United States Patent [19]

Mase et al.

[11] Patent Number: 4,987,132
[45] Date of Patent: Jan. 22, 1991

[54] SATURATED HETEROCYCLIC CARBOXAMIDE DERIVATIVES

[75] Inventors: Toshiyasu Mase, Chiba; Hiromu Hara, Saitama; Hitoshi Nagaoka, Tokyo; Takumi Takahashi, Tokyo; Takeshi Suzuki, Tokyo; Kenichi Tomioka, Saitama; Toshimitsu Yamada, Tokyo, all of Japan

[73] Assignee: Yamanouchi Pharmaceutical Co., Ltd., Tokyo, Japan

[21] Appl. No.: 232,899

[22] Filed: Aug. 16, 1988

Related U.S. Application Data

[63] Continuation-in-part of Ser. No. 157,406, Feb. 17, 1988, abandoned.

[30] Foreign Application Priority Data

Feb. 20, 1987 [JP] Japan .................................. 62-36950
May 21, 1987 [JP] Japan ................................ 62-125259
Oct. 1, 1987 [JP] Japan ................................ 62-249499

[51] Int. Cl.$^5$ .................. A61K 31/495; C07D 417/04
[52] U.S. Cl. ......................................... 514/252; 514/8; 514/226.8; 514/228.8; 514/235.2; 514/235.5; 514/235.8; 514/236.8; 514/253; 514/254; 514/314; 514/316; 514/317; 514/318; 514/326; 514/330; 514/340; 514/342; 514/343; 514/365; 514/432; 514/433; 514/436; 514/439; 514/440; 514/444; 514/452; 514/459; 514/467; 514/471; 514/474; 544/54; 544/55; 544/96; 544/120; 544/124; 544/128; 544/129; 544/130; 544/133; 544/138; 544/141; 544/146; 544/148; 544/149; 544/152; 544/238; 544/237; 544/295; 544/353; 544/357; 544/360; 544/363; 544/364; 544/367; 544/368; 544/369; 544/370; 544/371; 544/372; 544/373; 544/376; 544/379; 544/405; 546/167; 546/187; 546/189; 546/193; 546/200; 546/207; 546/208; 546/209; 546/212; 546/213; 546/214; 546/275; 546/277; 546/280; 546/281; 546/283; 546/284; 548/200; 548/215; 548/517; 548/518; 548/527; 549/13; 549/14; 549/22; 549/29; 549/39; 549/60; 549/370; 549/414; 549/448; 549/473; 549/487

[58] Field of Search ............... 544/357, 363, 364, 360, 544/367, 369, 372, 379, 238, 237, 295, 353, 376, 54, 55, 96; 514/252, 253, 254, 226.8, 228.8, 235.2, 235.5, 235.8, 236.8

[56] References Cited

U.S. PATENT DOCUMENTS

4,656,190  4/1987  Shen et al. ........................ 514/529
4,840,936  6/1989  Della Bella et al. ............... 548/200

FOREIGN PATENT DOCUMENTS

256687    2/1988  European Pat. Off. ............ 546/280
2729414   1/1978  Fed. Rep. of Germany .
60-90012  7/1981  Japan ................................. 546/280

OTHER PUBLICATIONS

Oeriu, Chem. Abst., 88-121163f (1978).
Braquet et al, Chem. Abst. 103-189808d (1985).
Biftu et al, Chem. Abst. 104-5761z (1986).
Fabre et al, Chem. Abst. 101-230510z (1984).
Mase et al, Chem. Abst. 110-23877v (1989).

Primary Examiner—Cecilia Shen
Attorney, Agent, or Firm—Burgess, Ryan & Wayne

[57] ABSTRACT

A saturated heterocyclic carboxamide derivative of the following general formula (I) and salts thereof which have platelet activating factor (PAF) antagonizing activity.

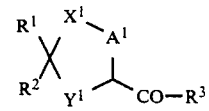

17 Claims, No Drawings

SATURATED HETEROCYCLIC CARBOXAMIDE DERIVATIVES

This application is a continuation-in-part of U.S. application Ser. No. 157,406, filed Feb. 17 1988, now abandoned the entire contents of which is incorporated herein by reference.

FIELD OF THE INVENTION

This invention relates to novel saturated heterocyclic carboxamide derivatives and salts thereof which have platelet activating factor (PAF) antagonizing (anti-PAF) activity.

BACKGROUND OF THE INVENTION

PAF is a chemical substance released from human and other animal cells and is an acetylglyceryl ether of phosphorylcholine as represented by the following formula

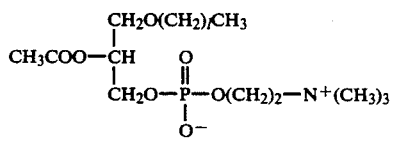

wherein $\gamma$ is the integer 15 or 17.

PAF is physiologically active and causes contraction of the airway smooth muscle, increased vascular permeation, platelet aggregation and blood pressure fall, among others. It is thought to be a factor inducing asthma, inflammation, thrombosis, shock and other symptoms. Therefore, studies of substances capable of antagonizing the physiological activities of PAF are under way and several anti-PAF agents have been reported (e.g. European Patent Application No. 178,261 (A), U.S. Pat. Nos. 4,539,332; 4,656,190 and 4,621,038 European Pat. No. 115,979 (B), and British Patent Application No. 2,162,062 (A)).

The present inventors found that novel saturated heterocyclic carboxamide derivatives differing in chemical structure from the known anti-PAF agents having platelet activating factor antagonizing activity and, based on this finding, they have now completed the present invention.

SUMMARY OF THE INVENTION

The invention thus provides saturated heterocyclic carboxamide derivatives of the following general formula (I) and salts thereof

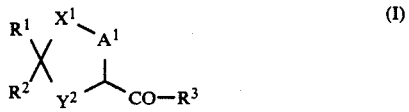

In the above formula (I) $R^1$ represents a substituted or unsubstituted 5- or 6-membered heterocyclic group, which may be condensed with benzene ring; $R^2$ represents a hydrogen atom, a lower alkyl group, or an $R^1$ group defined above; $X^1$ represents an oxygen atom, a sulfur atom, or a methylene group, which may be substituted by a lower alkyl group; $Y^1$ represents an oxygen atom, a sulfur atom, or a group of the formula $>N-R^4$ wherein $R^4$ is a hydrogen atom, a lower alkyl, a carboxyl group, an acyl group or a lower alkoxycarbonyl group; $A^1$ represents a methylene group or an ethylene group, each of which may be substituted by a lower alkyl group; $R^3$ represents a group of the formulae

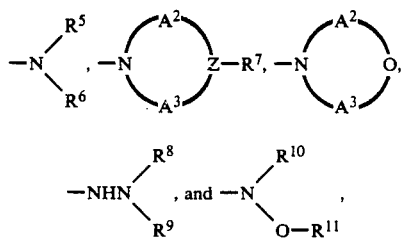

wherein one of $R^5$ and $R^6$ is a hydrogen atom, or a substituted or unsubstituted hydrocarbon group, and the other is a substituted or unsubstituted hydrocarbon group or a substituted or unsubstituted 5- or 6-membered heterocyclic group, which may be condensed with a benzene ring, $A^2$ and $A^3$, which may be the same or different, each represents a substituted or unsubstituted lower alkylene group, Z is a methine group ($>CH-$) or a nitrogen atom, $R^7$ is a hydrogen atom, a substituted or unsubstituted hydrocarbon group or a carboxyl, acyl, lower alkoxycarbonyl, carbamoyl, or mono- or di-lower alkylaminocabonyl group, and $R^8$ $R^9$ $R^{10}$ and $R^{11}$, which may be the same or different, each represents a hydrogen atom, a lower alkyl group, an aralkyl group or an aryl group.

In the above formula (I), it is preferred that $R^1$ is a pyridyl group, a quinolyl group, a pyrrolyl group, a piperidyl group, a pyrazinyl group or a furyl group, each of which may be substituted by one or two substituents each selected from the group consisting of a lower alkyl group, a lower alkoxy group, a lower alkoxycarbonyl group and a dimethylamino group, said pyridyl group may be in the pyridone form; $R^2$ is a hydrogen atom, a lower alkyl group, or a pyridyl group; $X^1$ is a sulfur atom, an oxygen atom or a methylene group; $Y^1$ is an oxygen atom or $>N-R^4$ wherein $R^4$ is a hydrogen atom, a lower alkyl group, an acyl group or a lower alkoxycarbonyl group; $A^1$ is a methylene or ethylene group, which may be substituted by one or two lower alkyl group; $R^3$ is

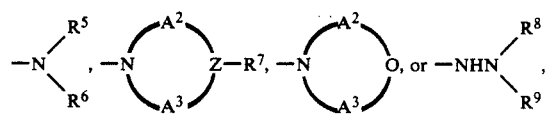

in which one of $R^5$ and $R^6$ is a hydrogen atom or a lower alkyl group and the other is a substituted or unsubstituted hydrocarbon group or a substituted or unsubstituted 5- or 6-membered heterocyclic group; $A^2$ and $A^3$, which may be the same or different, each is a substituted or unsubstituted alkylene group; Z is a methine group or a nitrogen atom; $R^7$ is a hydrogen atom, a substituted or unsubstituted hydrocarbon group, or an acyl group, a lower alkoxycarbonyl group, a carbamoyl group, or a mono- or di-alkylaminocarbonyl group; and $R^8$ and $R^9$, which may be the same or different, each is a hydrogen atom, a lower alkyl group or an aryl group. Further, it is more preferred that $R^1$ is a pyridyl group, which may be substituted by one or two substituents each selected from the group consisting of a lower alkyl group, a lower alkoxycarbonyl group, or a dimethylamino group; $R^2$ is a hydrogen atom; $X^1$ is a sulfur atom; $Y^1$ is >N-$R^4$, in which $R^4$ is a hydrogen atom, a lower alkyl, an acyl group or a lower alkoxycarbonyl group; $A^1$ is a methylene group, which may be substituted by one or two lower alkyl group; $R^3$ is

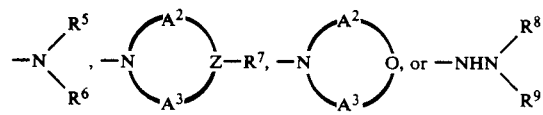

as defined above, preferably

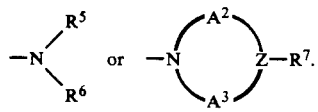

Among these substituents in the above formula (I), it is particularly preferred that $R^1$ is a pyridyl group; $R^2$ is a hydrogen atom; $X^1$ is a sulfur atom; $Y^1$ is >NH; $A^1$ is a methylene group; and $R^3$ is

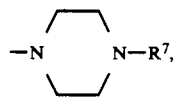

in which $R^7$ is an aryl-lower alkyl group.

From the chemical structure viewpoint, the compounds of the invention are characterized in that they are saturated heterocyclic carboxamide derivatives whose specific saturated heterocycle is always substituted by a specific heterocycle and a specific carboxamide at respective specific positions. More specifically, the chemical structure of the compounds according to the invention, which are represented by formula (I)

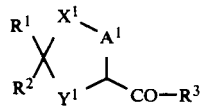

is characterized in that the saturated heterocycle

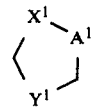

which is a 5- or 6-membered saturated heterocycle, is always substituted, at a specific position thereof, by a specific heterocycle, namely the group RI which is a 5- or 6-membered heterocycle, which may be condensed with a benzene ring, and, at another specific position, by the group —$COR^3$ which is a specific substituted carboxamide group.

Various saturated heterocyclic carboxamide derivatives similar to the compounds (I) according to the invention have been known so far. For instance, German Pat. No. 2,729,414 discloses that compounds of the formula

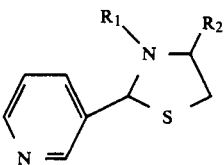

wherein $R_1$ is an alkanoyl group of 2 to 17 carbon atoms and $R_2$ is a carboxyl group or an ester or amide thereof, have litholytic activity and U.S. Pat. No. 3,592,905 discloses that compounds of the formula

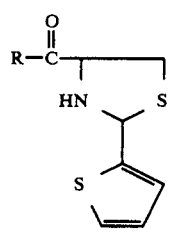

wherein R is a hydroxy, alkoxy or amino group, have antiinflammatory activity. However, those compounds that have the chemical structure characteristics mentioned hereinbefore in accordance with the invention have not been known in any specific manner.

DETAILED DESCRIPTION OF THE INVENTION

The compounds of the invention are described in more detail hereinbelow.

In the definitions of the substituents used herein in the general formulas, the term "lower" means, unless otherwise specified, than the relevant group includes a straight or branched carbon chain containing 1 to 6 carbon atoms.

Accordingly, the "lower alkyl group" includes, among others, methyl, ethyl, propyl, isopropyl, butyl, isobutyl, sec-butyl, tert-butyl, pentyl (amyl), isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The "mono- or di-lower alkylaminocarbonyl group" means a carbamoyl group whose amino group is mono- or di-substituted by the above-mentioned "lower alkyl group or groups" and, more specifically, includes methylaminocarbonyl, ethylaminocarbonyl, propylaminocarbonyl, isopropylaminocarbonyl, butylaminocarbonyl, isobutylaminocarbonyl, pentylaminocarbonyl, isopentylaminocarbonyl, hexylaminocarbonyl, isohexylaminocarbonyl, dimethylaminocarbonyl, diethylaminocarbonyl, dipropylaminocarbonyl, diisopropylaminocarbonyl, dibutylaminocarbonyl, dipentylaminocarbonyl, dihexylaminocarbonyl, ethylmethylaminocarbonyl, methylpropylaminocarbonyl, ethylpropylaminocarbonyl, ethylisopropylaminocarbonyl, butylmethylaminocarbonyl and butylpropylaminocarbonyl, among others.

The term "hydrocarbon group" as used herein means a monovalent group derived from a hydrocarbon, which is a generic name of a compound consisting of carbon and hydrogen atoms, by removal of one hydrogen atom therefrom. Preferred examples of the hydrocarbon group are acyclic hydrocarbon groups such is an alkyl group, which is a saturated monovalent hydrocarbon group, and cyclic hydrocarbon groups such as a cycloalkyl group, which is a monocyclic saturated monovalent hydrocarbon group, an aryl group, which is an aromatic monocyclic or polycyclic monovalent hydrocarbon group, a nonaromatic condensed polycyclic hydrocarbon group, and an aralkyl or aralkenyl group, which is a monovalent group derived from an aromatic monocyclic or polycyclic hydrocarbon having a side chain by removal of one hydrogen atom from said side chain.

The "alkyl group" mentioned above is preferably a straight or branched alkyl group containing 1 to 20 carbon atoms and includes, in addition to the above-mentioned examples of the "lower alkyl group", heptyl, 5-methylhexyl, octyl, 6-methylheptyl, nonyl, 7-methyloctyl, decyl, 8-methylnonyl, undecyl, 9-methyldecyl, dodecyl, 10-methylundecyl, tridecyl, 11-methyldodecyl, tetradecyl, 12-methyltridecyl, pentadecyl, 13-methyltetradecyl, hexadecyl, 14-methylpentadecyl, heptadecyl, 15-methylhexadecyl, octadecyl, 16-methylheptadecyl, nonadecyl, 17-methyloctadecyl, eicosyl, 18-methylnonadecyl and so forth.

The "cycloalkyl group" preferably contains 3 to 7 carbon atoms and includes cyclopropyl, cyclobutyl, cyclopentyl cyclohexyl, cycloheptyl, etc.

Preferred examples of the "aryl group" are phenyl and naphthyl.

The "aralkyl group" is preferably a group derived from the above-mentioned "lower alkyl group" by substitution of any hydrogen atom by the above-mentioned "aryl group" and includes, among others, benzyl, phenethyl, 1-phenylethyl, 3-phenylpropyl, 2-phenylpropyl, 1-phenylpropyl, 1-methyl-2-phenylethyl, 4-phenylbutyl, 3-phenylbutyl, 2-phenylbutyl, 1-phenylbutyl, 2-methyl-3-phenylpropyl, 2-methyl-2-phenylpropyl, 2-methyl-1-phenylpropyl, 1-methyl-3-phenylpropyl, 1-methyl-2-phenylpropyl, 1-methyl-1-phenylpropyl, 1-ethyl-2-phenylethyl, 1,1-dimethyl-2-phenylethyl, 5-phenylpentyl, 4-phenylpentyl, 3-phenylpentyl, 2-phenylpentyl, 1-phenylpentyl, 3-methyl-4-phenylbutyl, 3-methyl-3-phenylbutyl, 3-methyl-2-phenylbutyl, 3-methyl-1-phenylbutyl, 6-phenylhexyl, 5-phenylhexyl, 4-phenylhexyl, 3-phenylhexyl, 2-phenylhexyl, 1-phenylhexyl, 4-methyl-5-phenylpentyl, 4-methyl-4-phenylpentyl, 4-methyl-3-phenylpentyl, 4-methyl-2-phenylpentyl, 4-methyl-1-phenylpentyl, 1-naphthylmethyl, 2-naphthylmethyl, 2-(1-naphthyl)ethyl, 2-(2-naphthyl)ethyl, 1-(1-naphthyl)ethyl, 1-(2-naphthyl)ethyl, 3-(1-naphthyl)propyl, 3-(2-naphthyl)propyl, 2-(1-naphthyl)propyl, 2-(2-naphthyl)propyl, 1-(1-naphthyl)propyl, 1-(2-naphthyl)propyl, 1-methyl-2-(1-naphthyl)ethyl, 1-methyl-2-(2-naphthyl)ethyl, 4-(1-naphthyl)butyl, 4-(2-naphthyl)butyl, 3-(1-naphthyl)butyl, 3-(2-naphthyl)butyl, 2-(1-naphthyl)butyl, 2-(2-naphthyl)butyl, 1-(1-naphthyl)butyl, 1-(2naphthyl)butyl, 2-methyl-3-(1-naphthyl)propyl, 2-methyl-3-(2-naphthyl)propyl, 2-methyl 2-(1-naphthyl)propyl, 2-methyl-2-(2-naphthyl)propyl, 2-methyl-1-(1-naphthyl)propyl, 2-methyl-1-(2-naphthyl)propyl, 5-(1-naphthyl)pentyl, 5-(2-naphthyl)pentyl, 4-(1-naphthyl)pentyl, 4-(2-naphthyl)pentyl, 3-methyl-4-(1-naphthyl)butyl, 3-methyl-4-(2-naphthyl)butyl, 6-(1-naphthyl)hexyl, 6-(2-naphthyl)hexyl, 5-(1-naphthyl)hexyl, 5-(2-naphthyl)hexyl, 4-methyl-5-(1-naphthyl)pentyl, 4-methyl-5-(2-naphthyl)pentyl, diphenylmethyl (benzhydryl) and trityl (triphenylmethyl).

The "aralkenyl group" is a group resulting from binding of the above-mentioned "aryl group" to a lower alkenyl group and includes, among others, 2-phenylethyl, 3-phenyl-1-propenyl, 3-phenyl-2-propenyl, 1-methyl-2-phenylbutenyl, 4-phenyl-1-butenyl, 4-phenyl-2-butenyl, 4-phenyl-3-butenyl, 5-phenyl-1-pentenyl, 5-phenyl-2-pentenyl, 5-phenyl-3-pentenyl, 5-phenyl-4-pentenyl, 6-phenyl-1-hexenyl, 6-phenyl-2-hexenyl, 6-phenyl-3-hexenyl, 6-phenyl-4-hexenyl, 6-phenyl-5-hexenyl, 2-(1-naphthyl)ethenyl, 2-(2-naphthyl)ethenyl, 3-(1-naphthyl)-2-propenyl, 3-(2-naphthyl)-2-propenyl, 4-(1-naphthyl)-3-butenyl, 4-(2-naphthyl)-3-butenyl, 5-(1-naphthyl)-2-pentenyl, 5-(2-naphthyl)-2-pentenyl, 5-(1-naphthyl)-4-pentenyl, 5-(2-naphthyl)-4-pentenyl, 6-(1-naphthyl) 2-hexenyl, 6-(2-naphthyl)-2-hexenyl, 6-(1-naphthyl)-5-hexenyl and 6-(2-naphthyl)-5-hexenyl.

Examples of the nonaromatic condensed polycyclic hydrocarbon group are indanyl, which may be represented by the formula

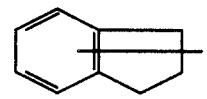

which is available for binding at any optional position on the benzene ring or saturated ring (the same shall apply when the same manner of formula representation is used), indenyl (e.g.

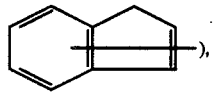), tetrahydronaphthyl

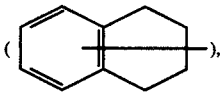), dihydronaphthyl (e.g.

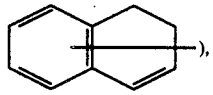), 1,2-benzo-1-cycloheptenyl

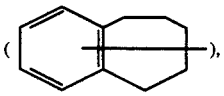), fluorenyl (e.g.

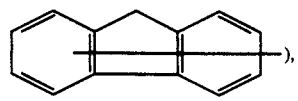), 2,3-dihydro-1H-benz[f]indenyl

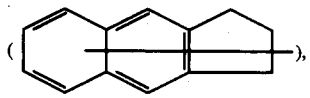

1H-benz[f]indenyl

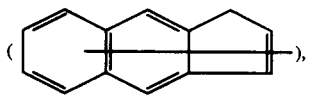

and the like condensed polycyclic hydrocarbon groups ether than aromatic hydrocarbon groups.

In the compounds or the invention, the "5- or 6-membered heterocyclic group, which may be condensed with a benzene ring" represented by $R^1$ $R^2$, $R^5$ or $R^6$ is preferably an oxygen-, sulfur- and/or nitrogen-containing, saturated or unsaturated heterocyclic group and, more specifically, includes pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, indolyl, benzimidazolyl, indazolyl, pyridyl, dihydropyridyl, tetrahydropyridyl, piperidinyl, pyrimidinyl, pyridazinyl, pyrazinyl, piperazinyl, quinolyl, quinazolinyl, quinoxalinyl, phthalazinyl, cinnolinyl and other monocyclic or bicyclic, saturated unsaturated heterocyclic groups containing one or more nitrogen atoms alone as hetero atoms; thiazolinyl, thiazolidinyl, isothiazolyl, thiadiazolyl, benzothiazolyl, benzoisothiazolyl and other nitrogen and sulfur atoms containing, mono- or bicyclic, saturated or unsaturated heterocyclic groups; oxazolyl, oxazolinyl, oxazolidinyl, isoxazolyl, oxadiazolyl, benzoxazolyl, benzisoxazolyl and other nitrogen and oxygen atoms-containing, mono- or bicyclic, saturated or unsaturated heterocyclic groups; and, furthermore, heterocyclic groups containing one or more sulfur or oxygen atoms, such as thienyl, tetrahydrothienyl, furyl, tetranhydrofuryl, pyranyl, tetrahydropyranyl, dioxolyl, benzofuryl, benzopyranyl and benzodioxolyl.

These heterocyclic groups are available for bonding at any optional position, either on the heterocycle or on the benzene ring, through a ring-forming carbon atom or a ring-forming nitrogen atom.

The "lower alkylene group" represented by each of $A^2$ and $A^3$ is preferably a straight alkylene group containing 1 to 3 carbon atoms and, more specifically, includes methylene, ethylene and trimethylene.

As the "acyl group", there may be made particular mention of lower alkanoyl groups such as formyl, acetyl, propionyl, butyryl isobutyryl, valeryl, isovaleryl, pivaloyl and hexanoyl, aralkanoyl groups such as benzylcarbonyl, 3-phenylpropanoyl, 2-phenylpropanoyl, 1-phenylpropanoyl, 4-phenylbutanoyl, 3-phenylbutanoyl, 2-phenylbutanoyl, 1-phenylbutanoyl, 2-methyl-3-phenylpropanoyl, 5-phenylpentanoyl, 4-phenylbutanoyl, 3-phenylpentanoyl, 2-phenylpentanoyl, 1-phenylhentanoyl, 3-methyl-4-phenylbutanoyl, 3-methyl-2-phenylbutanoyl, 6-phenylhexanoyl, 5-phenylhexanoyl, 4-phenylhexanoyl, 3-phenylhexanoyl, 2-phenylhexanoyl, 1-phenylhexanoyl, 4-methyl-5-phenylpentanoyl, 4-methyl-3-phenylhexanoyl and 4-methyl-2-phenylhexanoly, and substituted or unsubstituted arylcarbonyl groups such as benzoyl, 1-naphthoyl, 2-naphthoyl, (o-, m- or p-)toluoyl, (o-, m- or p-)fluorobenzoyl, (o-, m- or p-)chlorobenzoyl, (o-, m- or p-)bromobenzoyl and various fluoronaphthoyl, chloronaphthoyl, bromonaphthoyl, methoxalyl and ethoxalyl groups. The "lower alkoxycarbonyl group" includes, among others, methoxycarbonyl, ethoxycarbonyl, isobutoxycarbonyl, sec-butoxycarbonyl, tertbutoxycarbonyl, pentyloxycarbonyl, 3-methylbutoxycarbonyl, hexyloxycarbonyl and 4-methylpentyloxycarbonyl.

As preferred examples of the "aralkyl group" or "aryl group" represented by any or $R^8$, $R^9$, $R^{10}$ and $R^{11}$, there may be mentioned those aralkyl groups or aryl groups specifically mentioned in relation to the term "hydrocarbon group".

The above-mentioned "hydrocarbon group" and/or "5- or 6-membered heterocyclic group, which may be condensed with a benzene ring" may further have, on any of $R^5$, $R^6$, $R^7$, $R^1$ and $R^2$, one or more substituents each selected from among halogen atom, lower alkyl group, hydroxy and related groups (hydroxy, mercapto, alkoxy, lower alkylthio, cycloalkyl-lower alkoxy, cycloalkyl-lower alkylthio, aryl, aralkyloxy, aralkylthio, aryloxy, arylthio, arylsulfinyl, arylsulfonyl, aryloxy-lower alkoxy, aryloxy-lower alkylthio, arylthio-lower alkoxy, arylthio-lower alkylthio), oxo and related groups (oxo, thioxo), carboxyl and related groups (carboxyl, lower alkoxycarbonyl, acyl), cyano, carbamoyl and related groups (carbamoyl, mono- or di-lower alkylaminocarbonyl), nitro, amino and related groups (amino, mono- or di-lower alkylamino, mono- or diaralkylamino, N-aralkyl-N-lower alkylamino) and, for $R^5$ or $R^6$, nitrogen-containing heterocyclic groups.

Preferred as the "halogen atom" is a fluorine, chlorine or bromine atom. The "lower alkyl group" includes those mentioned hereinbefore.

The "alkoxy group" is suitably a straight or branched one containing 1 to 10 carbon atoms and includes methoxy, ethoxy, propoxy, isopropoxy, butoxy, isobutoxy, sec-butoxy, tert-butoxy, pentyloxy (amyloxy), isopentyloxy, tert-pentyloxy, neopentyloxy, 2-methylbutoxy, 1,2-dimethylpropoxy, 1-ethylpropoxy, hexyloxy, heptyloxy, 5-methylhexyloxy, octyloxy, 6-methylheptyloxy, nonyloxy, 7-methyloctyloxy, decyloxy, 8-methylnonyloxy, and so on.

The "lower alkoxy group" includes those alkoxy groups mentioned hereinbefore in relation to the "alkoxy group" which contain 1 to 6 carbon atoms.

The "lower alkylthio group" corresponds to the above-mentioned lower alkoxy group in the sense that the former contains a sulfur atom in place of the oxygen atom in the latter Examples are methylthio, ethylthio, propylthio, isopropylthio, butylthio, sec-butylthio, tert-butylthio, pentylthio, neopentylthio, 2-methylbutylthio, 1,2-dimethylpropylthio, 1-ethylpropylthio and hexylthio.

The "cycloalkyl-lower alkoxy group" or "cycloalkyl-lower alkylthio group" means a group resulting from substitution of one optical hydrogen atom of the above-mentioned "lower alkoxy group" or "lower alkylthio group", respectively, by the above-mentioned "cycloalkyl group" and specifically includes, among others, cyclopropylmethoxy (or methylthio) [for denoting cyclopropylmethoxy or cyclopropylmethylthio; hereinafter the same shall apply], 2-cyclopropyl-ethoxy (or ethylthio), 1-cyclopropyl-ethoxy (or ethylthio), 3-cyclopropyl-propoxy (or propylthio), 2-cyclopropyl-propoxy (or propylthio), 1-cyclopropyl-propoxy or propylthio), 2-cyclopropyl-1-methyl-ethoxy (or ethylthio), 4-cyclopropyl-butoxy (or butylthio), 5-cyclopropylpentyl-oxy (or thio), 6-cyclopropylhexyl-oxy (or thio), cyclobutyl-methoxy (or methylthio), 2-cyclobutyl-ethoxy (or ethylthio), 1-cyclobutylethoxy (or ethylthio), 3-cyclobutyl-propoxy (or propylthio), 2-cyclobutyl-propoxy (or propylthio), 1-cyclobutyl-propoxy (or propylthio), 2-cyclobutyl-1-methyl-ethoxy (or ethylthio), 4-cyclobutyl-butoxy or butylthio), 5-cyclobutylpentyl-oxy (or thio), 6-cyclobutylhexyl-oxy (or thio), cyclopentyl-methoxy (or methylthio), 2-cyclopentylethoxy (or ethylthio), 1-cyclopentyl-ethoxy (or ethylthio), 3-cyclopentyl-propoxy (or propylthio), 2-cyclopentyl-propoxy (or propylthio), 1-cyclopentyl-propoxy (or propylthio), 2 cyclopentyl-1-methyl-ethoxy (or ethylthio), 4-cyclopentyl-butoxy (or butylthio), 5-cyclopentylpentyl-oxy (or thio), 6-cyclopentylhexyl-oxy (or thio), cyclohexyl-methoxy (or methylthio), 2-cyclohexyl-ethoxy (or ethylthio), 1-cyclohexyl-ethoxy (or ethylthio), 3-cyclohexyl-propoxy (or propylthio), 2-cyclohexyl-propoxy (or propylthio), 1-cyclohexyl-propoxy (or propylthio), 2-cyclohexyl-1-methyl ethoxy (or ethylthio), 4-cyclohexylbutyoxy (or butylthio), 5-cyclohexylpentyl-oxy (or thio), 6-cyclohexylhexyl-oxy (or thio), cycloheptyl-methoxy (or methylthio), 2-cycloheptyl-ethoxy (or ethylthio), 1-cycloheptyl-ethoxy (or etnylthio), 3-cycloheptyl-propoxy (or propylthio), 2-cycloheptyl-propoxy (or propylthio), 1-cycloheptyl-propoxy (or propylthio), 2-cycloheptyl-1-methyl-ethoxy (or ethylthio), 4-cycloheptyl-butoxy (or butylthio), 5-cycloheptylpentyl-oxy (or thio) and 6-cycloheptylhexyl-oxy (or thio).

The "aralkyloxy group" or "aralkylthio group" means a group resulting from substitution of one optional hydrogen atom of the above-mentioned "lower alkoxy group" or "lower alkylthio group" by the above-mentioned "aryl group" and, more specifically, includes the following examples in which the "aryl group" is typified by a phenyl group alone: benzyloxy (or thio), phenethyl-oxy (or thio), 1-phenyl-ethoxy (or ethylthio), 3-phenyl-propoxy (or propylthio), 2-phenyl-propoxy (or propylthio), 1-phenyl-propoxy (or propylthio), 2-phenyl-1-methyl-ethoxy (or ethylthio), 4-phenyl-butoxy (or butylthio), 5-phenylpentyl-oxy (or thio) and 6-phenylhexyl-oxy (or thio).

Examples of the "aryloxy group" or "arylthio group" are phenoxy (or phenylthio), naphthyl-oxy (or thio) and other ether or thioether residues derived from aromatic mono- or polycyclic hydrocarbon hydroxy or mercapto compounds.

The "aryloxy-lower alkoxy group", "aryloxy-lower alkylthio group", "arylthio-lower alkoxy group" or "arylthio-lower alkylthio group" means a group resulting from substitution of one optional hydrogen atom of the above-mentioned "lower alkoxy group" or "lower alkylthio group" by the above-mentioned "aryloxy group" or "arylthio group" and, more specifically, includes the following examples wherein the "aryloxy group" or "arylthio group" is typified by a phenoxy (or phenylthio) group alone: phenoxy (or phenylthio)-methoxy (or methylthio), 2-phenoxy (or phenylthio)-ethoxy (or ethylthio), 1-phenoxy (or phenylthio)-ethoxy (or ethylthio), 3-phenoxy (or phenylthio)-propoxy (or propylthio), 2-phenoxy (or phenylthio)-propoxy (or propylthio), 1-phenoxy (or phenylthio)-propoxy or propylthio), 2-phenoxy (or phenylthio)-1-methyl-ethoxy (or ethylthio), 4-phenoxy (or phenylthio)-butoxy (or butylthio), 5-phenoxy (or phenylthio)pentyl-oxy (or thio) and 6-phenoxy (or phenylthio)hexyl-oxy (or thio).

As examples of the "acyl group" or "mono- or di-lower alkylaminocarbonyl group", there may be mentioned those specific groups that have already been given hereinabove.

The "mono- or di-lower alkylamino group" means a group resulting from substitution of one or two hydrogen atoms of an amino group by "lower alkyl groups" mentioned hereinbefore and, more specifically, includes monoalkylamino groups in which the substituent alkyl group is a straight or branched alkyl group containing 1 to 6 carbon atoms, such as methylamino, ethylamino, propylamino, isopropylamino, butylamino, isobutylamino, pentylamino, isopentylamino, hexylamino and isohexylamino, symmetrical dialkylamino groups in which the two substituent alkyl groups are the same and each is a straight or branched alkyl group containing 1 to 6 carbon atoms, such as dimethylamino, diethylamino, dipropylamino, diisopropylamino, dibutylamino, dipentylamino and dihexylamino, and asymmetrical dialkylamine groups in which the two substituent alkyl groups are different from each other and each is a straight or branched alkyl group containing 1 to 6 carbon atoms, such as ethylmethylamino, methylpropylamino, ethylpropylamino, burylmethylamino, butylethylamino and butylpropylamino.

As the "mono- or diaralkylamino group", there may be mentioned monoaralkylamino groups such as benzylamino, phenethylamino, 3-phenylpropylamino, 4-phenylbutylamino, 5-phenylpentylamino, 6 phenylhexylamino, 1-naphthylmethylamino, 2-naphthylmethylamio, 1-naphthylethylamino, 2-naphthylethylamino, 1-naphrhylpropylamino, 2-naphthylpropylamino, 1-naphthylbutylamino, 2-naphthylbutylamino, diphenylmethylamino, 2,2-diphenylethylamino, 3,3-diphenylpropylamino, 4,4-diphenylbutylamino and triphenylmethylamino, symmetrical diaralkylamino groups such as dibenzylamino, diphenethylamino, bis(3-phenylpropyl)amino, bis(4-phenylbutyl)amino, bis(5-phenylpentyl)amino and bis(6-phenylhexyl)amino, and asymmetrical diaralkylamino groups such as N-benzylphenethylamino, N-benzyl-3-phenylpropylamino, N-benzyl-4-phenylbutylamino, N-benzyl-5-phenylpentylamino, N-benzyl-6-phenylhexylamino, N-phenethyl-3-phenylpropylamino, N-phenethyl-4-phenylbutylamino, N-phenethyl-5-phenylpentylamino, N-phenethyl-6-phenylhexylamino, N-(3-phenylpropyl)-4-phenyloutylamino, N-(3-phenylpropyl)-5-phenylpentylamino, N-(3-phenylpropyl)-6-phenylhexylamino, N-(4-phenylbutyl)-5-phenylpentylamino, N-(4-phenylbutyl)-6-phenylhexylamino and N-(5-phenylpentyl)-6-phenylhexylamino.

The "N-aralkyl-N-lower alkyl group" means a group resulting from substitution of the above-mentioned "lower alkyl group" on the amino group of the above-mentioned "monoaralkylamino group" for rendering the amino group tertiary and typically includes N-methylbenzylamino, N-ethylbenzylamino, N-propylbenzylamino, N-butylbenzylamino, N-pentylbenzylamino, N-hexylbenzylamino, N-methylphenethylamino, N-ethylphenethylamino, N-propylphenethylamino, N-butylphenethylamino, N-pentylphenethylamino, N-hexylphenethylamino, N-methyl-3-phenylpropylamino, N-ethyl-3-phenylpropylamino, N-propyl-3-phenylpropylamino, N-butyl-3-phenylpropylamino, N-pentyl-3-phenylpropylamino, N-hexyl-3-phenylpropylamino, N-methyl-4-phenylbutylamino, N-ethyl-4-phenylbutylamino, N-propyl-4-phenylbutylamino, N-butyl-4-phenylbutylamino, N-pentyl-4-phenylbutylamino and N-hexyl-4-phenylbutylamino.

The "nitrogen-containing heterocyclic group" as a substituent on $R^5$ and/or $R^6$ means a saturated or unsaturated, 5- or 6-membered heterocyclic group which contains at least one nitrogen atom as a hetero atom and optionally a sulfur atom and/or an oxygen atom, and may be condensed with a benzene ring. As examples of said group, there may be mentioned those heterocyclic groups containing at least one nitrogen atom as selected from among the examples given hereinbefore as examples of the "5- or 6-membered heterocyclic group, which may be condensed with a benzene ring".

In this case, too, such heterocyclic groups may be available for bonding at any position on the heterocycle or benzene ring either via a ring-forming carbon atom or via a ring-forming nitrogen atom, as mentioned hereinabove.

Preferred as the substituent which $A^2$ and/or $A^3$ may have are lower alkyl, aralkyl and aryl groups and, in particular, those groups specifically mentioned in relation to the above-mentioned "lower alkyl group" and, in the case of aralkyl and aryl groups, in relation to the "hydrocarbon group".

The compounds (I) according to the invention can form salts. The scope of the invention includes salts of the compounds (I). Such salts include acid addition salts with inorganic acids such as hydrochloric acid, sulfuric acid, nitric acid, phosphoric acid, hydrobromic acid and hydroiodic acid and with organic acids such as acetic acid, oxalic acid, succinic acid, citric acid, maleic acid, malic acid, fumaric acid, tartaric acid, picric acid, methanesulfonic acid and ethanesulfonic acid, salts with acidic amino acids such as glutamic acid and aspartic acid, quaternary ammonium salts resulting from quaternization with alkyl halides such as methyl chloride, methyl bromide and methyl iodide, and so forth.

The compounds (I) provided by the present invention have at least two asymmetric carbon atoms and there can exist isomers due to the presence of such carbon atoms. In certain instances, keto-enol tautomerism may be encountered between a compound having a hydroxy or mercapto group on a heterocycle and a compound having an oxo or thioxo group on a heterocycle. Such iosmers all fall within the scope of the present invention either in each individual isolated form or in a mixture form.

Specific examples of particularly preferred compound (I) and salts thereof in the invention include 1-(3-phenylpropyl)-4-[2-(3-pyridyl)thiazolidin-4-ylcarbonyl]piperazine, 1-decyl-4-2-(3-pyridyl)thiazolidin-4-ylcarbonyl]piperazine, 1-(4-oxo-4-phenylbutyl)-4-[2-(3-pyridyl)thiazolidin-4-ylcarbonyl]piperazine or an acid addition salt thereof, etc., but the present invention should not be construed as being limited thereto.

The compounds (I) according to the invention can be produced by applying various synthetic methods taking advantage of the characteristics of the skeletal structure and various substituents. Typical examples of applicable production processes are given below.

Process 1 (Amidation A)

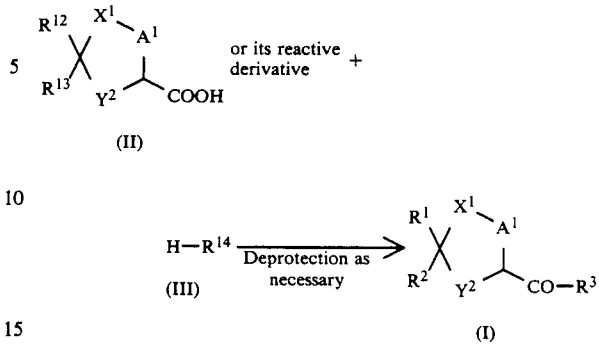

Process 2 (Amidation B)

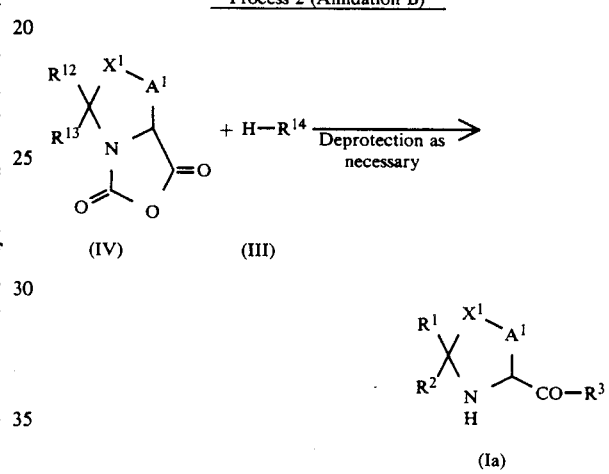

Process 3 (Amidation C)

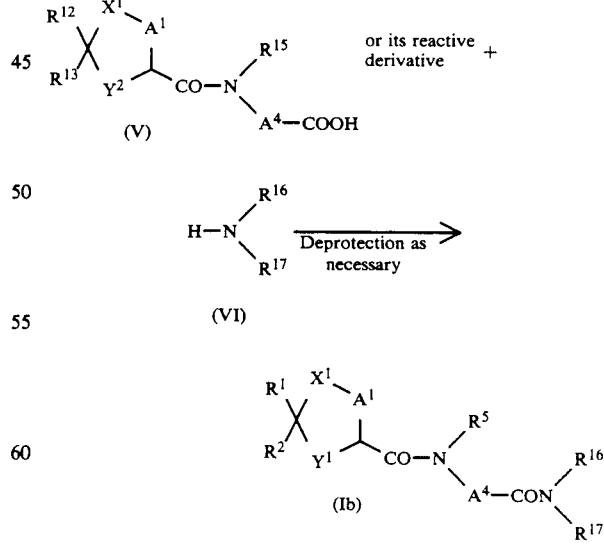

Process 4 (N-Acylation A)

-continued

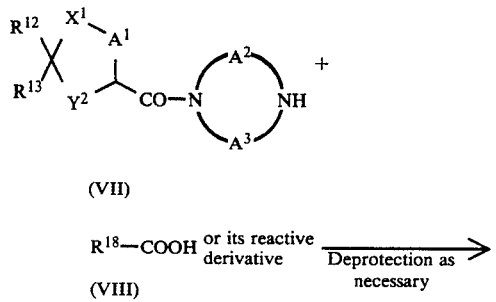
(VII)

$R^{18}$—COOH or its reactive derivative (VIII) $\xrightarrow{\text{Deprotection as necessary}}$

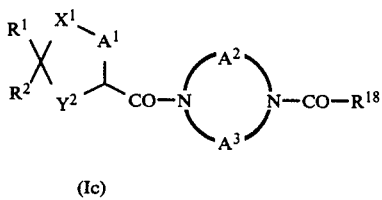
(Ic)

Process 5 (N-Acylation B)

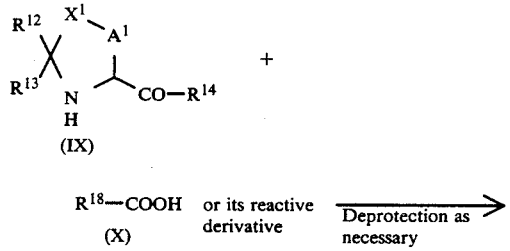
(IX)

$R^{18}$—COOH or its reactive derivative (X) $\xrightarrow{\text{Deprotection as necessary}}$

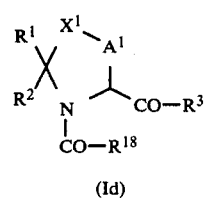
(Id)

Process 6 (N-Acylation C)

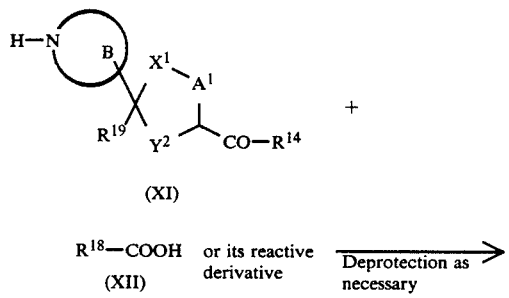
(XI)

$R^{18}$—COOH or its reactive derivative (XII) $\xrightarrow{\text{Deprotection as necessary}}$

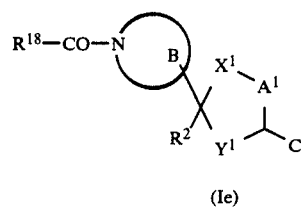
(Ie)

Process 7 (Etherification or thioetherification A)

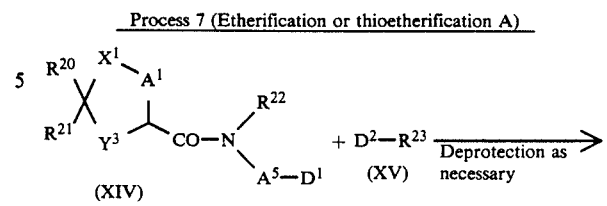
(XIV) + $D^2$—$R^{23}$ (XV) $\xrightarrow{\text{Deprotection as necessary}}$

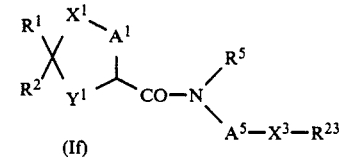
(If)

Process 8 (Etherification or thioetherification B)

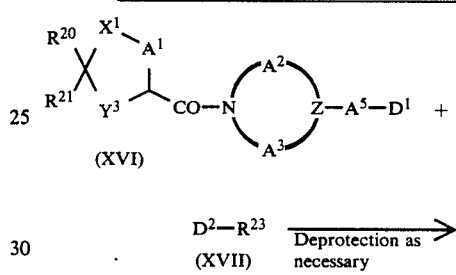
(XVI) +

$D^2$—$R^{23}$ (XVII) $\xrightarrow{\text{Deprotection as necessary}}$

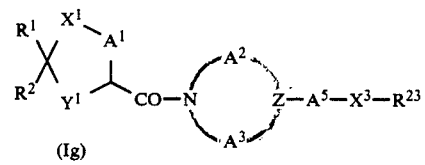
(Ig)

Process 9 (Etherification or thioetherification C)

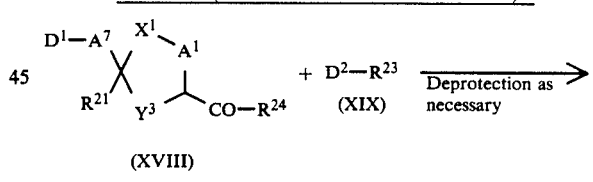
(XVIII) + $D^2$—$R^{23}$ (XIX) $\xrightarrow{\text{Deprotection as necessary}}$

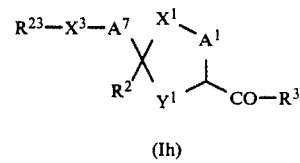
(Ih)

Process 10 (Cyclization)

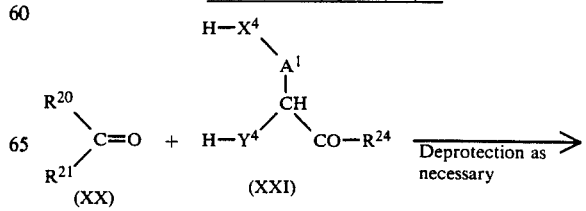
(XX) (XXI) $\xrightarrow{\text{Deprotection as necessary}}$

-continued

Process 10 (Cyclization)

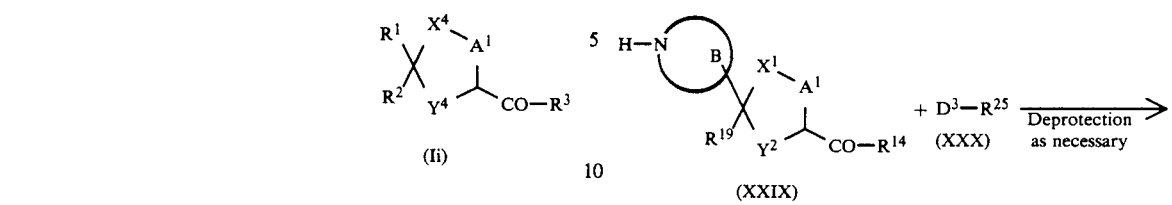

(Ii)

Process 11 (N-Alkylation A)

(XXII) $\xrightarrow{\text{D}^3-\text{R}^{25}\ (\text{XXIII})}_{\text{Deprotection as necessary}}$

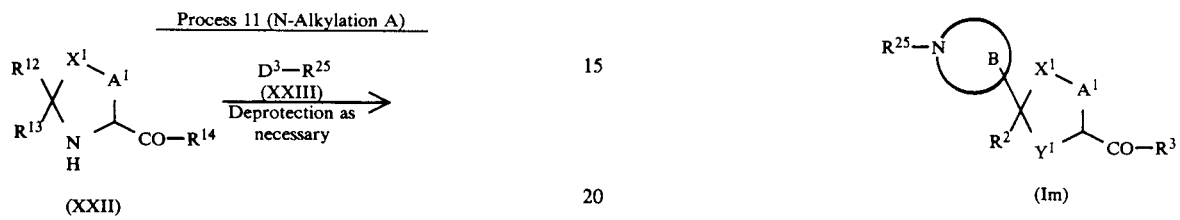

(Ij)

Process 12 (N-Alkylation B)

(XXIV) $\xrightarrow[\substack{(2)\ \text{D}^3-\text{R}^{27}\ (\text{XXVI}) \\ \text{as desired} \\ (3)\ \text{Deprotection as} \\ \text{necessary}}]{(1)\ \text{D}^5-\text{R}^{26}\ (\text{XXV})}$

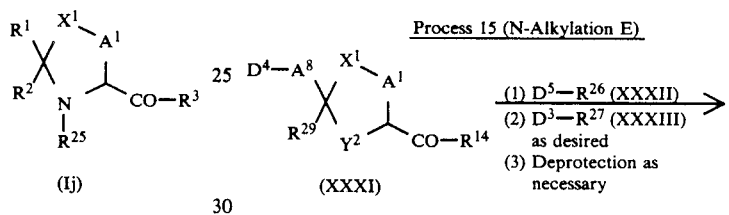

(Ik)

Process 13 (N-Alkylation C)

(XXVII) + D³—R²⁵ (XXVIII) $\xrightarrow{\text{Deprotection as necessary}}$

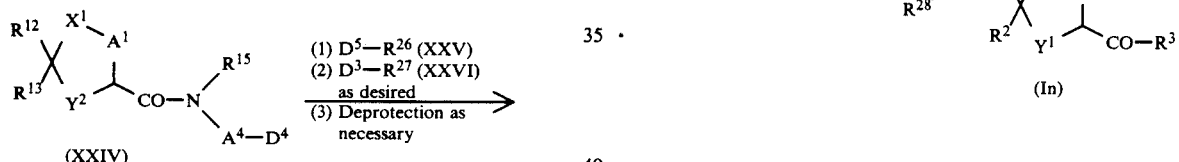

(Il)

Process 14 (N-Alkylation D)

(XXIX) + D³—R²⁵ (XXX) $\xrightarrow{\text{Deprotection as necessary}}$

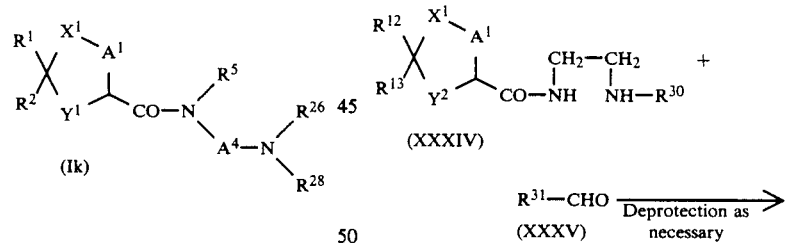

(Im)

Process 15 (N-Alkylation E)

(XXXI) $\xrightarrow[\substack{(2)\ \text{as desired} \\ (3)\ \text{Deprotection as} \\ \text{necessary}}]{(1)\ \text{D}^5-\text{R}^{26}\ (\text{XXXII})}$

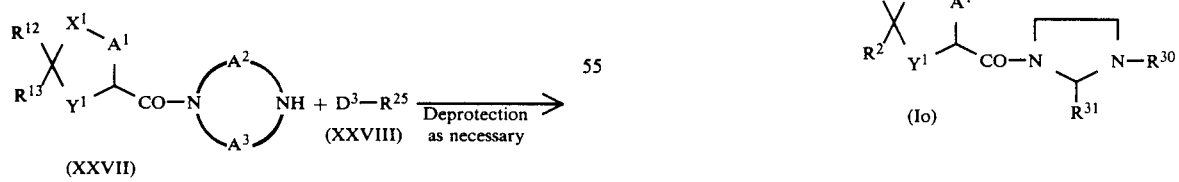

(In)

Process 16

(XXXIV) + R³¹—CHO (XXXV) $\xrightarrow{\text{Deprotection as necessary}}$

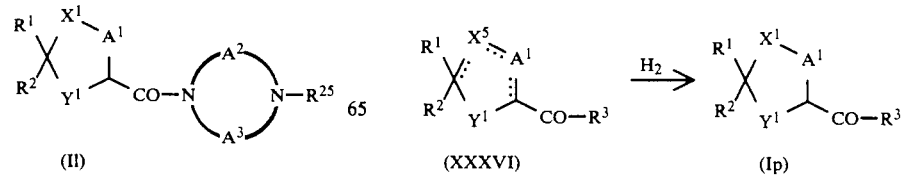

(Io)

Process 17 (Reduction)

(XXXVI) $\xrightarrow{\text{H}_2}$ (Ip)

In the above reaction formulas, $R^1$, $R^2$, $R^3$, $R^4$, $R^5$, $X^1$, $A^1$, $Y^1$ and Z each are as defined in above formula (I) and the other substituents are defined as follows:

$R^{12}$: the same group as $R^1$, which however may have a protective group;

$R^{13}$: the same group as $R^2$, which however may have a protective group;

$Y^2$: the same group as $Y^1$, which however may have a protective group;

$R^{14}$: the same group as $R^3$, which however may have a protective group;

$R^{15}$: the same group as $R^5$, which however may have a protective group;

$A^4$: a divalent hydrocarbon group;

$R^{16}$ and $R^{17}$: a hydrogen atom or a lower alkyl group; $R^{16}$ and $R^{17}$, which may be the same or different, a hydrogen atom or a lower alkyl group;

$R^{18}$: the residue of an acyl group after removal of the carbonyl group therefrom;

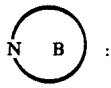

a nitrogen-containing 5- or 6-membered heterocyclic group in which the nitrogen atom is not a tertiary one and which may be condensed with a benzene ring; $R^{19}$: a hydrogen atom, a lower alkyl group or a group of the formula

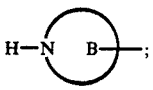

$R^{20}$: a the same group as $R^1$, which however may have a protective group;

$R^{21}$: the same group as $R^2$, which however may have a protective group;

$Y^3$: the same group as $Y^1$, which however may have a protective group;

$R^{22}$: the same group as $R^5$, which however may have a protective group;

$A^5$: the same group as $A^4$ or a divalent group of the formula $-A^4-X^2-A^6-$;

$X^2$: an oxygen atom or a sulfur atom;

$A^6$: a lower alkylene group;

$D^1$ and $D^2$: one is a hydroxy group, a mercapto group, or an alkali metal-substituted hydroxy or mercapto group and the other is a halogen atom or an organo sulfonyloxy group;

$R^{23}$: an alkyl group of 1 to 10 carbon atoms, a cycloalkyl-lower alkyl group, an aralkyl group, an aryl group, an aryloxy-lower alkyl group or arylthio-lower alkyl group;

$X^3$: an oxygen atom or a sulfur atom;

$A^7$: a divalent 5- or 6-membered heterocyclic group, which may be condensed with a benzene ring, or a group of the formula $-A^6-X^2-A^8-$;

$A^8$: a divalent 5- or 6-membered heterocyclic group, which may be condensed with a benzene ring;

$R^{24}$: the same group as $R^3$, which however may have a protective group;

$X^4$: an oxygen atom or a sulfur atom;

$Y^4$: an oxygen atom, a sulfur atom or an imino group (—NH—);

$D^3$: a halogen atom or an organo sulfonyloxy group;

$R^{25}$: a lower alkyl group, a lower alkoxycarbonyl group or an acyl group;

$D^4$ and $D^5$: one is an amino group, which may have a protective group, and the other is a halogen atom: or an organo sulfonyloxy group;

$R^{26}$: a hydrogen atom, a lower alkyl group or an aralkyl group when $D^5$ is an amino group which may have a protective group; a lower alkyl group or an aralkyl group when $D^5$ is a halogen atom or an organo sulfonyloxy acid group; $D^5$-$R^{26}$ may be potassium phthalamide, provided that $D^4$ is a halogen atom or an organo sulfonyloxy group;

$R^{27}$: a lower alkyl group or an aralkyl group, which may be the same as or different from $R^{26}$;

$R^{28}$: a hydrogen atom or the same group as $R^{26}$ or $R^{27}$;

$R^{29}$: a hydrogen atom, a lower alkyl group or a group of the formula $D^4-A^8-$;

$R^{30}$: a hydrogen atom, a lower alkyl group or an aralkyl or an aryl group;

$R^{31}$: a hydrogen atom, a lower alkyl group, an aralkyl group or an aryl group;

$X^5$: an oxygen or a sulfur atom, a methylene group which may have a lower alkyl group as a substituent or a methine group which may have a lower alkyl group as a substituent (i.e. H— or lower $$\text{alkyl-C}=\atop{|}$$

or H— or lower $$\text{alkyl-C}-\atop{\|}\text{);}$$

one bond is a double bond.

Referring to the above definitions, the protective group includes amino-protecting groups, carboxy-protecting groups, mercapto-protecting groups and hydroxy-protecting groups. As the amino-protecting groups, there may be mentioned urethane-forming protective groups such as benzyloxycarbonyl, p-methoxybenzyloxycarbonyl, p-methylbenzyloxycarbonyl, p-chlorobenzyloxycarbonyl, p-nitrobenzyloxycarbonyl, p-phenylazobenzyloxycarbonyl, p-methoxyphenylazobenzyloxycarbonyl, 3,5-dimethoxybenzyloxycarbonyl, 3,4,5-trimethoxybenzyloxycarbonyl, tert-butoxycarbonyl, tert-amyloxycarbonyl, p-biphenylisopropyloxycarbonyl and diisopropylmethyloxycarbonyl, acyl-type protective groups such as formyl, acyl, trifluoroacetyl, phthalyl, tosyl, o-nitrophenylsulfenyl, p-methoxy-o-nitrophenylsulfenyl, benzoyl and chloroacetyl, alkyl-type protective groups such as trityl, benzyl, 2-benzoyl-1-methylvinyl and trimethylsilyl, and allylidene-type protective groups such as benzylidene and 2-hydroxy-allylidene.

As the carboxy-protecting groups, there may be mentioned ester residues such as benzyl, p-nitrobenzyl, p-methoxybenzyl, 2,4,6-trimethylbenzyl, pentamethylbenzyl, methyl, ethyl, tert-butyl, benzhydryl, trityl, phthalimidomethyl, cyclopentyl, 2-methylthioethyl, phenacyl and 4-picolyl.

As the mercapto-protecting groups, there may be mentioned benzyl, p-methoxybenzyl, p-nitrobenzyl, benzhydryl, trityl, benzyloxycarbonyl, benzoyl, ethyl-carbamoyl, acetamidomethyl, ethylthio, benzylthiomethyl, and so forth. As the hydroxy-protecting groups, there may be mentioned benzyl, tert-butyl, acetyl, trifluoroacetyl, benzyloxycarbonyl, and so on.

The "divalent hydrocarbon group" corresponds to the substituted hydrocarbon group in $R^5$, $R^6$ or $R^7$ and preferably is an alkylene group, a cycloalkanediyl group, an arylene group, a divalent nonaromatic condensed polycyclic hydrocarbon group, an aralkylene group or an aralkenylene group.

The "alkylene group" preferably contains 1 to 20 carbon atoms, which may be straight or branched and, more specifically, includes, among others, methylene, methylmethylene, ethylene, trimethylene, propylene, tetramethylene, 1-methyltrimethylene, 2-methyltrimethylene, 3-methyltrimethylene, pentamethylene, 1-methyltetramethylene, 4-methyltetramethylene, hexamethylene, 5-methylpentamethylene, heptamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene, nonadecamethylene and eicosamethylene.

The "cycloalkanediyl group" includes various cyclopropanediyl groups, various cyclobutanediyl groups, various cyclopentanediyl groups, various cyclohexanediyl groups and various cycloheptanediyl groups.

As the "divalent nonaromatic condensed polycyclic hydrocarbon group", there may be mentioned various indanediyl groups, various indenediyl groups, various tetrahydronaphthalenediyl groups, various dihydronaphthalenediyl groups, various 1,2-benzo-1-cycloheptenediyl groups, various fluorenediyl groups, various 2,3-dihydro-1H-benz[f]indenediyl groups and various 1H-benz[f]indenediyl groups, among others.

As the "arylene group", there may be mentioned phenylene groups (o-, m- and p-). various naphthalenediyl groups, and so forth. The "aralkylene group" means a divalent group of an arylalkene as resulting from bonding of the above-mentioned "arylene group" to a lower alkylene group containing 1 to 6 carbon atoms and is, for example,

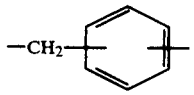

when the arylene group is phenylene and the lower alkylene group is methylene.

As the alkali metal atom for forming an alcoholate (phenolate) or thiolate (thiophenolate), there may be mentioned potassium and sodium, among others.

As said "residue of an acyl group after removal of the carbonyl group therefrom", lower alkyl groups, aralkyl groups, halo-substituted or unsubstituted aryl groups and lower alkoxy groups are particularly preferred. As specific examples of such groups, there may be mentioned those mentioned hereinbefore.

The "nitrogen-containing 5- or 6-membered heterocyclic group in which the nitrogen atom is not a tertiary one and which may be condensed with a benzene ring" means a group which belongs to the class of the "5- or 6-membered heterocyclic group, which may be condensed with a benzene ring" as represented by $R^1$ and/or $R^2$ and contains at least one nitrogen atom and in which at least one nitrogen atom is not yet a tertiary one. Examples of such group are thus as follows: 1H-pyrrolyl, $\Delta^2$- or $\Delta^3$-pyrrolinyl, pyrrolidinyl, imidazolyl, imidazolinyl, imidazolidinyl, pyrazolyl, pyrazolinyl, pyrazolidinyl, 1H-1,2,3-triazolyl, 2H-1,2,3-triazolyl, 1H-1,2,4-triazolyl, H-1,2,4-triazolyl, 1H-1,2,3,4-tetrazolyl, indoyl, benzimidazolyl, 1H-indazolyl, 2H-indazolyl, 1,4-dihydropyridyl, tetrahydropyridyl, piperidinyl, piperazinyl, $\Delta^4$-thiazolinyl, thiazolidinyl, $\Delta^4$-oxazolinyl, oxazolidinyl, $\Delta^4$-isoxazolinyl and isoxazolidinyl.

The "halogen atom" represented by $D^1$, $D^2$, $D^3$, $D^4$ or $D^5$ is, for example, an iodine, bromine or chlorine atom, whereas the "organo sulfonyloxy group" is, for example, an alkylsulfonyloxy group such as methanesulfonyloxy or ethnesulfonyloxy, a benzenesulfonyloxy, or an arylsulfonyloxy group such as toluene- (in particular p-toluene-)sulfonyloxy group.

The "cycloalkyl-lower alkyl group" represented by $R^{25}$ indicates a group resulting from substitution of one optional hydrogen atom of the above-mentioned "lower alkyl group" by the above-mentioned "cycloalkyl group". Thus, for instance, when the lower alkyl group is methyl and the cycloalkyl group is cyclohexyl, said group is cyclohexylmethyl.

Similarly, the "aryloxy-lower alkyl group" or "arylthio-lower alkyl group" means a group resulting from substitution of one optional hydrogen atom of the above-mentioned "lower alkyl group" by the above-mentioned "aryloxy group" or "arylthio group", respectively. Thus, for instance, when the lower alkyl group is propyl and the aryloxy or arylthio group is phenoxy (or phenylthio), the group in question is phenoxy- (or phenylthio-)propyl.

The "divalent 5- or 6-membered heterocyclic group, which may be condensed with a benzene ring" as represented by $A^7$ and/or $A^8$ corresponds to the "5- or 6-membered heterocyclic group, which may be condensed with a benzene ring" as represented by $R^1$ and/or $R^2$. Thus, more specifically for the pyridine ring, there may be mentioned various pyridinediyl groups, namely pyridine2,3-diyl, pyridine-2,4-diyl, pyridine-2,5-diyl, pyridine2,6-diyl, pyridine-3,4-diyl and pyridine-3,5-diyl, respectively represented by:

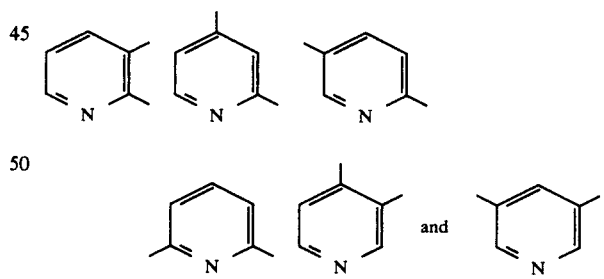

The other groups are as already mentioned in the above formula (I).

The production processes are now described in more detail.

PROCESS 1

The compounds (I) of the invention can be produced by reacting a heterocyclic carboxylic acid of general formula (II), which may have a protective group, or a reactive derivative thereof with an amine of general formula (III), which may have a protective group, if necessary followed by deprotecting (removing the protective group or groups).

As the reactive derivative of compound (II), there may be mentioned acid halides such as acid chloride and acid bromide; acid azide; active esters with N-hydroxybenzotriazole, N-hydroxysuccinimide, etc.; symmetric acid anhydride; and acid anhydrides with alkylcarbonic acids, p-toluenesulfonic acid, etc.

When the compound (II) is used in the free carboxylic acid form, it is advantageous to carry out the reaction in the presence of a condensing agent such as dicyclohexylcarbodiimide or 1,1'-carbonyldiimidazole.

The reaction conditions may vary to some extent depending on a starting compound, particularly on the kind of reactive derivative of compound (II). Generally, however, it is advantageous to carry out the reaction in an organic solvent inert to the reaction, such as pyridine, tetrahydrofuran, dioxane, ether, N,N-dimethylformamide, benzene, toluene, xylene, methylene chloride, dichloroethane, chloroform, ethyl acetate or acetonitrile, using the starting compounds (II) and (III) in equimolar amounts or using one of them in excess.

According to the kind of reactive derivative, or when the starting (III) is used in a salt form, it is in some instances advantageous to carry out the reaction in the presence of a base, for example an organic base such as trimethylamine, triethylamine, pyridine, picoline, lutidine, dimethylaniline or N-methylmorpholine, or an inorganic base such as potassium carbonate, sodium carbonate, sodium hydrogen carbonate, sodium hydroxide or potassium hydroxide. It is also possible to promote the reaction by using the starting compound (III) in excess. Pyridine can serve also as a solvent.

The reaction temperature may vary, hence should suitably be selected, depending on the kind of said reactive derivative.

It is favorable to the reaction that a mercapto group, a reactive amino group, a carboxyl group and a hydroxy group be absent. It is possible, however, to obtain desired compounds having such groups by means of protective group introduction prior to reaction and deprotection after reaction.

The method of deprotection may vary depending on the protective group.

For instance, when substituted or unsubstituted benzyloxycarbonyl is used as an amino-protecting group, the deprotection is preferably carried out in the manner of catalytic reduction and in certain instances in the manner of acid treatment with hydrobromic acid/acetic acid, hydrobromic acid/trifluoroacetic acid, hydrofluoric acid, etc. Other urethane-forming protective groups, e.g. tert-butoxycarbonyl, can advantageously be removed by acid treatment using hydrobromic acid/acetic acid, trifluoroacetic acid, hydrochloric acid, hydrochloric acid/acetic acid, hydrochloric acid/dioxane, etc.

When methyl or ethyl group is used as a carboxy-protecting group, deprotection can easily be effected by saponification. Benzyl and various substituted benzyl groups as carboxy-protecting groups can be eliminated with ease by catalytic reduction or saponification. Carboxy-protecting tert-butyl group can easily be removed by the same acid treatment as mentioned above, and trimethylsilyl group by contact with water.

Mercapto- or hydroxy-protecting groups can be removed in most cases by treatment with sodium liquid ammonia or with hydrofluoric acid. In some cases (e.g. o-benzyl, o-benzyloxycarbonyl, s-p-nitrobenzyl), they can be removed also by applying catalytic reduction.

When they are acyl groups, they can be eliminated by treatment with an acid or alkali.

The deprotection treatments mentioned above can be performed in the conventional manner.

PROCESS 2

Those compounds of general formula (Ia) in which $Y^1$ is an imino group can be produced also by reacting an oxazolidinedione ring-condensed heterocyclic compound of general formula (IV) with a compound (III).

The compound (IV) is a compound in which the C-terminus of compound (II) is in an activated form and at the same time the amino group of compound (II) is in a protected form. Hence, the reaction also fall under the category of amidation.

In respect to reaction conditions, protective groups and methods of deprotection, this process is substantially the same as in Process 1.

PROCESS 3

The compounds of the invention include those amide compounds in which $R^3$ is an amino group substituted by a hydrocarbon group having a carbamoyl, mono- or di-lower alkylaminocarbonyl group. Such compounds, which are represented by general formula (Ib), can be produced by reacting a side chain carboxylic acid of general formula (V) or a reactive derivative thereof with an amine of general formula (VI), if necessary followed by deprotecting.

In respect of reaction conditions and so forth, this process is substantially the same as in Process 1.

PROCESS 4

The compounds of the invention which have the general formula (Ic) can be produced by reacting a corresponding cyclic secondary amine (VII) with a carboxylic acid of general formula (VIII) or a reactive derivative thereof, if necessary followed by deprotecting.

This N-acylation reaction can be carried out in the same manner as in Process 1.

PROCESS 5

Those compounds of the invention which are represented by the general formula (Id) can be produced by reacting a corresponding heterocyclic secondary amine (IX) with a carboxylic acid of general formula (X) or a reactive derivative thereof, if necessary followed by deprotecting.

The reaction conditions and the like are substantially the same as in Process 1.

PROCESS 6

The compounds of the invention include those compounds (Ie) in which $R^1$ (or $R^1$ and $R^2$ each) is a heterocyclic group containing a cyclic secondary amineforming nitrogen atom with an acyl group bonded to the nitrogen atom. They can be produced by reacting a compound (XI) with a compound (XII) or a reactive derivative thereof in the same manner as in Process 1.

PROCESS 7

The compounds of the invention include ether or thioether compounds. Such compounds can be produced by applying a conventional method of etherification or thioetherification.

Among the conventional methods, the most general method which comprises reacting an alcohol or mercaptan or an alkali metal derivative thereof with a halide or sulfonate can be used most advantageously.

Thus, the ether or thioether compounds of general formula (If) can be produced by reacting a hydroxy or mercapto compound of general formula (XIV) or an alkali metal derivative thereof with a halide or sulfonate compound of general formula (XV) or reacting a halide or sulfonate compound of general formula (XIV) with a hydroxy or mercapto compound of general formula (XV) or an alkali metal derivative thereof.

The reaction is carried out in an organic solvent such as N,N-dimethylformamide, dimethyl sulfoxide, acetone, methyl ethyl ketone (2-butanone), methanol, ethanol, ethylene chloride, chloroform, ether, tetrahydrofuran or dioxane, or water, or in a mixed solvent composed of water and such an organic solvent, using the compounds (XIV) and (XV) in substantially equimolar amounts or using either of them in slight excess.

When the starting hydroxy or mercapto compound (XIV) or (XV) is not in the alkali metal-substituted form, the reaction is carried out in the presence of a base, preferred examples of which are sodium hydroxide, potassium hydroxide, sodium hydride, sodium carbonate, potassium carbonate and Triton B.

Although the reaction temperature is not critical, the reaction is usually carried out at room temperature or with heating.

When the starting compound. (XIV) contains an additional free or alkali metal-substituted mercapto group, thioetherification generally takes place simultaneously on the group.

According to the kind of substituent, it is preferable to carry out the reaction after introduction of a protective group so that the expected side reaction can be inhibited. In that case, postreaction deprotection can be effected by treating in the same manner as described in relation to Process 1.

PROCESS 8

The ether or thioether compounds of general formula (Ig) can be produced by reacting a compound (XVI) with a compound (XVII). The reaction conditions and the like are the same as in Process 7.

PROCESS 9

The ether or thioether compounds of general formula (Ih), too, can be produced by reacting and treating in the same manner as in Process 7 with a compound (XVIII) and a compound (XIX) as the starting compounds.

PROCESS 10

Among the compounds of the invention, those compounds (Ii) in which $X^1$ is an oxygen or sulfur atom can be produced by applying a cyclization or ring closure reaction using a ketone (or aldehyde) of general formula (XX) and a diol, dithiol, hydroxy-mercaptan, amino-alcohol or amino-mercaptan compound of general formula (XXI) as the starting compounds.

The reaction is carried out in a solvent such as an alcohol (e.g. methanol, ethanol, isopropanol) or an aqueous alcohol and generally at room temperature using the compounds (XX) and (XXI) in almost equimolar amounts or using either of them in slight excess. It is also possible to conduct the reaction while removing by-product water as an azeotrope with such a solvent as benzene or toluene using a Dean-Stark trap or the like. It is favorable to this reaction that additional reactive groups such as mercapto, amino and carboxyl are absent. Protection of such groups, however, renders the reaction practicable. In that case, deprotection can be effected in the same manner as in Process 1.

PROCESS 11

The N-substituted compounds of general formula (Ij) can be produced by reacting a corresponding cyclic secondary amine of general formula (XXII) with a halide or sulfonate of general formula (XXIII), if necessary followed by deprotecting.

When the starting compound (XXIII) is a halide, the reaction is advantageously carried out in a solvent such as mentioned above for Process 7, at room temperature or with heating or refluxing, using the compounds (XXII) and (XXIII) in approximately equimolar amounts or using either of them in slight excess.

In some instances, the addition of a secondary or tertiary base such as pyridine, picoline, N,N-dimethylaniline, N-methylmorpholine, trimethylamine, triethylamine or dimethylamine or of an inorganic base such as potassium carbonate, sodium carbonate, sodium hydrogen carbonate, sodium hydroxide or potassium hydroxide can advantageously cause the reaction to proceed smoothly.

When the starting compound (XXIII) is a compound substituted by an organo sulfonyloxy group, the reaction is advantageously carried out in a solvent such as mentioned above in relation to Process 7, with cooling or at room temperature, using the compounds (XXII) and (XXIII) in approximately equimolar amounts or using either of them in slight excess. The reaction period should be selected in due consideration of various reaction conditions.

The absence of such groups as mercapto, reactive carboxyl and reactive hydroxy group is favorable to this reaction, too. However, protective group introduction prior to the reaction makes it possible to obtained desired compounds. When there is additionally a reactive amino group, the amino group may also be subject to simultaneous N-alkylation. In that case, it is possible to obtain desired compounds when an easily eliminable protective group is introduced prior to the reaction and is removed after reaction.

Deprotection can be effected as described above relative to Process 1.

PROCESS 12

Those compounds of the invention in which $R^3$ is a diamine type substituent can be produced by applying the method comprising reacting an amine of general formula (XXIV) with a halide or sulfonate of general formula (XXV) or reacting a halide or sulfonate of general formula (XXIV) with an amino (XXV).

When symmetrically disubstituted amino compounds are produced, one of the compounds (XXIV) and (XXV) is used in an amount of about 2 moles per mole of the other, as the case may be. Preferably, the compound (XXIV) is an amine and the compound (XXV) is a halide or sulfonate, and the halide or sulfonate compound (XXV) is used in an amount of about 2 moles per mole of the amine compound (XXIV). When the desired compounds are monosubstituted amines or when disubstituted amines are to be produced using monosubstituted amines as starting materials, both the reactants are used in approximately equimolar amounts. Other reaction conditions, such as solvent, temperature, addition of base and deprotection conditions, are substantially the same as in Process 11.

In producing monosubstituted amines as the desired compounds, it is desirable to inhibit tertiary amine formation so that the desired products can be produced in good yields. For that purpose, the amino group of $D^4$ or $D^5$ should preferably be converted in advance to a secondary amine form by introducing a protective group for preventing tertiary amine formation, such as toluenesulfonyloxy, acetyl, phenacylsulfonyl, trifluoromethanesulfonyl or bisbenzenesulfonyl.

When primary amines are to be produced by using a halide or sulfonate compound (XXIV) in which $D^4$ is a halogen atom or an organo sulfonyloxy group as one starting material, the compound (XXV) may be an ammonia. It is advantageous, however, to apply the method comprising carrying out the reaction using the potassium salt of phthalimide and thereafter removing the protective group.

PROCESS 13

Those compounds of the invention which have the general formula (Il) can be produced by reacting a corresponding cyclic secondary amine (XXVII) with a compound (XXVIII). The reaction conditions and so forth are approximately the same as in Process 11.

PROCESS 14

The compounds (Im) can be derived from the starting compounds (XXIX) and (XXX) by treating in the same manner as in Process 11.

PROCESS 15

Those compounds of the invention which have the formula (In) and have an amino group, or a mono- or disubstituted amino group on $R^1$ and/or $R^2$ can be produced by treating the reactants in the same manner as in Process 12.

PROCESS 16

For producing those compounds (Io) of the invention in which $R^3$ is the group

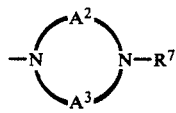

forming a 5-membered ring, namely imidazolidine compounds, various methods of synthesizing 1,3-diazoles are applicable. Among them, an advantageous method of producing the compounds (Io) comprises subjecting to ring closure or cyclization a corresponding ethylenediamine compound (starting compound) of general formula (XXXIV) in which one of the two ethylenediamine nitrogen atoms is in an amide form. While various carbonyl compounds can be used as ring closure reagents, an aldehyde of general formula (XXXV) is preferred when the introduction of a hydrocarbon-derived substituent is taken into consideration.

The reaction can be effected by heating the compounds (XXXIV) and (XXXV) in an inert organic solvent (e.g. toluene) with a molecular sieve added.

While the absence of additional reactive groups such as mercapto, amino, carboxyl in the starting compounds is favorable to the reaction, a starting compound having such a protective group can be submitted to the reaction without difficulty when said group is protected beforehand, as the case may be. In that case, deprotection can be carried out in the same manner as in Process 1.

PROCESS 17

Among the compounds of the invention, there are various compounds which can be obtained by applying a reductive means (e.g. reduction of C=C to C—C, C≡C to C=C or C—C, $NO_2$ to $NH_2$, S—S to SH).

In the process given above by way of example, the basic saturated heterocycle skeletons of the compounds according to the invention are formed by reduction of the corresponding unsaturated or incompletely hydrogenated heterocycles.

The reduction is advantageously carried out catalytically in the presence of a reduction catalyst such as platinum black, platinum oxide, palladium-on-carbon or Raney nickel.

OTHER PRODUCTION PROCESSES

In the foregoing, detailed mentioned has been made of amidation, etherification or thioetherification, cyclization and N-alkylation reactions, among others. However, the compounds of the invention contain various functional groups and therefore can be produced by applying various methods selected according to the characteristics of such groups.

For instance, the compounds (I) of the invention which has a free carboxyl group as a substituent can be produced from a corresponding ester by eliminating the ester residue by a conventional method. Conversely, those compounds which have a lower alkoxycarbonyl group, an esterified carboxyl group, as a substituent can be produced by reacting a corresponding carboxylic acid or a reactive derivative thereof with a lower alcohol or a reactive derivative thereof such as a lower alkyl halide in the conventional manner for ester formation.

The thus-produced compounds (I) of the invention are isolated in the free form or in the form of salts thereof and purified. The salts can be produced by subjecting the free-form compounds to a conventional salt formation reaction.

Isolation and purification can be performed by applying ordinary procedures in chemistry, such as extraction, concentration, crystallization, filtration, recrystallization and various forms of chromatography.

As already mentioned hereinabove, the compounds of the invention may occur as optical isomers such as racemic modifications, optically active substances and diastereomers, geometric isomers, namely cis and trans forms, and tautomeric isomers, namely keto and enol forms, either singly or in the form of a mixture. Racemic compounds can be led to stereochemically pure isomers by using appropriate starting compounds or by using a general method of optical resolution [e.g. the method which comprises conversion to diastereomer salts with an optically active acid in general use (e.g. tartaric acid)]. Separation of diastereomer mixtures can be realized in the conventional manner, for example by fractional crystallization or chromatography. Geometric isomers can be separated from each other by utilizing a difference in physicochemical property therebetween.

The compounds (I) and salts thereof according to the invention have PAF-antagonizing activity and are useful in the treatment and prevention of various diseases caused by PAF. In particular, they can be used as antiasthmatics, antiinflammatory agents, antiulcer agents, shock symptom alleviating agents, therapeutic agents for ischemic heart and brain diseases, liver diseases, thrombosis and nephritis, rejection inhibitors for use in organ transplantation, etc.

Some of the compounds of the invention have vasodilating activity and such compounds are useful as vasodilators as well.

The compounds of this invention shown by the general formula (I) or the salts thereof can be orally or parenterally administered as they are or as medical compositions composed of these compounds and pharmaceutically permissible carriers or excipients (e.g., tablets, capsules, powders, granules, pils, ointments, syrups, injections, inhalants, suppositories, etc.). The does depends upon the patients, administration routes, symptoms, etc., but is usually 0.1 to 500 mg, preferably 1 to 200 mg per adult per day and is orally or parenterally administered 2 or 3 times per day.

The following examples are further illustrative of the present invention.

The above-mentioned starting compounds contain novel compounds and their production are described in the reference examples.

In the following, NMR indicates a nuclear magnetic resonance spectrum with TMS as an internal standard, MS mass spectrum, LAH lithium aluminum hydride, HOBT 1-hydroxybenzotriazole, DCC dicyclohexylcarbodiimide, THF tetrahydrofuran, and DMF N,N-dimethylformamide.

REFERENCE EXAMPLE 1

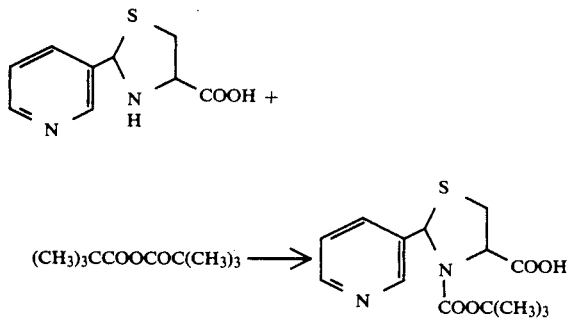

Di-tert-butyl dicarbonate (2.4 g) and 10 ml of 1N aqueous sodium hydroxide were added to a mixture of 2.1 g of 2-(3-pyridyl)thiazolidine-4-carboxylic acid (prepared from L-cysteine and pyridine-3-carbaldehyde), 20 ml of water and 40 ml of dioxane at a temperature not higher than 4° C., and the mixture was stirred at room temperature for 30 minutes. The reaction mixture was concentrated under reduced pressure, 30 ml of water was added, the pH was adjusted to 2 to 3 by addition of 0.5M aqueous citric acid, and the mixture was extracted with ethyl acetate. The extract was washed with water, dried over anhydrous sodium sulfate and concentrated under reduced pressure, and the residue was recrystallized from ethyl acetate to give 1 g of N-tert-butoxycarbonyl-2-(3-pyridyl)thiazolidine-4-carboxylic acid. Melting point 167°-169° C.

REFERENCE EXAMPLE 2

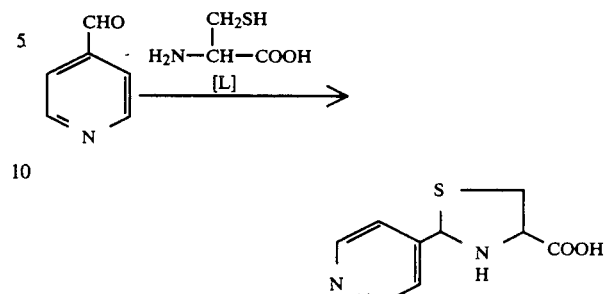

Pyridine-4-carbaldehyde (1.07 g) and 1.21 g of L-cysteine were heated in 60% ethanol at a refluxing temperature for 4 hours. Activated charcoal (100 mg) was added to the reaction mixture while it was warm. The mixture was filtered. After cooling, the resultant crystalline precipitate was collected by filtration and washed with ethanol to give 1.2 g of 2-(4-pyridyl)-thiazolidine-4-carboxylic acid. Melting point 171°-173° C.

NMR (DMSO-$d_6$) δ: 3.0~3.5 (2H), 3.9~4.2 (1H), 5.56 and 5.78 (s, respectively 1H), 7.4~7.6 (2H), 8.5~8.6 (2H)

REFERENCE EXAMPLE 3

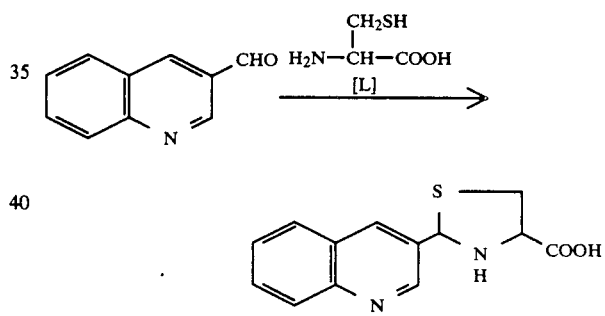

Quinoline-3-carbaldehyde (1.57 g ) and 1.21 g of L-cysteine were dissolved in 50 ml of 50% ethanol, and the solution was stirred at room temperature for 1 hour. The resultant crystalline precipitate was collected by suction filtration, washed with 50% ethanol and dried to give 1.95 g of 2-(3-quinolyl)thiazolidine-4-carboxylic acid. Melting point 173°-175° C. (decomposition).

REFERENCE EXAMPLE 4

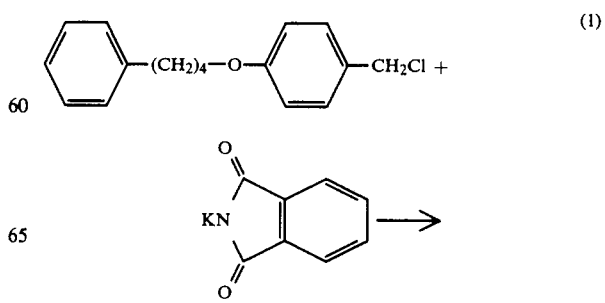

(1)

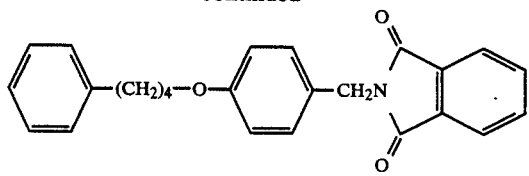

A solution of 1.20 g of p-chloromethyl-(4-phenylbutoxy)benzene and 1.15 g of potassium phthalimide in 20 ml of N,N-dimethylformamide was stirred at 100° C. for 3 hours. The reaction mixture was diluted with ethyl acetate, and the dilution was washed with three portions of water and then with saturated aqueous solution of sodium chloride, and dried over anhydrous magnesium sulfate. The solvent was distilled off under reduced pressure, and the residual solid was recrystallized from ethyl acetate to give 1.85 g of N-[p-(4-phenylbutoxy)benzyl]phthalimide. Melting point 106°–107.5° C.

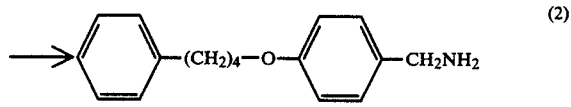

A solution of 920 mg of N-[p-4-phenylbutoxy)benzyl]phthalimide obtained in (1) and 200 mg of hydrazine hydrate in 10 ml of ethanol was refluxed for 3 hours. After cooling, the solid precipitate was filtered off, and the filtrate was concentrated. Chloroform was added to the residue, and the insoluble matter was filtered off. The filtrate was concentrated to give 190 mg of p-(4-phenylbutoxy)benzylamine.

NMR (CDCl$_3$) δ: 1.6~1.9 (4H), 2.5~2.8 (2H), 3.75 (2H, br), 3.8~4.0 (2H), 6.7~6.9 (2H), 7.1~7.3 (7H)

REFERENCE EXAMPLE 5

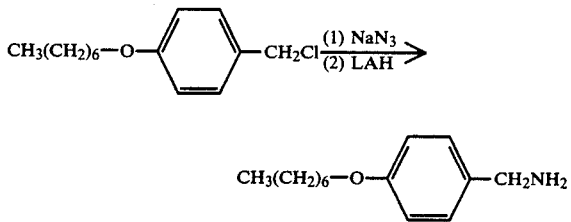

A solution of 1.25 g of sodium azide in 2.5 ml of water was added to a solution of 900 mg of p-chloromethyl(-heptyloxy)benzene in 25 ml of N,N-dimethylformamide, and the mixture was stirred at 100° C. for 6 hours. After cooling, the reaction mixture was diluted with water, and the product was extracted with ether. The ether layer was washed in sequence with water and saturated aqueous solution of sodium chloride, dried over anhydrous magnesium sulfate and concentrated under reduced pressure. A solution of the thus-obtained residual oil in 10 ml of tetrahydrofuran was added dropwise at 0° C. over 5 minutes to a suspension of 200 mg of lithium aluminum hydride in 15 ml of tetrahydrofuran. The resultant mixture was stirred at the same temperature for 1 hour and then at room temperature for 1 hour. Then, sodium sulfate decahydrate added to decompose the excess lithium aluminum hydride. The insoluble matter was filtered off, and the filtrate was concentrated under reduced pressure to give 860 mg of p-heptyloxybenzylamine.

MS: m/z 221 (M+)

NMR (CDCl$_3$) δ: 0.8~1.0 (3H), 1.2~1.5 (10H), 1.6~1.9 (2H), 3.80 (2H, s), 3.94 (2H, t), 6.87 (2H, d), 7.22 (2H, d)

REFERENCE EXAMPLE 6

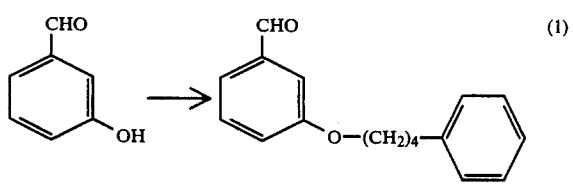

A solution of 380 mg of m-hydroxybenzaldehyde, 600 mg of 1-bromo-4-phenylbutane and 580 mg of potassium carbonate in 3 ml of N,N-dimethylformamide was stirred overnight at room temperature. After dilution with ethyl acetate, the reaction mixture was washed with water, 1N sodium hydroxide, water and saturated aqueous solution of sodium chloride, in that order, and then dried over anhydrous magnesium sulfate. The ethyl acetate layer was concentrated under reduced pressure to give 660 mg of m-(4-phenylbutoxy)benzaldehyde.

MS: m/z 254 (M+)

NMR (CDCl$_3$) δ: 1.6~1.9 (4H), 2.6~2.8 (2H), 4.06 (2H, t), 7.2~7.4 (9H), 9.96 (1H, s)

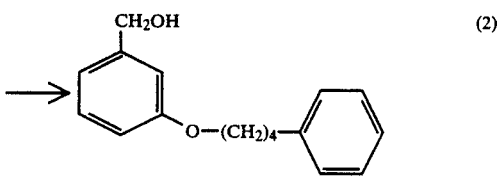

Sodium borohydride (200 mg) was added to a solution of 660 mg of m-(4-phenylbutoxy)benzaldehyde in 10 ml of methanol, and the mixture was stirred at room temperature for 2 hours. The reaction mixture was concentrated under reduced pressure, 5% hydrochloric acid was added to the residue, and the product was extracted with ethyl acetate. The ethyl acetate layer was washed with water, dried over anhydrous magnesium sulfate and concentrated under reduced pressure to give 510 mg of m-(4-phenylbutoxy)benzyl alcohol.

NMR (CDCl$_3$) δ: 1.6~1.9 (4H), 2.6~2.8 (2H), 3.9~4.1 (2H), 4.60 (2H, s), 7.2~7.5 (9H)

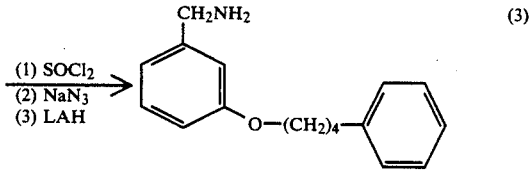

m-(4-Phenylbutoxy)benzyl alcohol (510 mg) was dissolved in 5 ml of benzene, 1.4 g of thionyl chloride was added, and the mixture was stirred at room temperature for 4 hours. The reaction mixture was concentrated under reduced pressure to give 520 mg of m-chloromethyl-(4-phenylbutoxy)benzene. This compound was then treated by the procedure of Reference Example 4 to give 470 mg of m-(4-phenylbutoxy)benzylamine.

MS: m/z 255 (M+)

NMR (CDCl$_3$) δ: 1.6~1.9 (4H), 2.6~2.8 (2H), 3.6~3.9 (2H), 3.9~4.1 (2H), 6.7~6.9 (3H), 7.2~7.4 (6H)

REFERENCE EXAMPLE 7

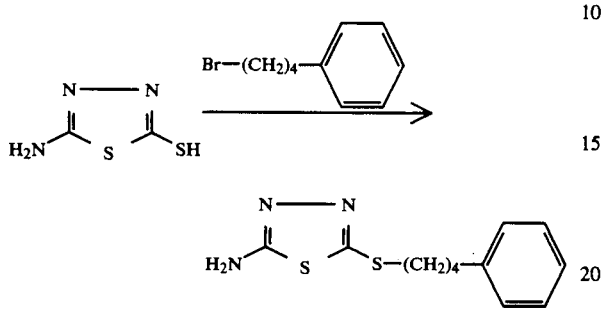

A solution of 320 mg of 2-amino-5-mercapto-1,3,4-thiadiazole, 430 mg of 1-bromo-4-phenylbutane and 350 mg of potassium carbonate in 5 ml of N,N-dimethylformamide was stirred overnight at room temperature. After dilution with ethyl acetate, the reaction mixture was washed in sequence with water, 1N sodium hydroxide, water and saturated aqueous solution of sodium chloride, then dried over anhydrous sodium sulfate and concentrated under reduced pressure. The residue obtained was recrystallized from ethyl acetate to give 300 mg of 2-amino-5-[(4-phenylbutyl)thio]-1,3,4-thiadiazole. Melting point 111° C.

| Elemental analysis (for C$_{12}$H$_{15}$N$_3$S$_2$): | | | | |
|---|---|---|---|---|
| | C (%) | H (%) | N (%) | S (%) |
| Calculated: | 54.31 | 5.70 | 15.83 | 24.16 |
| Found: | 54.29 | 5.69 | 15.88 | 23.90 |

REFERENCE EXAMPLE 8

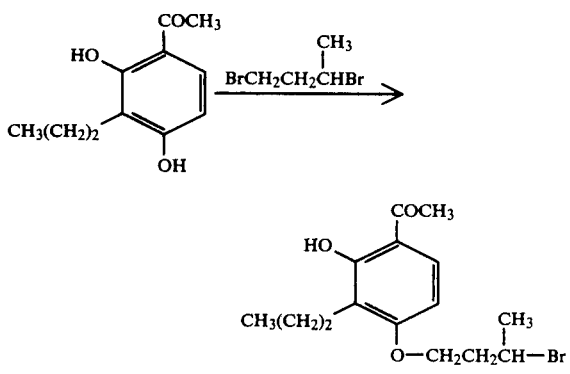

A mixture of 5.0 g of 2,4-dihydroxy-3-propylacetophenone, 11.1 g of 1,3-dibromobutane, 6.0 g of potassium carbonate and 50 mg of tetra-n-butylammonium bromide in 130 ml of acetone was refluxed overnight. After cooling, the insoluble matter was filtered off, and the filtrate was concentrated. The residue was purified by silica gel column chromatography (eluent:hexane-ethyl acetate=8:1) to give 2.47 g of 1-[4-(3-bromobutoxy)-2-hydroxy-3-propylphenyl]ethanone. Melting point 53°-55° C.

| Elemental analysis (for C$_{15}$H$_{21}$O$_3$Br): | | | |
|---|---|---|---|
| | C (%) | H (%) | Br (%) |
| Calculated: | 54.72 | 6.43 | 24.27 |
| Found: | 54.98 | 6.40 | 23.91 |

REFERENCE EXAMPLE 9

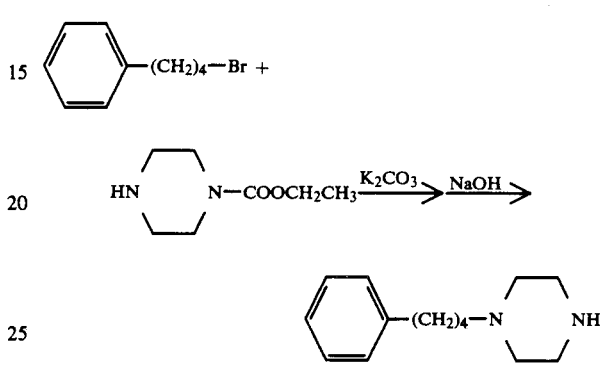

A solution of 2.47 g of 1-bromo-4-phenylbutane in 5 ml of 2-butanone was added to a mixture of 1.93 g of 1-ethoxycarbonylpiperazine, 1.76 g of potassium carbonate and 15 ml of 2-butanone at room temperature. After stirring at 80° C. for 12 hours, the mixture was cooled and, after addition of water, extracted with ethyl acetate. The extract was washed with water and saturated aqueous solution of sodium chloride in that order and dried over anhydrous sodium sulfate. The residue obtained after concentration under reduced pressure was purified by silica gel column chromatography (eluent:hexane-ethyl acetate=4:1) to give 1-ethoxycarbonyl-4-(4-phenylbutyl)piperazine. The compound obtained was dissolved in 20 ml of ethanol and 20 ml of 10% aqueous solution of sodium hydroxide, and the solution was stirred at 100° C. for 12 hours. After cooling, the reaction mixture was extracted with ethyl acetate, and the extract was washed with saturated aqueous solution of sodium chloride and dried over anhydrous sodium sulfate. After concentration under reduced pressure, the residue was purified by silica gel column chromatography (eluent:chloroform-methanol-25% aqueous ammonia=100:10:1) to give 1.5 g of 1-(4-phenylbutyl)piperazine as an oil.

NMR (CDCl$_3$) δ: 1.34~1.85 (4H, m), 2.20~3.04 (12H, m), 7.04~7.40 (5H, m)

MS: m/z 217 (M+)

REFERENCE EXAMPLE 10

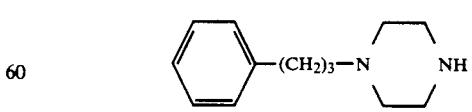

1-Ethoxycarbonylpiperazine and 1-bromo-3-phenylpropane were used as the starting materials and treated in the same manner as in Reference Example 9 to give 1-(3phenylpropyl)piperazine.

NMR (CDCl$_3$) δ: 1.63~1.97 (2H, m), 2.44~3.00 (12H, m), 7.04~7.44 (5H, m)

MS: m/z 203 (M+)

REFERENCE EXAMPLE 11

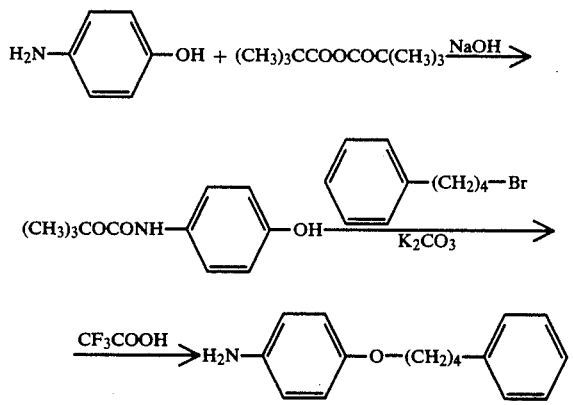

A solution of 6.43 g of di-tert-butyl dicarbonate in 5 ml of THF was added to a mixture of 3.06 g of p-aminophenol and 30 ml of 10% aqueous solution of sodium hydroxide at room temperature. The mixture was stirred at 80° C. for 12 hours, then cooled and extracted with ethyl acetate. The extract was dried over anhydrous sodium sulfate and concentrated under reduced pressure. The residue obtained was purified by silica gel column chromatography (eluent:hexane-ethyl acetate=4:1) to give 4.35 g of p-(tert butoxycarbonylamino)phenol. A mixture of 300 mg of the thus-obtained compound, 210 mg of potassium carbonate and 10 ml of 2-butanone was stirred at room temperature for 30 minutes, then a solution of 310 mg of 1-bromo-4-phenylbutane in 5 ml of 2-butanone was added, and the mixture was stirred at 80° C. for 12 hours. After cooling, water was added to the reaction mixture, and the organic matter was extracted with ethyl acetate. The extract was washed in sequence with water and saturated aqueous solution of sodium chloride, dried over anhydrous sodium sulfate and concentrated under reduced pressure. The residue was purified by silica gel column chromatography (eluent:hexane-ethyl acetate=10:1) to give 1-(tert-butoxycarbonylamino)-4-(4-phenylbutoxy)benzene (0.2 g). Trifluoroacetic acid (5 ml) was added to the compound obtained with ice cooling, and the mixture was stirred with ice cooling for 30 minutes. The reaction mixture was concentrated under reduced pressure, washed with saturated aqueous solution of sodium hydrogen carbonate and then with saturated aqueous solution of sodium chloride, dried over anhydrous sodium sulfate, and concentrated under reduced pressure to give 0.13 g of p-(4-phenylbutoxy)aniline.

NMR (CDCl$_3$) δ: 1.66~1.90 (4H, m), 2.67 (2H, t), 3.90 (2H, t), 6.56~6.82 (4H, m), 7.13~7.33 (5H, m)
MS: m/z 241 (M+)

REFERENCE EXAMPLE 12

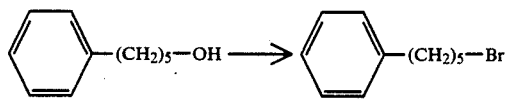

A mixture of 20 g of 5-phenylpentan-1-ol and 30 ml of 47% hydrobromic acid was refluxed for 6 hours. The reaction mixture was cooled and extracted with n-hexane The extract was washed with water, dried over anhydrous sodium sulfate and concentrated under reduced pressure. The residue was purified by silica gel column chromatography (eluent:n-hexane-ethyl acetate=100:1) to give 16.87 g of 1-bromo-5-phenylpentane.

NMR (CDCl$_3$) δ: 1.28~2.03 (6H, m), 2.63 (2H, t), 3.42 (2H, t), 7.08~7.40 (5H, m)
MS: m/z 228 (M++1)

REFERENCE EXAMPLE 13

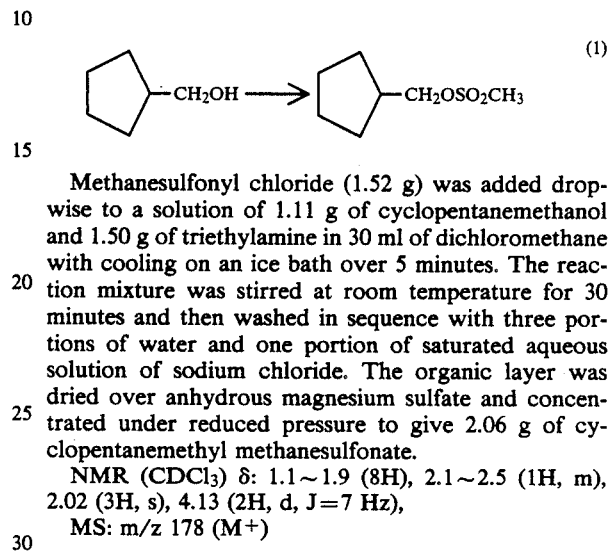

Methanesulfonyl chloride (1.52 g) was added dropwise to a solution of 1.11 g of cyclopentanemethanol and 1.50 g of triethylamine in 30 ml of dichloromethane with cooling on an ice bath over 5 minutes. The reaction mixture was stirred at room temperature for 30 minutes and then washed in sequence with three portions of water and one portion of saturated aqueous solution of sodium chloride. The organic layer was dried over anhydrous magnesium sulfate and concentrated under reduced pressure to give 2.06 g of cyclopentanemethyl methanesulfonate.

NMR (CDCl$_3$) δ: 1.1~1.9 (8H), 2.1~2.5 (1H, m), 2.02 (3H, s), 4.13 (2H, d, J=7 Hz),
MS: m/z 178 (M+)

A mixture of 0.80 g of cyclopentanemethyl methanesulfonate obtained in (1), 0.60 g of p-hydroxybenzaldehyde and 0.93 g of anhydrous potassium carbonate in 6 ml of N,N-dimethylformamide was stirred overnight at 70° C. The reaction mixture was diluted with ethyl acetate and washed with water. The organic layer was washed with 1N sodium hydroxide, water and saturated aqueous solution of sodium chloride in that order, then dried over anhydrous magnesium sulfate, and concentrated under reduced pressure to give 460 mg of p-cyclopentanemethoxybenzaldehyde.

NMR (CDCl$_3$) δ: 1.2~2.0 (8H), 2.40 (1H, quintet, J=7 Hz), 3.92 (2H, d, J=7 Hz), 6.99 (2H, d, J=10 Hz), 7.86 (2H, d, J=10 Hz), 9.88 (1H, s)
MS: m/z 204 (M+)

REFERENCE EXAMPLE 14

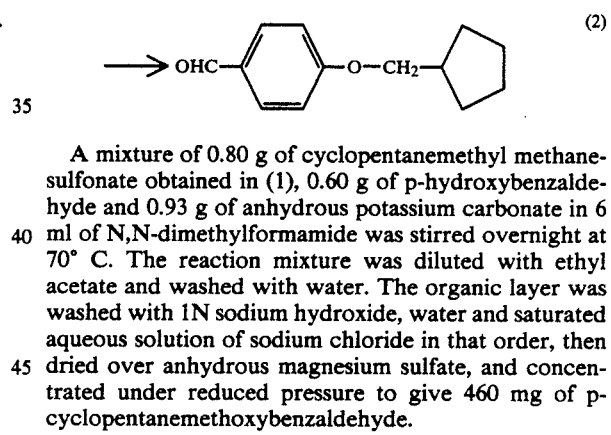

A mixture of 1.00 g of p-hydroxybenzaldehyde, 1.46 g of isoamyl iodide and 1.80 g of potassium carbonate in 15 ml of N,N-dimethylformamide was stirred at room temperature for 2 days. Water was added to the reaction mixture, and the product was extracted with ethyl acetate. The ethyl acetate layer was washed in sequence with 1N sodium hydroxide, water and saturated aqueous solution of sodium chloride, dried over anhydrous magnesium sulfate and concentrated under reduced pressure to give 1.34 g of p-(3-methylbutoxy)benzaldehyde.

NMR (CDCl₃) δ: 0.97 (6H, d, J=7 Hz), 1.6~1.9 (3H), 4.08 (2H, t, J=7 Hz), 6.99 (2H, d, J=8 Hz), 7.87 (2H, d, J=8 Hz), 9.90 (1H, s)

MS: m/z 192 (M+)

REFERENCE EXAMPLES 15 TO 17

The following compounds were obtained in the same manner as in Reference Example 14.

|  | Physicochemical properties |
|---|---|
| Ref. Ex. 15<br>OHC—⟨⟩—O—(CH₂)₃—⟨⟩<br>p-(3-Phenylpropoxy)benzaldehyde | NMR (CDCl₃)<br>δ: 2.18 (2H, m), 2.83 (2H, br t), 4.03 (2H, t, J=7Hz), 6.87 (2H, d, J=9Hz), 7.22 (5H, br), 7.82 (2H, d, J=9Hz), 9.88 (1H, s)<br>MS: m/z 240 (M+) |
| Ref. Ex. 16<br>OHC—⟨⟩—O—(CH₂)₃—⟨⟩<br>p-(3-Phenoxypropoxy)benzaldehyde | NMR (CDCl₃)<br>δ: 2.30 (2H, quintet, J=6Hz), 4.19 (2H, t, J=6Hz), 4.39 (2H, t, J=6Hz), 6.7~7.3 (7H), 7.87 (2H, d, J=9Hz), 9.93 (1H, s)<br>MS: m/z 256 (M+) |
| Ref. Ex. 17<br>OHC—⟨⟩—O—(CH₂)₄—⟨⟩<br>       OCH₃<br>3-Methoxy-4-(4-phenylbutoxy)benzaldehyde | NMR (CDCl₃)<br>δ: 1.6~2.0 (4H), 2.6~2.8 (2H), 3.90 (3H, s), 4.10 (2H, br, t), 6.93 (2H, d, J=9Hz), 7.1~7.5 (7H), 9.85 (1H, s)<br>MS: m/z 284 (M+) |

REFERENCE EXAMPLE 18

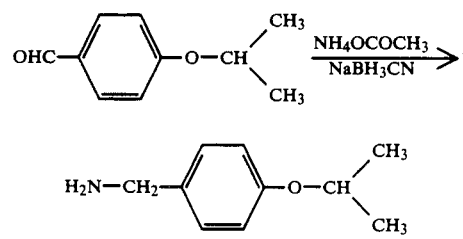

Sodium cyanoborohydride (330 mg) was added to a solution of 770 mg of p-isopropoxybenzaldehyde and 4.0 g of ammonium acetate in 20 ml of methanol, and the mixture was stirred at room temperature for 40 hours. The reaction mixture was adjusted to pH 2 or less by addition of concentrated hydrochloric acid, and then concentrated. The residue was dissolved in water and the solution was washed with ethyl acetate. The aqueous layer was adjusted to pH 11 or more by addition of solid potassium hydroxide, and the product was extracted with ethyl acetate. The ethyl acetate layer was washed with water and saturated aqueous solution of sodium chloride in that order, dried over anhydrous sodium sulfate and concentrated under reduced pressure to give 110 mg of p-isopropoxybenzylamine.

NMR (CDCl₃) δ: 1.28 (6H, d, J=6 Hz), 1.50 (2H, exchange with D₂O), 3.71 (2H, s), 4.46 (1H, hep., J=6 Hz), 6.75 (2H, d, J=8 Hz), 7.14 (2H, d, J=8 Hz)

MS: m/z 165 (M+)

REFERENCE EXAMPLES 19 TO 21

The following compounds were obtained in the same manner as in Reference Example 18.

|  | Physicochemical properties |
|---|---|
| Ref. Ex. 19<br>H₂N—CH₂—⟨⟩—O—CH₂CH(CH₃)₂<br>p-(2-Methylpropoxy)-benzylamine | NMR (CDCl₃)<br>δ: 1.02 (6H, d, J=7Hz), 1.5 (2H, exchange with D₂O), 2.06 (1H), 3.70 (2H, d, J=6Hz), 3.77 (2H, s), 6.84 (2H, d, J=9Hz), 7.20 (2H, d, J=9Hz)<br>MS: m/z 179 (M+) |
| Ref. Ex. 20<br>H₂N—CH₂—⟨⟩—O—CH₂CH₂CH₂CH(CH₃)₂<br>p-(4-Methylpentyloxy)-benzylamine | NMR (CDCl₃)<br>δ: 0.97 (6H, d, J=6Hz), 1.5 (2H, exchange with D₂O), 1.3~2.1 (5H), 3.78 (2H, s), 3.95 (2H, t, J=6Hz), 6.86 (2H, d, J=9Hz), 7.23 (2H, d, J=9Hz)<br>MS: m/z 207 (M+) |
| Ref. Ex. 21<br>H₂N—CH₂—⟨⟩—O—CH₂—⟨cyclopentyl⟩<br>p-Cyclopentylmethoxy-sd,21 | NMR (CDCl₃)<br>δ: 1.2~1.9 (10H), 1.38 (1H, m), 3.80 (2H, s), 3.83 (2H, d, J=7Hz), 6.87 (2H, d, J=9Hz), 7.23 (2H, d, J=9Hz)<br>MS: m/z 205 (M+) |

REFERENCE EXAMPLE 22

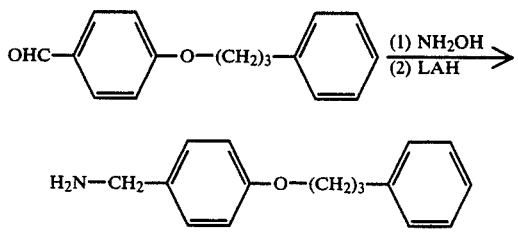

A solution of 750 mg of p-(3-phenylpropoxy)benzaldehyde and 2.3 g of hydroxylamine hydrochloride in 20 ml of methanol was adjusted to pH 8 by addition of 10% sodium hydroxide under cooling. The mixture was stirred for 1 hour and, then, the methanol was evaporated. Water was added to the residue, and the product was extracted with ethyl acetate. The ethyl acetate layer was washed with water and saturated aqueous solution of sodium chloride, dried over anhydrous sodium sulfate and concentrated to give 750 mg of p-(3-phenylpropoxy)benzaldehyde oxime. A solution of this compound in 10 ml of tetrahydrofuran was added dropwise to a suspension of 300 mg of lithium aluminum hydride in 6 ml of tetrahydrofuran at −30° C. After 20 minutes of stirring at −30° C., the temperature was raised to room temperature and stirring was continued for 2 hours. The excess lithium aluminum hydride was decomposed with sodium sulfate decahydrate, and the reaction mixture was filtered. The filtrate was diluted with ethyl acetate and washed with 10% hydrochloric acid. The hydrochloric acid layer was made alkaline with solid potassium hydroxide, and the product was extracted with ethyl acetate. The ethyl acetate layer was washed in sequence with water and saturated aqueous solution of sodium chloride, dried over anhydrous sodium sulfate and concentrated under reduced pressure to give 260 mg of p-(3-phenylpropoxy)benzylamine.

NMR (CDCl$_3$) δ: 1.6 (2H, exchange with D$_2$O), 2.00~2.35 (2H, m), 2.70~3.00 (2H, m), 3.81 (2H, s), 3.97 (2H, t, J=6 Hz), 6.87 (2H, d, J=9 Hz), 7.24 (2H, d, J=9 Hz), 7.25 (5H, s)

MS: m/z 241 (M+)

REFERENCE EXAMPLES 23 TO 27

The following compounds were obtained in the same manner as in Reference Example 22.

| | Physicochemical Properties |
|---|---|
| Ref. Ex. 23<br>H$_2$N—CH$_2$—⟨phenyl⟩—O—(CH$_2$)$_3$—O—⟨phenyl⟩<br>2-(3-Phenoxypropoxy)-benzylamine | NMR (CDCl$_3$)<br>δ: 1.75 (2H, exchange with D$_2$O), 2.23 (2H, quintet, J=6Hz), 3.76 (2H, s), 4.14 (4H, t, J=6Hz), 6.8~7.4 (9H)<br>MS: m/z 257 (M+) |
| Ref. Ex. 24<br>H$_2$N—CH$_2$—⟨phenyl⟩—(CH$_2$)$_3$CH$_3$<br>p-Butylbenzylamine | NMR (CDCl$_3$)<br>δ: 0.91 (3H, t, J=7Hz), 1.2~1.7 (4H), 1.6 (2H, exchange with D$_2$O), 2.60 (2H, t, J=7Hz), 3.82 (2H, s), 7.1~7.3 (4H)<br>MS: m/z 163 (M+) |
| Ref. Ex. 25<br>H$_2$N—CH$_2$—⟨phenyl⟩—CH(CH$_3$)$_2$<br>p-Isopropylbenzylamine | NMR (CDCl$_3$)<br>δ: 1.24 (6H, d, J=7Hz), 1.60 (2H, exachange with D$_2$O), 2.90 (1H, heptet, J=7Hz), 3.83 (2H, s), 7.23 (4H, br s)<br>MS: m/z 149 (M+) |
| Ref. Ex. 26<br>H,CH$_3$N—CH$_2$—⟨phenyl⟩—O—(CH$_2$)$_3$—⟨phenyl⟩<br>N-Methyl-N-[p-(3-phenyl-propoxy)benzyl]amine | NMR (CDCl$_3$)<br>δ: 2.0~2.3 (2H), 2.2 (1H, exchange with D$_2$O), 2.43 (3H, s), 2.7~2.9 (2H), 3.69 (2H, s), 3.96 (2H, t, J=7Hz), 6.85 (2H, d, J=9Hz), 7.23 (2H, d, J=9Hz), 7.24 (5H)<br>MS: m/z 255 (M+) |
| Ref. Ex. 27 | NMR (CDCl$_3$) |

-continued

| | Physicochemical Properties |
|---|---|
| 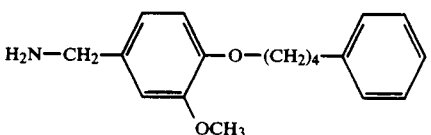<br>[3-Methoxy-4-(4-phenyl-butoxy)]benzylamine | δ: 1.5~1.9 (6H), 2.7 (2H, m), 3.49 (2H, br s), 3.87 (3H, s), 4.0 (2H, m), 6.8~7.0 (3H), 7.2~7.3 (5H)<br>MS: m/z 285 (M+) |

REFERENCE EXAMPLE 28

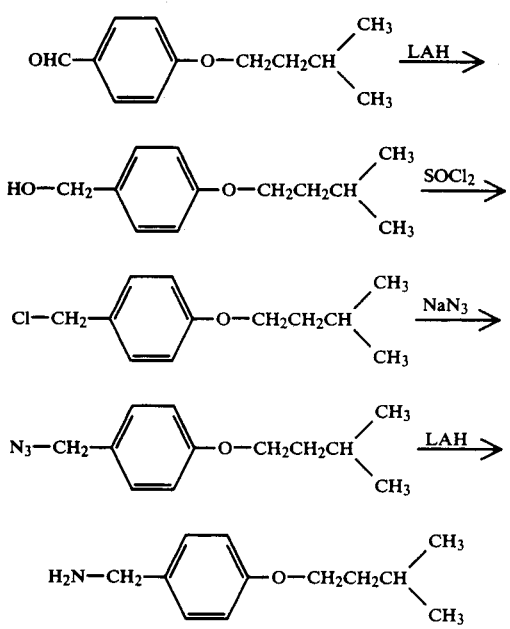

Lithium aluminum hydride (350 mg) was added gradually to a solution of 1.35 g of p-(3-methylbutoxy)-benzaldehyde in 50 ml of tetrahydrofuran at −10° C. After stirring at room temperature for 1 hour, the excess lithium aluminum hydride was decomposed with sodium sulfate decahydrate. The insoluble matter was filtered off from the mixture, and the filtrate was concentrated to give 1.33 g of p-(3-methylbutoxy)benzyl alcohol. Thionyl chloride (3 g) was added to a solution of the compound obtained in 25 ml of benzene, and the mixture was stirred at room temperature for 2 hours. The reaction mixture was concentrated under reduced pressure to give 1.45 g of p-(3-methylbutoxy)benzyl chloride. To a solution of this compound in 50 ml of N,N-dimethylformamide, there was added a solution of 3.3 g of sodium azide in 14 ml of water with ice cooling. After overnight stirring at room temperature, the reaction mixture was diluted with water, and the product was extracted with ethyl acetate. The ethyl acetate layer was washed with water and saturated aqueous solution of sodium chloride, dried over anhydrous magnesium sulfate and concentrated under reduced pressure to give 1.48 g of p-(3-methylbutoxy)benzyl azide. To a solution of this compound in 30 ml of tetrahydrofuran was added 500 mg of lithium aluminum hydride with ice cooling. The temperature of the reaction mixture was allowed to gradually rise to room temperature, and the mixture was stirred for 2 hours. The excess lithium aluminum hydride was decomposed with sodium sulfate decahydrate. The insoluble matter was filtered off, and the filtrate was concentrated under reduced pressure to give 1.13 g of p-(3-methylbutoxy)benzylamine.

NMR (CDCl₃) δ: 0.95 (6H, d, J=7 Hz , 1.5 (2H, exchange with D₂O), 1.6~1.9 (3H), 3.80 (2H, s), 3.98 (2H, t, J=7 Hz), 6.87 (2H, d, J=9 Hz), 7.24 (2H, d, J=9 Hz)

MS: m/z 193 (M+)

REFERENCE EXAMPLE 29

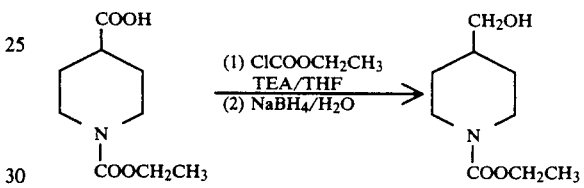

A solution of 0.67 g of ethyl chloroformate in 2 ml of tetrahydrofuran was added to a solution of 1.01 g of ethyl 4-carboxypiperidine-1-carboxylate and 0.72 g of triethylamine in 20 ml of tetrahydrofuran at −10° to −5° C., and the mixture was stirred for 30 minutes. The resultant crystalline precipitate was filtered off, the filtrate was added to a solution of 0.57 g of sodium borohydride in 10 ml of water with ice cooling over 30 minutes, and the mixture was stirred at room temperature for 30 minutes. The reaction mixture was made acidic with 1N hydrochloric acid with ice cooling and then extracted with ether. The ether layer was washed in sequence with water, saturated aqueous solution of sodium hydrogen carbonate and saturated aqueous solution of sodium chloride, then dried over anhydrous magnesium sulfate, and concentrated under reduced pressure. The residue was subjected to silica gel column chromatography. Elution with a hexane-ethyl acetate (1:1 v/v) mixture gave 0.69 g of ethyl 4-hydroxymethyl-piperidine-1-carboxylate NMR (CDCl₃) δ: 0.88~1.42 (1H, br), 1.30 (3H, t, J=7.0 Hz), 1.42~2.00 (5H, m), 2.77 (2H, dt, J=12.0, 3.0 Hz), 3.52 (2H, d, J=6.0 Hz), 4.15 (2H, q, J=7.0 Hz), 4.00~4.36 (2H, m)

MS: m/z 187 (M+)

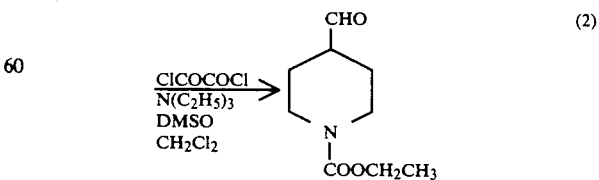
(2)

A solution of 1.97 g of dimethyl sulfoxide in 5 ml of dichloromethane was added to a solution of 1.59 g of oxalyl chloride in 30 ml of dichloromethane at a temperature within the range of −60° to −50° C. Five minutes layer, a solution of 2.11 g of ethyl 4-hydroxylethylpiperidine-1-carboxylate in 10 ml of dichloromethane was added dropwise, and the resultant mixture was stirred for 15 minutes. Triethylamine (5.73 g) was added to the reaction mixture, the whole mixture was stirred for 5 minutes and then at room temperature for 15 minutes. Water was added to the reaction mixture, and the resultant mixture was extracted with dichloromethane. The organic layer was washed in sequence with 1N hydrochloric acid and saturated aqueous solution of sodium chloride, dried over anhydrous magnesium sulfate and concentrated under reduced pressure to give 1.97 g of ethyl 4-formylpiperidine-1-carboxylate.

NMR (CDCl₃) δ: 1.25 (3H, t, J=7.0 Hz), 1.42~2.10 (4H, m), 2.24~2.65 (1H, m), 2.65~3.24 (2H, m), 3.82~4.41 (4H, m), 9.68 (1H, s)

MS m/z 185 (M+)

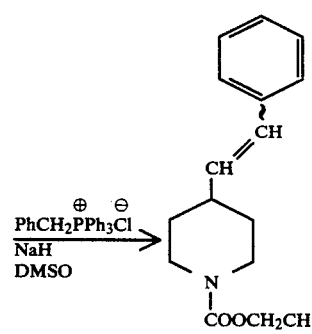

(3)

Sodium hydride (0.24 g) was added to 6 ml of dimethyl sulfoxide, the mixture was stirred at 75° C. for 30 minutes and then cooled to room temperature. Thereto was added a suspension of 2.1 g of benzyltriphenylphosphonium chloride in 5 ml of dimethyl sulfoxide at room temperature, and the mixture was stirred for 15 minutes. To this mixture was added a solution of 0.93 g of ethyl 4-formylpiperidine-1-carboxylate in 5 ml of dimethyl sulfoxide, and the mixture was stirred for 1 hours. After addition of water, the mixture was extracted with ether, and the organic layer was washed with saturated aqueous solution of sodium chloride, dried over anhydrous magnesium sulfate and concentrated under reduced pressure. The residue was subjected to purification by silica gel column chromatography (35 g). Elution with a hexane-ethyl acetate (3:1) mixture gave 1.13 g of ethyl 4-styrylpiperidine-1-carboxylate.

NMR (CDCl₃) δ: 1.29 (3H, t, J=7.0 Hz), 1.10~1.95 (4H, m), 2.03~2.58 (1H, m), 2.58~3.05 (2H, m), 4.16 (2H, q, J=7.0 Hz), 3.88~4.40 (2H, m), 5.46 (1/7H, dd, J=12.0, 10.0 Hz), 6.13 (6/7H, dd, J=16.0, 6.0 Hz), 6.42 (1/7H, d, J=12.0 Hz), 6.43 (6/7H, d, J=16.0 Hz), 7.08~7.45 (5H, m)

MS: m/z 259 (M+)

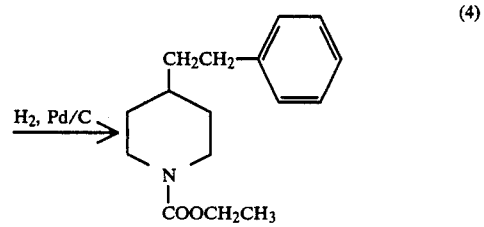

(4)

A mixture of 0.80 g of ethyl 4-styrylpiperidine-1carboxylate and 80 mg of 10% palladium-on-carbon in ethyl acetate (40 ml) was subjected to catalytic reduction at room temperature until stopping of hydrogen absorption. The catalyst was filtered off, and the filtrate was concentrated under reduced pressure to give 0.80 g of ethyl 4-(2-phenylethyl)piperidine-1-carboxylate.

NMR (CDCl₃) δ: 1.28 (3H, t, J=8.0 Hz), 0.72~2.01 (7H, m), 2.50~2.98 (4H, m), 3.89~4.42 (2H, m), 4.14 (2H, q, J=8.0 Hz), 7.02~7.54 (5H, m)

MS: m/z 261 (M+)

(5)

A mixture of 0.70 g of ethyl 4-(2-phenylethyl)piperidine-1-carboxylate in 6 ml of 47% hydrobromic acid was heated under reflux at 100° C. for 6 hours. A small amount of water was added for dissolution of the resultant crystals, the solution was washed with ether, and the aqueous layer was made alkaline with 20% sodium hydroxide. After salting out with sodium chloride, the aqueous layer was extracted with ether. The organic layer was washed with saturated aqueous solution of sodium chloride, dried over anhydrous sodium sulfate and concentrated under reduced pressure to give 0.42 g of 4-(2-phenylethyl)piperidine.

NMR (CDCl₃) δ: 0.78~2.06 (8H, m), 2.30~2.86 (4H, m), 2.86~3.32 (2H, m), 6.95~7.50 (5H, m)

MS: m/z 189 (M+)

REFERENCE EXAMPLES 30 TO 32

The ethyl 1-(4-formyl)piperidinecarboxylate of Reference Example 29 (2) and Ph(CH₂)ᵤP⊕Ph₃.Br⊖(u=2 to 4) were used and treated in the same manner as in Reference Example 29 (3) to (5) to give the following compounds:

| | Physicochemical Properties |
|---|---|
| Ref. Ex. 30 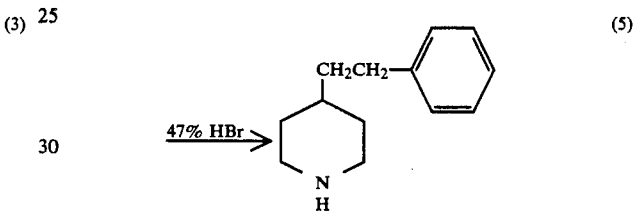 4-(3-Phenylpropyl)-piperidine | NMR (CDCl₃) δ: 0.75~2.05 (10H, m), 2.30~2.76 (4H, m), 2.83~3.24 (2H, m), 7.04~7.49 (5H, m) MS: m/z 203 (M+) |
| Ref. Ex. 31 | NMR (CDCl₃) |

| | Physicochemical Properties |
|---|---|
| 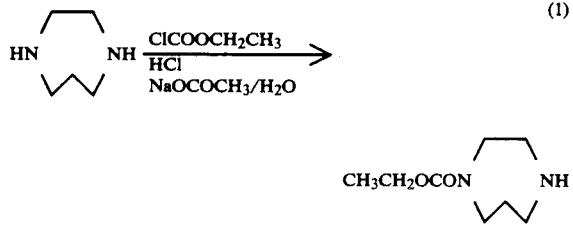 4-(4-Phenylbutyl)-piperidine | δ: 0.78~1.82 (11H, m), 1.12 (1H, s), 2.35~2.75 (4H, m), 2.84~3.21 (2H, m), 7.04~7.45 (5H, m) MS: m/z 217 (M+) |
| Ref. Ex. 32 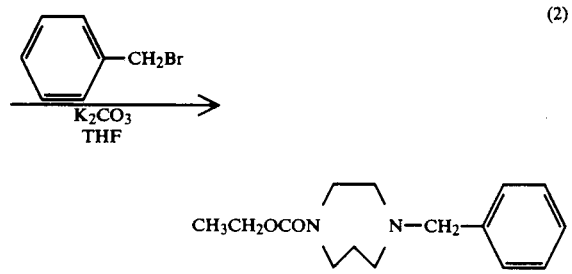 4-(5-Phenylpentyl)-piperidine | NMR (CDCl₃) δ: 0.81~1.90 (14H, m), 2.35~2.80 (4H, m), 2.86~3.23 (2H, m), 7.02~7.42 (5H, m) MS: m/z 231 (M+) |

REFERENCE EXAMPLE 33

(1)

HN⌒NH $\xrightarrow[\text{NaOCOCH}_3/\text{H}_2\text{O}]{\text{ClCOOCH}_2\text{CH}_3 \; / \; \text{HCl}}$

CH₃CH₂OCON⌒NH

2N Hydrochloric acid was added to a solution of 1.10 g of homopiperazine in 15 ml of water at room temperature until a pH of 2 was attained. Then, 40% aqueous sodium acetate and 1.28 g of ethyl chloroformate were added alternately in portions within the pH range of 2.0 to 3.5, and the resultant mixture was stirred at room temperature for 2 hours. The reaction mixture was washed with ethyl acetate, and the aqueous layer was saturated with potassium carbonate and extracted with ethyl acetate. The organic layer was washed with saturated aqueous solution of sodium chloride, dried over anhydrous sodium sulfate and concentrated under reduced pressure to give 1.27 g of ethyl 1-homopiperazinecarboxylate.

NMR (CDCl₃) δ: 1.28 (3H, t, J=7 Hz), 1.60~1.99 (3H, m) 2.75~3.04 (4H, m), 3.30~3.65 (4H, m), 4.15 (2H, q, J=7 Hz)

MS: m/z 172 (M+)

(2)

⌬—CH₂Br $\xrightarrow[\text{THF}]{\text{K}_2\text{CO}_3}$

CH₃CH₂OCON⌒N—CH₂—⌬

Potassium carbonate (0.80 g) was added to a solution of 0.86 g of ethyl 1-homopiperazinecarboxylate and 0.90 g of benzylbromide in 5 ml of tetrahydrofuran, and the mixture was refluxed for 4 hours. Thereafter, water was added, and the mixture was extracted with ethyl acetate, and the organic layer was washed with saturated aqueous solution of sodium chloride, dried over anhydrous sodium sulfate and concentrated under reduced pressure. The residue was subjected to silica gel column chromatography. Elution with a hexane-ethyl acetate (2:1) mixture gave 1.06 g of ethyl 4-benzylhomopiperazine-1-carboxylate.

NMR (CDCl₃) δ: 1.25 (3H, t, J=7 Hz), 1.62~2.05 (2H, m), 2.50~2.81 (4H, m), 3.32~3.75 (4H, m), 3.61 (2H, s), 4.14 (2H, q, J=7 Hz), 7.29 (5H, s)

MS: m/z 262 (M+)

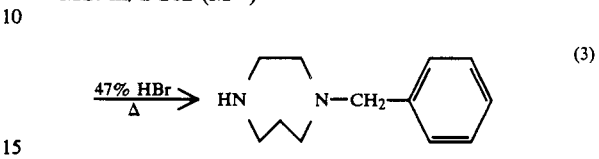

(3)

A mixture of 0.85 g of ethyl 4-benzylhomopiperazine-1-carboxylate and 5 ml of 47% hydrobromic acid was heated at 100° C. for 10 hours. After addition of a small amount of water, the reaction mixture was washed with ethyl acetate. The aqueous layer was made alkaline with 30% sodium hydroxide and, after salting out with sodium chloride, extracted with ethyl acetate. The organic layer was washed with saturated aqueous solution of sodium chloride, dried over anhydrous sodium sulfate and concentrated under reduced pressure to give 0.55 g of 1-benzylhomopiperazine.

NMR (CDCl₃) δ: 1.60~1.96 (2H, m), 1.91 (1H, s), 2.52~2.80 (4H, m), 2.80~3.07 (4H, m), 3.68 (2H, s), 7.12~7.45 (5H, m)

MS: m/z 190

REFERENCE EXAMPLES 34 TO 37

The following compounds were obtained in the same manner as in Reference Example 33 (2) and (3).

| | Physicochemical Properties |
|---|---|
| Ref. Ex. 34 HN⌒N—(CH₂)₂—⌬ 1-(2-Phenylethyl)homo-piperazine | NMR (CDCl₃) δ: 1.60~1.92 (2H, m), 2.03 (1H, s), 2.58~3.09 (12H, m), 7.05~7.43 (5H, m) MS: m/z 204 (M+) |
| Ref. Ex. 35 HN⌒N—(CH₂)₃—⌬ 1-(3-Phenylpropyl)homo-piperazine | NMR (CDCl₃) δ: 1.58~1.98 (4H, m), 2.08 (1H, s), 2.16~2.78 (8H, m), 2.78~3.02 (4H, m), 6.95~7.45 (5H, m) MS: m/z 218 (M+) |
| Ref. Ex. 36 HN⌒N—CH₂CH₂CH₂CH(CH₃)₂ 1-(4-Methylpentyl)homo-piperazine | NMR (CDCl₃) δ: 0.89 (6H, d, J=6Hz), 0.96~2.91 (7H, m), 2.11 (1H, s), 2.35~2.57 (2H, m), 2.57~2.79 (4H, m), 2.80~3.04 (4H, m) MS: m/z 184 (M+) |
| Ref. Ex. 37 HN⌒N—(CH₂)₆CH₃ 1-Heptylhomopiperazine | NMR (CDCl₃) δ: 0.73~1.01 (3H, m), 1.08~1.61 (11H, m), 1.63~1.93 (2H, m), 2.32~2.80 (6H, m), 2.82~3.08 (4H, m). |

REFERENCE EXAMPLE 38

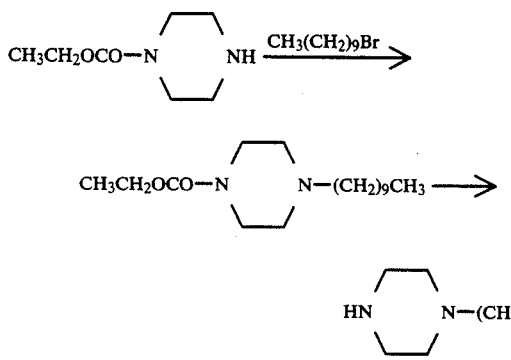

A mixture of 2.02 g of ethyl 1-piperazinecarboxylate, 1.92 g of anhydrous potassium carbonate, 3.08 g of decyl bromide and 20 ml of 2-butanone was stirred overnight at 80° C. After addition of water, the reaction mixture was extracted with ethyl acetate. The ethyl acetate layer was extracted with 3N hydrochloric acid. The extract was made alkaline with potassium carbonate and then extracted with ethyl acetate. The extract was washed with water, dried over anhydrous sodium sulfate and concentrated under reduced pressure Ethanol (20 ml) and ml of 10% aqueous sodium hydroxide were added to the residue, and the mixture was stirred overnight at 100° C. The reaction mixture was cooled and extracted with ethyl acetate. The extract was washed with water, dried over anhydrous sodium sulfate and concentrated under reduced pressure to give 0.38 g of 1-decylpiperazine as an oil.

NMR (CDCl$_3$) δ: 0.73~1.74 (19H, m), 2.16~2.52 (6H, m), 2.84~2.98 (4H, m)
MS: m/z 226 (M$^+$)

REFERENCE EXAMPLES 39 TO 50

The following compounds were obtained in the same manner as in Reference Example 38.

| | Physiochemical Properties |
|---|---|
| Ref. Ex. 39<br>HN−(piperazine)−N−(CH$_2$)$_2$CH(CH$_3$)$_2$<br>1-(3-Methylbutyl)piperazine | NMR (CDCl$_3$)<br>δ: 0.89 (6H, d),<br>1.12~1.74 (3H, m),<br>2.13~2.52 (6H, m),<br>2.80~3.00 (4H, m)<br>MS: m/z 156 (M$^+$) |
| Ref. Ex. 40<br>HN−(piperazine)−N−CH$_2$CH$_2$CH$_2$CH(CH$_3$)$_2$<br>1-(4-Methylpentyl)piperazine | NMR (CDCl$_3$)<br>δ: 0.88 (6H, d, J=7Hz),<br>1.00~1.73 (5H, m),<br>2.09 (1H, s),<br>2.17~2.56 (4H, m),<br>2.78~3.05 (4H, m) |
| Ref. Ex. 41<br>HN−(piperazine)−N−(CH$_2$)$_5$CH$_3$<br>1-Hexylpiperazine | NMR (CDCl$_3$)<br>δ: 0.90 (3H, t),<br>1.12~1.72 (8H, m),<br>2.20~2.52 (6H, m),<br>2.82~3.00 (4H, m)<br>MS: m/z 170 (M$^+$) |
| Ref. Ex. 42<br>HN−(piperazine)−N−(CH$_2$)$_6$CH$_3$<br>1-Heptylpiperazine | NMR (CDCl$_3$)<br>δ: 0.90 (3H, t),<br>1.14~1.72 (10H, m),<br>2.20~2.56 (6H, m),<br>2.80~3.04 (4H, m)<br>MS: m/z 184 (M$^+$) |
| Ref. Ex. 43<br>HN−(piperazine)−N−(CH$_2$)$_7$CH$_3$<br>1-Octylpiperazine | NMR (CDCl$_3$)<br>δ: 0.90 (6H, d),<br>1.12~1.40 (12H, m),<br>2.16~2.56 (6H, m),<br>2.80~3.00 (4H, m)<br>MS: m/z 178 (M$^+$) |
| Ref. Ex. 44<br>HN−(piperazine)−N−CH$_2$−(cyclopentyl)<br>1-Cyclopentylmethylpiperazine | NMR (CDCl$_3$)<br>δ: 1.04~2.52 (15H, m),<br>2.80~3.00 (4H, m) |

-continued

| | Physiochemical Properties |
|---|---|
| Ref. Ex. 45 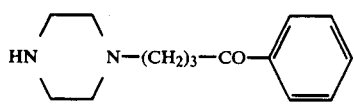<br>1-(4-Oxo-4-phenylbutyl)piperazine | NMR (CDCl$_3$)<br>δ: 1.72~3.20 (14H, m),<br>7.26~7.64 (3H, m),<br>7.90~8.10 (2H, m)<br>MS: m/z 231 (M$^+$) |
| Ref. Ex. 46 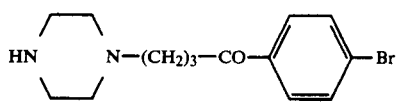<br>1-[4-(p-Bromophenyl)-4-oxobutyl]piperazine | NMR (CDCl$_3$)<br>δ: 1.80~2.10 (4H, m),<br>2.26~2.50 (6H, m),<br>2.72~2.90 (4H, m),<br>7.52~7.72 (2H, m),<br>7.76~8.00 (2H, m) |
| Ref. Ex. 47 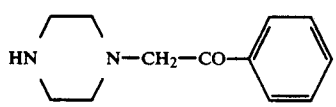<br>1-(2-Oxo-2-phenylethyl)piperazine | NMR (CDCl$_3$)<br>δ: 2.40~2.76 (4H, m),<br>2.76~3.12 (4H, m),<br>3.80 (2H, s),<br>7.22~7.64 (3H, m),<br>7.88~8.14 (2H, m)<br>MS: m/z 204 (M$^+$) |
| Ref. Ex. 48 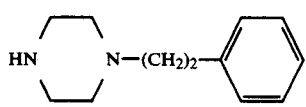<br>1-(2-Phenylethyl)piperazine | NMR (CDCl$_3$)<br>δ: 2.23~2.97 (12H, m),<br>7.10~7.36 (5H, m)<br>MS: m/z 189 (M$^+$) |
| Ref. Ex. 49 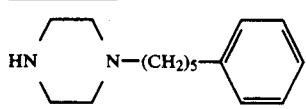<br>1-(5-Phenylpentyl)piperazine | NMR (CDCl$_3$)<br>δ: 1.14~1.84 (6H, m),<br>2.16~2.72 (8H, m),<br>2.78~3.02 (4H, m),<br>7.04~7.40 (5H, m)<br>MS: m/z 231 (M$^+$) |
| Ref. Ex. 50 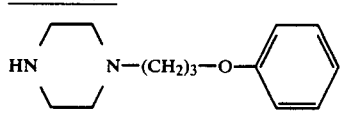<br>1-(3-Phenoxypropyl)piperazine | NMR (CDCl$_3$)<br>δ: 1.6~2.3 (2H, m),<br>2.4~3.2 (10H, m),<br>4.06 (2H, t),<br>6.7~7.5 (5H, m) |

REFERENCE EXAMPLE 51

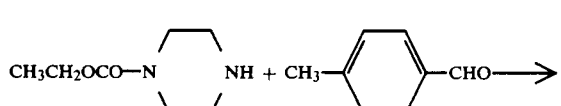

Sodium borohydride (500 mg) was added to a mixture of 1.6 g of ethyl 1-piperazinecarboxylate, 1.3 g of p-tolualdehyde and 30 ml of ethanol, and the mixture was stirred overnight at room temperature. The reaction mixture was concentrated under reduced pressure, 50 ml of water was added, and the resultant mixture was extracted with ethyl acetate. The ethyl acetate extract was then extracted with diluted hydrochloric acid. The diluted hydrochloric acid extract was washed with ethyl acetate, made alkaline with sodium hydrogen carbonate and extracted with ethyl acetate. The extract was washed with water, dried over anhydrous potassium carbonate and concentrated under reduced pressure to give 0.8 g of ethyl 4-p-tolylmethyl-1-piperazinecarboxylate as an oil. This was deprived of the carboethoxy group by the method described in Reference Example 38 to give 0.36 g of 1-ptolylmethylpiperazine as an oil.

NMR (CDCl$_3$) δ: 2.42 (3H, s, CH$_3$), 2.3~2.6 (4H, m), 2.7~3.1 (4H, m), 3.43 (2H, s, CH$_2$), 7.14 (4H, s)

REFERENCE EXAMPLE 52

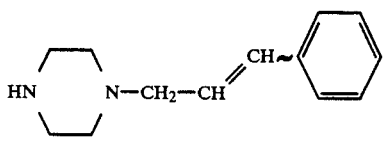

Ethyl 1-piperazinecarboxylate and cinnamaldehyde were used as the starting materials and treated in the same manner as in Reference Example 51 to give 1-cinnamylpiperazine as an oil.

NMR (CDCl$_3$) δ: 2.2~2.6 (4H, m), 2.8~3.0 (4H, m), 3.16 (2H, d, CH$_2$), 6.28 (1H, dt), 6.56 (1H, d), 7.0~7.5 (5H, m)

REFERENCE EXAMPLE 53

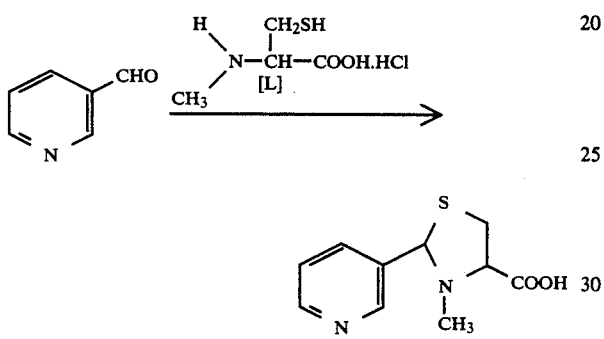

A mixture of 1.72 g of L-N-methylcysteine, 1.07 g of nicotinaldehyde and 2 ml of water was stirred at room temperature for 24 hours. Pyridine (0.8 ml) and 1 ml of ethanol were added to the reaction mixture, and the resultant crystalline precipitate was collected by filtration, washed with ethanol and dried to give 0.74 g of 3-methyl-2-(3-pyridyl)thiazolidine-4-carboxylic acid.

NMR (DMSO-d$_6$) δ: 2.24, 2.32 (3H/2×2, s, N—CH$_3$), 3.00~3.64 (5/2H, m), 4.16~4.32 (H/2, m), 4.92, 5.36 (H/2×2, s), 7.10~7.32 (1H, m), 7.80~8.00 (1H, m), 8.44~8.72 (2H, m)

MS (FAB): m/z 225 (M+H)+

REFERENCE EXAMPLE 54

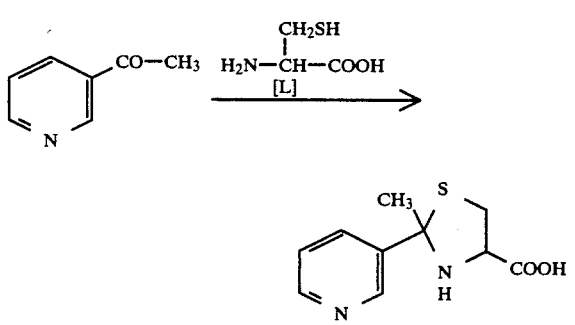

A mixture of 3.63 g of 3-acetylpyridine, 3.63 g of L-cysteine, 25 ml of water and 25 ml of ethanol was refluxed for 24 hours. The reaction mixture was concentrated under reduced pressure, isopropanol was added to the residue, and the resultant powder was collected by filtration. Ethanol was added to the powder, the insoluble matter was filtered off, and the filtrate was concentrated to dryness. The residue was dissolved in water and adjusted to pH 6 by addition of diluted hydrochloric acid under ice colling and stirring, and the resultant powder was collected by filtration, washed with ethanol and dried to give 2.54 g of 2-methyl-2-(3-pyridyl)thiazolidine-4-carboxylic acid.

NMR (DMSO-d6) δ: 1.78 and 1.88 (s, respectively 3H), 2.92~3.56 (2H, m), 3.56~4.38 (1H, m), 7.20~7.44 (1H, m), 7.80~9.08 (1H, m), 9.32~9.52 (1H, m), 9.68~9.86 (1H, m)

MS (FAB): m/z 225 (M+H)+

REFERENCE EXAMPLE 55

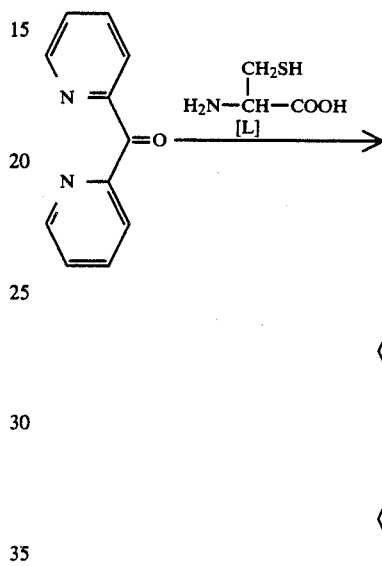

A mixture of 3.68 g of di-2-pyridyl ketone, 2.42 g of L-cysteine, 25 ml of water and 25 ml of ethanol was refluxed for 3.5 hours. After allowing the mixture to cool, the insoluble matter was filtered off, and the filtrate was concentrated to dryness under reduced pressure. The residue was washed in sequence with ethyl acetate and ether to give 0.63 g of 2,2-di(2-pyridyl)-thiazolidine-4-carboxylic acid.

NMR (DMSO-d6) δ: 2.85~4.15 (3H, m), 7.20~8.90 (8H, m)

REFERENCE EXAMPLE 56

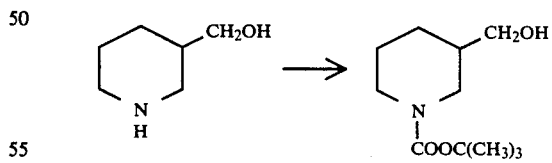

Di-tert-butyl dicarbonate (7.85 g) and 35 ml of 1 N sodium hydroxide were added to a solution of 4.00 g of 3-piperidinemethanol in 50 ml of dioxane plus 30 ml of water at 0° C. The reaction mixture was allowed to rise to room temperature and then stirred for 1.5 hours. The product was extracted with ethyl acetate. The ethyl acetate layer was washed in sequence with water and saturated aqueous solution of sodium chloride, dried over anhydrous magnesium sulfate and concentrated under reduced pressure to give 7.20 g of 1-tert-butoxycarbonylpiperidine-3-methanol. Melting point 77°-79° C.

NMR (CDCl₃) δ: 1.48 (9H, s), 1.4~1.9 (4H), 2.6~3.2 (4H), 3.6~3.9 (4H)
MS: m/z 215 (M+)

REFERENCE EXAMPLE 57

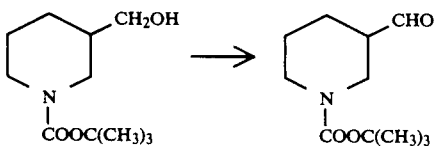

Dimethyl sulfoxide (0.85 ml) was added to a solution of 0.50 ml of oxalyl chloride in 10 ml of dichloromethane at −60° C. and, 3 minutes later, a solution of 1.08 g of 1-tert-butoxycarbonylpiperidine-3-methanol in 10 ml of dichloromethane was added dropwise over 5 minutes. After stirring for 15 minutes, 3.0 ml of triethylamine was added to the reaction mixture. After further 5 minutes of stirring, water (20 ml) was added to the reaction mixture and, after shaking, the dichloromethane layer was separated. The dichloromethane layer was washed with 1N hydrochloric acid, water, saturated aqueous solution of sodium hydrogen carbonate, water and saturated aqueous solution of sodium chloride in that order, then dried over anhydrous magnesium sulfate, and concentrated under reduced pressure to give 0.98 g of 1-tert-butoxycarbonylpiperidine-3-carbaldehyde.

NMR (CDCl₃) δ: 1.46 (9H, s), 1.4~2.0 (4H), 2.40 (1H, m, w/z=21 Hz), 3.10 (1H, dd, J=8.5 and 14 Hz), 3.65 (1H, ddd, J=4, 5 and 12.5 Hz), 3.94 (1H, dd, J=4 and 14 Hz), 9.68 (1H, s)
MS: m/z 213 (M+)

REFERENCE EXAMPLES 58 TO 67

The following compounds were obtained in the same manner as in Reference Example 2.

| Chemical Structure and Chemical Name | Desired Product Physicochemical Properties |
|---|---|
| Ref. Ex. 58<br>2-[3-(4-Dimethylaminopyridyl]thiazolidine-4-carboxylic acid | NMR (DMSO-d₆)<br>δ: 2.85 (6H, s), 2.98~3.56 (2H, m), 3.72~4.44 (1H, m), 5.68, 5.92 (1H, s), 6.80~7.00 (1H, m), 8.16~8.34 (1H, m), 8.60~8.75 (1H, m)<br>MS (FAB): m/z 254 (M+H)+ |
| Ref. Ex. 59<br>2-[3-(5,6-Dimethoxy-pyridyl)]thiazolidine-4-carboxylic acid | Melting point: 154~155° C. (decomposition)<br>MS (FAB): m/z 271 (M+H)+ |
| Ref. Ex. 60<br>2-[3-(2-Methylpyridyl)]-thiazolidine-4-carboxylic acid | NMR (DMSO-d₆)<br>δ: 2.60 (3H, s), 2.80~4.60 (3H, m), 5.70, 6.00 (1H, s), 7.00~8.50 (3H, m) |
| Ref. Ex. 61<br>2-(1-tert-Butoxycarbonyl-4-piperidinyl)thiazolidine-4-carboxylic acid | Melting point: 169~171° C. (decomposition)<br>NMR (CDCl₃+DMSO-d₆)<br>δ: 1.48 (9H, s), 1.4~2.1 (5H), 2.6~3.0 (1H), 2.95 (1H, dd, J=7 and 10Hz), 3.22 (1H, dd, J=7 and 10Hz), 3.6~4.0 (1H), 3.96 (1H, t, J=7Hz), 4.49 (1H, d, J=8Hz), 6.3 (2H, br, exchange with D₂O) |
| Ref. Ex. 62 | |

-continued

| Desired Product | |
|---|---|
| Chemical Structure and Chemical Name | Physicochemical Properties |

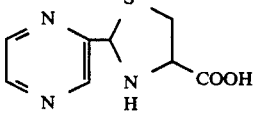

2-(2-Pyrazyl)thiazolidine-4-carboxylic acid

Melting point: 144~146° C. (decomposition)
Elemental analysis
(for $C_8H_9N_3O_2S$):

| | C(%) | H(%) | N(%) | S(%) |
|---|---|---|---|---|
| Calcd: | 45.49 | 4.29 | 19.89 | 15.18 |
| Found: | 45.20 | 4.18 | 19.76 | 15.43 |

Ref. Ex. 63

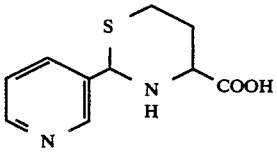

2-[3-Pyridyl)-3,4,5,6-tetrahydro-2H-thiazine-4-carboxylic acid

Melting point: 204~207° C.
MS: m/z 225 ($M^+ +1$)

Ref. Ex. 64

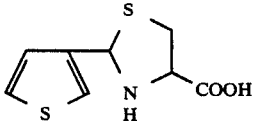

2-(3-Thienyl)thiazolidine-4-carboxylic acid

Melting point: 165~167° C.
Elemental analysis
(for $C_8H_9NO_2S_2$):

| | C(%) | H(%) | N(%) | S(%) |
|---|---|---|---|---|
| Calcd: | 44.63 | 4.21 | 6.51 | 29.79 |
| Found: | 44.57 | 4.23 | 6.49 | 29.99 |

Ref. Ex. 65

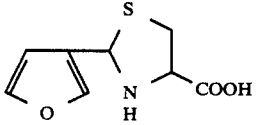

2-(3-Furyl)thiazolidine-4-carboxylic acid

Melting point: 169~170° C. (decomposition)
Elemental analysis
(for $C_8H_9NO_3S$):

| | C(%) | H(%) | N(%) | S(%) |
|---|---|---|---|---|
| Cald: | 48.23 | 4.55 | 7.03 | 16.09 |
| Found: | 48.03 | 4.51 | 7.00 | 16.28 |

Ref. Ex. 66

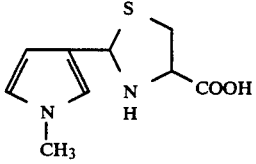

2-[3-(1-Methylpyrrolyl)]-thiazolidine-4-carboxylic acid

Melting point: 148~147° C. (decomposition)
MS (FAB): m/z 213 ($M^+ +1$)

Ref. Ex. 67

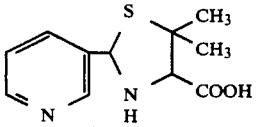

5,5-Dimethyl-2-(3-pyridyl)-thiazolidine-4-carboxylic acid

Melting point: 143~144° C.
MS (FAB): m/z 1239 ($M^+ +1$)

REFERENCE EXAMPLE 68

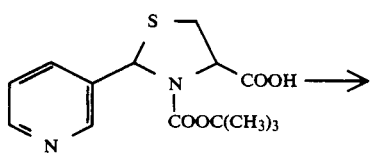

Oxalyl chloride (1.31 ml) and 50 mg of N,N-dimethylformamide were added to a solution of 3.10 g of 3-tert-butoxycarbonyl-2-(3-pyridiyl)thiazolidine-4-carboxylic acid in 30 ml of dichloromethane at −78° C. The reaction mixture was slowly warmed to room temperature and then stirred for 12 hours. The resultant precipitate was collected by filtration and dried to give 1.90 g of 1,3-dioxo-5-(3-pyridyl)thiazolidino[3,4-c]oxazolidine hydrochloride. Melting point 170° C. (decomposition).

| Elemental analysis (for $C_{10}H_9ClN_3O_3S$): | | | | | |
|---|---|---|---|---|---|
| | C (%) | H (%) | N (%) | S (%) | Cl (%) |
| Calculated: | 44.04 | 3.33 | 10.27 | 11.76 | 13.00 |
| Found: | 43.94 | 3.37 | 10.24 | 11.76 | 13.30 |

REFERENCE EXAMPLE 69

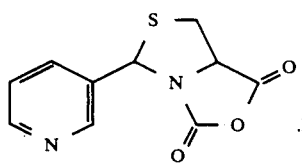

10% Palladium-on-carbon (200 mg) was added to a solution of 5.34 g of 4-methoxycinnamic acid in methanol, and the mixture was stirred under hydrogen until hydrogen gas absorption ceased. The catalyst was filtered off, and the filtrate was concentrated under reduced pressure to give 5.43 g of 3-(4-methoxyphenyl)-propionic acid.

NMR (CDCl$_3$) δ: 2.34~3.15 (4H), 3.76 (3H, s), 6.64~7.30 (4H), 11.00 (1H, s)

RFFERENCE EXAMPLE 70

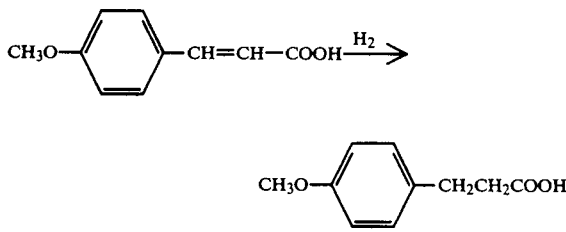

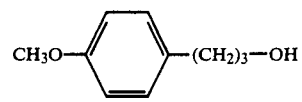

A solution of the 3-(4-methoxyphenyl)propionic acid in 100 ml of anhydrous ether was added dropwise to a suspension of 1.10 g of lithium aluminum hydride in 50 ml of anhydrous ether with stirring at room temperature over 20 minutes. After stirring at room temperature for 30 minutes, the mixture was refluxed for 1 hours. After cooling, water was added with ice cooling, and the mixture was made acidic by further addition of 10% hydrochloric acid and then extracted with ether. The organic layer was washed with saturated aqueous solution of sodium chloride, driven over anhydrous magnesium sulfate and concentrated under reduced pressure to give 5.06 g of 3-(4-methoxyphenyl)propanol.

NMR (CDCl$_3$) δ: 1.60~2.16 (2H), 2.38~2.95 (3H), 3.69 (2H, t, J=6 Hz), 3.80 (3H, s), 6.71~7.30 (4H)

REFERENCE EXAMPLES 71 TO 74

The following compounds were obtained in the same manner as in Reference Examples 69 and 70. In Reference Examples 73 and 74, platinum oxide was used as a catalyst for the catalytic reduction.

| Desired Compound | |
|---|---|
| Chemical Structure and Chemical Name | Physicochemical Properties |
| Ref. Ex. 71<br>H$_3$C—⌬—(CH$_2$)$_3$—OH<br>3-(4-Methylphenyl)propanol | MMR (CDCl$_3$)<br>δ: 1.58~2.10 (2H), 2.26 (3H, s), 2.49~2.83 (3H), 3.60 (2H, t, J=6Hz), 7.00 (4H, s) |
| Ref. Ex. 72<br>CH$_3$O—⌬—(CH$_2$)$_3$—OH<br>     CH$_3$O<br>3-(3,4-Dimethoxyphenyl)-propanol | MMR (CDCl$_3$)<br>δ: 1.60~2.14 (2H), 2.49~2.90 (3H), 3.65 (2H, t), 3.82 (6H, s), 6.73 (3H, s) |
| Ref. Ex. 73<br>Cl—⌬—(CH$_2$)$_3$—OH<br>3-(4-Chlorophenyl)propanol | MMR (CDCl$_3$)<br>δ: 1.60~2.14 (2H), 1.77 (1H, s), 2.54~2.90 (2H), 3.65 (2H, t), 6.95~7.40 (4H) |
| Ref. Ex. 74<br>F—⌬—(CH$_2$)$_3$—OH<br>3-(4-Fluorophenyl)propanol | MMR (CDCl$_3$)<br>δ: 1.55~2.16 (2H), 2.01 (1H, s), 2.48~2.88 (2H), 3.65 (2H, t), 6.65~7.31 (4H) |

REFERENCE EXAMPLE 75

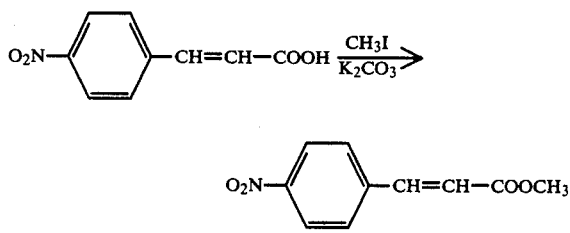

A mixture of 5.80 g of p-nitrocinnamic acid, 10.4 g of methyl iodide, 10.4 g of anhydrous potassium carbonate and 200 ml of acetone was stirred at room temperature for 2 days. The resultant precipitate was filtered off, the filtrate was concentrated under reduced pressure and, after addition of water, the residue was extracted with ethyl acetate. The organic layer was washed with saturated solution of sodium hydrogen carbonate and saturated aqueous solution of sodium chloride, dried over anhydrous magnesium sulfate and concentrated under reduced pressure to give 3.30 g of methyl 4-nitrocinnamate.

NMR (CDCl$_3$) δ: 3.83 (3H, s), 6.52 (1H, d, J=16 Hz), 7.50~7.95 (3H), 8.21 (2H, d, J=9 Hz).

REFERENCE EXAMPLE 76

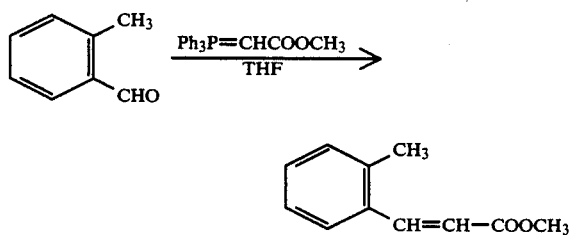

A solution of 1.20 g of o-tolualdehyde in 20 ml of anhydrous tetrahydrofuran was added to a suspension of 3.67 g of methyl (triphenylphosphoranylidene)acetate in 20 ml of anhydrous tetrahydrofuran at room temperature, and the mixture was refluxed for 15 hours. The solvent was then distilled off under reduced pressure, and the residue was subjected to silica gel column chromatography (40 g). Elution with hexane-ethyl acetate (2:1) gave 1.65 g of methyl 2-methylcinnamate.

NMR (CDCl$_3$) δ: trans-form, 2.45 (3H, s), 3.80 (3H, s), 6.34 (1H, d, J=16 Hz), 6.99~7.66 (4H), 7.97 (1H, d, J=16 Hz) cis-form, 2.29 (s), 3.63 (s), 6.03 (d J=12 Hz)

REFERENCE EXAMPLES 77 AND 78

The following compounds were synthesized in the same manner as in Reference Examples 69 and 70.

| Desired Compound | |
|---|---|
| Chemical Structure and Chemical Name | Physicochemical Properties |
| Ref. Ex. 77<br><br>![structure]<br>3-(2-Methylphenol)propanol | MMR (CDCl$_3$)<br>δ: 1.57~2.11 (2H), 1.86 (1H, s), 2.51~2.90 (2H), 3.69 (2H, t, J=6Hz), 7.10 (4H, s). |
| Ref. Ex. 78<br><br>H$_2$N-⟨C$_6$H$_4$⟩-(CH$_2$)$_3$-OH<br>3-(4-Aminophenyl)propanol | MMR (CDCl$_3$)<br>δ: 1.54~2.10 (2H), 2.40-3.10 (5H), 3.62 (2H, t, J=6Hz), 6.46~7.10 (4H). |

REFERENCE EXAMPLE 79

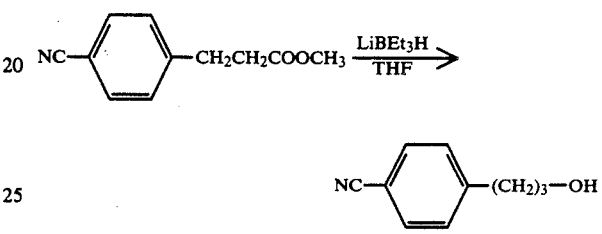

A solution of 1M superhydride/tetrahydrofuran (3.3 ml) in anhydrous tetrahydrofuran (5 ml) was cooled to −50° to −60° C. under an argon gas stream. Thereto was added dropwise a solution of 210 mg of methyl 3-(4-cyanophenyl)propionate synthesized from 4-cyanobenzaldehyde and methyl (triphenylphosphoranylidene)acetate by the procedure of Reference Examples 69 and 76) in 2 ml of tetrahydrofuran. The resultant mixture was stirred at that temperature for 10 minutes, then made acidic by addition of water and 1N hydrochloric acid in that order at the same temperature, and extracted with ethyl acetate. The organic layer was washed with saturated aqueous solution of sodium chloride, dried over anhydrous magnesium sulfate and concentrated under reduced pressure to give 120 mg of 3-(4-cyanophenyl)propanol.

NMR (CDCl$_3$) δ: 1.61~2.20 (3H), 2.60~3.06 (2H), 3.68 (2H, t, J=6 Hz), 7.10~7.75 (4H)

REFERENCE EXAMPLE 80

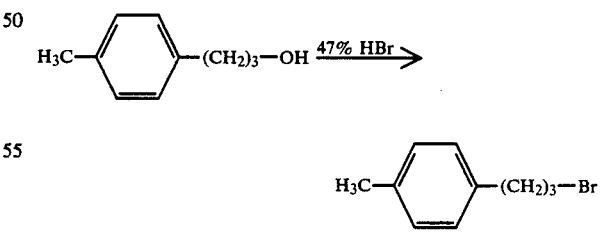

3-(4-Methylphenyl)propanol (2.13 g) was heated in 7 ml of 47% aqueous hydrobromic acid under reflux for 5 hours. The solvent was then distilled off under reduced pressure and, after addition of water, the residue was extracted with ether. The organic layer was washed with saturated aqueous solution of sodium chloride, dried over anhydrous magnesium sulfate and concentrated under reduced pressure. The residue was distilled under reduced pressure to give 1.75 g of 3-(4-methylphenyl)propyl bromide. Boiling point: 65° C./0.7 mmHg.

NMR (CDCl₃) δ: 1.85–2.43 (2H), 2.32 (3H, s), 2.55~2.95 (2H, 3.39 (2H, t, J=6 Hz), 7.04 (4H, s)

REFERENCE EXAMPLE 81

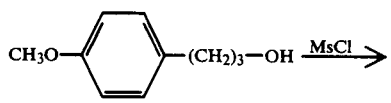

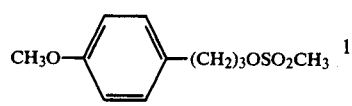

Methanesulfonyl chloride (3.8 g) was gradually added dropwise to a solution of 5 g of 3-(4-methoxyphenyl)propanol in 50 ml of anhydrous pyridine with ice cooling, and the resultant mixture was stirred at the same temperature for 3 hours. The solvent was distilled off under reduced pressure and, after addition of water, the residue was made acidic with 10% hydrochloric acid and then extracted with ethyl acetate. The organic layer was washed with 1N hydrochloric acid, saturated aqueous solution of sodium hydrogen carbonate and saturated aqueous solution of sodium chloride in that order, dried over anhydrous magnesium sulfate and concentrated under reduced pressure to give 6.32 g of 3-(4-methoxyphenyl)propylmethanesulfonate.

NMR (CDCl₃) δ: 1.75~2.36 (2H), 2.55~2.93 (2H), 3.00 (3H, s), 3.80 (3H, s), 4.24 (2H, t, J=6 Hz), 6.70~7.30 (4H).

REFERENCE EXAMPLE 82

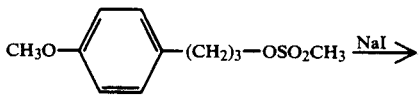

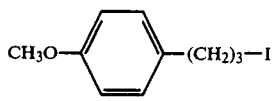

A solution of 6.30 g of 3-(4-methoxyphenyl)propyl methanesulfonate and 11.1 g of sodium iodide in 100 ml of acetone was refluxed for 15 hours. The reaction mixture was concentrated under reduced pressure and, after addition of water, the residue was extracted with ether. The organic layer was washed with saturated aqueous solution of sodium chloride, dried over anhydrous magnesium sulfate and concentrated under reduced pressure to give 6.62 g of 3-(4-methoxyphenyl)propyl iodide.

NMR (CDCl₃) δ: 1.81~2.35 (2H), 2.18 (2H, br t, J=7 Hz), 3.16 (2H, t, J=6 Hz), 3.80 (3H, s), 6.71~7.30 (4H).

REFERENCE EXAMPLE 83

The following compound was obtained in the same manner as in Reference Example 82.

| Desired Compound | |
|---|---|
| Chemical Structure and Chemical Name Ref. Ex. 83 | Physicochemical Properties |
| 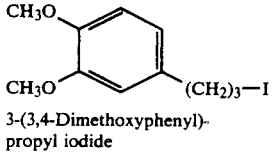<br>3-(3,4-Dimethoxyphenyl)-propyl iodide | MMR (CDCl₃)<br>δ: 1.80~2.34 (2H), 2.66 (2H, br t, J=7Hz), 3.12 (2H, t, J=6Hz), 3.81 (6H, s), 6.59 (3H, s). |

REFERENCE EXAMPLE 84

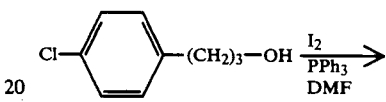

To a solution of 1.55 g of 3 (4-chlorophenyl)propanol and 2.51 g of triphenylphosphine in 10 ml of N,N-dimethylformamide, there was gradually added dropwise at room temperature a solution of 2.42 g of iodine in 8 ml of N,N-dimethylformamide while confirming the consumption of iodine. When the color of the reaction mixture ceased to disappear any more, water was added to the reaction mixture, the excess iodine was reduced by addition of 5% aqueous sodium thiosulfate, and the mixture was extracted with ethyl acetate. The organic layer was washed with saturated aqueous solution of sodium chloride, dried over anhydrous magnesium sulfate and concentrated under reduced pressure. The residue was subjected to silica gel column chromatography (20 g). Elution with hexane gave 1.82 g of 3-(4-chlorophenyl)propyl iodide.

NMR (CDCl₃) δ: 1.92~2.40 (2H), 2.71 (2H, br t, J=7 Hz) 3.13 (2H, t, J=6 Hz), 6.91~7.40 (4H).

REFERENCE EXAMPLES 85 TO 87

The following compounds were obtained in the same manner as in Reference Example 84.

| Desired Compound | |
|---|---|
| Chemical Structure and Chemical Name | Physicochemical Properties |
| Ref. Ex. 85<br>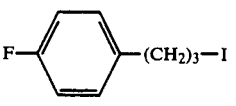<br>3-(4-Fluorophenyl)propyl iodide | MMR (CDCl₃)<br>δ: 1.79~2.35 (2H), 2.70 (2H, t, J=7Hz), 3.13 (2H, t, J=6Hz), 6.55~7.45 (4H). |
| Ref. Ex. 86<br>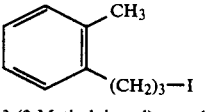<br>3-(2-Methylphenyl)propyl iodide | MMR (CDCl₃)<br>δ: 1.90~2.47 (2H), 2.32 (3H, s), 2.55~2.90 (2H), 3.22 (2H, t, J=6Hz), 7.11 (4H, s). |

-continued

| Desired Compound | |
|---|---|
| Chemical Structure and Chemical Name | Physicochemical Properties |
| Ref. Ex. 87<br>NC—⟨benzene⟩—(CH$_2$)$_3$—I<br>3-(4-Cyanophenyl)propyl iodide | MMR (CDCl$_3$)<br>δ: 1.86~2.42 (2H),<br>2.14~3.00 (2H), 3.16 (2H, t, J=6Hz), 7.13~7.71 (4H). |

REFERENCE EXAMPLE 89

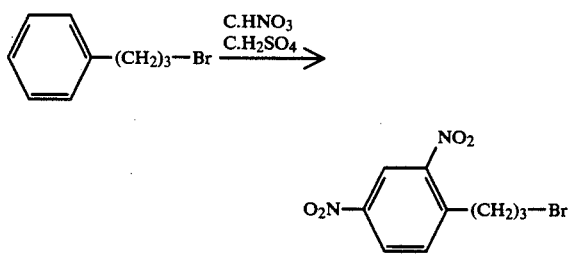

Phenylpropyl bromide (5.01 g) was added dropwise to a mixture of 10 ml of concentrated nitric acid (65%) and 10 ml of concentrated sulfuric acid with ice cooling over 5 minutes. The mixture was stirred at the same temperature for 1 hour and then allowed to stand at room temperature for 1 week. The reaction mixture was poured into water and extracted with ethyl acetate. The organic layer was washed with saturated aqueous solution of sodium chloride, dried over anhydrous magnesium sulfate and concentrated under reduced pressure. The residue was subjected to silica gel column chromatography (150 g). Elution with hexane-ethyl acetate (10:1) gave 5.50 g of 2,3-dinitrophenylpropyl bromide.

NMR (CDCl$_3$) δ: 2.08~2.51 (2H) 3.20 (2H, dd, J=7 Hz, J=9 Hz) 3.50 (2H, t, J=6 Hz) 7.68 (1H, d, J=9 Hz) 8.42 (1H, dd, J=3 Hz, J=9 Hz) 8.79 (1H, d, J=3 Hz)

REFERENCE EXAMPLE 90

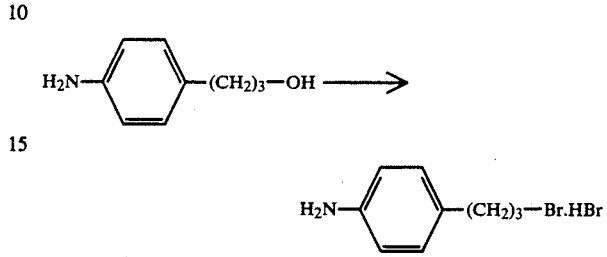

A solution of 0.51 g of 3-(4-aminophenyl)propanol in 5 ml of 47% aqueous hydrobromic acid was refluxed for 6 hours. The solvent was then distilled off under reduced pressure. Methanol and toluene were added, and the solvents were distilled off under reduced pressure, and this procedure was repeated, whereupon 1.04 g of 3-(4aminophenyl)propyl bromide hydrobromide was obtained.

NMR (DMSO-d$_6$+CDCl$_3$ (3:1)) δ: 1.91~2.47 (2H) 2.64~3.03 (2H) 3.43 (2H, t, J=6 Hz) 4.85 (3H, br s) 7.40 (4H, s)

REFERENCE EXAMPLES 91 TO 101

The following compounds were obtained in the same manner as in Reference Example 33 (2) and (3).

| Desired Product | |
|---|---|
| Chemical Structure and Chemical Name | Physicochemical Properties |
| Ref. Ex. 91<br>HN⟨piperazine⟩N—(CH$_2$)$_3$—⟨benzene⟩—OH<br>1-[3-(4-Hydroxyphenyl)propyl]piperazine | (1) NMR (DMSO-d$_6$)<br>δ: 1.92~1.84 (2H, m)<br>2.04~2.93 (12H, m)<br>4.50~5.20 (2H, br)<br>6.65 (1H, d, J=9Hz)<br>6.96 (1H, d, J=9Hz)<br>(2) MS: m/z 216 (M$^+$) |
| Ref. Ex. 92<br>HN⟨piperazine⟩N—(CH$_2$)$_3$—⟨benzene⟩—Cl<br>1-[3-(4-Chlorophenyl)propyl]piperazine | (1) NMR (CDCl$_3$)<br>δ: 1.50~2.05 (2H, m)<br>1.64 (1H, s)<br>2.06~3.01 (8H, m)<br>2.90 (4H, t, J=5Hz)<br>6.80~7.51 (4H, m)<br>(2) MS: m/z 238, 240 (M$^+$) |
| Ref. Ex. 93<br>HN⟨piperazine⟩H—(CH$_2$)$_3$—⟨benzene⟩—F<br>1-[3-(4-Fluorophenyl)propyl]piperazine | (1) NMR (CDCl$_3$)<br>δ: 1.56~2.04 (2H, m)<br>1.80 (1H, s)<br>2.19~2.78 (8H, m)<br>2.95 (4H, t, J=5Hz)<br>6.80~7.36 (4H, m)<br>(2) MS: m/z 223 (M$^+$+1) |
| Ref. Ex. 94<br>HN⟨piperazine⟩N—(CH$_2$)$_3$—⟨benzene with NO$_2$, NO$_2$⟩<br>1-[3-(2,4-Dinitrophenyl)propyl]piperazine | (1) NMR (CDCl$_3$)<br>δ: 1.64~2.13 (2H, m)<br>2.04 (1H, s)<br>2.22~2.53 (6H, m)<br>2.88 (4H, t, J=5Hz)<br>3.05 (2H, t, J=7Hz)<br>7.61 (1H, d, J=9Hz)<br>8.38 (1H, dd, J=3Hz, 9Hz)<br>8.64 (1H, dd, J=3Hz) |

-continued

Desired Product

| Chemical Structure and Chemical Name | Physicochemical Properties |
|---|---|
| Ref. Ex. 95<br>HN(piperazine)N—(CH$_2$)$_3$—C$_6$H$_4$—NH$_2$<br>1-[3-(4-Aminophenyl)propyl]piperazine | (1) NMR (CDCl$_3$)<br>δ: 1.56~1.93 (2H, m)<br>2.18~2.64 (11H, m)<br>2.89 (4H, t, J=5Hz)<br>6.60 (2H, d, J=9Hz)<br>6.95 (2H, d, J=9Hz)<br>(2) MS: m/z 219 (M$^+$) |
| Ref. Ex. 96<br>HN(piperazine)N—(CH$_2$)$_3$—C$_6$H$_4$(CH$_3$)<br>1-[3-(2-Methylphenyl)propyl]piperazine | (1) NMR (CDCl$_3$)<br>δ: 1.53~1.92 (2H, m)<br>2.28 (3H, s)<br>2.20~2.70 (8H, m)<br>2.88 (4H, t, J=5Hz)<br>7.09 (4H, s)<br>(2) MS: m/z 218 (M$^+$) |
| Ref. Ex. 97<br>HN(piperazine)N—(CH$_2$)$_5$CH$_3$<br>1-Hexylpiperazine | NHR (CDCl$_3$)<br>δ: 0.90 (3H, t)<br>1.12~1.72 (8H, m)<br>2.20~2.52 (6H, m)<br>2.82~3.00 (4H, m)<br>MS: m/z 170 (M$^+$) |
| Ref. Ex. 98<br>HN(piperazine)NCH(C$_6$H$_5$)$_2$<br>1-Diphenylmethylpiperazine | NMR (CDCl$_3$)<br>δ: 2.20~2.48 (4H, m)<br>2.76~3.04 (4H, m)<br>4.23 (1H, s)<br>7.04~7.52 (10H, m)<br>MS: m/z 252 (M$^+$) |
| Ref. Ex. 99<br>HN(piperazine)N—(CH$_2$)$_3$—C$_6$H$_4$—CH$_3$<br>1-[3-(4-Methylphenyl)propyl]piperazine | NMR (CDCl$_3$)<br>δ: 1.62~1.98 (2H, m),<br>1.76 (1H, s),<br>2.20~2.48 (6H, m),<br>2.35 (3H, s),<br>2.57 (2H, t, J=8Hz),<br>2.88 (4H, t, J=5Hz),<br>7.08 (4H, s).<br>MS: m/z 218 (M$^+$) |
| Ref. Ex. 100<br>HN(piperazine)N—(CH$_2$)$_3$—C$_6$H$_4$—OCH$_3$<br>1-[3-(4-Methylphenyl)propyl]piperazine | NMR (CDCl$_3$)<br>δ: 1.60~2.01 (2H, m),<br>1.92 (1H, s),<br>2.18~2.65 (8H, m),<br>2.87 (4H, t, J=5Hz),<br>3.77 (3H, s),<br>6.80 (1H, d, J=9Hz),<br>7.04 (1H, d, J=9Hz).<br>MS: m/z 234 (M$^+$) |
| Ref. Ex. 101<br>HN(piperazine)N—(CH$_2$)$_3$—C$_6$H$_3$(OCH$_3$)$_2$<br>1-[3-(3,4-Dimethoxyphenyl)propyl]piperazine | NMR (CDCl$_3$)<br>δ: 1.58~2.00 (2H, m),<br>1.86 (1H, s),<br>2.23~2.71 (8H, m),<br>2.91 (4H, t, J=5Hz),<br>3.84 (6H, s),<br>6.60~6.90 (3H, m).<br>MS: m/z 264 (M$^+$) |

REFERENCE EXAMPLE 102

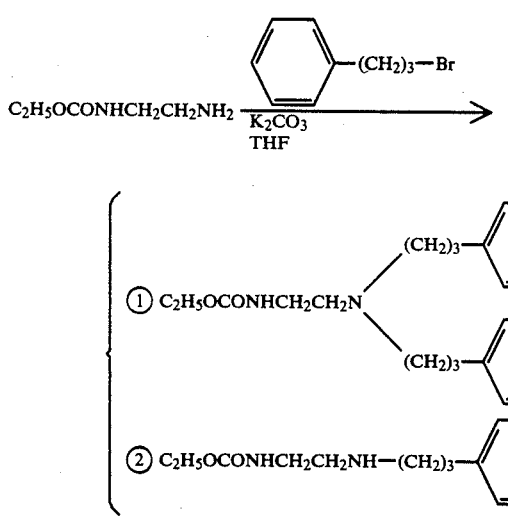

A solution of 0.88 g of carboethoxyethylenediamine, 1.33 g of 3-phenylpropyl bromide and 1.0 g of anhydrous potassium carbonate in 10 ml of tetrahydrofuran was heated overnight under reflux. The insoluble matter was filtered off, the filtrate was concentrated under reduced pressure, and the residue was subjected to alumina column chromatography (25 g). Elution with hexane-ethyl acetate (3:1 v/v) gave 0.54 g of N-carboethoxy-N,,N,-bis(3-phenylpropyl)ethylenediamine (1) and 0.60 g of N-carboethoxy-N'-(3-phenylpropyl)ethylenediamine (2).

NMR (CDCl$_3$) δ: 1.23 (3H, t, J=7 Hz), 1.56~2.02 (4H m) 2.20~2.87 (1OH, m), 3.00~3.45 (2H, m), 4.12 (2H, t, J=7 Hz), 5.13 (1H, br), 7.21 (10H, s)

NMR (CDCl$_3$) δ: 1.21 (1H, s), 1.25 (3H, t, J=7 Hz), 1.61~2.10 (2H, m), 2.45~2.93 (6H, m), 3.29 (2H, q, J=6 Hz), 4.15 (2H, t, J=7 Hz), 5.15 (1H, br), 7.21 (5H, s)

REFERENCE EXAMPLE 103

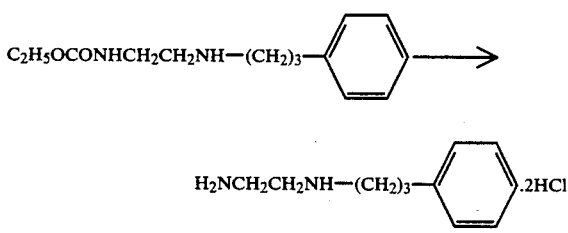

A solution of 580 mg of N-carboethoxy-N'-(3-phenylpropyl)ethylenediamine in 10 ml of concentrated hydrochloric acid was heated in a sealed tube at 120° C. overnight. The mixture was concentrated under reduced pressure. Toluene was added and the mixture was again concentrated. Two repetitions of this procedure gave 630 mg of N-(3-phenylpropyl)ethylenediamine dihydrochloride. This product was submitted to the next step without purification.

NMR (DMSO-d$_6$) δ: 1.76~2.20 (2H,m), 2,48~3.10 (2H, m), 3.22 (4H, s), 7.28 (5H,2), 8.0~10.0 (5H,br).

MS: m/z 179 (M$^+$+1)

REFERENCE EXAMPLE 104

The following compound was obtained in the same manner as in Reference Examples 102 and 103.

| Desired Product | |
|---|---|
| Chemical Structure and Chemical Name | Physicochemical Properties |
| 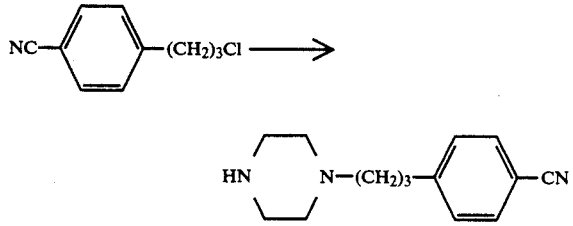 N,N-Di(3-phenylpropyl)ethylenediamine dihydrochloride | (1) NMR: (DMSO-d$_6$) δ: 1.76~2.24 (4H, m), 2.45~2.81 (4H, m), 2.92~3.60 (4H, m), 3.38 (4H, s), 7.26 (10H, s) (2) MS: m/z 297 (M$^+$+1) |

REFERENCE EXAMPLE 105

NC—⟨⟩—(CH$_2$)$_3$Cl ⟶

HN⟨N—(CH$_2$)$_3$—⟨⟩—CN

A solution of 250 mg of 3-(4-cyanophenyl)propyl iodide, 0.85 g of anhydrous piperazine and 0.5 g of potassium carbonated in 10 ml of tetrahydrofuran was refluxed for 2 hours. The reaction mixture was concentrated under reduced pressure and, after addition of saturated aqueous solution of sodium chloride, the residue was extracted with ethyl acetate. The organic layer was washed with saturated aqueous solution of sodium chloride, dried over anhydrous sodium sulfate and concentrated under reduced pressure to give 140 mg of 1-[3-(4-cyanophenyl)propyl]piperazine.

NMR (CDCl$_3$) δ: 1.60~2.10 (2H, m), 2.04 (1H, s), 2.19~2.54 (6H, m), 2.69 (2H, t, J=8 Hz), 2.89 (4H, t, J=5 Hz), 7.27 (2H, d, J=9 Hz), 7.56 (2H, d, J=9 Hz)

MS: m/z 229 (M$^+$)

REFERENCE EXAMPLE 106

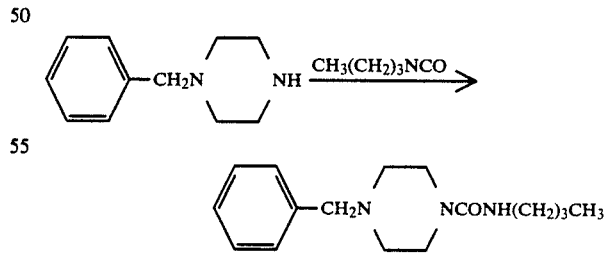

A solution of 1.0 g of n-butyl isocyanate in 5 ml of tetrahydrofuran was added to a solution of 1.76 g of 1-benzylpiperazine in 20 ml of tetrahydrofuran with ice cooling. The mixture was stirred at room temperature for 2 hours and, then, concentrated under reduced pressure to give 2.8 g of crude 1-benzyl-4-butylaminocarbonylpiperazine. The intermediate was submitted to the next step without purification.

NMR (CDCl₃) δ: 0.90 (3H, t), 1.1~1.7 (4H, m), 2.2~2.6 (4H, m), 3.0~3.6 (6H, m), 3.50 (2H, s), 4.5 (1H, br s), 7.0~7.5 (5H, m)

REFERENCE EXAMPLE 107

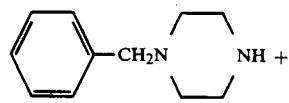

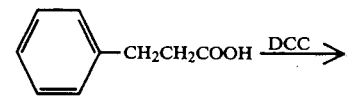

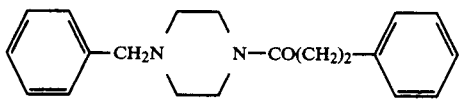

Dicyclohexylcarbodiimide (4.5 g) was added to a mixture of 3.52 g of 1-benzylpiperazine, 3.5 g of 3-phenylpropionic acid and 20 ml of tetrahydrofuran, and the mixture was stirred overnight at room temperature. The resultant dicyclohexylurea was filtered off, and the mother liquor was concentrated under reduced pressure. Ethyl acetate (100 ml) and 50 ml of water were added to the residue, and the mixture was made alkaline with potassium carbonate and then allowed to undergo phase separation. The ethyl acetate layer was washed in sequence with water and saturated aqueous solution of sodium chloride, dried over anhydrous sodium sulfate and concentrated under reduced pressure to give 6 g of 1-benzyl-4-(3-phenylpropionyl)piperazine.

NMR (CDCl₃) δ: 2.1~2.5 (4H, m), 2.4~3.2 (4H, m), 3.3~3.8 (4H, m), 3.45 (2H, s), 7.1~7.4 (10H, m)

REFERENCE EXAMPLE 108

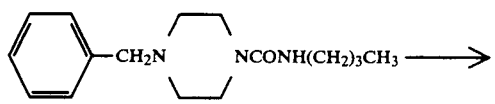

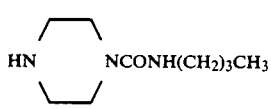

10% Palladium-on-carbon (250 mg) was added to a solution of 2.8 g of 1-benzyl-4-butylaminocarbonylpiperazine in 15 ml of ethanol, and catalytic reduction was carried out until cessation of hydrogen absorption. The catalyst was then filtered off, and the filtrate was concentrated under reduced pressure to give 2.2 g of 1-butylaminocarbonylpiperazine. This product was submitted to the next step without purification.

NMR (CDCl₃) δ: 0.92 (3H, t), 1.1~1.7 (4H, m), 2.7~3.0 (4H, m), 3.0~3.5 (6H, m)

REFERENCE EXAMPLE 109

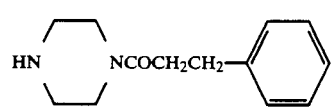

1-(3-Phenylpropionyl)piperazine was obtained in the same manner as in Reference Example 108 using 1-benzyl-4-(3-phenylpropionyl)piperazine as the starting material MS: m/z 218 (M+)

REFERENCE EXAMPLE 110

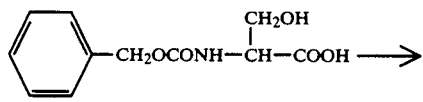

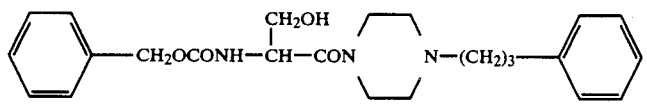

Dicyclohexylcarbodiimide (1.58 g) was added to an ice-cooled solution of 2.0 g of N-carbobenzyloxyserine, 1.57 g of 1-(3-phenylpropyl)piperazine and 1.04 g of 1-hydroxybenzotiazole in 30 ml of N,N-dimethylformamide. The mixture was stirred at room temperature for 24 hours, then diluted with ethyl acetate, washed in sequence with two portions of 4% aqueous sodium hydrogen carbonate, one portion of water and one portion of saturated aqueous solution of sodium chloride, dried over anhydrous sodium sulfate and concentrated under reduced pressure. The residue was purified by silica gel column chromatography to give 2.39 g of 1-[2-(benzyloxycarbonylamino)-3-hydroxypropionyl]-4-(3-phenylpropyl)piperazine. Melting point 95°–97° C.

| Elemental analysis (for C₂₄H₃₁N₃O₄): | | | |
|---|---|---|---|
| | C (%) | H (%) | N (%) |
| Calculated: | 67.74 | 7.34 | 9.87 |
| Found: | 67.74 | 7.26 | 9.88 |

REFERENCE EXAMPLE 111

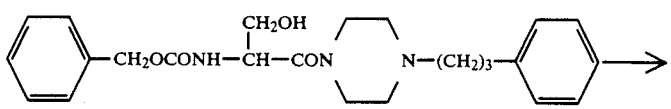

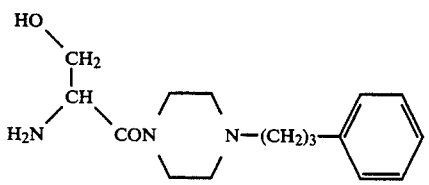

10% Palladium-on-carbon (100 mg) was added to a solution of 1.12 g of 1-[2-(benzyloxycarbonylamino)-3-hydroxypropionyl]-4-(3-phenylpropyl)piperazine in 30 ml of ethanol, and the mixture was stirred under a hydrogen gas stream until cessation of hydrogen absorption. The catalyst was then filtered off, and the filtrate was concentrated under reduced pressure to give 800 mg of 1-(2-amino-3-hydroxypropionyl)-4-(3-phenylpropyl)piperazine.

NMR (CDCl$_3$) δ: 1.7~2.0 (2H), 1.8~2.6 (3H, exchange with D$_2$O) 2.3~2.8 (8H), 3.4~3.8 (7H), 7.1~7.3 (5H) MS m/z 291 (M+)

REFERENCE EXAMPLE 112

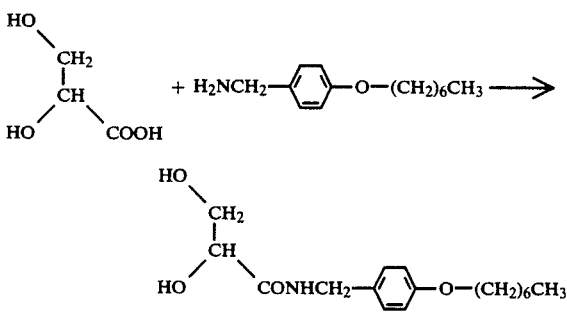

Dicyclohexylcarbodiimide (160 mg) was added to a solution of 200 mg of p-heptyloxybenzylamine, 150 mg of glyceric acid (65% aqueous solution) and 110 mg of 1-hydroxybenzotriazole in 2 ml of N,N-dimethylformamide. The reaction mixture was stirred at room temperature for 16 hours, then diluted with ethyl acetate, washed in sequence with saturated aqueous solution of sodium hydrogen carbonate, water and saturated aqueous solution of sodium chloride, dried over anhydrous magnesium sulfate, and concentrated under reduced pressure. The residue was purified by preparative silica gel thin layer chromatography to give 80 mg of N-(p-heptyloxybenzyl)glyceramide.

NMR (CDCl$_3$) δ: 0.90 (3H, br t), 1.2~1.5 (8H), 1.7~1.9 (2H), 3.0 (1H, exchange with D$_2$O), 3.8~4.0 (2H), 3.9 (1H, exchange with D$_2$O), 4.1~4.3 (1H), 4.38 (2H, d, J=6 Hz), 6.88 (2H, d, J=8 Hz), 7.18 (2H, d, J=8 Hz), 7.0~7.3 (1H, exchange with D$_2$O) MS: m/z 309 (M+)

REFERENCE EXAMPLE 113

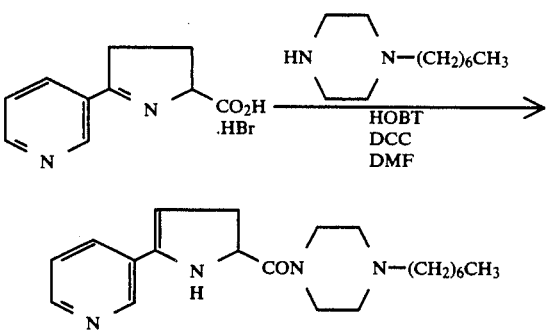

A mixture of 1.15 g of 2-(3-pyridyl)-1-pyrroline-4-carboxylic acid monohydrobromide, 770 mg of 1-heptylpiperazine, 860 mg of dicyclohexylcarbodiimide and 560 mg of 1-hydroxybenzotriazole in 15 ml of N,N-dimethylformamide was stirred at room temperature for 3 days. After dilution of the reaction mixture with ethyl acetate, the insoluble matter was filtered off, the filtrate was concentrated under reduced pressure and, after addition of 0.5N aqueous sodium hydroxide, the residue was extracted with ethyl acetate. The organic layer was extracted with 1N hydrochloric acid. The aqueous layer was adjusted to pH 10 by addition of potassium carbonate and extracted again with ethyl acetate. The organic layer was washed with saturated aqueous solution of sodium chloride, dried over anhydrous sodium sulfate and concentrated under reduced pressure. The residue was subjected to silica gel column chromatography (15 g). Elution with ethyl acetate gave 1.01 g of 1-heptyl-4-[2-(3-pyridyl)-2-pyrrolin-5-ylcarbonyl]piperazine.

NMR (CDCl$_3$) δ: 0.91 (3H, t, J=6 Hz), 1.12~1.72 (10H, m), 1.92~2.93 (9H, m), 2.95~3.26 (2H, m), 3.37~4.30 (3H, m), 5.04~5.30 (1H, m), 7.26~7.46 (1H, ddd, J=1 Hz, J=5 Hz, J=8 Hz), 8.18 (1H, dt, J=2 Hz, J=8 Hz), 8.68 (1H, dd, J=2 Hz, J=5 Hz), 9.05 (1H, dd, J=1 Hz, J=2 Hz)

MS: m/z 356 (M+)

REFERENCE EXAMPLE 114

The following compounds was obtained in the same manner as in Reference Example 113.

| Chemical Structure and Chemical Name | Desired Product Physicochemical Properties |
|---|---|
| 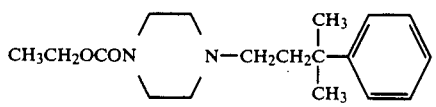<br>1-(3-Phenylpropyl)-4-[2-(3-pyridyl)-2-pyrrolin-5-ylcarbonyl]piperazine | (1) NMR (CDCl$_3$)<br>δ: 1.67~2.08 (2H, m),<br>2.08~2.93 (9H, m),<br>2.93~3.28 (2H, m),<br>3.30~4.32 (3H, m),<br>5.00~5.33 (1H, m),<br>(2) 7.05~7.52 (6H, m),<br>8.19 (1H, dt, J=2Hz, J=8Hz),<br>8.69 (1H, dd, J=2Hz, J=5Hz),<br>9.05 (1H, dd, J=2Hz, J=2Hz)<br>MS: m/z 376 (M$^+$) |

REFERENCE EXAMPLE 115

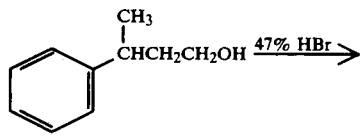

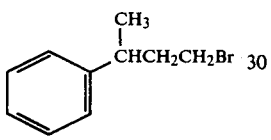

1-Bromo-3-phenylbutane was obtained in the same manner as in Reference Example 80.

NMR (CDCl$_3$) δ: 1.29 (3H, d, J=7 Hz), 2.11 (2H, q, J=7 Hz), 2.64~3.50 (3H, m), 7.24 (5H, s)

REFERENCE EXAMPLE 116

The following compound was obtained in the same manner as in Reference Example 102.

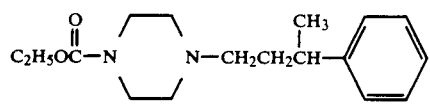

Ethyl 4-(3-phenylbutyl)-piperazine-1-carboxylate
NMR (CDCl$_3$) δ: 1.11~1.50 (6H, m), 1.56~3.05 (7H, m), 3.50 (4H, t, J=6 Hz), 4.19 (2H, q, J=7 Hz), 7.24 (5H s)

REFERENCE EXAMPLE 117

The following compound was obtained in the same manner as in Reference Example 103.

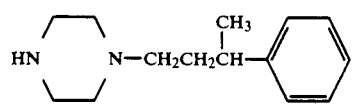

1-(3-Phenylbutyl)piperazine

NMR (CDCl$_3$) δ: 1.24 (3H, d, J=7 Hz), 1.76 (2H, q, J=7 Hz), 1.93 (1H, s), 2.10~2.46 (6H, m), 2.51~2.97 (5H, m), 7.00~7.38 (5H, m)
MS (m/z): 218 (M$^+$)

REFERENCE EXAMPLE 118

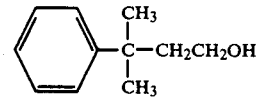

3-Methyl-3-phenylbutanoic acid (0.90 9) was dropwise added to a suspension of lithium alminum hydride (0.2 g) in 15 ml of tetrahydrofuran at room temperature and the mixture was stirred for 30 minutes. To the reaction mixture was added a saturated aqueous solution of sodium bicarbonate under ice cooling, and the reaction solution was extracted with ethyl acetate. The organic layer was washed with a saturated aqueous solution of sodium chloride,, dried over anhydrous magnesium sulfate and concentrated under reduced pressure. The resultant residue was subjected to silica gel column chromatography (20 g). Elution with a hexane ethyl acetate (5:1) mixture gave 0.75 g of 3-metyl-3-phenylbutanol.

NMR (CDCl$_3$) δ: 1.10 (1H,s), 1.34[6H,s) 1.92(2H,t, J=7 Hz), 4.48[2H,t, J=7 Hz) 7.03-7.52(5H,m)

REFERENCE EXAMPLE 119

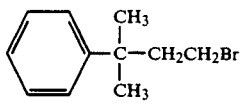

3-Metyl-3-phenylbutanol (0.82 g) was refluxed in 47% hydrobromic acid (5 ml) under heating for 7 hours. To the reaction solution was added water and the solution was extracted with ether. After washing with a saturated aqueous solution of sodium chloride, the ether layer was dried over anhydrous magnesium sulfate, and the residue was then subjected to silica gel column chromatography. Elution with a hexane - ethyl acetate 10:1) mixture gave 1.02 of 1-bromo-3-methyl-3-phenylbutane.

NMR (CDCl$_3$) δ: 1.33 (6H,s), 2.04-2.33(2H,m) 2.95-3.21(2H,m), 7.02.-7.43(5H,m)

REFERENCE EXAMPLE 120

A solution of 1-bromo-3-methyl-3-phenylbutane (0.73 g), ethyl piperazinecarboxylate (0.51 g) and anhydrous potassium carbonate (0.50 g) in tetrahydrofuran (5 ml) was refluxed under heating for 36 hours. To the reaction solution was added water and the solution was extracted with ethyl acetate. After washing with a saturated aqueous solution of sodium chloride, the ethyl acetate layer was dried over anhydrous sodium sulfate and concentrated under reduced pressure. The resultant residue was subjected to silica gel column chromatography (15 g) and elution with a hexane-ethyl acetate (2:1) mixture gave 0.80 g of ethyl 4-(3-methyl-3-phenyl-butyl)piperazine-1-carboxylate.

NMR (CDCl$_3$) δ: 1.42 (3H,t, J=7 Hz), 1.32(6H,s) 1.60–2.15(2H,m), 2.15–2.46(6H,m) 3.43(4H,t, J=6 Hz) 4.13(2H,q, J=7 Hz), 7.03–7.50(5H, m)

REFERENCE EXAMPLE 121

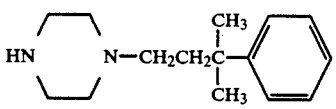

A solution of ethyl 4-(3-methyl-3-phenylbutyl)piperazine-1-carboxylate (1.17 g) in conc. hydrochloric acid (15 ml) was heated in a sealed tube for 12 hours at 120° C. The solution was concentrated and to the resultant residue was added 10% sodium hydroxide to make basic. The mixture thus obtained was saturated with sodium chloride and extracted with ethyl acetate. The ethyl acetate layer was washed with a saturated aqueous solution of sodium chloride, dried over anhydrous sodium sulfate and concentrated to give 0.85 g of 1-(3-methyl-3-phenylbutyl)piperazine.

NMR (CDCl$_3$) δ: 1.31 (6H,s), 1.60(1H,s) 1.65–1.96(2H,m), 1.96–2.20(2H,m) 2.30(4H,t, J=6 Hz), 2.85(4H,t, J=6 Hz) 7.03–7.46(5H,m)

MS (m/z) : 232 (M+)

REFERENCE EXAMPLE 122

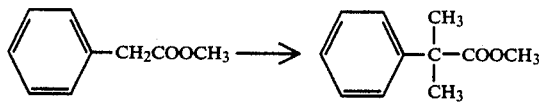

A solution of methyl phenylacetate (7.50 g) and 60% sodium hydride (2.1 g) in N,N-dimethylformamide (70 ml) was stirred for one hour at room temperature. To the resultant mixture was dropwise added methyl iodide (10 g) under ice cooling and stirred for 3 hours at 50° C. After cooling, the resultant crystals were filtered off. To the filtrate was added 60% sodium hydride (2.1 g) and then the resultant mixture was treated as mentioned above Again, to the resultant filtrate was added 60% sodium hydride (0.4 g) and the mixture was heated for one hour at 50° C. To the mixture was added methyl iodide (2.0 g) under ice cooling and stirred for 15 hours. After adding dropwise water to the reaction solution under ice cooling, the solution was concentrated under reduced pressure. To the residue was added water and the mixture was extracted with ether. After washing twice with water, the ether layer was washed with a saturated aqueous solution of sodium chloride, dried over anhydrous magnesium sulfate and concentrated under reduced pressure. The residue thus obtained was subjected to silica gel column chromatography (200 g).

Elution with a hexane-ethyl acetate (10:1) mixture gave 8.04 g of methyl 2-methyl-2-phenylpropionate.

NMR (CDCl$_3$) : 1.60 (6H,s), 3.68(3H,s) 7.35(5H,br.s)

REFERENCE EXAMPLE 123

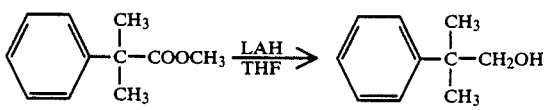

To a suspension of lithium aluminum hydride (1.71 g) in tetrahydrofuran (50 ml) was dropwise added a solution of methyl 2-methyl-2-phenylpropionate (7.97 g) in tetrahydrofuran (20 ml) under ice cooling and the mixture was stirred at room temperature for 30 minutes. To the reaction solution was dropwise added water and then a saturated aqueous solution of sodium bicarbonate, and the solution was extracted with ether. The ehter layer was washed with a saturated aqueous solution of sodium chloride, dried over anhydrous magnesium sulfate and concentrated under reduced pressure. The resultant residue was subjected to silica gel (100 g) column chromatography. Elution with a mixture solution of hexane-ethyl acetate (2:1) gave 6.32 9 of 2-methyl-2-phenylpropanol.

NMR (CDCl$_3$) δ: 1.32 (6H,s), 1.72(1H,s) 3.61(2H,s,), 7.10–7.61(5H,m)

REFERENCE EXAMPLE 124

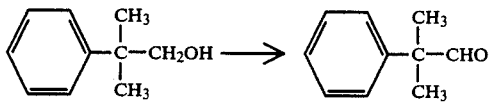

To a solution of oxalylchloride (4.1 ml) in dichloromethane (100 ml) was added dropwise a solution of dimethylsufoxide (7.14 g) in dichloromethane (10 ml) at −60° C., and the mixture was stirred for 10 minutes. To the resultant mixture was added a solution of 2-methyl-2-phenylpropanol (6.16 g) in dichloromethane (15 ml) at the same temperature. After stirring for one hour, to the mixture was added triethylamine (20.7 g). The mixture was further stirred for 30 minutes and allowed to room temperature. After adding water, the mixture was extracted with dichloromethane. The extract was washed with a saturated aqueous solution of sodium chloride, dried over anhydrous magnesium sulfate and concentrated under reduced pressure. The resultant residue was subjected to silica gel (40 g) column chromatography and elution with 2% ethyl acetate hexane solution gave 4.93 g of 2-methyl-2-phenylpropanal.

NMR (CDCl$_3$) δ: 1.46 (6H,s), 7.32(5H,s) 9.51(1H,s)

REFERENCE EXAMPLE 125

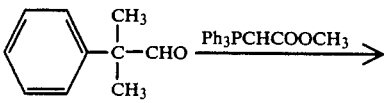

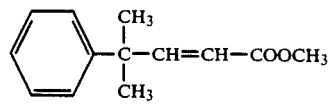

A solution of 2-methyl-2-phenylpropanal (0.30 g) and methyl triphenylphosphylideneacetate (0.74 g) in tetrahydrofuran (7 ml) was refluxed under heating for 6 hours and the reaction solution was concentrated under reduced pressure. The resultant residue was subjected to silica gel (25 g) column chromatography and elution with a hexane-ethyl acetate (2:1) mixture gave 0.37 g of methyl 4-methyl-4-phenyl-2-pentenoate.

NMR (CDCl$_3$) δ: 1.46 (6H,s), 3.75(3H,s) 5.82(1H,d, J=17 Hz) 7.19(1H,d, J=17 Hz) 7.30(5H,s)

REFERENCE EXAMPLE 126

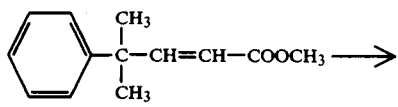

To a solution of methyl 4-methyl-4-phenyl-2-pentenoate (0.3 g) in absolute methanol (10 ml) was added metallic magnesium ribbons (0.36 g) and the mixture was stirred at room temperature for 2 hours. To the reaction mixture was added 10% hydrochloric acid and then the mixture was extracted with ethyl acetate. The extract was washed with a saturated aqueous solution of sodium chloride, dried over anhydrous magnesium sulfate and concentrated under reduced pressure to yield 0.30 g of methyl 4-methyl-4-phenylpentanoate.

NMR (CDCl$_3$) δ: 1.35 (6H,s), 2.05(4H s) 3.63(3H,s), 7.01–7.52(5H,m)

REFERENCE EXAMPLE 127

The following compound was obtained in the same manner as in Reference Example 118.

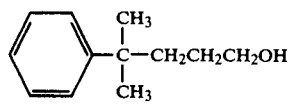

4-Methyl-4-phenyl-pentanol

NMR (CDCl$_3$) δ: 1.32 (6H,s), 1.10–1.92(4H,m) 1.56(1H,s , 3.51(2H,t, J=7 Hz) 7.05–7.50(5H,m)

REFERENCE EXAMPLE 128

The following compound was obtained in the same manner as in Reference Example 119.

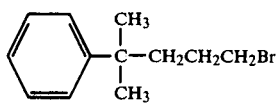

1-Bromo-4-methyl-4-phenylpentane

NMR (CDCl$_3$) δ: 1.32 (6H,s), 1.40–1.91(4H,m) 3.29(2H,t, J=6 Hz), 7.11–7.48(5H,m)

REFERENCE EXAMPLE 129

The following compound was obtained in the same manner as in Reference Example 120.

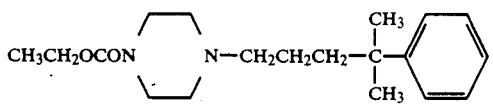

Ethyl 1-(4-methyl-4-phenylpentyl)-piperazine-4-carboxylate

NMR (CDCl$_3$) δ: 1.25 (3H,t, J=7 Hz), 1.32(6H s) 1.08–1.93(4H,m), 2.08–2.53(6H,m) 3.48(4H,t, J=6 Hz), 4.29(2H,q, J=7 Hz) 7.09–7.52(5H,m)

REFERENCE EXAMPLE 130

The following compound was obtained in the same manner as in Reference Example 120.

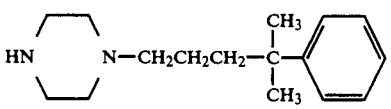

1-(4-Methyl-4-phenylpentyl)piperazine

NMR (CDCl$_3$) δ: 1.07–1.45(2H,m), 1.32(6H,s) 1.45–1.77(2H,m , 1.70(1H,s) 2.08–2.45(6H,m), 2.87(4H,t, J=6 Hz) 7.01–7.43(5H,m)

MS (m/z) : 246 (M+)

EXAMPLE 1

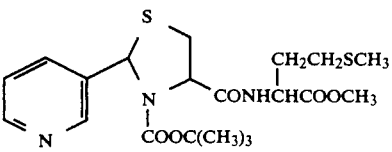

To a solution of 600 mg of N-tert-butoxycarbonyl-2-(3-pyridyl)thiazolidine-4-carboxylic acid in 10 ml of tetrahydrofuran, there were added, at 4° C. or below, 390 mg of L-methionine methyl ester hydrochloride, 390 mg of 1-hydroxybenzotriazole, 190 mg of N-methylmorpholine and 440 mg of dicyclohexylcarbodiimide, in that order. The mixture was stirred at 4° C. or below for 1 hour and then at room temperature for 1 hour. The resultant precipitate was filtered off, the filtrate was concentrated under reduced pressure, 50 ml of ethyl acetate was added, the insoluble matter was filtered off, and the filtrate was washed in sequence with 0.5M aqueous citric acid, water, 5% aqueous sodium hydrogen carbonate and water, dried over anhydrous sodium sulfate and concentrated under reduced pressure to give 440 mg of [N-tert-butoxycarbonyl-2-(3-pyridyl)thiazolidine-4-carbonyl]-L-methionine methyl ester as an oil.

NMR (CDCl$_3$) δ: 1.36 (9H, s), 1.8 2.2 (3H, m), 2.2~2.6 (2H, m), 3.26 (1H, dd), 3.6 (1H, dd), 3.78 (3H, s), 4.6~4.8 (1H, m), 4.86 (1H, dd), 6.02 (1H, s), 7.3 (1H, dd), 7.8~8.0 (1H, m), 8.52 (1H, dd), 8.65 (1H, dd)

EXAMPLE 2

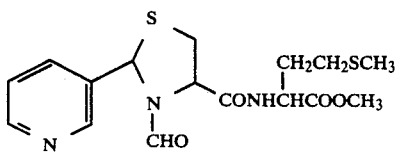

To a solution of 1.3 g of N-formyl-2-(3-pyridyl)-thiazolidine-4-carboxylic acid in 50 ml of tetrahydrofuran plus 10 ml of N,N-dimethylformamide, there were added, at 4° C. or below, 1.16 g of L-methionine methyl ester hydrochloride, 1.17 g of 1-hydroxybenzotriazole, 560 mg of N-methylmorpholine and 1.32 g of dicyclohexylcarbodiimide, in that order. The mixture was stirred at 4° C. or below for 1 hour and then at room temperature for 1 hour. The reaction mixture was then treated in the same manner as in Example 1. Purification by silica gel column chromatography [eluent: chloroform-methanol (9:1)] gave 820 g of [N-formyl-2-(3-pyridyl)thiazolidine-4-carbonyl]-L-methionine methyl ester as an oil.

| Elemental analysis (for $C_{16}H_{21}N_3O_4S_2$) | |
|---|---|
| | N (%) |
| Calculated: | 10.96 |
| Found: | 10.62 |

NMR (CDCl$_3$) δ: 2.08 (3H, s), 1.8~2.6 (4H, m), 3.2~3.5 (1H, m), 3.8 (3H, s), 3.5~3.8 (1H, m), 4.5~4.8 (1H, m), 4.8~5.1 (1H, m), 6.1 and 6.41 (s, respectively 1H), 7.2~7.5 (1H, m), 7.8~8.0 (1H, m), 8.34 (1H, s), 8.4~8.9 (2H, m)

EXAMPLE 3

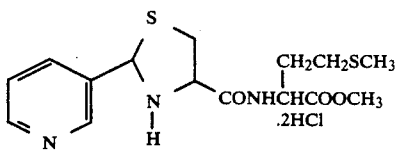

Trifluoroacetic acid (5 ml) was added to 430 mg of [N-tert-butoxycarbonyl-2-(3-pyridyl)thiazolidine-4-carbonyl]-L-methionine methyl ester with ice cooling, and the mixture was stirred at room temperature for 2 hours. The reaction mixture was concentrated under reduced pressure. Ethyl acetate was added to the residue, and the mixture was again concentrated under reduced pressure. The residue was dissolved in 5 ml of ethyl acetate, and 1 ml or 4N hydrochloric acid in dioxane was added with ice cooling. The resultant crystalline precipitate was collected by filtration, washed with ethyl acetate and dried to give 300 mg of [2-(3-pyridyl)thiazolidine-4-carbonyl]-L-methionine methyl ester dihydrochloride. Melting point 110° C.

| Elemental analysis (for $C_{15}H_{25}N_3O_4S_2Cl_2$): | | | |
|---|---|---|---|
| | C (%) | H (%) | N (%) |
| Calculated: | 40.36 | 5.64 | 9.41 |
| Found: | 40.00 | 5.35 | 9.24 |

EXAMPLE 4

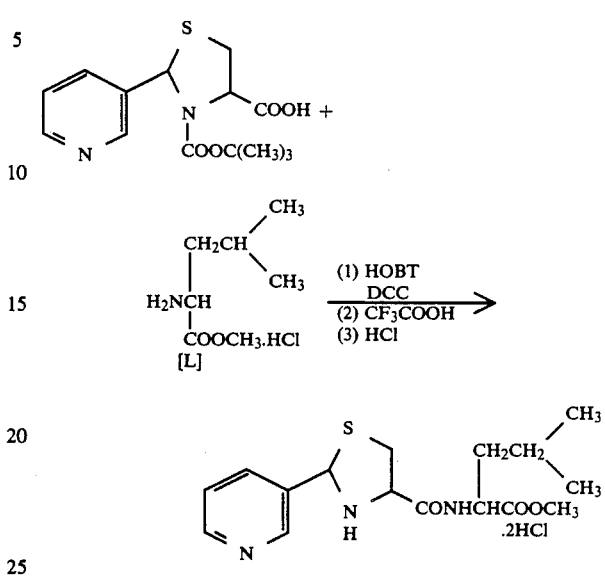

To a solution of 600 mg of N-tert-butoxycarbonyl-2-(3-pyridyl)thiazolidine-4 carboxylic acid in 5 ml of tetrahydrofuran, there were added, at 4° C. or below, 350 mg of L-leucine methyl ester hydrochloride, 390 mg of 1-hydroxybenzotriazole, 190 mg of N-methylmorpholine and 440 mg of dicyclohexylcarbodiimide, in that order, and the mixture was stirred overnight in an icehouse. The resultant precipitate was filtered off, the filtrate was concentrated under reduced pressure, 50 ml of ethyl acetate was added, the insoluble matter was filtered off, and the filtrate was washed in sequence with 0.5M aqueous citric acid, water, saturated aqueous solution of sodium hydrogen carbonate and water, dried over anhydrous sodium sulfate and concentrated under reduced pressure to give 830 mg of oily [N-tert-butoxycarbonyl-2-(3-pyridyl)thiazolidine-4-carbonyl]-L-leucine methyl ester. Trifluoroacetic acid (3 ml) was added to 800 mg of the thus obtained compound with ice cooling, and the mixture was stirred at room temperature for 3 hours. The reaction mixture was concentrated under reduced pressure, 10 ml of ethyl acetate was added and the solution was again concentrated under reduced pressure. The residue was dissolved in 10 ml of ethyl acetate, 3 ml of 2.2N hydrogen chloride solution in dioxane was added with ice colling, and the mixture was allowed to stand overnight in an icehouse. The resultant crystals were collected by filtration, washed with ethyl acetate and dried to give 510 mg of [2-(3-pyridyl)thiazolidine-4-carbonyl]-L-leucine methyl ester dihydrochloride. Melting point 97°-100° C.

| Elemental analysis (for $C_{16}H_{23}N_3O_3S.2HCl.4/5 H_2O$) | | | | |
|---|---|---|---|---|
| | C (%) | H (%) | N (%) | S (%) |
| Calculated: | 45.24 | 6.31 | 9.89 | 7.55 |
| Found: | 45.21 | 5.98 | 9.85 | 7.55 |

EXAMPLE 5

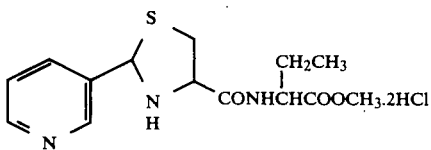

N-tert-Butoxycarbonyl-2-(3-pyridyl)thiazolidine-4-carboxylic acid and D,L-α-aminobutyric acid methyl ester hydrochloride were used as the starting materials and treated in the same manner as in Example 4 to give 2-[2-(3-pyridyl)thiazolidin-4-yl]carbonylaminobutyric acid methyl ester dihydrochloride. Melting point 98°–100° C.

| Elemental analysis (for $C_{14}H_{19}N_3O_3S.2HCl.H_2O$) | |
|---|---|
| | C (%) |
| Calculated: | 42.00 |
| Found: | 42.08 |

EXAMPLE 6

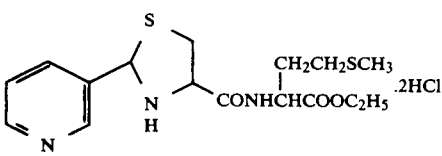

N-tert-Butoxycarbonyl-2-(3-pyridyl)thiazolidine-4-carboxylic acid and D-methionine ethyl ester hydrochloride were used as the starting materials and treated in the same manner as in Example 4 to give [2-(3-pyridyl)thiazolidine-4-carbonyl]-D-methionine ethyl ester dihydrochloride. Melting point 94°–96° C.

| Elemental analysis (for $C_{16}H_{23}N_3O_3S_2.2HCl.4/5H_2O$) | | | | |
|---|---|---|---|---|
| | C (%) | H (%) | N (%) | S (%) | Cl (%) |
| Calculated: | 42.07 | 5.87 | 9.20 | 14.04 | 15.52 |
| Found: | 42.17 | 5.89 | 8.89 | 13.77 | 15.68 |

EXAMPLE 7

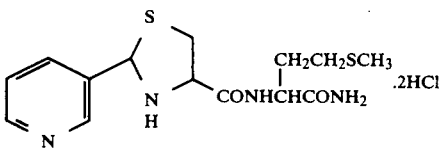

N-tert-Butoxycarbonyl-2-(3-pyridyl)thiazolidine-4-carboxylic acid and L-methioninamide hydrochloride were used as the starting materials and treated in the same manner as in Example 4 to give [2-(3-pyridyl)-thiazolidine-4-carbonyl]-L-methioninamide dihydrochloride. Melting point 131° C.

MS: m/z 340 (M+-2HCl)

EXAMPLE 8

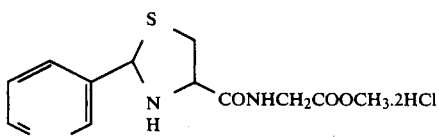

N-tert-Butoxycarbonyl-2-(3-pyridyl)thiazolidine-4-carboxylic acid and glycine methyl ester hydrochloride were used as the starting materials and treated in the same manner as in Example 4 to give [2-(3-pyridyl)-thiazolidine-4-carbonyl]gylcine methyl ester dihydrochloride. Melting point 116°–118° C.

| Elemental analysis (for $C_{12}H_{15}N_3O_3S.2HCl.H_2O$) | | | |
|---|---|---|---|
| | C (%) | H (%) | N (%) |
| Calculated: | 38.72 | 5.14 | 11.29 |
| Found: | 38.99 | 4.62 | 10.99 |

EXAMPLE 9

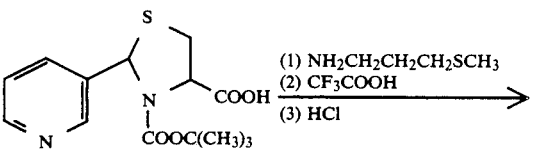

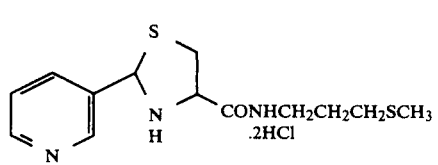

To a solution of 600 mg of N-tert-butoxycarbonyl-2-(3-pyridyl)thiazolidine-4-carboxylic acid in 10 ml of tetrahydrofuran, there were added, at 4° C. or below, 200 mg of 3-methylthiopropylamine, 390 mg of 1-hydroxybenzotriazole and 440 mg of dicyclohexylcarbodiimide, in that order, and the mixture was stirred at room temperature for 3 hours. The resultant precipitate was filtered off, the filtrate was concentrated under reduced pressure, and the residue was dissolved in 50 ml or ethyl acetate. The ethyl acetate solution was washed in sequence with 0.5M aqueous citric acid, water, saturated aqueous solution of sodium carbonate and water, dried over anhydrous sodium sulfate and concentrated under reduced pressure to give 250 mg of N-(3-methylthiopropyl)-3-tert-butoxycarbonyl-2-(3-pyridyl)-thiazolidine-4-carboxamide. Trifluoroacetic acid (2 ml) was added to 250 mg of the thus-obtained compound with ice cooling, and the mixture was treated in the same manner as in Example 4 to give 130 mg of N-(3-methylthiopropyl)-2-(3-pyridyl)thiazolidine-4-carboxamide dihydrochloride as an oil.

NMR (DMSO-$d_6$) δ: 1.6~1.9 (2H), 2.08 (3H), 2.4 2.6 (2H), 3.0~3.7 (4H), 4,05~4.50 (1H), 5.9~6.1 (1H), 7.4~9.2(4H)

EXAMPLE 10

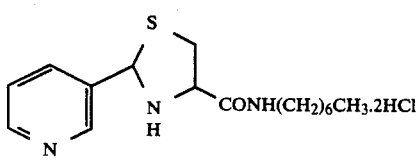

N-tert-Butoxycarbonyl-2-(3-pyridyl)thiazolidine-4-carboxylic acid and n-heptylamine were used as the starting materials and treated in the same manner as in Example 9 to give N-n-heptyl-2-(3-pyridyl)thiazolidine-4-carboxamide dihydrochloride.

NMR (DMSO-$d_6$) δ: 0.6~1.1 (3H), 1.1~1.8 (10H), 2.9~3.9 (4H), 4.4~4.7 (1H), 6.20 (1H), 8.0~8.3 (1H), 8.6~9.3 (3H)

EXAMPLE 11

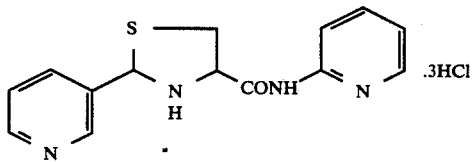

N-tert-Butoxycarbonyl-2-(3-pyridyl)thiazolidine-4-carboxylic acid and 2-aminopyridine were used and treated in the same manner as in Example 9 to give N-(2-pyridyl)-2-(3-pyridyl)thiazolidine-4-carboxamide trihydrochloride. Melting point 145° C.

| Elemental analysis (for $C_{14}H_{17}N_4OSCl_3$) | | | |
|---|---|---|---|
| | C (%) | H (%) | S (%) |
| Calculated: | 42.49 | 4.33 | 8.10 |
| Found: | 42.83 | 4.58 | 8.03 |

EXAMPLE 12

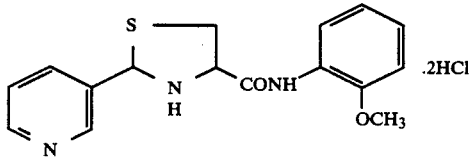

N-tert-Butoxycarbonyl-2-(3-pyridyl)thiazolidine-4-carboxylic acid and o-anisidine were used and treated in the same manner as in Example 9 to give N-(2-methoxyphenyl)-2-(3-pyridine)thiazolidine-4-carboxamide dihydrochloride. Yield, 68%. Melting point 129° C.

| Elemental analysis (for $C_{16}H_{19}N_3O_2SCl_2$) | | | |
|---|---|---|---|
| | C (%) | H (%) | N (%) |
| Calculated: | 49.49 | 4.93 | 10.82 |
| Found: | 49.29 | 5.18 | 10.38 |

EXAMPLE 13

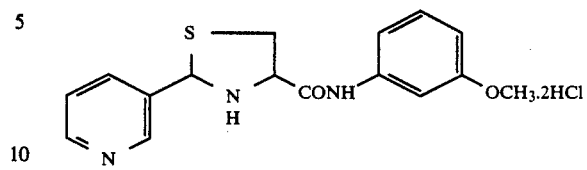

A mixture of 630 mg of 2-(3-pyridyl)thiazolidine-4-carboxylic acid, 350 mg of m-anisidine, 650 mg of dicyclohexylcarbodiimide and 430 mg of 1-hydroxybenzotriazole in 8 ml of dimethylformamide was stirred overnight at room temperature. The reaction mixture was diluted with 50 ml of ethyl acetate, and the insoluble matter was filtered off. The filtrate was washed with two portions of water, and then with aqueous solution of sodium hydrogen carbonate, water and saturated aqueous solution of sodium chloride in that order, dried over anhydrous sodium sulfate and concentrated under reduced pressure. The residue thus obtained was purified by preparative thin layer chromatography to give 230 mg of N-(3-methoxyphenyl)-2-(3-pyridyl)thiazolidine-4-carboxamide. This compound was dissolved in ethyl acetate, and 1 ml of 2N hydrogen chloride solution in dioxane was added. The resultant solid was collected by filtration, washed with ethyl acetate and dried to give 250 mg of N-(3-methoxyphenyl)-2-(3-pyridyl)-thiazolidine-4-carboxamide dihydrochloride. Melting point 129° C.

| Elemental analysis (for $C_{16}H_{19}N_3O_2SCl_2$): | | | | |
|---|---|---|---|---|
| | C (%) | H (%) | N (%) | S (%) |
| Calculated: | 49.49 | 4.93 | 10.82 | 8.26 |
| Found: | 49.49 | 5.08 | 10.56 | 8.24 |

EXAMPLE 14

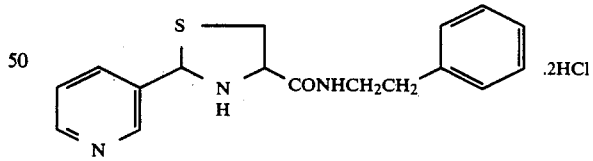

The procedure of Example 13 was followed using 2-(3-pyridyl)thiazolidine-4-carboxylic acid and 2-phenylethylamine to give N-(2-phenylethyl)-2-(3-pyridyl)thiazolidine-4-carboxamide dihydrochloride. Yield, 81%. Melting point 115° C.

| Elemental analysis (for $C_{17}H_{21}N_3OSCl_2$): | | | | |
|---|---|---|---|---|
| | C (%) | H (%) | N (%) | S (%) |
| Calculated: | 52.85 | 5.48 | 10.88 | 8.30 |
| Found: | 52.25 | 5.74 | 10.77 | 8.16 |

EXAMPLE 15

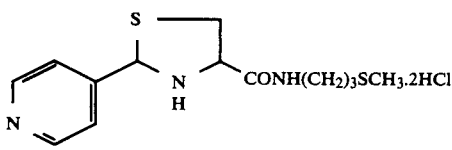

N-(3-Methylthiopropyl)-2-(4-pyridyl)thiazolidine-4-carboxamide dihydrochloride was obtained from the compound obtained in Reference Example 2 and 3-methylthiopropylamine by following the procedure of Example 13. Melting point 70° C.

| Elemental analysis (for $C_{13}H_{21}N_3OS_2Cl_2$): | | | |
|---|---|---|---|
| | C (%) | H (%) | N (%) |
| Calculated: | 42.16 | 5.72 | 11.35 |
| Found: | 41.65 | 5.83 | 10.87 |

EXAMPLE 16

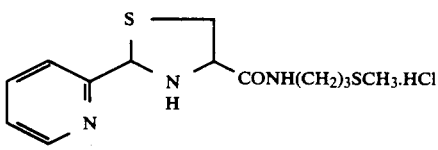

A solution of 1.50 g of pyridine-2-carboxaldehyde and 1.70 g of L-cysteine in 50% ethanol was stirred at room temperature for 4 hours. The insoluble matter was filtered off, and the filtrate reaction mixture was concentrated under reduced pressure. The thus-obtained syrupy substance was dissolved in 35 ml of tetrahydrofuran. To the solution were added 2.89 g of dicyclohexylcarbodiimide, 1.89 g of 1-hydroxybenzotriazole and 1.62 g of 3-methylthiopropylamine, and the mixture was stirred overnight at room temperature. The reaction mixture was diluted with ethyl acetate, and the insoluble matter was filtered off. The filtrate was washed with water (twice), aqueous sodium hydrogen carbonate, water (twice) and saturated aqueous solution of sodium chloride in that order, dried over anhydrous sodium sulfate and concentrated under reduced pressure. The residue obtained was purified by column chromatography (eluent: tolueneethyl acetate=1:1) to give 1.50 g of N-(3-methylthiopropyl)-2-(2-pyridyl)thiazolidine-4-carboxamide. A 800-mg portion of this compound was dissolved in ethyl acetate, and 2N hydrogen chloride solution in dioxane was added. The solvent was distilled off, and the residue was dried to give 830 mg of N-(3-methylthiopropyl)-2-(2-pyridyl)thiazolidine-4-carboxamide hydrochloride. Melting point 65° C.

| Elemental analysis (for $C_{13}H_{22}N_3O_2S_2Cl$): | | | | |
|---|---|---|---|---|
| | C (%) | H (%) | N (%) | S (%) |
| Calculated: | 44.37 | 6.30 | 11.94 | 18.22 |
| Found: | 44.59 | 6.09 | 11.79 | 18.38 |

EXAMPLE 17

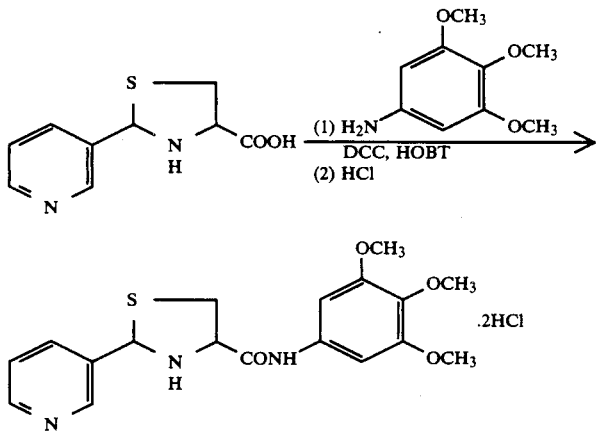

A mixture of 630 mg of 2-(3-pyridyl)thiazolidine-4-carboxylic acid, 520 mg of 3,4,5-trimethoxyaniline, 650 mg of dicyclohexylcarbodiimide and 430 mg of 1-hydroxybenzotriazole in 8 ml of N,N-dimethylformamide was stirred overnight at room temperature. The reaction mixture was diluted with ethyl acetate, and the insoluble matter was filtered off. The filtrate was washed in sequence with aqueous sodium hydrogen carbonate, water and saturated aqueous solution of sodium chloride, dried over anhydrous magnesium sulfate and concentrated under reduced pressure. Purification of the residue by silica gel column chromatography (eluent: ethyl acetate) gave 370 mg of N-(3,4,5-trimethoxyphenyl)-2-(3-pyridyl)thiazolidine-4-carboxamide. This compound was dissolved in 10 ml of ethyl acetate, and 2 ml of 2N hydrogen chloride solution in dioxane was added. The resultant solid was collected by filtration, washed with ethyl acetate and dried to give mg of N-(3,4,5-trimethoxyphenyl)-2-(3-pyridyl)thiazolidine-4-carboxamide dihydrochloride. Melting point 130°-132° C.

| Elemental analysis (for $C_{18}H_{23}N_3O_4SCl_2$): | | | | |
|---|---|---|---|---|
| | C (%) | H (%) | N (%) | S (%) |
| Calculated: | 48.22 | 5.17 | 9.37 | 7.15 |
| Found: | 48.23 | 5.35 | 9.02 | 7.12 |

EXAMPLE 18

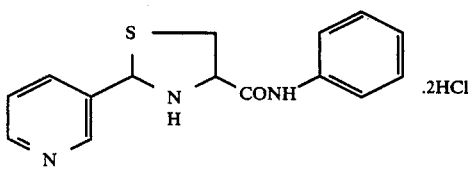

N-Phenyl-2-(3-pyridyl)thiazolidine-4-carboxamide dihydrochloride was obtained from 2-(3-pyridyl)-thiazolidine-4-carboxylic acid and aniline by following the procedure of Example 17. Melting point 145°–148° C. NMR (DMSO-d$_6$) δ: 3.4 4.2 (2H), 4.96 (1H, t), 6.31 and 6.35 (respectively 1H), 7.0 7.4 (3H), 7.6 7.8 (2H), 8.10 (1H, dd), 8.9 9.0 (2H), 9.3 (1H)

EXAMPLE 19

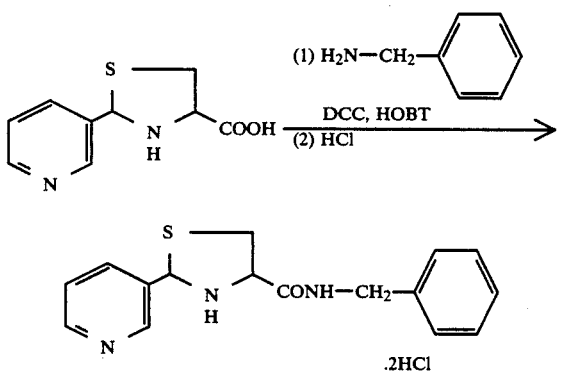

N-Benzyl-2-(3-pyridyl)thiazolidine-4-carboxamide dihydrochloride was obtained from 2-(3-pyridyl)-thiazolidine-4-carboxylic acid and benzylamine by following the procedure of Example 17. Melting point 126°–130° C.

NMR (DMSO-d$_6$) δ: 3.2~3.7 (2H), 4.3~4.6 (3H), 6.08 and 6.14 (respectively 1H), 7.3 (5H), 8.06 (1H, dd), 8.7~9.0 (2H), 9.1~9.2 (1H)

EXAMPLE 20

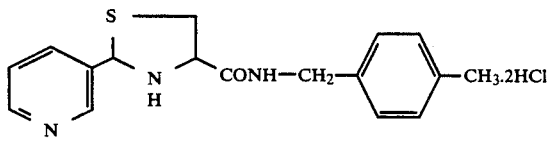

N-(p-Methylbenzyl)-2-(3-pyridyl)thiazolidine-4-carboxamide dihydrochloride was obtained from 2-(3-pyridyl)thiazolidine-4-carboxylic acid and p-methylbenzylamine by following the procedure of Example 17. Yield, 58%. Melting point 130°–136° C.

| Elemental analysis (for $C_{17}H_{21}N_3OSCl_2$): | | | | |
|---|---|---|---|---|
| | C (%) | H (%) | N (%) | S (%) |
| Calculated: | 52.85 | 5.48 | 10.88 | 8.30 |
| Found: | 52.64 | 5.56 | 10.81 | 8.38 |

EXAMPLE 21

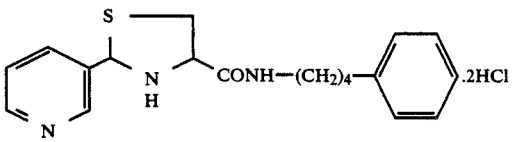

N-(4-Phenylbutyl)-2-(3-pyridyl)thiazolidine-4-carboxamide dihydrochloride was obtained from 2-(3-pyridyl)thiazolidine-4-carboxylic acid and 4-phenylbutylamine by following the procedure of Example 17. Yield, 63%. Melting point 100°–104° C.

| Elemental analysis (for $C_{19}H_{25}N_3OSCl_2 \cdot 0.2H_2O$): | | | | | |
|---|---|---|---|---|---|
| | C (%) | H (%) | N (%) | S (%) | Cl (%) |
| Calculated: | 54.36 | 6.15 | 10.01 | 7.64 | 16.84 |
| Found: | 54.44 | 6.16 | 10.08 | 7.68 | 16.59 |

EXAMPLE 22

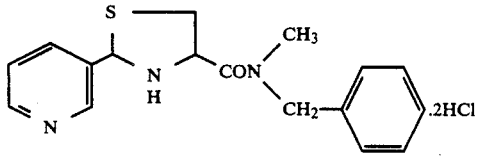

N-benzyl-N-methyl-2-(3-pyridyl)thiazolidine-4-carboxamide dihydrochloride was obtained from 2-(3-pyridyl)thiazolidine-4-carboxylic acid and N-methylbenzylamine by following the procedure of Example 17. Melting point 105°–110° C.

| Elemental analysis (for $C_{17}H_{21}N_3OSCl_2 \cdot H_2O$): | | | | | |
|---|---|---|---|---|---|
| | C (%) | H (%) | N (%) | S (%) | Cl (%) |
| Calculated: | 50.50 | 5.73 | 10.39 | 7.93 | 17.54 |
| Found: | 50.63 | 5.60 | 10.43 | 7.98 | 17.26 |

EXAMPLE 23

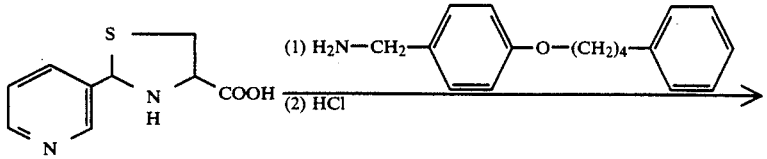

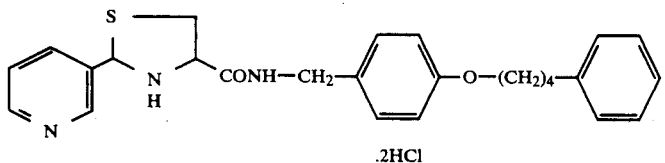

N-2-(3-pyridyl)thiazolidine-4-carboxamide dihydrochloride was obtained from 2-(3-pyridyl)thiazolidine-4-carboxylic acid was p-(4-phenylbutoxy)benzylamine by following the procedure of Example 17. Yield, 72%. Melting point 133°–135° C.

| Elemental analysis (for $C_{26}H_{31}N_3O_2SCl_2.0.2H_2O$): | | | | | |
|---|---|---|---|---|---|
| | C (%) | H (%) | N (%) | S (%) | Cl (%) |
| Calculated: | 59.58 | 6.04 | 8.02 | 6.12 | 13.53 |
| Found: | 59.58 | 6.02 | 7.96 | 6.23 | 13.58 |

EXAMPLE 24

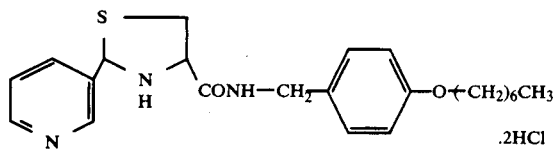

N-(p-Heptyloxybenzyl)-2-(3-pyridyl)thiazolidine-4-carboxamide dihydrochloride was obtained from 2-(3-pyridyl)thiazolidine-4-carboxylic acid and p-heptyloxybenzylamine by following the procedure of Example 17. Melting point 155°–160° C.

| Elemental analysis (for $C_{23}H_{33}N_3O_2Cl_2.0.3H_2O$): | | | | | |
|---|---|---|---|---|---|
| | C (%) | H (%) | N (%) | S (%) | Cl (%) |
| Calculated: | 56.16 | 6.88 | 8.54 | 6.52 | 14.41 |
| Found: | 56.11 | 6.84 | 8.47 | 6.53 | 14.50 |

EXAMPLE 25

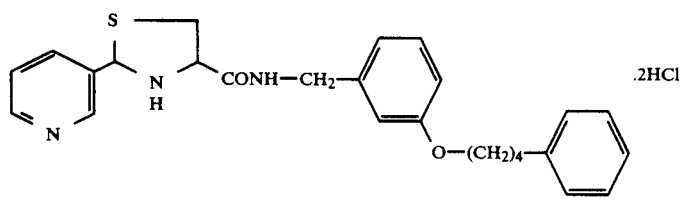

N-[m-(4-phenylbutoxy)benzyl]-2-(3-pyridyl)thiazolidine-carboxamide dihydrochloride was obtained from 2-(3-pyridyl)thiazolidine-4-carboxylic acid and m-(4-phenylbutoxy)benzylamine by following the procedure of Example 17. Yield, 41%. Melting point 88°–93° C.

| Elemental analysis (for $C_{26}H_{31}N_3O_2SCl_2.0.5H_2O$): | | | | | |
|---|---|---|---|---|---|
| | C (%) | H (%) | N (%) | S (%) | Cl (%) |
| Calculated: | 58.97 | 6.09 | 7.94 | 6.06 | 13.39 |
| Found: | 58.96 | 6.07 | 7.96 | 6.11 | 13.36 |

EXAMPLE 26

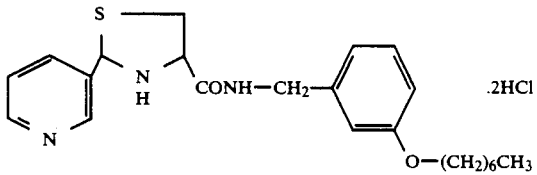

N-(m-Heptyloxybenzyl)-2-(3-pyridyl)thiazolidine-4-carboxamide dihydrochloride was obtained from 2-(3-pyridyl)thiazolidine-4-carboxylic acid and m-heptyloxybenzylamine by following the procedure of Example 17. Melting point 135°–140° C.

| Elemental analysis (for $C_{23}H_{33}N_3O_2SCl_2$): | | | | |
|---|---|---|---|---|
| | C (%) | H (%) | N (%) | S (%) |
| Calculated: | 56.76 | 6.84 | 8.64 | 6.59 |
| Found: | 56.68 | 6.85 | 8.69 | 6.62 |

EXAMPLE 27

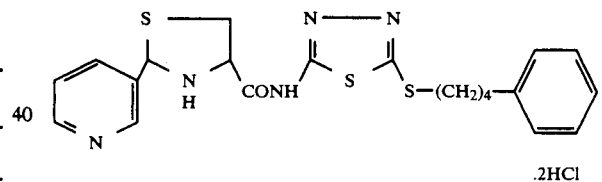

N-[5-[[(4-phenylbutyl)thio]-1,3,4-thiadiazol-2-yl]-2-(3-pyridyl)thiazolidine-4-carboxamide dihydrochloride was obtained from 2-(3-pyridyl)thiazolidine-4-carboxylic acid and 2-amino-5-[(4-phenylbutyl)thio]-1,3,4-thiadiazole by the following the procedure of Example 17. Melting point 99°–105° C.

| Elemental analysis (for $C_{21}H_{25}OS_3Cl_2$): | | | | |
|---|---|---|---|---|
| | C (%) | H (%) | N (%) | S (%) |
| Calculated: | 47.54 | 4.75 | 13.20 | 18.13 |
| Found: | 47.58 | 4.84 | 13.09 | 18.28 |

EXAMPLE 28

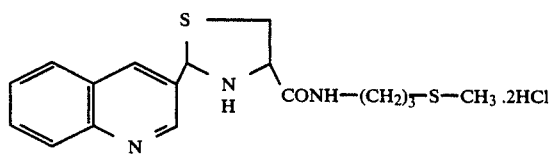

N-(3-Methylthiopropyl)-2-(3-quinolyl)thiazolidine-4-carboxamide dihydrochloride was obtained from 2-(3-quinolyl)thiazolidine-4-carboxalic acid and 3-methylthiopropylamine. Melting point 122°–126° C.

| Elemental analysis (for $C_{17}H_{23}N_3OS_2Cl_2.0.5H_2O$): | | | | |
|---|---|---|---|---|
| C (%) | H (%) | N (%) | S (%) | Cl (%) |
| Calculated: 47.55 | 5.63 | 9.78 | 14.93 | 16.51 |
| Found: 47.57 | 5.72 | 9.75 | 15.02 | 16.47 |

EXAMPLE 29

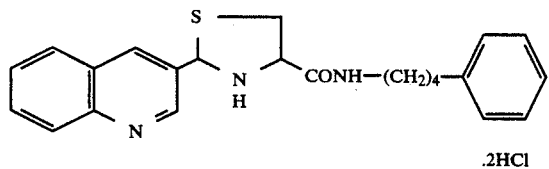

N-(4-Phenylbutyl)-2-(3-quinolyl)thiazolidene-4-carboxamide dihydrochloride was obtained from 2-(3-quinolyl)thiazolidine-4-carboxylic and 4-phenylbutylamine by following the procedure of Example 17. Melting point 116°–122° C.

| Elemental analysis (for $C_{23}H_{27}N_3OSCl_2$): | | | |
|---|---|---|---|
| C (%) | H (%) | N (%) | S (%) |
| Calculated: 59.48 | 5.86 | 9.05 | 6.90 |
| Found: 59.13 | 5.84 | 8.99 | 7.14 |

EXAMPLE 30

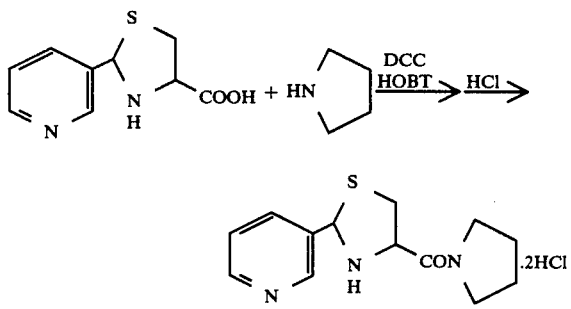

2-(3-Pyridyl)thiazolidine-4-carboxylic acid and pyrrolidine were used as the starting materials and treated in the same manner as in Example 17 to give 1-[ 2-(3-pyridyl)thiazolidin-4-ylcarbonyl]pyrrolidine dihydrochloride. Melting point 136° C.

NMR (DMSO-$d_6$) δ: 1.60~2.13 (4H, m), 3.0~3.90 (6H, m), 4.55~4.71 (1H, m), 6.09 and 6.26 (s, respectively 1H), 8.08 (1H, dd), 8.72 9.20 (3H, m)

EXAMPLE 31

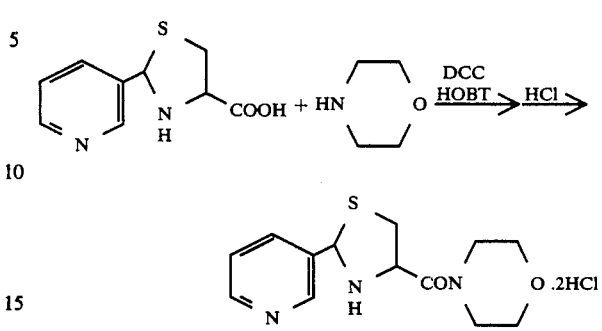

2-(3-Pyridyl)thiazolidine-4-carboxylic acid and morpholine were used as the starting materials and treated in the same manner as in Example 17 to give 4-[2-(3-thiazolidin-4-ylcarbonyl]morpholine dihydrochloride. Melting point 143° C.

NMR (DMSO-$d_6$) δ: 2.97 3.78 (10H, m), 4.62~4.78 (1H, m), 6.00 and 6.23 (s, resepectively 1H), 8.05 (1H, dd), 8.71~9.10 (3H, m)

EXAMPLE 32

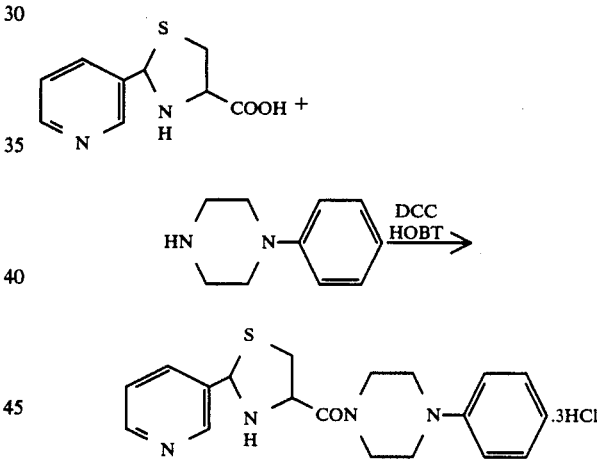

2-(3-Pyridyl)thiazolidine-4-carboxylic acid and 1-phenylpiperazine were used as the starting materials and treated in the same manner as in Example 17 to give 1-phenyl-4-[2-(3-pyridyl)thiazolin-4-ylcarbonyl]piperazine trihydrochloride. Yield, 79%. Melting point 169° C.

NMR (DMSO-$d_6$) δ: 3.04~4.20 (10H, m), 4.64~4.84 (1H, m), 6.00 and 6.23 (s, respectively 1H), 7.04~7.64 (5H, m), 7.99~8.14 (1H, m), 8.70~9.16 (3H, m)

EXAMPLE 33

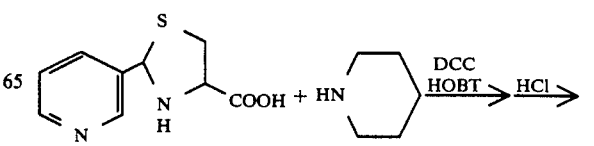

-continued

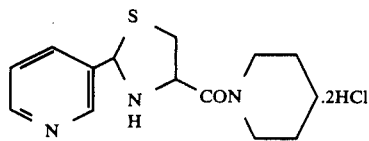

2-(3-Pyridyl)thiazolidine-4-carboxylic acid and piperidine were used as the starting materials and treated in the same manner as in Example 17 to give 1-[2-(3-pyridyl)thiazolin-4-ylcarbonyl]piperidine dihydrochloride. Yield, 48%. Melting point 172° C.

Elemental analysis (for $C_{14}H_{21}N_3OSCl_2 \cdot 0.3H_2O$):

|  | C (%) | H (%) | N (%) | S (%) | Cl (%) |
|---|---|---|---|---|---|
| Calculated: | 47.27 | 6.12 | 11.81 | 9.01 | 19.93 |
| Found: | 47.36 | 6.03 | 11.75 | 9.01 | 19.71 |

EXAMPLE 34

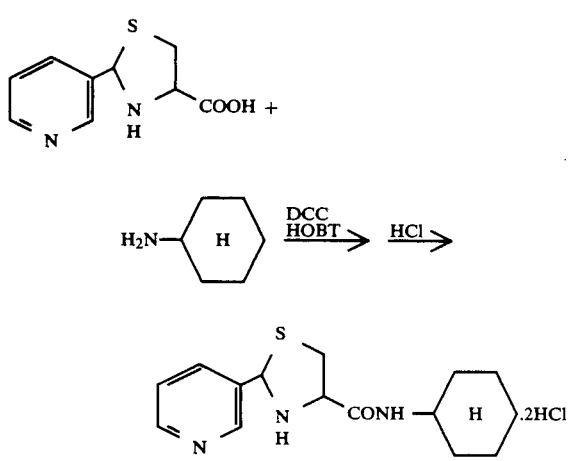

2-(3-Pyridyl)thiazolidine-4-carboxylic acid and cyclohexylamine were used as the starting materials and treated in the same manner as in Example 17 to give N-cyclohexyl-2-(3-pyridyl)thiazolidine-4-carboxamide dihydrochloride. Melting point 139° C.

NMR (DMSO-$d_6$) δ: 0.90~1.95 (11H, m), 3.06~3.69 (3H, m), 4.39 (1H, dd), 6.07 and 6.14 (s, respectively 1H), 8.03 (1H, dd), 8.46 9.13 (3H, m)

EXAMPLE 35

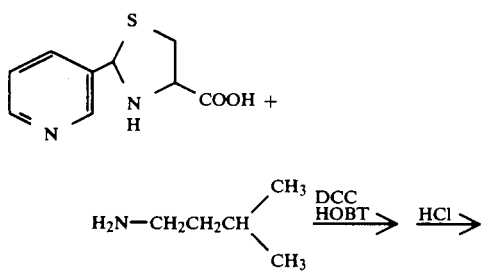

2-(3-Pyridyl)thiazolidine-4-carboxylic acid and isoamylamine were used as the starting materials and in the same manner as in Example 17 to give N-(3-methylbutyl)-2-(3-pyridyl)thiazolidine-4-carboxamide dihydrochloride. Yield, 47%. Melting 115° C.

Elemental analysis (for $C_{14}H_{22}N_3OSCl_2 \cdot 0.3H_2O$):

|  | C (%) | H (%) | N (%) | S (%) |
|---|---|---|---|---|
| Calculated: | 47.14 | 6.39 | 11.78 | 8.99 |
| Found: | 47.24 | 6.59 | 11.56 | 9.10 |

EXAMPLE 36

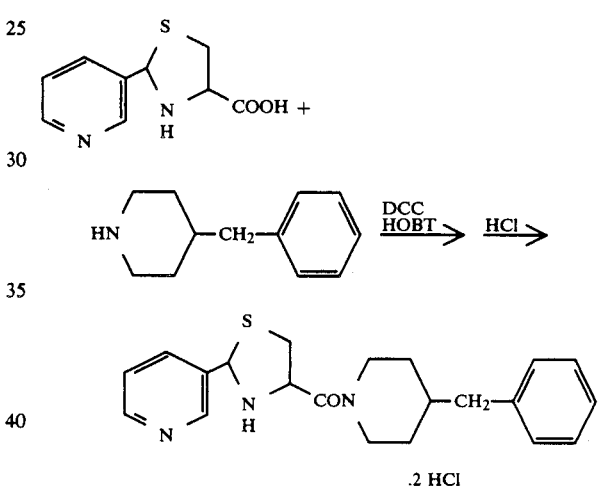

2-(3-Pyridyl)thiazolidine-4-carboxylic acid and 4-benzylpiperidine were used as the starting materials and treated in the same manner as in Example 17 to give 4-benzyl-1-[2-(3-pyridyl)thiazolidin-4-ylcarbonyl]-piperidine dihydrochloride. Yield, 60%. Melting point 135° C.

NMR (DMSO-$d_6$)
δ: 0.76~2.06 (5H, m), 2.35~4.54 (8H, m), 4.68~5.08 (1H, m), 6.08 and 6.28 (s, respectively 1H), 7.06~7.28 (5H, m), 8.07 (1H, dd), 8.71~9.30 (3H, m)

EXAMPLE 37

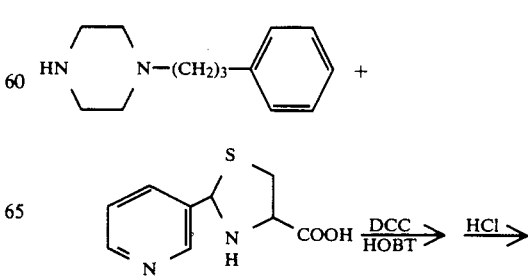

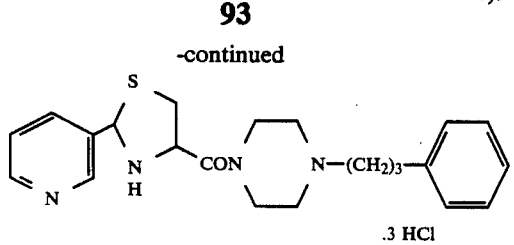

.3 HCl 2-(3-Pyridyl)thiazolidine-4-carboxylic acid and 1-(3-phenylpropyl)piperazine were used as the starting materials and treated in the same manner as in Example 17 to give 1-(3-phenylpropyl)-4-[2-(3-pyridyl)thiazolidin-4-ylcarbonyl]piperazine trihydrochloride. Yield, 60%. Melting point 144° C.

NMR (DMSO-$d_6$) δ: 1.85~4.86 (17H, m), 5.97 and 6.18 (s, respectively 1H), 7.10~7.48 (5H, m), 8.06 (1H, 8.65~9.12 (3H, m)

EXAMPLE 38

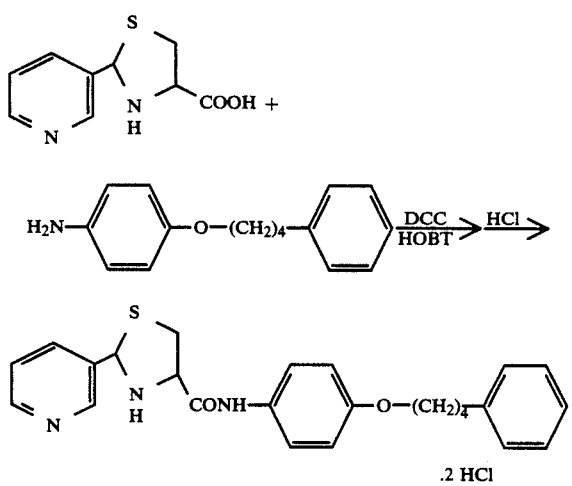

.2 HCl 2-(3-Pyridyl)thiazolidine-4-carboxylic acid and p-(4-phenylbutoxy)aniline were used as the starting materials and treated in the same manner as in Example 17 give N-[p-(4-phenylbutoxy)phenyl]-2-(3-pyridyl)thiazolidine-4-carboxyamide dihydrochloride. Melting point 117° C.

| Elemental analysis (for $C_{25}H_{29}N_3O_2SCl_2$): | | | | |
|---|---|---|---|---|
| | C (%) | H (%) | N (%) | S(%) |
| Calculated: | 59.28 | 5.77 | 8.30 | 6.33 |
| Found: | 59.65 | 5.76 | 8.40 | 6.39 |

EXAMPLE 39

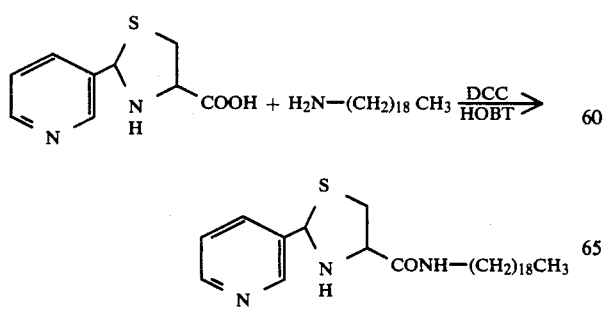

A solution of 500 mg of dicyclohexylcarbodiimide in 3 ml of tetrahydrofuran was added dropwise to a mixture of 510 mg of 2-(3-pyridyl)thiazolidine-4-carboxylic acid, 490 mg of 1-hydroxybenzotriazole, 680 mg of nonadecylamine and 12 ml of tetrahydrofuran with ice cooling, and the resulting mixture was stirred with ice cooling for 1 hour and then at room temperature for 12 hours. The reaction mixture was diluted with 30 ml of ethyl acetate, and the insoluble matter was filtered off. The filtrate was washed in sequence with saturated aqueous solution of sodium hydrogen carbonate, water and saturated aqueous solution of sodium chloride, dried over anhydrous sodium sulfate and concentrated under reduced pressure. The residue was purified by silica gel column chromatography (eluent: ethyl acetate) and recrystallized from ethyl acetate to give 250 mg of N-nonadecyl-2-(3-pyridyl)thiazolidine-4-carboxamide. Melting point 108°-110° C.

| Elemental analysis (for $C_{28}H_{48}N_3OS.1/5\ H_2O$): | | | | |
|---|---|---|---|---|
| | C (%) | H (%) | N (%) | S (%) |
| Calculated: | 70.30 | 10.20 | 8.78 | 6.70 |
| Found: | 70.37 | 10.34 | 8.83 | 6.80 |

EXAMPLE 40

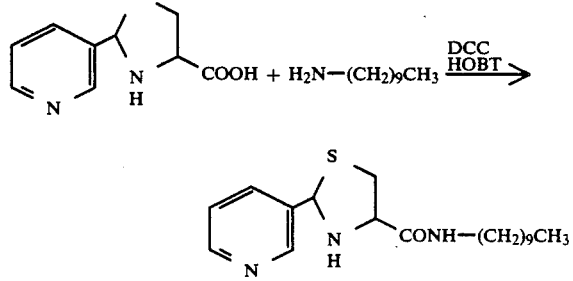

2-(3-Pyridyl)thiazolidine-4-carboxylic acid and decylamine were used as the starting materials and treated the same manner as in Example 39 to give N-decyl-2-(3-pyridyl)thiazolidine-4-carboxamide. Yield, 80%. Melting point 88° C.

| Elemental analysis (for $C_{19}H_{30}N_3OS$): | | | | |
|---|---|---|---|---|
| | C (%) | H (%) | N (%) | S (%) |
| Calculated: | 65.48 | 8.68 | 12.06 | 9.20 |
| Found: | 65.16 | 8.80 | 11.91 | 9.04 |

EXAMPLE 41

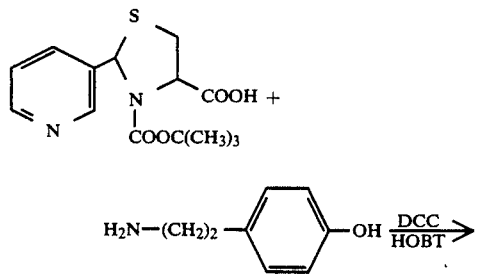

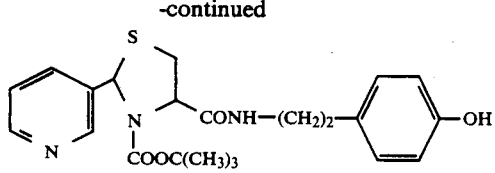

N-tert-Butoxycarbonyl-2-(3-pyridyl)thiazolidine-4-carboxylic acid and tyramine were used as the starting materials and treated in the same manner as in Example 39 to give N-[2-(p-hydroxyphenyl)ethyl]-3-tert-butoxycarbonyl-2-(3-pyridyl)thiazolidino-4-carboxamide. Yield, 100%. Melting point 76° C.

NMR (CDCl$_3$) δ: 1.34 (9H, s), 2.72 (2H, t), 3.22 (1H, dd), 3.43~3.70 (3H, m), 4.80 (1H, dd), 5.99 (1H, s), 6.70~7.03 (4H, m), 7.19~7.32 (1H, m), 7.75~7.84 (1H, m), 8.51 (1H, dd), 8.63 (1H, d)

EXAMPLE 42

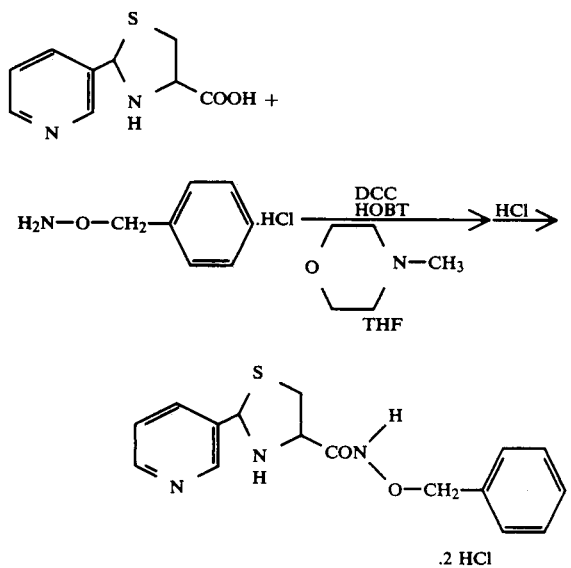

A solution of 490 mg of dicyclohexylcarbodiimide in 5 ml of tetrahydrofuran was added dropwise to a mixture of 500 mg of 2-(3-pyridyl)thiazolidine-4-carboxylic acid, mg of O-benzylhydroxylamine, 480 mg of 1-hydroxybenzotriazole, 240 mg of N-methylmorpholine and 15 ml of tetrahydrofuran with ice cooling, and the resultant mixture was stirred with ice cooling for 1 hour and then at room temperature for 12 hours. The reaction mixture was diluted with 30 ml of ethyl acetate, and the insoluble matter was filtered off. The filtrate was washed in sequence with saturated aqueous solution of sodium hydrogen carbonate and saturated aqueous solution of sodium chloride, dried over anhydrous sodium sulfate and concentrated under reduced pressure. Purification of the residue by silica gel column chromatography (eluent:ethyl acetate) gave 260 mg of N-benzyloxy-2-(3-pyridyl)thiazolidine-4-carboxamide. This compound was dissolved in ethyl acetate, and 1.5 ml of 2N hydrogen chloride solution in dioxane was added. The resultant solid was collected by filtration, washed with ethyl acetate and dried to give 240 mg of N-benzyloxy-2-(pyridin-3-yl)thiazolidine-4-carboxamide dihydrochloride. Melting point 115° C.

NMR (DMSO-d$_6$) δ: 3.02~3.52 (2H, m), 4.07~4.20 (1H, m), 4.90 (2H, s), 6.00 and 6.08 (s, respectively 1H), 7.28~7.53 (5H, m), 8.07 (1H, dd), 8.64~9.26 (3H, m)

EXAMPLE 43

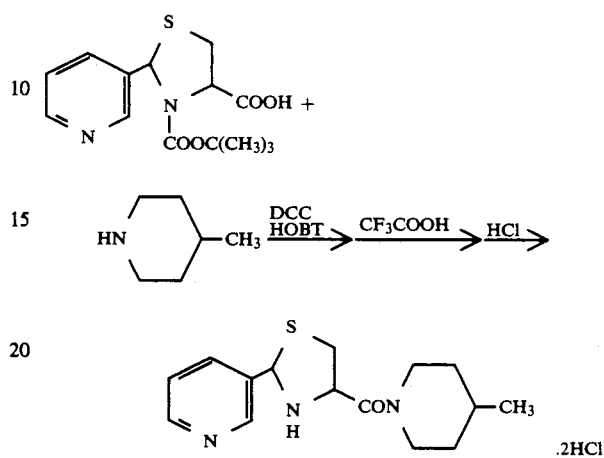

A solution of 540 mg of dicyclohexylcarbodiimide in 5 ml of tetrahydrofuran was added dropwise to a mixture of 810 mg of N-tert-butoxycarbonyl-2-(3-pyridyl)-thiazolidine-4-carboxylic acid, 260 mg of 4-methylpiperidine, 530 mg of 1-hydroxybenzotriazole and 10 ml of tetrahydrofuran with ice cooling, and the mixture was stirred with ice cooling for 1 hour and then at room temperature for 12 hours. The reaction mixture was diluted with 30 ml of ethyl acetate, and the insoluble matter was filtered off. The filtrate was washed in sequence with saturated aqueous solution of sodium hydrogen carbonate and saturated aqueous solution of sodium chloride, dried over anhydrous sodium sulfate and concentrated under reduced pressure to give 4-methyl-1-[3-tert-butoxycarbonyl-2-(3-pyridyl)thiazolidin-4-ylcarbonyl]piperidine. Trifluoroacetic acid (5 ml) was added to the thus-obtained compound, and the mixture was stirred at room temperature for 1 hour. The reaction mixture was concentrated under reduced pressure, the residue was dissolved in ethyl acetate, and the solution was washed in sequence with saturated aqueous solution of sodium hydrogen carbonate and saturated aqueous solution of sodium chloride, dried over anhydrous sodium sulfate and concentrated under reduced pressure The residue thus obtained was purified by silica gel column chromatography (eluent: ethyl acetate) to give 4-methyl-1-[2-(3-pyridyl)thiazolidin-4-ylcarbonyl]piperidine. This compound was dissolved in ethyl acetate, and 3 ml of 2N hydrogen chloride solution in dioxane was added The resultant solid was collected by filtration, washed with ethyl acetate and dried to give 530 mg of 4-methyl-1-(3-pyridyl)thiazolidin-3-ylcarbonyl]piperidine dihydrochloride. Melting point 130° C.

| Elemental analysis (for $C_{15}H_{23}N_3OSCl_2$): | | | | |
|---|---|---|---|---|
| | C (%) | H (%) | N (%) | S (%) |
| Calculated: | 49.45 | 6.39 | 11.53 | 8.80 |
| Found: | 49.59 | 6.60 | 11.47 | 8.63 |

EXAMPLE 44

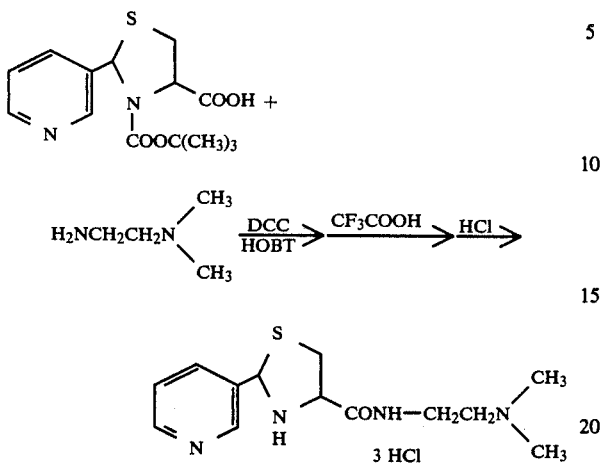

N tert-Butoxycarbonyl-2-(3-pyridyl)thiazolidine-4-carboxylic acid and N,N-dimethylethylenediamine were used as the starting materials and treated in the same manner as in Example 43 to give N-[2-(N',N'-dimethylamino)ethyl]-(3-pyridyl)thiazolidine-4-carboxamide trihydrochloride. Melting point 150° C.

NMR (DMSO-d$_6$) δ: 2.63~3.80 (12H, m), 4.26~4.50 (1H, m), 6.01 and 6.08 (s, respectively 1H), 8.06 (1H, dd), 8.70~9.18 (3H, m)

EXAMPLE 45

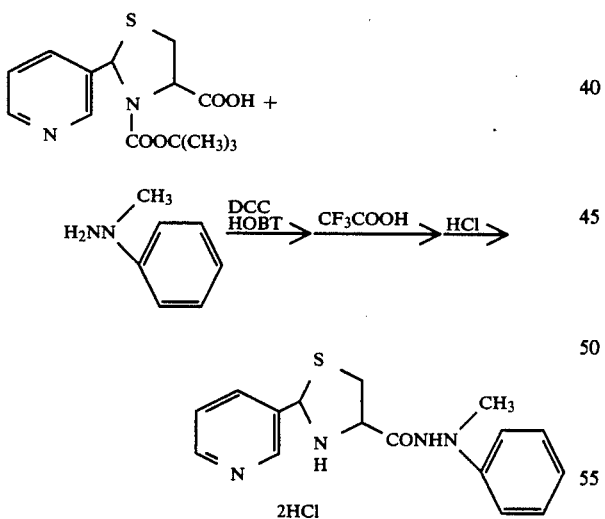

N-tert-Butoxycarbonyl-2-(3-pyridyl)thiazolidine-4-carboxylic acid and N-methyl-N-phenylhydrazine were used as the starting materials and treated in the same manner as in Example 43 to give N'-methyl-N'-phenyl-2-(3-pyridyl)thiazolidine-4-carbohydrazine dihydrochloride. Yield, 58%. Melting point 145° C.

NMR (DMSO-d$_6$) δ: 3.04~3.72 (5H, m , 4.28~4.50 (1H m) 6.03 and 6.12 (s, respectively 1H), 6.70~7.32 (5H, m), 8.07 (1H, dd), 8.69~9.17 (3H, m)

EXAMPLE 46

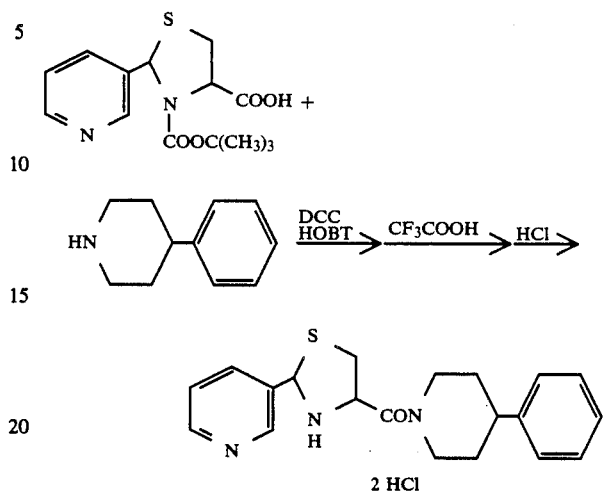

N-tert-Butoxycarbonyl-2-(3-pyridyl)thiazolidine-4-carboxylic acid and 4-phenylpiperidine were used as the starting materials and treated in the same manner as in Example 43 to give 4-phenyl-1-[2-(3-pyridyl)thiazolidin-4-ylcarbonyl]piperidine dihydrochloride. Yield, 48%. Melting point 115° C.

NMR (DMSO-d$_6$) δ: 1.32~2.08 (4H, m), 2.58~3.82 (6H, m), 3.96~5.00 (2H, m), 6.04 and 6.28 (s, respectively 1H), 7.08~7.44 (5H, m), 8.06 (1H, dd), 8,68~9.16 (3H, m)

EXAMPLE 47

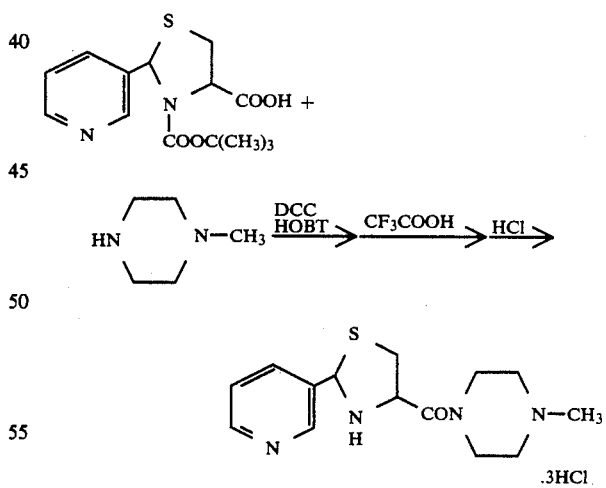

N-tert-Butoxycarbonyl-2-(3-pyridyl)thiazolidine-4-carboxylic acid and 1-methylpiperazine were used as the starting material and treated in the same manner as in Example 43 to give 1-methyl-4-[2-(3-pyridyl)thiazolidin-4-ylcarbonyl]piperazine trihydrochloride. Melting point 182° C.

NMR (DMSO-D$_6$) δ2.62~5.00 (14H, m), 6.03 and 6.22 (s, respectively 1H), 8.09 (1H, dd), 8.70~9.20 (3H, m)

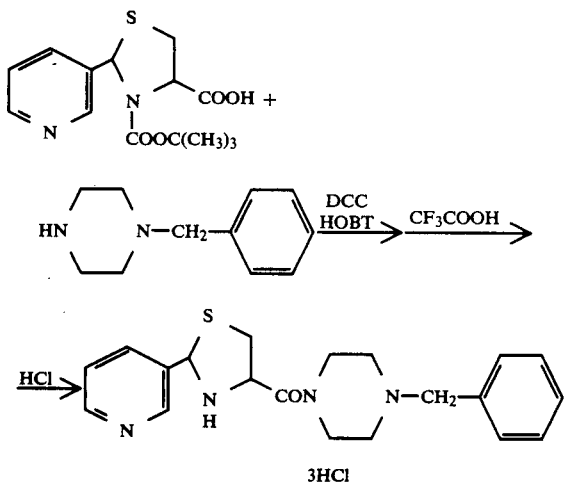

N-tert-Butoxycarbonyl-2-(3-pyridyl)thiazolidine-4-carboxylic acid and 1-benzylpiperazine were used as the starting materials and treated in the same manner as in Example 43 to give 1-benzyl-4-[2(3-pyridyl)thiazolidin-4-ylcarbonyl]piperazine trihydrochloride. Yield, 63%. Melting point 165° C.

NMR (DMSO-d$_6$) δ: 2.76~4.80 (13H, m), 5.93 and 6.15 (s, respectively 1H), 7.36~7.80 (5H, m), 8.03 (1H, dd), 8.62~9.10 (3H, m)

EXAMPLE 49

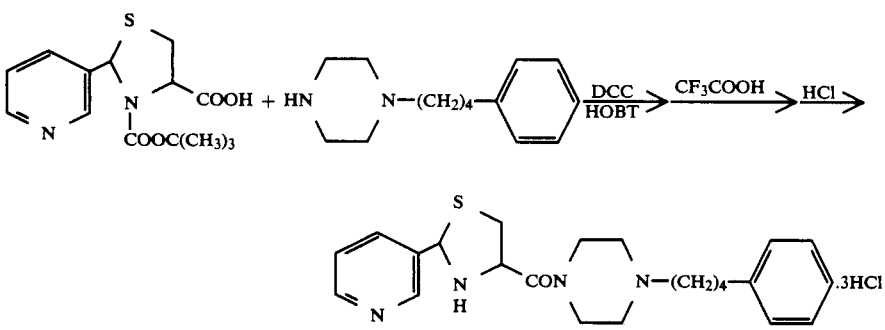

N-tert-Butoxycarbonyl-2-(3-pyridyl)thiazolidine-4-carboxylic acid and 1-(4-phenylbutyl)piperazine were used as the starting materials and treated in the same manner as in Example 43 to give 1-(4-phenylbutyl)-4-[2-(3-pyridyl)thiazolidin-4-ylcarbonyl]piperazine trihydrochloride. Yield, 98%. Melting point 157° C.

NMR (DMSO-d$_6$) δ: 1.33~1.85 (4H, m), 2.30~2.76 (8H, m), 2.86~3.78 (6H, m), 3.99~4.30 (1H, m), 5.96 and 6.17 (s respectively 1H), 7.12~7.44 (6H, m), 8.12 (1H, dd), 8.72~9.17 (2H, m)

EXAMPLE 50

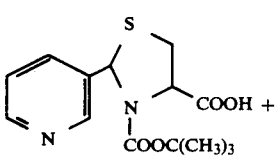

A solution of 450 mg of dicyclohexylcarbodiimide in 5 ml of tetrahydrofuran was added dropwise to a mixture of 680 mg of N-tert-butoxycarbonyl-2-(3-pyridyl)-thiazolidine-4-carboxylic acid, 240 mg of phenylhydrazine, 450 mg of 1-hydroxybenzotriazole and 20 ml of tetrahydrofuran with ice cooling, and the resultant mixture was stirred with ice cooling for 1 hour and then at room temperature for 12 hours. The reaction mixture was diluted with 30 ml of ethyl acetate, and the insoluble matter was filtered off. The filtrate was washed in sequence with saturated aqueous solution of sodium hydrogen carbonate and saturated aqueous solution of sodium chloride, and dried over anhydrous sodium sulfate Concentration under reduced pressure gave 840 mg of. N'-phenyl-3-tert-butoxycarbonyl-2-(3-pyridyl)-thiazolidine-4-carbohydrazide. Trifluoroacetic acid (5 ml) was added to the thus-obtained compound, and the mixture was stirred at room temperature for 1 hour. The reaction mixture was concentrated under reduced pressure, the residue was dissolved in ethyl acetate, and the solution was washed in sequence with saturated aqueous solution of sodium hydrogen carbonate and saturated aqueous solution of sodium chloride, and dried over anhydrous sodium sulfate Concentration under reduced pressure gave crystals, which were recrystallized from ethyl acetate. Thus was obtained 180 mg of N'-phenyl- 2-(3-pyridyl)thiazolidine-4-carbohydrazide. Melting point 155° C.

NMR (CDCl$_3$+DMSO-d$_6$) δ: 3.22~3.56 (2H, m), 4.22~4.36 (1H, m), 5.60 and 5.72 (s, respectively 1H), 6.72~7.44 (6H, m), 7.81~7.95 (1H, m), 8.56 (1H, dd), 8.79 (1H, d)

EXAMPLE 51

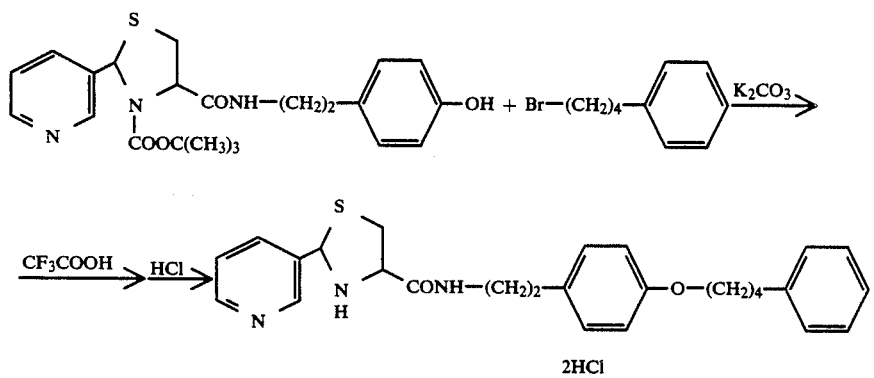

A solution of 280 mg of 1-bromo-4-phenylbutane in 5 ml of N,N-dimethylformamide was added to a mixture of 540 mg of N-[2-(p-hydroxyphenyl)ethyl]-3-tert-butoxycarbonyl-2(3-pyridyl)thiazolidine-4-carboxamide, 180 mg of potassium carbonate and 10 ml of N,N-dimethylformamide at room temperature. The mixture was stirred at 80° C. for 3 days. After cooling, 20 ml of water was added to the reaction mixture, and the organic matter was extracted with ethyl acetate. The organic layer was washed in sequence with water and saturated aqueous solution of sodium chloride, and dried over anhydrous sodium sulfate and concentrated under reduced pressure. Purification of the residue by silica gel column chromatography (eluent: hexane-ethyl acetate = 1:3) gave 360 mg of N-[2-[p-(4-phenylbutoxy)phenyl]ethyl]-3-tert-butoxycarbonyl-2-(3-pyridyl)-thiazolidine-4-carboxamide. Trifluoroacetic acid (5 ml) was added to the compound obtained, and the mixture was stirred at room temperature for 1.5 hour. The reaction mixture was concentrated under reduced pressure, the residue was dissolved in ethyl acetate, and the solution was washed in sequence with saturated aqueous solution of sodium hydrogen carbonate and saturated aqueous solution of sodium chloride, and dried over anhydrous sodium sulfate and concentrated under reduced pressure. The residue was purified by silica gel column chromatography (eluent: ethyl acetate) to give 230 mg of N-[2-[p-(4-penylbutoxy)phenyl]ethyl]-2-(3-pyridyl)-thiazolidine-4-carboxamide. This compound was dissolved in ethyl acetate, and 1 ml of 2N hydrogen chloride solution in dioxane was added. The resultant solid was collected by filtration, washed with ethyl acetate and dried to give 130 mg of N-[2-[p-(4-phenylbutoxy)phenyl]ethyl]-2-(3-pyridyl) thiazolidine-4-carboxamide dihydrochloride. Melting point 102° C.

Elemental analysis (for $C_{27}H_{33}N_3O_2SCl_2$):

|  | C (%) | H (%) | N (%) | S (%) |
|---|---|---|---|---|
| Calculated: | 60.67 | 6.22 | 7.86 | 6.00 |
| Found: | 60.51 | 6.15 | 7.94 | 5.97 |

EXAMPLE 52

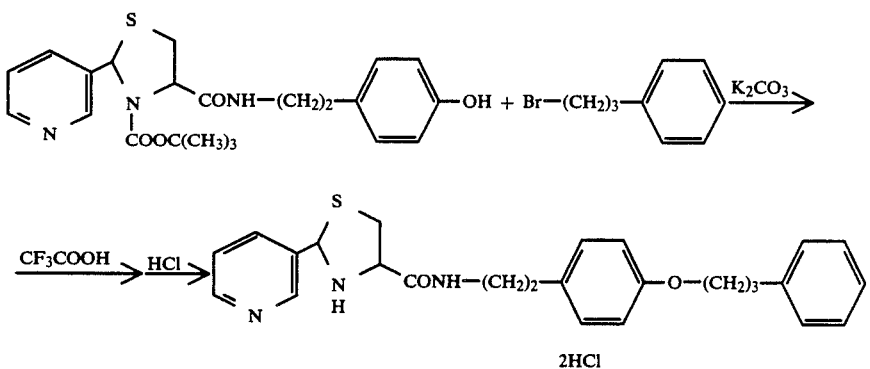

N-[2-(p-Hydroxyphenyl)ethyl]-3-tert-butoxycarbonyl-2-(3-pyridyl)thiazolidine-4-carobxamide and 1-bromo-3-phenylpropane were used as the starting materials and treated in the same manner as in Example 51 to give N-[2-[p-)3-phenylpropoxy)phenyl]ethyl]-2-(3-pyridyl)thiazolidine-4-carboxamide dihydrochloride. Melting point 98° C.

Elemental analysis (for $C_{26}H_{31}N_3O_2SCl_2.0.3H_2O$)):

|  | C (%) | H (%) | N (%) | S (%) | Cl (%) |
|---|---|---|---|---|---|
| Calculated: | 59.38 | 6.06 | 7.99 | 6.10 | 13.48 |
| Found: | 59.37 | 6.05 | 8.01 | 6.09 | 13.31 |

EXAMPLE 53

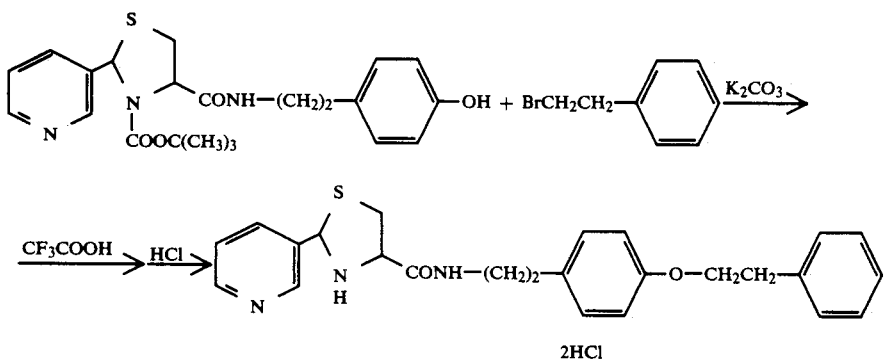

N-[2-(p-Hydroxyphenyl)ethyl]-3-tert-butoxycarbonyl-2-(3-pyridyl)thiazolidine-4-carboxamide and 1-bromo-2-phenylethane were used as the starting materials and treated in the same manner as in Example 51 to give N-[2-p-(2-phenylethoxy)phenyl]ethyl]-2-(3-pyridyl)thiazolidine-4-carboxamide dihydrochloride.

NMR (DMSO-d$_6$) δ: 2.58~3.64 (8H, m), 4.11~4.40 (3H, m), 6.03 (1H, s), 6.83~7.35 (5H, m), 8.02 (1H, dd), 8.66~8.85 (1H, m), 8.88~9.01 (1H, m), 9.07 (1H, dd)
MS: m/z 433 (M+-2xHCl)

EXAMPLE 54

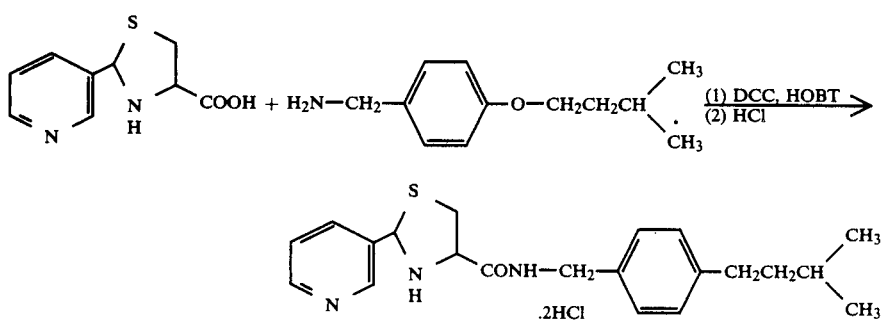

A mixture of 1.13 g of p-(3 methylbutoxy)benzylamine, 1.29 g of 2-(3-pyridyl)thiazolidine-4-carboxylic acid, 1.25 g of dicyclohexylcarbodiimide and 0.82 g of 1-hydroxybenzotriazole in 20 ml of N,N-dimethylformamide was stirred overnight at room temperature. The reaction mixture was diluted with 100 ml of ethyl acetate, and the insoluble matter was filtered off. The filtrate was washed in sequence with saturated aqueous solution of sodium hydrogen carbonate, water and saturated aqueous solution of sodium chloride, dried over anhydrous magnesium sulfate, and concentrated under reduced pressure Purification of the thus-obtained residue by silica gel column chromatography (eluent: ethyl acetate) gave 2.20 g of N-[p-(3-methylbutoxy)benzyl]-2-(3-pyridyl)thiazolidine-4-carboxamide. To a solution of this compound in 60 ml of ethyl acetate was added 4 ml of 4N hydrogen chloride solution in dioxane. The precipitate solid was collected by filtration, washed with ethyl acetate and dried under reduced pressure to give 2.30 g of N-[p-(3-methylbutoxy)benzyl]-2-(3-pyridyl)-thiazolidine-4-carboxamide dihydrochloride. Melting point 120°-128° C.

| Elemental analysis (for $C_{21}H_{29}N_3O_2SCl_2.0.4H_2O$): | | | | |
|---|---|---|---|---|
| C (%) | H (%) | N (%) | S (%) | Cl (%) |
| Calculated: 54.17 | 6.45 | 9.02 | 6.89 | 15.23 |
| Found: 54.23 | 6.37 | 8.96 | 7.00 | 15.16 |

REFERENCE EXAMPLES 55 TO 80

The following compounds were obtained in the same manner as in Example 54.

| Desired Product | |
|---|---|
| p-2-Methylpropxy)benzyl]Structure and Chemical Name | Physicochemical Properties |
| Ex. 55 ![structure] N-[P-2-Methylpropoxy)benzyl]-2-(3-pyridyl)thiazolidine-3-carboxamide dihydrochloride | (1) Melting point: 125~133° C. (2) Elemental analysis (for $C_{20}H_{27}N_3O_2SCl_2$): C H N S Calculated: 54.05 6.12 9.45 7.22 (%) Found: 53.69 6.19 9.32 6.97 (%) |
| Ex. 56 | (1) Melting point: 124~128° C. |

-continued

| Desired Product | |
|---|---|
| p-2-Methylpropxy)benzyl]Structure and Chemical Name | Physicochemical Properties |

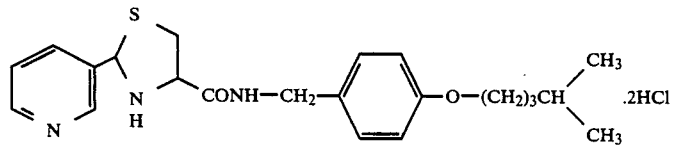

N-[p-(4-Methylpentyloxy)benzyl]-2-(3-pyridyl)thiazolidine-4-carboxamide dihydrochloride (2) Elemental analysis (for $C_{22}H_{31}N_3O_2SCl_2$):

| | C | H | N | S | Cl |
|---|---|---|---|---|---|
| Calculated: (%) | 54.88 | 6.70 | 8.73 | 6.66 | 14.73 |
| Found: (%) | 54.79 | 6.69 | 8.70 | 6.48 | 14.80 |

Ex. 57

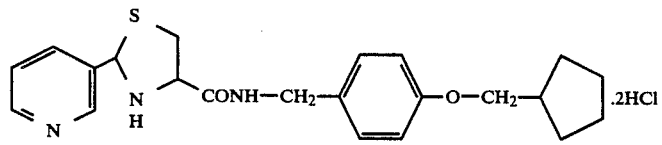

N-(p-Cyclopentylmethoxybenzyl)-2-(3-pyridyl)thiazolidine-4-carboxamide dihydrochloride (1) Melting point: 55~60° C.
(2) Elemental analysis (for $C_{22}H_{20}N_3O_2SCl_2$):

| | C | H | N | S |
|---|---|---|---|---|
| Calculated: (%) | 56.17 | 6.21 | 8.93 | 6.82 |
| Found: (%) | 55.83 | 6.11 | 8.65 | 6.84 |

Ex. 58

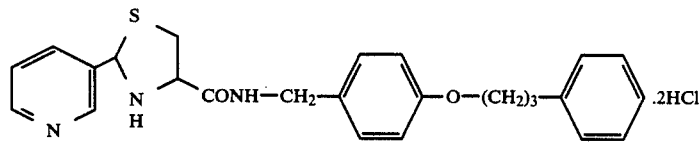

N-[p-(3-Phenylpropoxy)benzyl]-2-(3-pyridyl)thiazolidine-4-carboxamide dihydrochloride (1) Melting point: 110~116° C.
(2) Elemental analysis (for $C_{25}H_{20}N_3O_2SCl_2$):

| | C | H | N | S | Cl |
|---|---|---|---|---|---|
| Calculated: (%) | 59.28 | 5.77 | 8.30 | 6.33 | 14.00 |
| Found: (%) | 58.95 | 5.74 | 8.21 | 6.36 | 13.93 |

Ex. 59

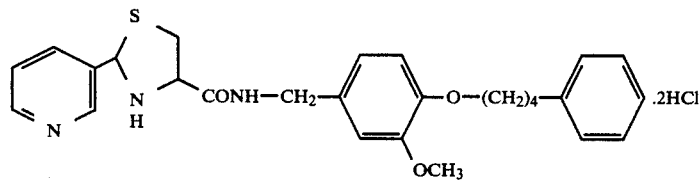

N-[3-Methoxy-4-(4-phenylbutoxy)-benzyl]-2-(3-pyridyl)thiazolidine-4-carboxamide dihydrochloride (1) Melting point: 88~95° C.
(2) Elemental analysis (for $C_{27}H_{33}N_3O_3SCl_2$):

| | C | H | N | S | Cl |
|---|---|---|---|---|---|
| Calculated: (%) | 58.90 | 6.04 | 7.63 | 5.82 | 12.88 |
| Found: (%) | 58.52 | 6.02 | 7.59 | 5.82 | 12.48 |

Ex. 60

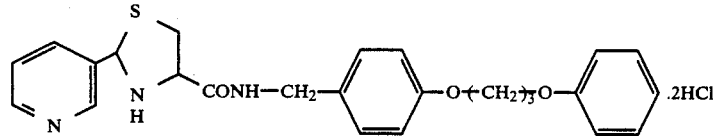

N-[p-(3-Phenoxypropoxy)benzyl]-2-(3-pyridyl)thiazolidine-4-carboxamide dihydrochloride (1) Melting point: 101~110° C.
(2) Elemental analysis (for $C_{25}H_{29}N_3O_3SCl_2$):

| | C | H | N | S | Cl |
|---|---|---|---|---|---|
| Calculated: (%) | 57.47 | 5.59 | 8.04 | 6.14 | 13.57 |
| Found: (%) | 57.42 | 5.77 | 7.90 | 5.98 | 13.35 |

Ex. 61

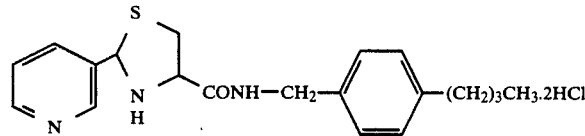

N-(p-Butylbenzyl)-2-(3-pyridyl)-thiazolidine-4-carboxamide dihydrochloride (1) Melting point: 110~115° C.
(2) Elemental analysis (for $C_{20}H_{27}N_3OSCl_2.0.4H_2O$):

| | C | H | N | S | Cl |
|---|---|---|---|---|---|
| Calculated: (%) | 55.14 | 6.43 | 9.65 | 7.36 | 16.28 |
| Found: (%) | 55.27 | 6.50 | 9.69 | 7.23 | 16.06 |

Ex. 62

(1) Melting point: 133~142° C.

-continued

| Desired Product p-2-Methylpropxy)benzyl]Structure and Chemical Name | Physicochemical Properties |
|---|---|
| 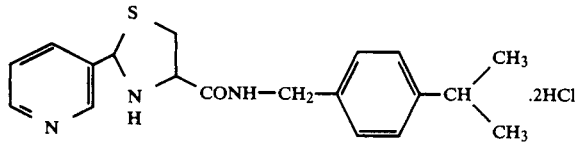<br>N-[p-(1-Methylethyl)benzyl]-2-<br>(3-pyridyl)thiazolidine-4-carboxamide dihydrochloride | (2) Elemental analysis<br>(for $C_{19}H_{25}N_3OSCl_2.0.6H_2O$):<br>          C    H    N    S    Cl<br>Calculated: 53.67  6.21  9.88  7.54  16.68<br>(%)<br>Found:     53.75  6.17  9.83  7.52  16.37<br>(%) |
| Ex. 63<br>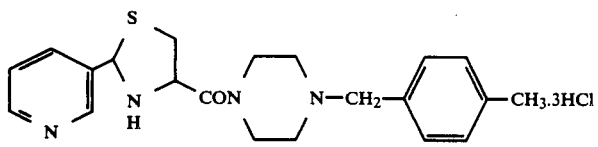<br>1-(p-Methylbenzyl)-4-[2-(3-pyridyl)-<br>thiazolidin-4-ylcarbonyl]piperazine trihydrochloride | (1) Melting point: 168° C.<br>(2) NMR (DMSO-$d_6$)<br>δ: 2.38 (3H, s), 2.5~3.5 (8H, m),<br>4.0~4.6 (4H, m), 4.4~4.9 (1H, m),<br>5.96 and 6.18 (s, respectively<br>1H), 7.26 and 7.56 (4H, dd,<br>ABq), 6.9~7.2 (1H, m), 7.6~8.2<br>(3H, m) |
| Ex. 64<br>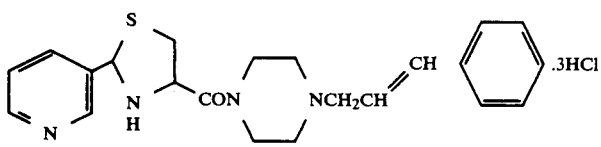<br>1-(3-Phenyl-2-propenyl)-4-[2-(3-<br>pyridyl)thiazolidin-4-ylcarbonyl]piperazine trihydrochloride | (1) Melting point: 180° C.<br>(2) NMR (DMSO-$d_6$)<br>δ: 2.38~3.8 (8H, m), 3.8~4.1 (2H, m),<br>4.0~4.8 (3H, m), 5.98 and 6.18<br>(s, respectively 1H), 6.3~6.7<br>(1H, m), 6.8 and 6.86 (s,<br>respectively 1H), 7.2~7.6 (5H,<br>m), 8.0~8.2 (1H, m), 8.6~9.2 (3H,<br>m) |
| Ex. 65<br>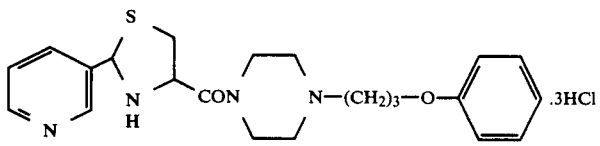<br>1-(3-Phenoxypropyl-4-[2-(3-<br>pyridyl)thiazolidin-4-ylcarbonyl]piperazine trihydrochloride | (1) MS: m/z 412 ($M^+$-3HCl)<br>(2) NMR (DMSO-$d_6$)<br>δ: 2.0~2.6 (2H, m), 2.6~3.9 (10H, m),<br>4.09 (2H, t), 4.0~4.9 (3H, m),<br>6.0 and 6.2 (s, respectively<br>1H), 6.8-7.1 (3H, m), 6.2~6.42<br>(2H, m), 8.0~8.2 (1H, m), 8.6~9.2<br>(3H, m) |
| Ex. 66<br>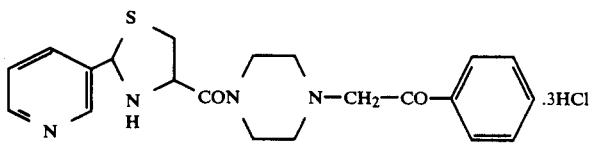<br>1-[(2-Oxo-2-phenyl)ethyl]-4-[2-(3-<br>pyridyl)thiazolidin-4-ylcarbonyl]piperazine trihydrochloride | (1) Melting point: 147° C.<br>(2) NMR (DMSO-$d_6$)<br>δ: 2.94~4.32 (12H, m), 4.52~4.80 (1H,<br>m), 5.96 and 6.16 (s,<br>respectively 1H), 7.44~7.84 (3H,<br>m), 7.94~8.20 (3H, m), 8.60~9.20<br>(3H, m) |
| Ex. 67<br>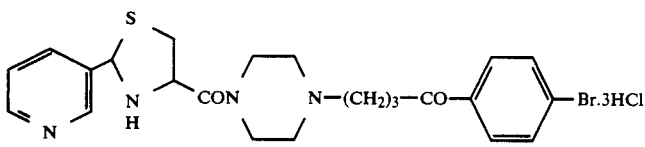<br>1-[4-(p-Bromophenyl)-4-oxobutyl]-4-[2-(3-pyridyl)thiazolidin-4-<br>ylcarbonyl]piperazine trihydrochloride | (1) Melting point: 139° C.<br>(2) Elemental analysis<br>(for $C_{23}H_{30}N_4O_2SBrCl_3$):<br>          C    H    N    S    Br+Cl<br>Calculated: 45.08  4.93  9.14  5.23  30.39<br>(%)<br>Found:     44.90  5.17  9.24  5.41  30.29<br>(%) |
| Ex. 68 | (1) Melting point: 129° C. |

-continued

Desired Product p-2-Methylpropxy)benzyl]Structure
and Chemical Name

Physicochemical Properties

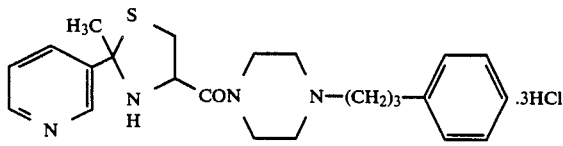

1-[2-Methyl-2-(3-pyridyl)thiazol-
idin-4-ylcarbonyl]-4-(3-phenylpropyl)piperazine trihydrochloride (2) NMR (DMSO-$d_6$)
δ: 1.88 and 1.96 (s, respectively
3H), 1.68~2.28 (2H, m), 2.44~2.80
(2H, m), 2.88~4.64 (13H, m),
7.12~7.48 (6H, m), 7.96~8.18 (1H,
m), 8.64~9.04 (2H, m)

Ex. 69

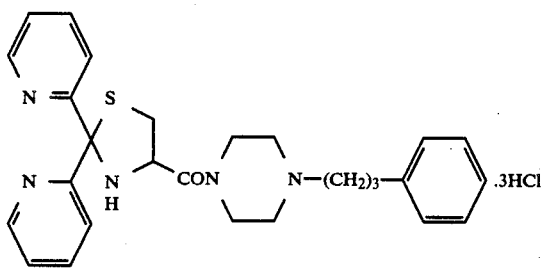

1-[2,2-Di(2-pyridyl)thiazolidin-
4-ylcarbonyl]-4-(3-phenylpropyl)piperazine trihydrochloride (1) Melting point: 111° C.
(2) NMR (DMSO-$d_6$)
δ: 1.90~2.28 (2H, m), 2.46~2.80 (2H,
m), 2.86~3.74 (12H, m), 4.12~4.68
(1H, m), 7.16~7.40 (5H, m),
7.44~8.88 (8H, m)

Ex. 70

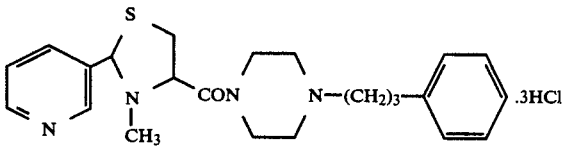

1-[3-Methyl-2-(3-pyridyl)thiazol-
idin-4-ylcarbonyl]-4-(3-phenylpropyl)piperazine trihydrochloride (1) Melting point: 130° C.
(2) NMR (DMSO-$d_6$)
δ: 1.88~2.24 (2H, m), 2.36 and 2.52
(s, respectively 3H), 2.56~2.78
(2H, m), 2.78~4.60 (13H, m), 5.58
and 5.82 (s, respectively 1H),
7.08~7.44 (6H, m), 7.86~8.20 (1H,
m), 8.58~9.02 (2H, m)

Ex. 71

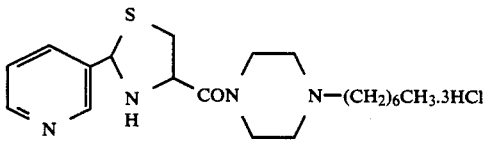

1-Heptyl-4-[2-(3-pyridyl)thiazol-
idin-4-ylcarbonyl]piperazine trihydrochloride (1) Melting point: 139° C.
(2) Elemental analysis
(for $C_{20}H_{35}N_4OSCl_3 \cdot 1.5H_2O$):

| | C | H | N | S | Cl |
|---|---|---|---|---|---|
| Calculated: (%) | 46.83 | 7.47 | 10.92 | 6.25 | 20.73 |
| Found: (%) | 47.09 | 7.29 | 11.09 | 6.36 | 20.47 |

Ex. 72

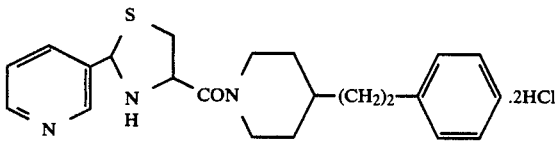

4-(2-Phenylethyl)-1-[2-(3-pyridyl)-
thiazolidin-4-ylcarbonyl]piperidine dihydrochloride (1) Melting point: 110~117° C.
(2) Elemental analysis
(for $C_{22}H_{29}N_3OSCl_2 \cdot 0.8H_2O$):

| | C | H | N | S | Cl |
|---|---|---|---|---|---|
| Calculated: (%) | 56.36 | 6.58 | 8.96 | 6.84 | 15.12 |
| Found: (%) | 56.27 | 6.55 | 8.92 | 6.94 | 15.02 |

Ex. 73

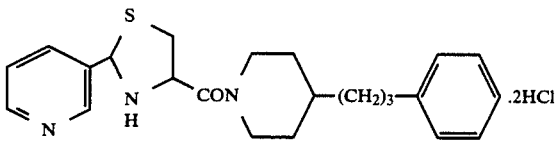

4-(3-Phenylpropyl)-1-[2-(3-
pyridyl)thiazolidin-4-ylcarbonyl]piperidine dihydrochloride (1) Melting point: 104~112° C.
(2) Elemental analysis
(for $C_{23}H_{31}N_3OSCl_2 \cdot 0.4H_2O$):

| | C | H | N | S | Cl |
|---|---|---|---|---|---|
| Calculated: (%) | 58.07 | 6.74 | 8.83 | 6.74 | 14.91 |
| Found: (%) | 58.03 | 6.64 | 8.80 | 6.81 | 14.96 |

Ex. 74

(1) Melting point: 108~116° C.

-continued

Desired Product p-2-Methylpropxy)benzyl]Structure
and Chemical Name | Physicochemical Properties

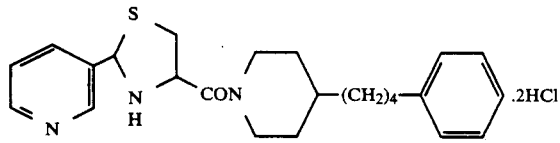

4-(4-Phenylbutyl)-1-[2-(3-pyridyl)-
thiazolidin-4-ylcarbonyl]piperidine dihydrochloride (2) Elemental analysis
(for $C_{24}H_{33}N_3OSCl_2 \cdot 0.8H_2O$):

| | C | H | N | S | Cl |
|---|---|---|---|---|---|
| Calculated: (%) | 58.01 | 7.02 | 8.46 | 6.45 | 14.27 |
| Found: (%) | 57.89 | 6.77 | 8.43 | 6.59 | 14.42 |

Ex. 75

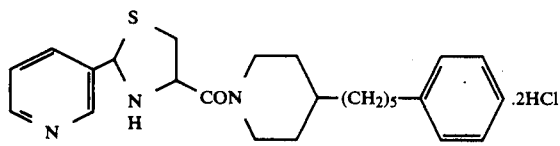

4-(5-Phenylpentyl)-1-[2-(3-pyridyl)-
thiazolidin-4-ylcarbonyl]piperidine dihydrochloride Melting point: 110~118° C.

Elemental analysis
(for $C_{25}H_{33}N_3OSCl_2 \cdot 0.5H_2O$):

| | C | H | N | S | Cl |
|---|---|---|---|---|---|
| Calculated: (%) | 59.40 | 7.18 | 8.31 | 6.36 | 14.03 |
| Found: (%) | 59.56 | 7.21 | 8.36 | 6.47 | 13.89 |

Ex. 76

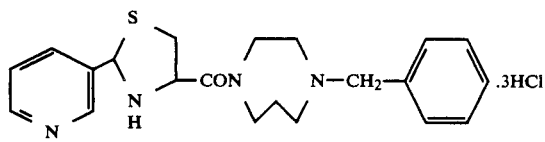

4-Benzyl-1-[2-(3-pyridyl)thiazolidin-
4-ylcarbonyl]homopiperazine trihydrochloride (1) Melting point: 168~175° C.
(2) NMR (DMSO-$d_6$)
δ: 1.80~2.50 (2H, m), 2.82~3.86 (8H, m), 3.86~4.73 (3H, m), 4.36 (2H, brs), 5.50~6.45 (3H, br), 5.94 and 6.16 (s, respectively 1H), 7.35~7.57 (3H, m), 7.57~7.81 (2H, m), 7.92~8.17 (1H, m), 8.57~9.14 (3H, m), 11.08~11.60 (1H, br)
(3) MS: m/z 382 (M$^+$-3HCl)

Ex. 77

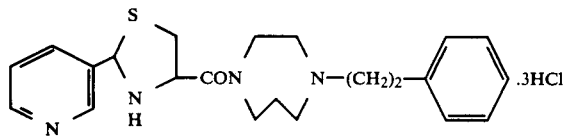

4-2-Phenylethyl)-1-[2-(3-pyridyl)-
thiazolidin-4-ylcarbonyl]homopiperazine trihydrochloride (1) Melting point: 161~169° C.
(2) NMR (DMSO-$d_6$)
δ: 1.91~2.45 (2H, m), 2.95~4.34 (14H, m), 4.45~4.92 (1H, br), 6.02 and 6.21 (s, respectively 1H), 6.40~7.09 (3H, br), 7.31 (5H, s), 7.95~8.20 (1H, m), 8.67~9.22 (3H, m), 11.36~11.87 (1H, br)
(3) MS: m/z 396 (M$^+$-3HCl)

Ex. 78

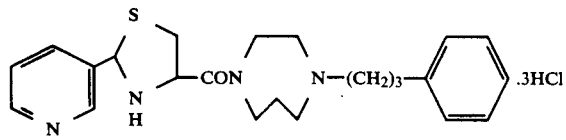

4-(3-Phenylpropyl)-1-[2-(3-pyridyl)-
thiazolidin-4-ylcarbonyl]homopiperazine trihydrochloride (1) Melting point: 162~170° C.
(2) NMR (DMSO-$d_6$)
δ: 1.79~2.30 (4H, m), 2.64 (2H, t, J=7Hz), 2.85~4.31 (12H, m), 4.36~4.75 (1H, br), 5.25~6.10 (3H, br), 5.94 and 6.16 (s, respectively 1H), 7.29 (5H, s), 7.92~8.16 (1H, m), 8.59~9.15 (3H, m), 11.15~11.60 (1H, br)
(3) MS: m/z 410 (M$^+$-3HCl)

Ex. 79

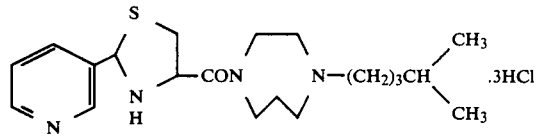

4-(4-Methylpentyl)-1-[2-(3-pyridyl)-
thiazolidin-4-ylcarbonyl]homopiperazine trihydrochloride (1) NMR (DMSO-$d_6$)
δ: 0.87 (6H, d, J=7Hz), 1.02~1.30 (2H, m), 1.39~2.42 (3H, m), 2.82~4.28 (14H, m), 4.50~4.93 (1H, br), 6.03 and 6.21 (s, respectively 1H), 6.11~6.90 (3H, br), 7.96~8.22 (1H, m), 8.66~9.20 (3H, m), 10.95~11.40 (1H, br)
(2) MS: m/z 376 (M$^+$-3HCl)

Ex. 80

(1) NMR (DMSO-$d_6$)

-continued

| Desired Product | |
|---|---|
| p-2-Methylpropxy)benzyl]Structure and Chemical Name | Physicochemical Properties |
| 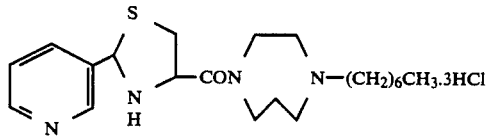<br>4-Heptyl-1-[2-(3-pyridyl)thiazolidin-4-ylcarbonyl]homopiperazine trihydrochloride | δ: 0.87 (3H, t, J=6Hz), 1.08∼1.46 (8H, br s), 1.54∼1.89 (2H, m), 2.04∼2.61 (2H, m), 2.83∼4.36 (14H, m), 4.52∼4.96 (1H, m), 6.05 and 6.24 (s, respectively 1H), 7.97∼8.23 (1H, m), 8.67∼9.60 (6H, m), 11.20∼11.65 (1H, br)<br>(2) MS: m/z 390 (M+-3HCl) |

EXAMPLE 81

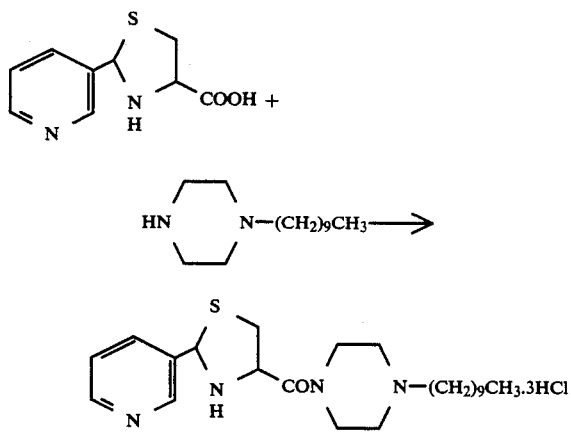

Dicyclohexylcarbodiimide (0.34 g) was added to a mixture of 0.34 g of 2-(3-pyridyl)thiazolidine-4-carboxylic acid, 0.37 g of 1-decylpiperazine, 0.33 g of 1-hydroxybenzotriazole and 10 ml of N,N-dimethylformamide with ice cooling, and the resultant mixture was stirred overnight at room temperature. The reaction mixture was diluted with ethyl acetate, and the insoluble matter was filtered off. The filtrate was washed with saturated aqueous solution of sodium hydrogen carbonate and then with saturated aqueous solution of sodium chloride, dried over anhydrous sodium sulfate and concentrated under reduced pressure Ethyl acetate (5 ml) was added to the residue, and the insoluble matter was filtered off. 2N Hydrogen chloride solution in dioxane was added to the filtrate. The resultant crystals were collected by filtration, washed with ethyl acetate and dried to give 0.63 g of 1-decyl-4-[2-(3-pyridyl)thiazolidin-4-ylcarbonyl]piperazine trihydrochloride. Melting point 170° C.

| Elemental analysis (for $C_{23}H_{41}N_4OSCl_3.H_2O$): | | | | | |
|---|---|---|---|---|---|
| | C (%) | H (%) | N (%) | S (%) | Cl (%) |
| Calculated: | 50.59 | 7.94 | 10.26 | 5.87 | 19.48 |
| Found: | 50.50 | 7.81 | 10.22 | 6.07 | 19.47 |

EXAMPLES 82 TO 85

The following compounds were obtained in the same manner as in Example 81.

| Desired Product | |
|---|---|
| Chemical Structure and Chemical Name | Physicochemical Properties |
| Ex. 82<br><br>1-(3-Methylbutyl)-4-[2-(3-pyridyl)thiazolidin-4-ylcarbonyl]piperazine trihydrochloride | (1) Melting point: 153° C.<br>(2) Elemental analysis<br>(for $C_{18}H_{31}N_4OSCl_3.1.7H_2O$):<br>        C    H    N    S    Cl<br>Calculated: 44.26  7.10  11.47  6.56  21.77 (%)<br>Found:      44.28  6.97  11.47  6.74  21.57 (%) |
| Ex. 83<br><br>1-(4-Oxo-4-phenylbutyl)-4-[2-(3-pyridyl)thiazolidin-4-ylcarbonyl]piperazine trihydrochloride | (1) Melting point: 145° C.<br>(2) Elemental analysis<br>(for $C_{23}H_{30}N_4O_2SCl_3.3/2H_2O$):<br>        C    H    N    S    Cl<br>Calculated: 49.25  6.11  9.99  5.72  18.96 (%)<br>Found:      49.40  5.97  9.79  5.92  18.81 (%) |
| Ex. 84 | (1) Melting point: 155° C. |

| Chemical Structure and Chemical Name | Desired Product Physicochemical Properties |
|---|---|
| 1-(2-Phenylethyl)-4-[2-(3-pyridyl)thiazolidin-4-ylcarbonyl]piperazine trihydrochloride | (2) Elemental analysis (for $C_{21}H_{28}N_4OSCl_3.2/5H_2O$):<br>　　　　　C　　H　　N　　S<br>Calculated: 50.64　5.83　11.25　6.44 (%)<br>Found:　　 50.74　6.11　11.21　6.44 (%) |
| Ex. 85<br>1-(5-Phenylpentyl)-4-[2-(3-pyridyl)thiazolidin-4-ylcarbonyl]piperazine trihydrochloride | (1) Melting point: 136° C.<br>(2) Elemental analysis (for $C_{24}H_{35}N_4OSCl_3.H_2O$):<br>　　　　　C　　H　　N　　S　　Cl<br>Calculated: 52.22　6.76　10.15　5.81　19.27 (%)<br>Found:　　 51.98　6.71　10.12　5.93　19.46 (%) |

EXAMPLE 86

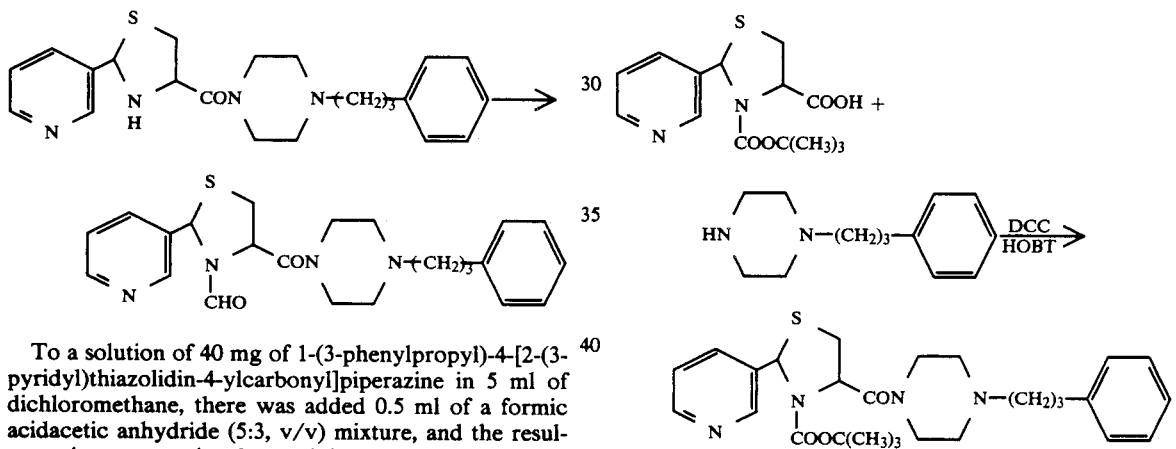

To a solution of 40 mg of 1-(3-phenylpropyl)-4-[2-(3-pyridyl)thiazolidin-4-ylcarbonyl]piperazine in 5 ml of dichloromethane, there was added 0.5 ml of a formic acid-acetic anhydride (5:3, v/v) mixture, and the resultant mixture was stirred overnight at room temperature. Ethyl acetate (20 ml) was added to the reaction mixture, the dilution was washed with 5% aqueous sodium hydrogen carbonate and with water, dried over anhydrous magnesium sulfate and concentrated under reduced pressure to give 30 mg of 1-[3-formyl-2-(3-pyridyl)-thiazolidin-4-ylcarbonyl]-(3-phenylpropyl)piperazine as an oil.

NMR (CDCl$_3$) δ: 1.6~2.0 (2H, m), 2.2~2.8 (8H, m), 3.0~3.4 (2H, m), 3.6~3.9 (4H, m), 5.0~5.7 (1H, m), 6.14 and 6.4 (s, respectively 1H), 7.0~7.5 (5H, m), 7.6~7.9 (1H, m), 8.24 (1H, s), 8.4~8.8 (3H, m)

MS: m/z 424 (M+)

EXAMPLE 87

3-tert-Butoxycarbonyl-2-(3-pyridyl)thiazolidine-4-carboxylic acid (650 mg) and 1-(3-phenylpropyl)piperazine (400 mg) were used as the starting materials and treated in the same manner as in Example 54. Without conversion to the hydrochloride, the product was purified by silica gel column chromatography (eluent ethyl acetate) Thus was obtained 1-[3-(tert-butoxycarbonyl)-2-(3 pyridyl)thiazolidin-4-ylcarbonyl]-4-(3-phenylpropyl)piperazine (560 mg) as an oil.

NMR (CDCl$_3$) δ1.40 (9H, s), 1.6~2.1 (2H, m), 2.2~2.8 (8H, m), 3.0~3.4 (2H, m), 3.4~4.0 (6H, m), 5.08 (1H, br t), 6.16 (1H, br s), 7.0~7.5 (5H, m), 8.4~8.8 (4H, m)

MS: m/z 496 (M+)

EXAMPLES 88 AND 89

The following compounds were obtained in the same manner as in Example 87.

| Chemical Structure and Chemical Name | Desired Product Physicochemical Properties |
|---|---|
| Ex. 88 | (1) MS: m/z 357 (M+) |

-continued

| Desired Product | |
|---|---|
| Chemical Structure and Chemical Name | Physicochemical Properties |
| 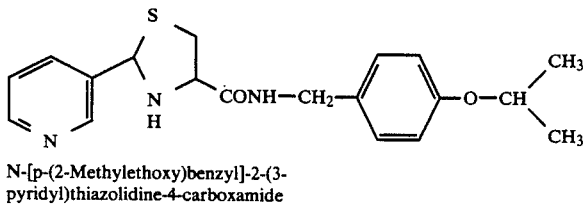<br>N-[p-(2-Methylethoxy)benzyl]-2-(3-pyridyl)thiazolidine-4-carboxamide | (2) NMR (CDCl$_3$)<br>δ: 1.34 (6H, d, J=7Hz), 2,5 (1H, br, exchange with D$_2$O), 3.38 (1H, dd, J=13, 8Hz), 3.73 (1H, dd, J=13, 5Hz), 3.98 and 4.40 (m, respectively 1H), 4.3~4.6 (3H), 5.40 and 5.60 (s, respectively 1H), 6.8~6.9 (2H), 7.1~7.4 (3H), 7.4 (1H, br, exchange with D$_2$O), 7.80 (1H, m), 8.54 (1H, m), 8.68 (1H, m) |
| Ex. 89<br>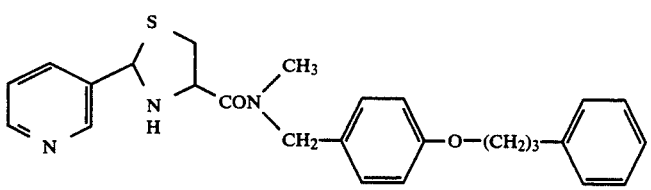<br>N-Methyl-N-[p-(3-phenylpropoxy)benzyl]-2-(3-pyridyl)thiazolidine-4-carboxamide | (1) MS: m/z 447 (M$^+$)<br>(2) NMR (CDCl$_3$)<br>δ: 2.0~2.3 (2H), 2.6~3.5 (5H), 3.01 and 3.03 (s, respectively 3H), 3.96 (2H, t, J=7Hz), 3.9~4.1 (1H), 4.6 (2H, br s), 5.58 and 5.98 (s, respectively 1H), 6.8~7.4 (10H), 7.7~8.0 (1H), 8.4~8.7 (1H), 8.75 (1H, br s) |

EXAMPLE 90

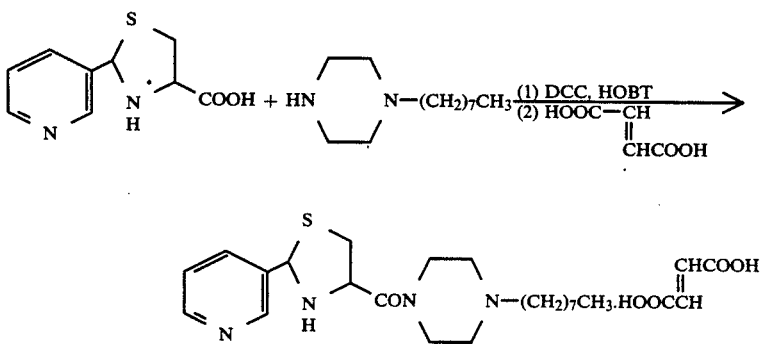

Dicyclohexylcarbodiimide (0.82 g) was added to a mixture of 0.84 g of 2-(3-pyridyl)thiazolidine-4-carboxylic acid, 0.79 g of 1-octylpiperazine, 0.54 g of 1-hydroxybenzotriazole and 20 ml of N,N-dimethylformamide with ice cooling, and the resultant mixture was stirred overnight at room temperature. The reaction mixture was diluted with ethyl acetate, and the insoluble matter was filtered off. The filtrate was washed in sequence with saturated aqueous solution of sodium hydrogen carbonate, water and saturated aqueous solution of sodium chloride, and dried over anhydrous magnesium sulfate. The solvent was then distilled off under reduced pressure. Ethyl acetate was added to the residue, the insoluble matter was filtered off, and the filtrate was concentrated under reduced pressure. The residue was purified by silica gel column chromatography (eluent 10% methanol-ethyl acetate), the oil obtained was dissolved in 25 ml of ethanol, and 0.32 g of fumaric acid was added. After allowing the mixture to stand for 2 days, the resultant crystals were collected by filtration, washed with cold ethanol and dried. Thus was obtained 0.72 g of 1-octyl-4-[2-(3-pyridyl)thiazolidin-4-ylcarbonyl]piperazine fumarate. Melting point 135° C.

| Elemental analysis (for C$_{25}$H$_{38}$N$_4$O$_5$S): | | | | |
|---|---|---|---|---|
| | C (%) | H (%) | N (%) | S (%) |
| Calculated: | 59.27 | 7.56 | 11.06 | 6.33 |
| Found: | 59.01 | 7.66 | 10.95 | 6.27 |

EXAMPLES 91 TO 94

The following compounds were obtained in the same manner as in Example 90.

| Desired Product | |
|---|---|
| Chemical Structure and Chemical Name | Physicochemical Properties |
| Ex. 91 | (1) Melting point: 175° C. |

-continued

| Chemical Structure and Chemical Name | Desired Product Physicochemical Properties |
|---|---|
| 1-(3-Phenylpropyl)-4-[2-(3-pyridyl)thiazolidin-4-ylcarbonyl]piperazine fumarate | (2) Elemental analysis (for $C_{26}H_{32}N_4O_5S$):<br>          C    H    N    S<br>Calculated: 60.92  6.29  10.93  6.26 (%)<br>Found:    60.62  6.25  10.79  6.17 (%) |
| Ex. 92<br>1-Hexyl-4-[2-(3-pyridyl)thiazolidin-4-ylcarbonyl]piperazine fumarate | (1) Melting point: 128° C.<br>(2) Elemental analysis (for $C_{23}H_{34}N_4O_5S$):<br>          C    H    N    S<br>Calculated: 57.72  7.16  11.71  6.70 (%)<br>Found:    57.60  7.22  11.61  6.60 (%) |
| Ex. 93<br>1-(4-Methylpentyl)-4-[2-(3-pyridyl)thiazolidin-4-ylcarbonyl]piperazine fumarate | (1) Melting point: 148° C.<br>(2) Elemental analysis (for $C_{23}H_{34}N_4O_5S$):<br>          S<br>Calculated: 6.70 (%)<br>Found:    6.78 (%) |
| Ex. 94<br>1-Heptyl-4-[2-(3-pyridyl)thiazolidin-4-ylcarbonyl]piperazine fumarate | (1) Melting point: 153° C.<br>(2) Elemental analysis (for $C_{24}H_{36}N_4O_5S$):<br>          C    H    N    S<br>Calculated: 58.51  7.37  11.37  6.51 (%)<br>Found:    58.46  7.38  11.28  6.63 (%) |

EXAMPLES 95 TO 131

The following compounds of Examples 95 to 105 compounds of Examples 106 to 116 and compounds of Examples 117 to 131 were obtained in the same manner as in Examples 54, 87 and 90, respectively.

| Chemical Structure and Chemical Name | Desired Product Physicochemical Properties |
|---|---|
| Ex. 95<br>1-[5,5-Dimethyl-2-(3-pyridyl-thiazolidin-4-ylcarbonyl]-4-(3-phenylpropyl)piperazine trihydrochloride | (1) NMR (DMSO-$d_6$)<br>δ: 1.22~1.80 (6H, m), 1.92~2.28 (1H, m), 2.44~2.80 (2H, m), 2.84~4.88 (11H, m), 6.00~6.18 (1H), 7.12~7.48 (5H, m), 7.92~8.12 (1H, m), 8.52~8.72 (1H, m), 8.78~9.04 (2H, m)<br>(2) MS: (FAB) m/z 452 ($M^+$ +1-3HCl) |
| Ex. 96 | (1) Melting point: 143~145° C. |

-continued

| | Desired Product | |
|---|---|---|
| Chemical Structure and Chemical Name | | Physicochemical Properties |

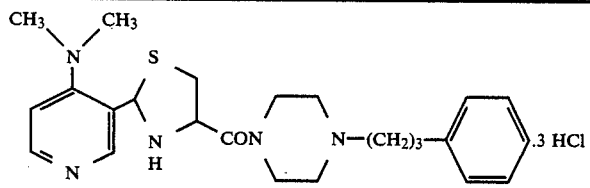

1-[2-(4-Dimethylamino-3-pyridyl-thiazolidin-4-ylcarbonyl]-4-(3-phenylpropyl)piperazine trihydrochloride (2) Elemental analysis
(for $C_{24}H_{36}N_5OSCl_3 \cdot 2H_2O$):

| | C | H | N | S | Cl |
|---|---|---|---|---|---|
| Calculated: (%) | 49.27 | 6.89 | 11.97 | 5.48 | 18.18 |
| Found: (%) | 49.35 | 6.50 | 11.56 | 5.65 | 17.91 |

Ex. 97

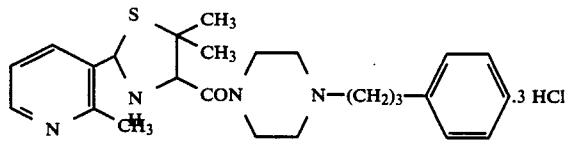

1-[2-(2-Methyl-3-pyridyl)thiazolidin-4-ylcarbonyl]-4-(3-phenylpropyl)-piperazine trihydrochloride (1) Melting point: 138~140° C.
(2) Elemental analysis (for $C_{23}H_{33}N_4OSCl_3$):

| | C | H | N | S |
|---|---|---|---|---|
| Calculated: (%) | 49.69 | 6.71 | 10.08 | 5.77 |
| Found: (%) | 49.78 | 6.51 | 9.97 | 5.74 |

Ex. 98

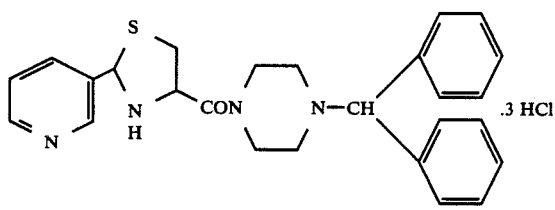

1-Benzhydryl-4-[2-(3-pyridyl)thiazolidin-4-ylcarbonyl]piperazine trihydrochloride (1) Melting point: 173~174° C.
(2) Elemental analysis
(for $C_{26}H_{31}N_4O_2SCl_3 \cdot 1.8H_2O$):

| | C | H | N | S |
|---|---|---|---|---|
| Calculated: (%) | 53.25 | 5.95 | 9.55 | 5.47 |
| Found: (%) | 53.41 | 5.83 | 9.48 | 5.27 |

Ex. 99

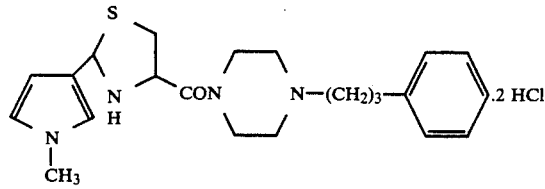

1-[2-(1-Methyl-3-pyrrolyl)thiazolidin-4-ylcarbonyl]-4-(3-phenylpropyl)piperazine dihydrochloride (1) Melting point: 125° C.
(2) Elemental analysis
(for $C_{22}H_{32}N_4OSCl_2 \cdot 1.5H_2O$):

| | C | H | N | S | Cl |
|---|---|---|---|---|---|
| Calculated: (%) | 53.01 | 7.08 | 11.24 | 6.43 | 14.22 |
| Found: (%) | 52.97 | 6.89 | 10.93 | 6.60 | 14.35 |

Ex. 100

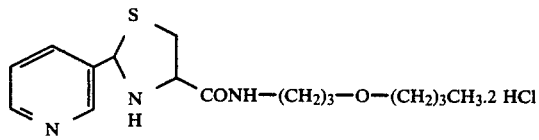

N-(3-Butoxypropyl)-2-(3-pyridyl)thiazolidine-4-carboxamide dihydrochloride (1) Melting point: 125~130° C.
(2) Elemental analysis
(for $C_{16}H_{27}N_3O_2SCl_2$):

| | C | H | N | S |
|---|---|---|---|---|
| Calculated: (%) | 48.48 | 6.87 | 10.60 | 8.09 |
| Found: (%) | 48.18 | 6.85 | 10.26 | 8.17 |

Ex. 101

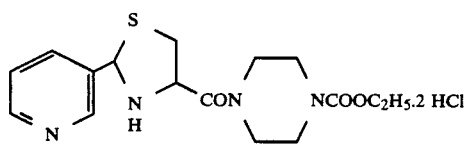

1-Ethoxycarbonyl-4-[2-(3-pyridyl)thiazolidin-4-ylcarbonyl]-piperazine dihydrochloride (1) Melting point: 168° C.
(2) Elemental analysis (for $C_{16}H_{24}N_4O_3SCl_2$):

| | C | H | N |
|---|---|---|---|
| Calculated: (%) | 45.39 | 5.71 | 13.23 |
| Found: (%) | 45.12 | 5.52 | 13.02 |

Ex. 102

(1) Melting point: 65~70° C.

-continued

Desired Product

| Chemical Structure and Chemical Name | Physicochemical Properties |
|---|---|
| 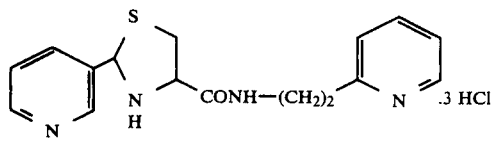<br>N-[2-(2-Pyridyl)ethyl]-2-(3-pyridyl)thiazolidine-4-carboxamide trihydrochloride | (2) Elemental analysis (for $C_{16}H_{21}N_4OSCl_3 \cdot 1.6H_2O$):<br>         C    H    N    S    Cl<br>Calculated: 42.46  5.39  12.38  7.08  23.50 (%)<br>Found:     42.41  5.33  12.13  6.91  23.46 (%) |
| Ex. 103<br>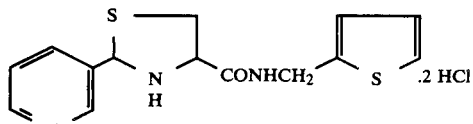<br>N-(2-Thienylmethyl)-2-(3-pyridyl)thiazolidine-4-carboxamide dihydrochloride | (1) Melting point: 109~111° C.<br>(2) Elemental analysis (for $C_{14}H_{17}N_3OS_2Cl_2 \cdot 0.9H_2O$):<br>         C    H    N    S<br>Calculated: 42.62  4.80  10.65  16.25 (%)<br>Found:     42.80  4.77  10.74  16.00 (%) |
| Ex. 104<br>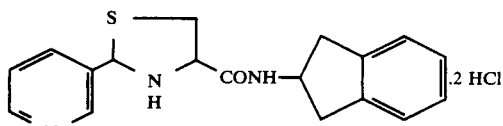<br>N-(2- Indanyl)-2-(3-pyridyl)thiazolidine-4-carboxamide dihydrochloride | (1) Melting point: 124~127° C.<br>(2) Elemental analysis (for $C_{18}H_{21}N_3OSCl_2$):<br>         C    H    N    S<br>Calculated: 54.27  5.31  10.55  8.05 (%)<br>Found:     54.11  5.36  10.31  7.95 (%) |
| Ex. 105<br>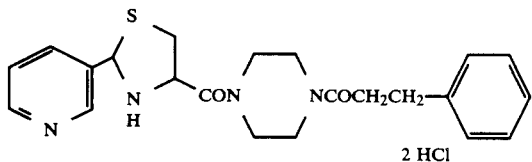<br>1-(3-Phenylpropionyl)-4-[2-(3-pyridyl)thiazolidin-4-ylcarbonyl]-piperazine dihydrochloride | (1) Melting point: 130° C.<br>(2) NMR (DMSO-$d_6$)<br>δ: 2.6~2.8 (4H, m), 3.3~3.8 (8H, m), 4.5~4.9 (1H, m), 5.98 and 6.20 (s, respectivley 1H), 7.26 (5H, s), 7.9~8.2 (1H, m), 8.6~9.2 (3H, m) |
| Ex. 106<br>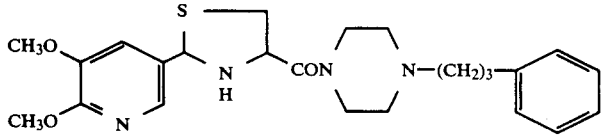<br>1-[2-(5,6-Dimethoxy-3-pyridyl)thiazolidin-4-ylcarbonyl]-4-(3-phenylpropyl)piperazine | (1) NMR (DMSO-$d_6$)<br>δ: 1.52~1.96 (2H, m), 2.18~2.72 (8H, m), 2.90~4.40 (13H, m), 5.40~5.84 (1H, m), 7.12~7.40 (5H, m), 7.40~7.50 (1H, m), 7.70~7.84 (1H, m)<br>(2) MS: m/z 456 ($M^+$) |
| Ex. 107<br>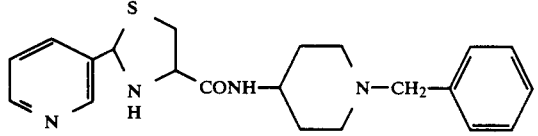<br>N-(1-Benzyl-4-piperidinyl)-2-(3-pyridyl)thiazolidine-4-carboxamide | (1) Melting point: 131~134° C.<br>(2) Elemental analysis (for $C_{21}H_{26}N_4OS$):<br>         C    H    N    S<br>Calculated: 65.94  6.85  14.65  8.38 (%)<br>Found:     65.69  6.83  14.46  8.43 (%) |
| Ex. 108<br>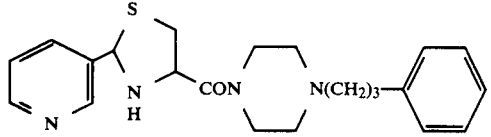<br>1-(3-Phenylpropyl)-4-[2-(3-pyridyl)thiazolidin-4-ylcarbonyl]piperazine | (1) NMR (CDCl$_3$)<br>δ: 1.6~2.0 (2H, m), 2.2~3.8 (14H, m), 3.8~4.2 (1H, m), 5.62 and 5.98 (d, respectively 1H), 7.0~7.5 (6H, m), 7.7~8.0 (1H, m), 8.4~8.7 (1H, m), 8.7~8.9(1H, m) |
| Ex. 109 | (1) Melting point: 169~170° C. |

-continued

| Chemical Structure and Chemical Name | Physicochemical Properties |
|---|---|
| 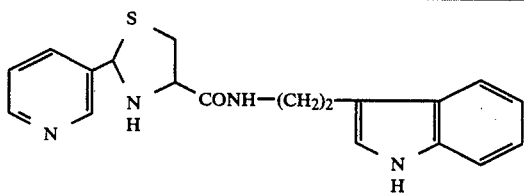<br>N-[2-(3-Indolyl)ethyl]-2-(3-pyridyl)thiazolidine-4-carboxamide | (2) Elemental analysis (for $C_{19}H_{20}N_4OS$):<br>　　　　　　C　　H　　N　　S<br>Calculated: 64.75　5.72　15.90　9.10<br>(%)<br>Found:　　64.52　5.67　15.70　9.07<br>(%) |
| Ex. 110<br>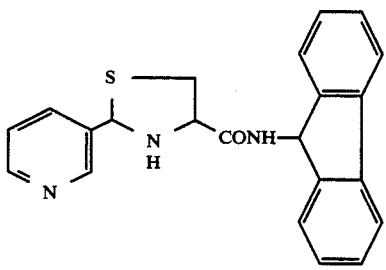<br>N-(9-Fluorenyl)-2-(3-pyridyl)thiazolidine-4-carboxamide | (1) Melting point: 194~196° C.<br>(2) Elemental analysis (for $C_{22}H_{19}N_3OS$):<br>　　　　　　C　　H　　N　　S<br>Calculated: 70.75　5.13　11.25　8.59<br>(%)<br>Found:　　70.51　5.16　10.99　8.51<br>(%) |
| Ex. 111<br>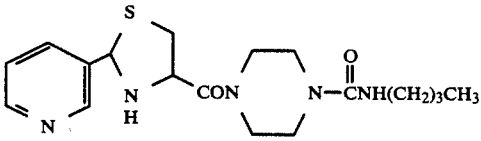<br>1-Butylaminocarbonyl-4-[2-(3-pyridyl)thiazolidin-4-ylcarbonyl]piperazine | (1) NMR (CDCl$_3$)<br>δ: 0.94 (3H, t), 1.1~1.7 (4H, m),<br>3.0~3.8 (12H, m), 3.9~4.3 (1H, m),<br>5.58 and 5.94 (s, respectively<br>1H), 7.2~7.4 (1H, m), 7.7~8.0 (1H,<br>m), 8.4~8.6 (1H, m), 8.6~8.8 (1H,<br>m)<br>(2) MS: m/z 378 (M$^+$+1) |
| Ex. 112<br>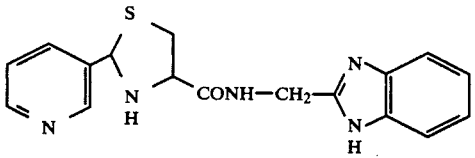<br>N-(2-Benzimidazolyl)methyl-2-(3-pyridyl)thiazolidine-4-carboxamide | (1) Melting point: 96~99° C.<br>(2) NMR (CDCl$_3$)<br>δ: 3.2~3.7 (2H), 4.3 (1H, m), 4.6~4.8<br>(2H), 5.5~5.6 (1H), 7.2~7.4 (3H),<br>7.5~7.6 (3H), 7.7~7.9 (1H), 8.4~8.6<br>(2H), 8.66 (1H, d, J=3Hz)<br>(3) MS: m/z 339 (M$^+$) |
| Ex. 113<br>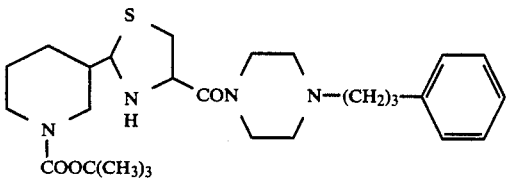<br>1-[2-(1-tert-Butoxycarbonyl-3-piperidinyl)thiazolidin-4-ylcarbonyl]-4-(3-phenylpropyl)piperazine | (1) Elemental analysis (for $C_{27}H_{42}N_4O_3S$):<br>　　　　　　C　　H　　N　　S<br>Calculated: 64.51　8.42　11.14　6.38<br>(%)<br>Found:　　64.21　8.45　10.83　6.38<br>(%)<br>(2) MS: m/z 502 (M+) |
| Ex. 114<br>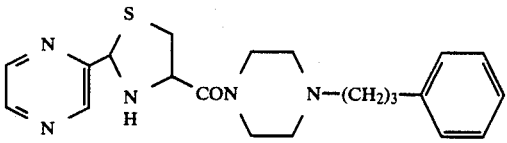<br>1-(3-Phenylpropyl)-4-[2-(2-pyrazyl)thiazolidine-4-ylcarbonyl]piperazine | (1) NMR (CDCl$_3$)<br>δ: 1.6~2.0 (2H, m), 2.2~2.8 (8H, m),<br>3.0~3.4 (2H, m), 3.5~4.0 (4H, m),<br>4.0~4.2 (1H, m), 5.67 and 5.80<br>(s, respectively 1H), 7.1~7.3<br>(5H, m), 8.6~8.8 (3H, m)<br>(2) MS: m/z 397 (M+) |
| Ex. 115 | (1) NMR (CDCl$_3$) |

-continued

Desired Product

| Chemical Structure and Chemical Name | Physicochemical Properties |
|---|---|
| 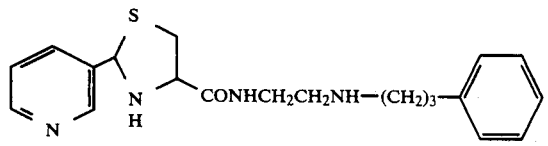<br>N-(3-Phenylpropylaminoethyl)-2-(3-pyridyl)thiazolidine-4-carboxamide | δ: 1.45~2.16 (4H, m), 2.45~3.05 (6H, m), 3.10~3.75 (4H, m), 4.08~4.40 (1H, br), 5.36~5.70 (1H, br d, J=10Hz), 6.92~7.41 (6H, m), 7.53 (1H, br s), 7.68~7.96 (1H, m), 8.40~8.82 (2H, m)<br>(2) MS: m/z 371 (M⁺+1) |
| Ex. 116<br>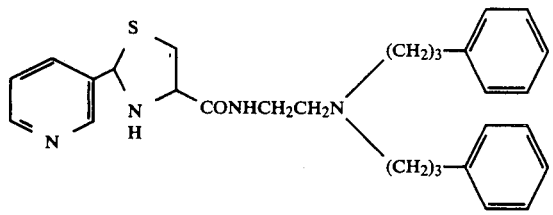<br>N-Di(3-phenylpropyl)aminoethyl)-2-(3-pyridyl)thiazolidine-4-carboxamide | (1) NMR (CDCl₃)<br>δ: 1.52~2.10 (5H, m), 2.32~2.75 (10H, m), 3.14~3.77 (4H, m), 4.15~4.40 (1H, m), 5.43 (0.7H, d, J=12Hz), 5.55 (0.3H, d, J=12Hz), 7.00~7.41 (11H, m), 7.41~7.93 (2H, m), 8.46~8.74 (2H, m)<br>(2) MS: m/z 489 (M⁺+1) |
| Ex. 117<br>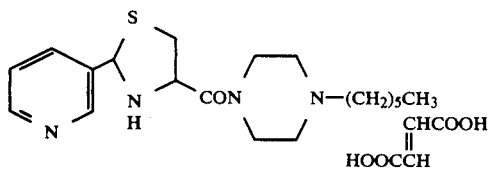<br>1-Hexyl-4-[2-(3-pyridyl)thiazolidin-4-yl-carbonyl]piperazine fumarate | (1) Melting point: 128° C.<br>(2) Elemental analysis (for C₂₃H₃₄N₄O₅S):<br>　　　　　C　　H　　N　　S<br>Calculated: 57.72　7.16　11.71　6.70 (%)<br>Found:　　 57.60　7.22　11.61　6.61 (%) |
| Ex. 118<br>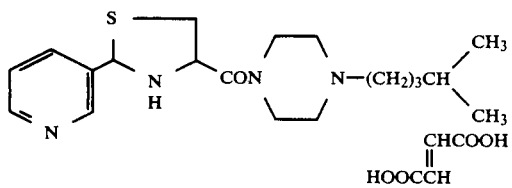<br>1-(4-Methylpentyl)-4-[2-(3-pyridyl)thiazolidin-4-yl-carbonyl]piperazine fumarate | (1) Melting point: 145~148° C.<br>(2) NMR (DMSO-d₆)<br>δ: 0.83 (6H, d, J=6Hz), 0.97~1.16 (5H, m), 2.24~2.76 (6H, m), 2.84~3.90 (6H, m), 4.29 (1H, q, J=7Hz), 5.58 (0.5H, s), 5.88 (0.5H, s), 6.61 (2H, s), 7.25~7.57 (1H, m), 7.75~8.08 (1H, m), 8.39~8.80 (2H, m)<br>(3) MS: m/z 362 (M⁺—C₄H₄O₄) |
| Ex. 119<br>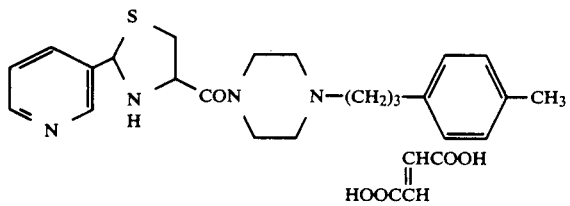<br>1-[2-(3-Pyridyl)thiazolidin-4-ylcarbonyl]-4-[3-(p-tolyl)-propyl]piperazine fumarate | (1) Melting point: 178~181° C.<br>(2) Elemental analysis (for C₂₇H₃₄N₄O₅S):<br>　　　　　C　　H　　N　　S<br>Calculated: 61.58　6.51　10.64　6.09 (%)<br>Found:　　 61.20　6.47　10.52　6.26 (%) |
| Ex. 120<br>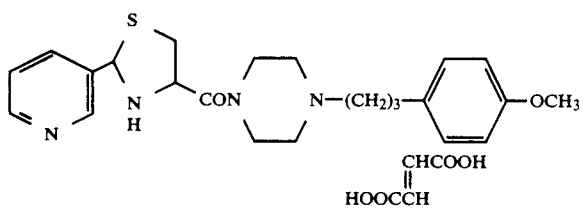<br>1-[3-(p-Methoxyphenyl)propyl]-4-[2-(3-pyridyl)thiazolidin-4-ylcarbonyl]piperazine fumarate | Melting point: 141~143° C.<br>Elemental analysis (for C₂₇H₃₄N₄O₆S):<br>　　　　　C　　H　　N　　S<br>Calculated: 59.76　6.32　10.32　5.91 (%)<br>Found:　　 59.50　6.31　10.28　5.98 (%) |

-continued

Desired Product

| Chemical Structure and Chemical Name | Physicochemical Properties |
|---|---|
| Ex. 121 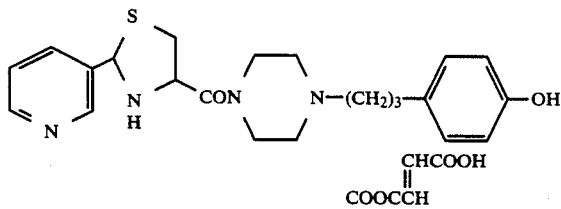<br>1-[3-(p-Hydroxyphenyl)propyl]-4-[2-(3-pyridyl)thiazolidin-4-ylcarbonyl]piperazine fumarate | (1) Melting point: 182~185° C.<br>(2) Elemental analysis (for $C_{26}H_{32}N_4O_6S$):<br>            C     H     N     S<br>Calculated: 59.07  6.10  10.60  6.07 (%)<br>Found:     58.68  6.03  10.44  6.07 (%) |
| Ex. 122 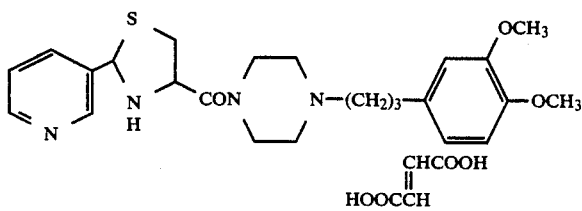<br>1-[3-(3,4-Dimethoxyphenyl)propyl]-4-[2-(3-pyridyl)thiazolidin-4-yl-carbonyl]piperazine fumarate | (1) NMR (DMSO-$d_6$)<br>δ: 1.53~1.95 (2H, m), 2.20~2.68 (8H, m), 2.83~3.89 (6H, m), 3.72 (3H, s), 3.74 (3H, s), 4.28 (1H, q, J=7Hz), 5.55 (0.5H, s), 5.88 (0.5H, s), 6.65 (2H, s), 6.69~6.95 (3H, m), 7.25~7.51 (1H, m), 7.74~8.05 (1H, m), 8.39~8.74 (2H, m)<br>(2) MS: m/z 457 ($M^+$ + 1-$C_4H_4O_4$) |
| Ex. 123 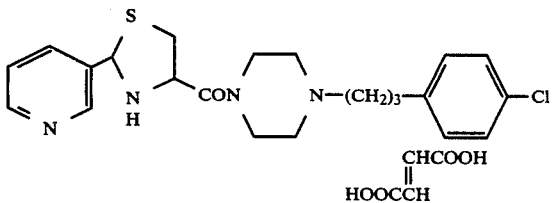<br>1-[3-(p-Chlorophenyl)propyl]-4-[2-(3-pyridyl)thiazolidin-4-ylcarbonyl]piperazine fumarate | (1) Melting point: 187~189° C.<br>(2) Elemental analysis (for $C_{26}H_{31}N_4O_5SCl$):<br>           C    H    N    Cl    S<br>Calculated: 57.08  5.71  10.24  6.48  5.86 (%)<br>Found:     57.27  5.77  10.17  6.20  5.82 (%) |
| Ex. 124 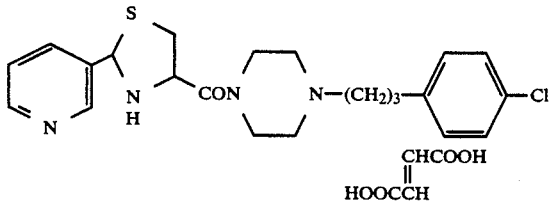<br>1-[3-(p-Fluorophenyl)propyl]-4-[2-(3-pyridyl)thiazolidin-4-ylcarbonyl]piperazine fumarate | (1) Melting point: 171~172° C.<br>(2) Elemental analysis (for $C_{26}H_{31}N_4O_5FS$):<br>           C    H    N    F    S<br>Calculated: 58.85  5.89  10.56  3.58  6.04 (%)<br>Found:     58.82  5.93  10.50  3.33  6.21 (%) |
| Ex. 125 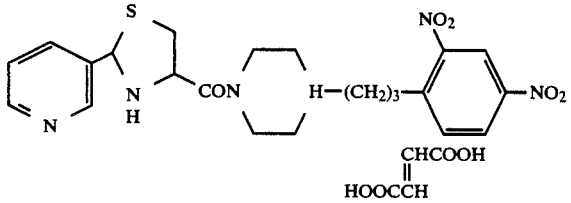<br>1-[3-(2,4-Dinitrophenyl)propyl]-4-[2-(3-pyridyl)thiazolidin-4-ylcarbonyl]piperazine fumarate | (1) NMR (DMSO-$d_6$)<br>δ: 1.60~2.05 (2H, m), 2.19~2.66 (6H, m), 2.80~3.78 (8H, m), 4.10~4.42 (1H, m), 5.58 (0.5H, s), 5.89 (0.5H, s), 6.63 (2H, s), 7.26~7.57 (1H, m), 7.72~8.08 (2H, m), 8.35~8.84 (4H, m)<br>(2) MS: m/z 487 ($M^+$ + 1-$C_4H_4O_4$) |
| Ex. 126 | (1) NMR (DMSO-$d_6$) |

-continued

| | Desired Product | |
|---|---|---|
| Chemical Structure and Chemical Name | | Physicochemical Properties |

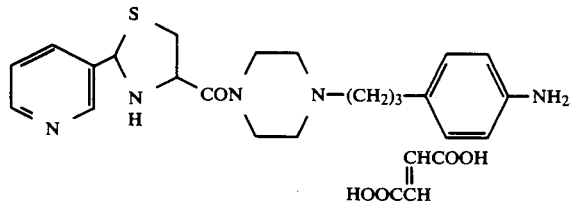

1-[3-(p-Aminophenyl)propyl]-4-[2-(3-pyridyl)thiazolidin-4-ylcarbonyl]piperazine fumarate δ: 1.48~1.89 (2H, m), 2.18~2.68 (8H, m), 2.81~3.76 (6H, m), 4.16~4.43 (1H, m), 5.58 (0.5H, s), 5.89 (0.5H, s), 6.49 (1H, d, J=9Hz), 6.63 (2H, s), 6.83 (1H, d, J=9Hz), 7.25~7.52 (1H, m), 7.74~8.15 (1H, m), 8.41~8.81 (2H, m)
(2) MS: m/z 411 ($M^+ - C_4H_4O_4$)

Ex. 127

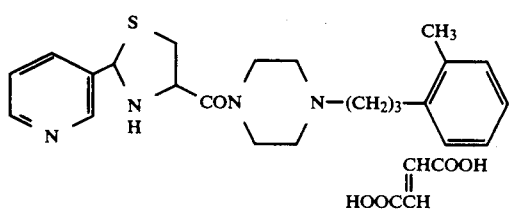

1-[3-(o-Methylphenyl)propyl]-4-[2-(3-pyridyl)thiazolidin-4-ylcarbonyl]piperazine fumarate (1) Melting point: 151~153° C.
(2) Elemental analysis (for $C_{27}H_{34}N_4O_5S$):

| | C | H | N | S |
|---|---|---|---|---|
| Calculated (%): | 61.58 | 6.51 | 10.64 | 6.09 |
| Found (%): | 61.33 | 6.41 | 10.58 | 6.10 |

Ex. 128

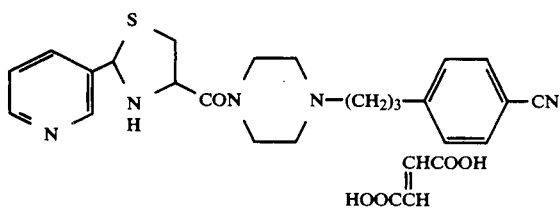

1-[3-(p-Cyanophenyl)propyl]-4-[2-(3-pyridyl)thiazolidin-4-ylcarbonyl]piperazine fumarate (1) NMR (DMSO-d$_6$)
δ: 1.58~1.92 (2H, m), 2.16~2.80 (8H, m), 2.80~3.68 (6H, m), 4.12~4.42 (1H, m), 5.55 (0.3H, s), 5.87 (0.7H, s), 6.65 (2H, s), 7.25~7.53 (3H, m), 7.65~8.03 (3H, m), 8.36~8.73 (2H, m)
(2) MS: m/z 421 ($M^+ - C_4H_4O_4$)

Ex. 129

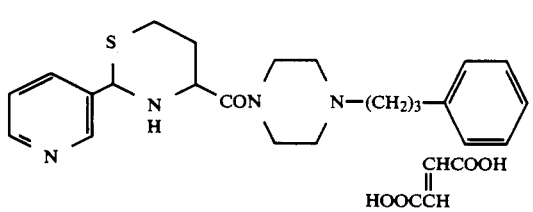

1-(3-Phenylpropyl)-4-[2-(3-pyridyl)-3,4,5,6-tetrahydro-2H-thiazin-4-yl-carbonyl]piperazine fumarate (1) NMR (DMSO-d$_6$)
δ: 1.59~1.9 (4H, m), 2.2~2.8 (8H, m), 2.8~3.6 (6H, m), 3.9~4.2 (1H, m), 5.6 (1H, s), 6.66 (2H, s), 7.1~7.6 (6H, m), 7.6~8.0 (1H, m), 8.4~8.8 (2H, m)
(2) MS: m/z 410 ($M^+ - C_4H_4O_4$)

Ex. 130

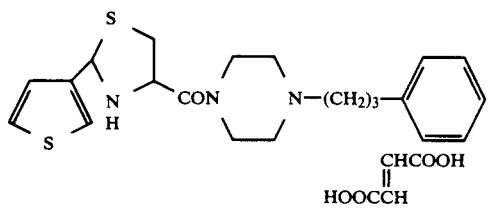

1-(3-Phenylpropyl)-4-[2-(3-thienyl)thiazolidin-4-ylcarbonyl]piperazine fumarate (1) Melting point: 152~155° C. (decomposition)
(2) Elemental analysis (for $C_{25}H_{31}N_3O_5S_2$):

| | C | H | N | S |
|---|---|---|---|---|
| Calculated (%): | 58.01 | 6.04 | 8.12 | 12.39 |
| Found (%): | 58.04 | 6.04 | 8.11 | 12.62 |

Ex. 131

(1) Melting point: 173~175° C.

-continued

Desired Product

| Chemical Structure and Chemical Name | Physicochemical Properties |
|---|---|
| 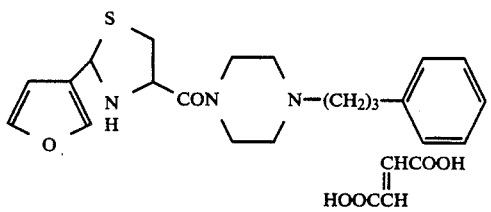<br>1-(3-Phenylpropyl)-4-[2-(3-furyl)thiazolidin-4-ylcarbonyl]piperazine fumarate | (2) Elemental analysis (for $C_{25}H_{31}N_3O_6S$):<br>　　　　　　　C　　H　　N　　S<br>Calculated: 59.86　6.23　8.38　6.39<br>(%)<br>Found:　　59.76　6.14　8.37　6.47<br>(%) |

EXAMPLE 132

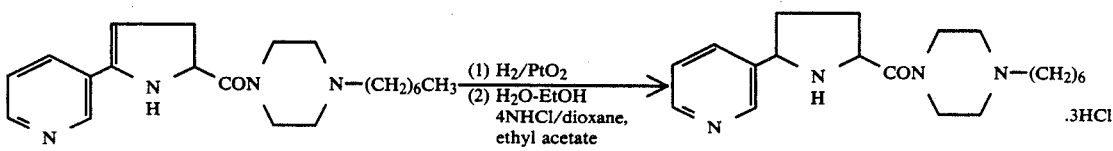

1-Heptyl-4-[2-(3-pyridyl)-2-pyrrolin-5-ylcarbonyl]-piperazine (570 mg) was catalytically reduced in 20 ml of water plus 20 ml of ethanol in the presence of platinum oxide as the catalyst until cessation of the absorption of hydrogen. The catalyst was filtered off, the filtrate was concentrated under reduced pressure, and the residue was subjected to silica gel column chromatography (5 g). Elution with methanol ethyl acetate (1:10, v/v) gave 250 mg of 1-heptyl-4-[5-(3-pyridyl)pyrrolidin-2-ylcarbonyl]piperazine. This product was converted to its trihydrochloride (180 mg) in the same manner as in Example 54. Melting point 138°–143° C.

| Elemental analysis (for $C_{21}H_{37}N_4OCl_3 \cdot 1.8H_2O$): | | | |
|---|---|---|---|
| C (%) | H (%) | N (%) | Cl (%) |
| Calculated: 50.41 | 8.18 | 11.20 | 21.26 |
| Found:　　50.49 | 7.83 | 11.09 | 21.10 |

EXAMPLE 133

The following compound was obtained in the same manner as in Example 132 except that the treatment with a hydrogen chloride was not carried out.

Desired Product

| Chemical Structure and Chemical Name | Physicochemical Properties |
|---|---|
| 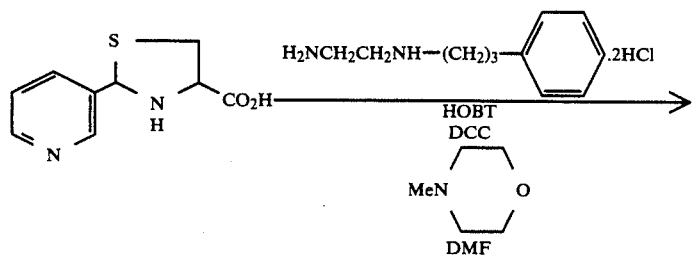<br>1-(3-Phenylpropyl)-4-[5-(3-pyridyl)pyrrolidin-2-ylcarbonyl]piperazine | (1) NMR ($CDCl_3$)<br>δ: 1.56~2.88 (15H, m),<br>3.43~3.90 (4H, m),<br>3.99~4.34 (2H, m),<br>7.04~7.44 (6H, m), 7.91<br>(1H, dt, J=2Hz,<br>J=8Hz), 8.53 (1H, dd,<br>J=2Hz, J=5Hz), 8.65<br>(1H, d, J=2Hz).<br>(2) MS: m/z 378 ($M^+$) |

EXAMPLE 134

-continued

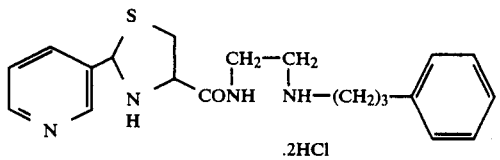
.2HCl

To a solution of 200 mg of 3-phenylpropylethylenediamine and 81 mg of N-methylmorpholine in 5 ml of dimethylformamide, there were added in sequence 120 mg of 1-hydroxybenzotriazole, 180 mg of dicyclohexylcarbondiimide and 170 mg of 2-(3-pyridyl)thiazolidine-4-carboxylic acid. The mixture was stirred overnight at room temperature. The reaction mixture was diluted with ethyl acetate, the insoluble matter was filtered off, and the filtrate was concentrated under reduced pressure. After addition of 0.5N aqueous sodium hydroxide, the residue was extracted with ethyl acetate. The organic layer was extracted with 1N hydrochloric acid, and the aqueous layer was adjusted to pH 10 with potassium carbonate and extracted again with ethyl acetate The organic layer was washed with saturated aqueous solution of sodium chloride, dried over anhydrous sodium sulfate and concentrated under reduced pressure. The residue was subjected to alumina column chromatography (20 g). Elution with methanol-ethyl acetate (1:10) gave 160 mg of N-(3-phenylpropylaminoethyl)-2-(3-pyridyl)thiazolidine-4-carboxamide. The NMR and MS data for this compound were in agreement with those given in Examples 115.

EXAMPLE 135

-continued

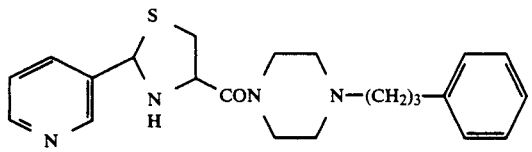

A solution of 40 mg of 1-(3-phenylpropyl)piperazine in 0.5 ml of dimethyl sulfoxide was added to a solution of 50 mg of 1,3-dioxo-5-(3-pyridyl)thiazolidino[3,4-c]oxazolidine hydrochloride in 1 ml of dimethyl sulfoxide at room temperature. The reaction mixture was stirred for 2 hours at room temperature, then diluted with ethyl acetate, washed in sequence with saturated aqueous solution of sodium hydrogen carbonate, water and saturated aqueous solution of sodium chloride, dried over anhydrous sodium sulfate and concentrated under reduced pressure to give 70 mg of 1-(3-phenylpropyl)-4-[2-(3-pyridyl)thiazolidin-4-ylcarbonyl]piperazine. The physicochemical properties of this product were in agreement with those of the compound of Example 108.

EXAMPLE 136

The following compound was obtained in the same manner as in Example 135.

| Desired Product | |
|---|---|
| Chemical Structure and Chemical Name | Physicochemical Properties |
| ![structure] CONH—(CH$_2$)$_3$—N◯ O.3HCl<br>N-(3-morpholinopropyl)-2-(3-pyridyl)thiazolidine-4-carboxamide trihydrochloride | (1) Melting point: 92~96° C.<br>(2) Elemental analysis<br>(for C$_{16}$H$_{27}$N$_4$O$_2$SCl$_3$.1.5 H$_2$O):<br>          C    H    N    S    Cl<br>Calculated: 40.64  6.39  11.85  6.78  22.49<br>(%)<br>Found:      40.72  6.12  11.58  6.90  22.62<br>(%) |

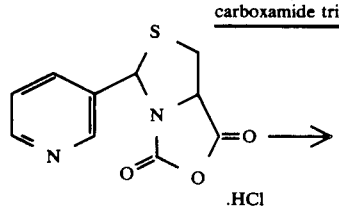
.HCl

EXAMPLE 137

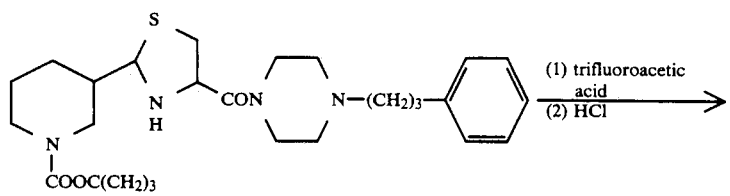

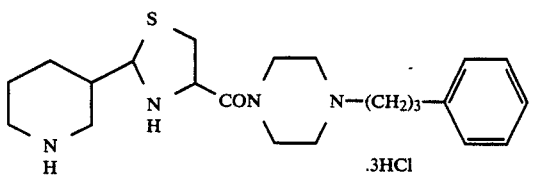
.3HCl

1-[2-(1-tert-Butoxycarbonyl-3-piperidinyl)thiazolidin-4-ylcarbonyl]-4-(3-phenylpropyl)piperazine (430 mg) was dissolved in 3 ml of dichloromethane, followed by addition of 2 ml of trifluoroacetic acid. The mixture was stirred at room temperature for 6 hours. The reaction mixture was poured into 60 ml of saturated aqueous solution of sodium hydrogen carbonate, and the product was extracted with ethyl acetate. The ethyl acetate layer was washed with saturated aqueous solution of sodium chloride, dried over anhydrous sodium sulfate and concentrated under reduced pressure to give 280 mg of 1-(3-phenylpropyl)-4-[2-(3-piperidinyl)thiazolidin-4-ylcarbonyl]piperazine. This compound was dissolved in 8 ml of ethyl acetate, and 1 ml of 4N hydrogen chloride solution in dioxane was added. After 30 minutes of stirring, the resultant solid was collected by filtration and dried to give 200 mg of 1-(3-phenylpropyl)-4-[2-(3-piperidinyl)thiazolidin-4-ylcarbonyl]piperazine trihydrochloride. Melting point 174°–178° C.

| Elemental analysis (for $C_{22}H_{37}N_4OSCl_3.1.5H_2O$): | | | | |
|---|---|---|---|---|
| | C (%) | H (%) | N (%) | S (%) |
| Calculated: | 49.02 | 7.48 | 10.39 | 5.95 |
| Found: | 49.02 | 7.40 | 10.29 | 6.00 |

EXAMPLE 138

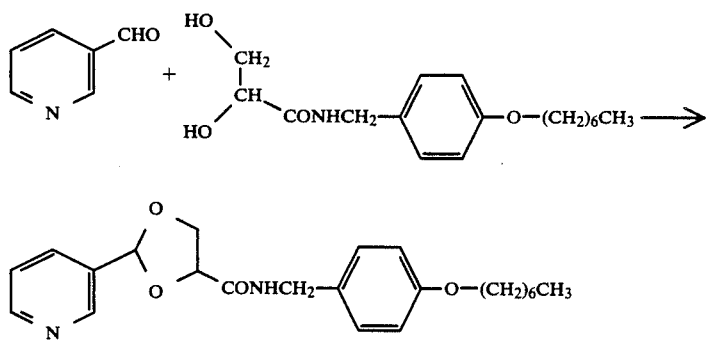

p-Toluenesulfonic acid (5 mg) was added to a solution of 70 mg of N (p-heptyloxybenzyl)glyceramide and mg of pyridine-3-carboxaldehyde in 70 ml of benzene plus 2.5 ml of pyridine, and the mixture was refluxed for 12 hours for azeotropic dehydration After cooling, the reaction mixture was washed with two portions of saturated aqueous solution of sodium hydrogen carbonate, three portions of water and one portion of saturated aqueous solution of sodium chloride, then dried over anhydrous sodium sulfate, and concentrated under reduced pressure. The residue obtained was purified by preparative silica gel thin layer chromatography to give 60 mg of N-(p-heptyloxybenzyl)-2-(3-pyridyl)-1,3-dioxolane-4-carboxamide.

NMR (CDCl$_3$) δ: 0.90 (3H, br t), 1.2 1.5 (8H), 1.6 2.0 (2H), 3.95 (2H, t, J=7 Hz), 4.1~4.8 (5H), 5.89 and 5.99 (respectively 1H), 6.6~7.2 (1H, exchange with D$_2$O), 6.8~7.4 (5H), 7.6~7.8 (1H), 8.6~8.7 (2H)

MS: m/z 398 (M+)

EXAMPLE 139

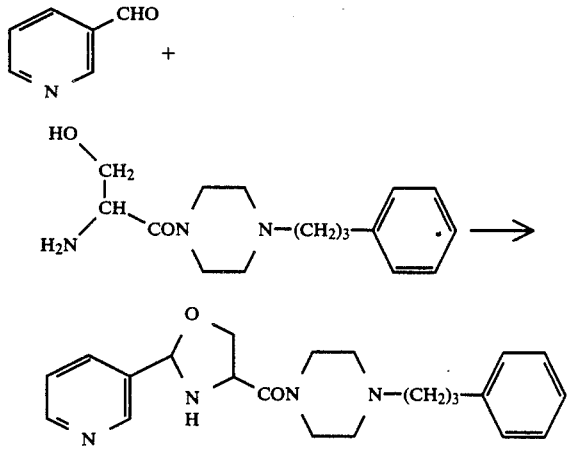

1-(3-Phenylpropyl)-4-[2-(3-pyridyl)oxazolidin-4-ylcarbonyl]piperazine was obtained from 1-(2-amino-3-hydroxypropionyl)-4-(3-phenylpropyl)piperazine and pyridine-3-carboxaldehyde by following the procedure of Example 138. Yield, 50%.

| Elemental analysis (for $C_{22}H_{28}N_4O_2$): | | |
|---|---|---|
| | C (%) | H (%) | N (%) |
| Calculated: | 69.45 | 7.42 | 14.72 |
| Found: | 69.16 | 7.38 | 14.58 |

MS: m/z 380 (M+)

EXAMPLE 140

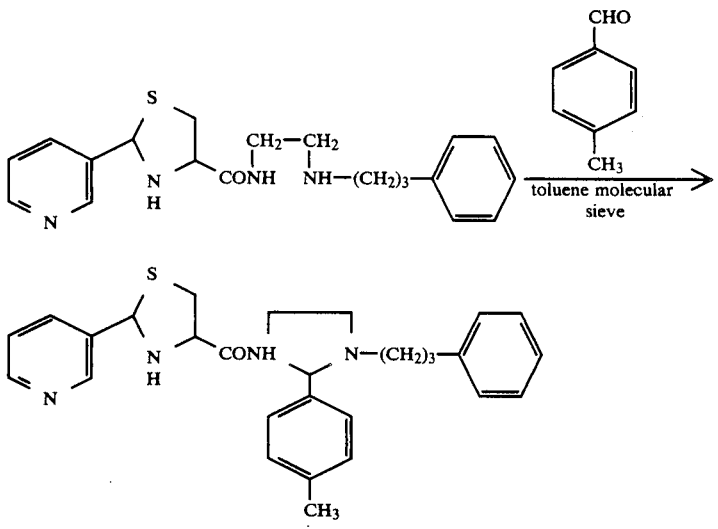

A mixture of 50 mg of N-(3-phenylpropylaminoethyl)-2-(3-pyridyl)thiazolidine-4-carboxamide, 17 mg of p-tolualdehyde, 100 mg of molecular sieve (4A) and 2 ml of toluene was heated in a sealed tube at 120° C. for 8 hours. The reaction mixture was filtered, the filtrate was concentrated under reduced pressure, and the residue was subjected to preparative thin layer chromatography (development with 2% methanol-ethyl acetate being made twice; $R_f$ value=0.15) to give 3.3 mg of 1-(3-phenylpropyl)-3-[2-(3-pyridyl)thiazolidin-4-ylcarbonyl]-2-(4-tolyl)imidazolidine.

NMR (CDCl$_3$) δ: 1.55~1.93 (3H, m), 2.39 (3H, s), 2.42~2.87 (8H, m), 3.09 (1H, dd, J=8 Hz, 12 Hz), 3.41 (1H, dd, J=4 Hz, J=12 Hz), 4.07~4.30 (1H, m), 5.16 (1H, s), 5.52 (1H, s), 7.03~7.42 (10H, m), 7.60 7.81 (1H, m), 8.44 (1H, dd, J=2 Hz, J=5 Hz), 8.63 (1H, d, J=2 Hz)

MS: m/z 472 (M+)

EXAMPLE 141 solved in 25 ml of ethyl acetate. To the solution was added with stirring at room temperature 2N hydrogen chloride solution in dioxane. The resultant powder was collected by filtration and dissolved in saturated sodium carbonate solution. Ethyl acetate was added, the organic layer was separated and washed with water, and the solvent was distilled off under reduced pressure. The residue was purified by silica gel column chromatography (silica gel 25 ml; 10% methanol-ethyl acetate) to give 210 mg of 1-[2-(5-methoxy-6 oxo 5,6-dihydro-3-pyridyl)thiazolidin-4-ylcarbonyl]-4-(3-phenylpropyl)piperazine.

NMR (DMSO-d$_6$) δ: 1.56~1.94 (2H, m), 2.20~2.80 (8H, m), 2.90~4.40 (10H, m), 5.28~5.66 (1H, m), 6.80~7.44 (7H, m)

MS: m/z 442 (M+)

EXAMPLE 142

The following compound was obtained in the same manner as in Example 90.

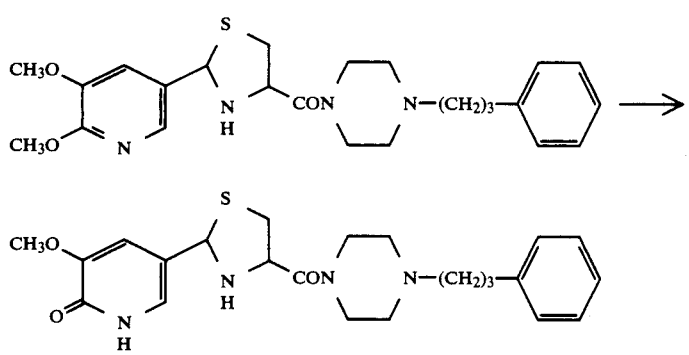

1-[2-(5,6-Dimethoxy-3-pyridyl)thiazolidin-4-ylcarbonyl]-4-(3-phenylpropyl)piperazine (730 mg) was dis-

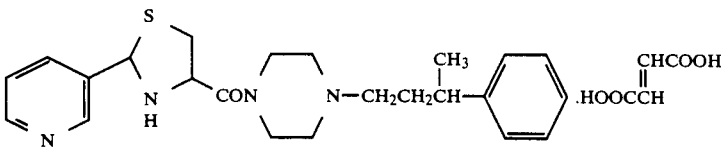

-continued
1-(3-Phenylbutyl)-4-[2-(3-pyridyl)thiazolidin-4-ylcarbonyl]piperazine fumarate Melting point 166°–168° C.

| Elemental analysis (for C<sub>27</sub>H<sub>34</sub>N<sub>4</sub>O<sub>5</sub>S): | | | | |
|---|---|---|---|---|
| | C (%) | H (%) | N (%) | S (%) |
| Calculated: | 61.58 | 6.51 | 10.64 | 6.09 |
| Found: | 61.21 | 6.45 | 10.58 | 6.42 |

MS: 410 (M+−C$_4$H$_4$O$_4$)

EXAMPLE 143

| Tablet composition (per tablet) | |
|---|---|
| The product obtained in Example 91 | 20 mg |
| Lactose | 57 mg |
| Corn starch | 38 mg |
| Hydroxypropylcellulose | 4 mg |
| Magnesium stearate | 1 mg |
| Total | 120 mg |

A homogeneous mixture is prepared from 20 g of the product obtained in Example 91, 57 g of lactose and 38 g of corn starch. Then, 40 g of 10% hydroxypropylcellulose solution is added, and the mixture is subjected to wet granulation. The granules are forced through a sieve and then dried. One gram of magnesium stearate is added to the thus-obtained granulation product. After thorough mixing, the mixture is formed into tablets using a tableting machine (die punch size: 7 mm, 5.6 R).

EXAMPLE 144

| Capsule composition (per capsule) | |
|---|---|
| The product obtained in Example 91 | 15 mg |
| Crystalline cellulose | 40 mg |
| Crystalline lactose | 144 mg |
| Magnesium stearate | 1 mg |
| Total | 200 mg |

A homogeneous mixture is prepared from 15 g of the product obtained in Example 91, 40 g of crystalline cellulose, 144 g of crystalline lactose and 1 g of magnesium stearate and filled into No. 3 capsules using a capsule-filling machine.

EXAMPLE 145

| Lyophilized preparation composition (per vial) | |
|---|---|
| The fumarate obtained in Example 91 | 1 mg |
| D-Mannitol | 5.0 mg |

In 800 ml of water are dissolved 1 g of the product obtained in Example 91 and 50 g of D-mannitol in that order. Water is added to make the whole volume 1 liter. This solution is aseptically filtered, then filled in 1-ml portions into vials, and lyophilized.

EXAMPLE 146

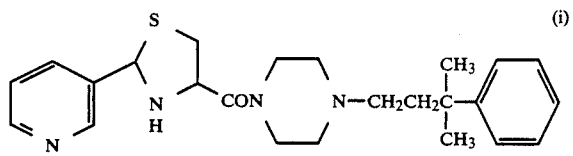
(i)

A solution of 2-(3-pyridyl)thiazolidin-4-carboxylic acid (0.81 g), 1-(3-methyl-3-phenylbutyl)-piperazine (0.73 g), 1-hydroxybenzotriazole (0.50 g) and dicyclohexylcarbodiimide (0.76 g) in N,N-dimethylformamide (7 ml) was stirred under room temperature for 12 hours. To the reaction solution was added ethyl acetate (10 ml) and the insoluble matter was filtered off. To the filtrate was added 0.5N sodium hydroxide and the solution was extracted with ethyl acetate. The ethyl acetate layer was extracted with 1N hydrochloric acid. The aqueous layer was made basic with potassium carbonate and extracted with ethyl acetate. The resultant ethyl acetate layer was washed with a saturated aqueous solution of sodium chloride, dried over anhydrous sodium sulfate and concentrated under reduced pressure. The residue was subjected to silica gel column chromatography and elution with an ethyl acetate-methanol (10:1) mixture gave 1.32 g of 1-(3-methyl-3-phenylbutyl)-4-[2-(3-pyridyl)thiazolidin-4-ylcarbonyl]piperazine.

NMR (CDCl$_3$) δ: 1.35 (6H,s), 1.65–1.97(2H,m) 1.97–2.48(7H,m), 2.78–3.73(6H,m) 3.78–4.30(1H,m) 5.57(0.5H,br.d, J=12 Hz) 5.95(0.5H,br.d, J=5 Hz) 7.05–7.43(6H,m), 7.71–7.96(1H,m) 8.43∼8.63(1H,m), 8.6

MS [m/z): 424 (M+)

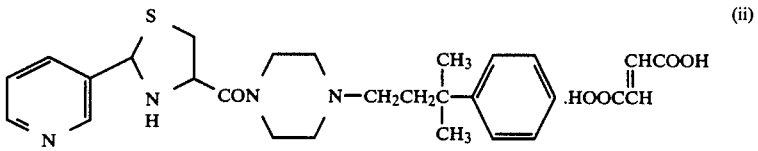
(ii)

To a solution of 1-(3-methyl-3-phenylbutyl)-4[2-(3-pyridyl)thiazolidin-4-ylcarbonyl]piperazine (1.22 g) in ethanol (6 ml) was added fumaric acid (0.32 g) and the mixture was dissolved. The solution was stirred at room temperature for 2 hours and allowed to stand at room temperature for a day. The resultant crystals were collected by filtration, washed with ethanol and then dried to give 1.08 g of 1-(3-methyl-3-phenylbutyl]-4-[2-(3-pyridyl)thiazolidin-4-ylcarbonyl]piperazine fumarate.

Melting point: 172°–173° C.

| Elemental analysis (for C<sub>28</sub>H<sub>36</sub>N<sub>4</sub>O<sub>5</sub>S) | | | | |
|---|---|---|---|---|
| | C (%) | H (%) | N (%) | S (%) |
| Calc. | 62.20 | 6.71 | 10.36 | 5.93 |
| Found | 61.92 | 6.67 | 10.17 | 6.09 |

EXAMPLE 147
The following compound was obtained in the same manner as in Example 146.
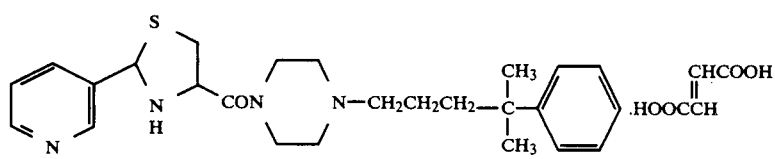
1-(4-Methyl-4-phenylpentyl)-4-[2-(3-pyridyl)thiazolidin-4-yl-carbonyl]piperazine fumarate
NMR (CDCl$_3$) δ: 1.05–1.47 (2H,m), 1.35(6H,s) 1.47–1.86(2H,m), 2.09–2.63(6H,m) 2.73–3.76(6H,m), 4.27(1H,q, J=6 Hz) 5.58(0.5H,s), 5.89(0.5H,s) 6.85[2H,s], 7.05–7.53[6H,m] 7.75–8.05(1H,m), 8.38–8.75[2H,m]
MS (m/z): 438 (M$^+$- C$_4$H$_4$O$_4$)

| Chemical Structure | Desired Product Physicochemical Properties |
|---|---|
| Ex. 148 [structure: pyridyl-thio compound with piperidine-N-CH2-phenyl-NH-CH(CH3)2 and HOOC-CH=CH-] | (1) NMR (DMSO-$d_6$)<br>δ: 1.20 (6H, d), 2.2–2.6 (4H, m), 2.6–3.5 (3H, m), 3.4–3.8 (6H, m), 4.1–4.4 (1H, m), 5.57, 5.89 (s, respectively 1H), 6.64 (2H, s), 7.12 (4H, s), 7.2–7.6 (1H, m), 7.7–8.1 (1H, m), 8.4–8.8 (2H, m)<br>(2) MS: m/z 410 (M$^+$ — C$_4$H$_4$O$_4$) |
| Ex. 149 [structure: pyridyl-thio compound with piperidine-N-CH2-phenyl-O-CH2CH2CH(CH3)2 and HOOC-CH=CH-] | (1) NMR (DMSO-$d_6$)<br>δ: 0.94 (6H, d), 1.4–1.9 (4H, m), 2.2–2.5 (4H, m), 2.6–3.2 (2H, m), 3.2–3.8 (7H, m), 3.96 (2H, t), 4.1–4.4 (1H, m), 5.56, 5.88 (s, respectively 1H), 6.65 (2H, s), 6.88, 7.25 (4H, ABq, J=3.7 Hz) 7.3–7.5 (1H, m), 7.7–8.0 (1H, m), 8.4–8.7 (2H, m)<br>(2) MS: m/z 454 (M$^+$ — C$_4$H$_4$O$_4$) |
| Ex. 150 [structure: pyridyl-thio compound N-COCH3, piperidine N-CH2CH2-C(CH3)2-phenyl] | (1) NMR (CDCl$_3$)<br>δ: 1.36 (6H, s), 2.07 (3H, s), 1.8–2.2 (2H, m), 2.3–2.6 (4H, m), 3.16 (2H, d), 3.4–4.0 (4H, m), 5.12 (1H, t), 6.10 (1H, s), 7.2–7.5 (6H, m), 8.4–8.8 (3H, m)<br>(2) MS: m/z 466 (M$^+$) |
| Ex. 151 [structure: pyridyl-thio compound with piperidine-NH·3HCl] | (1) Melting point: 165° C.<br>(2) NMR (DMSO-$d_6$)<br>δ: 2.9–3.3 (4H, m), 3.2–3.8 (2H, m), 3.6–4.2 (4H, m), 4.4–4.8 (2H, m), 5.92, 6.08 (s, respectively 1H), 7.9–8.2 (1H, m), 8.6–9.2 (3H, m) |
| Ex. 152 [structure: pyridyl-thio compound with piperidine-N-(CH2)3-phenyl and HOOC-CH=CH-] | (1) Melting point: 189–191° C.<br>(2) Elemental analysis (for C$_{26}$H$_{32}$N$_4$O$_5$S)<br><br>            C     H     N     S<br>Calculated: 60.92  6.29  10.93  6.26<br>(%)<br>Found:     60.68  6.15  10.86  6.13<br>(%)<br>[d-isomer] |
| Ex. 153 | (1) NMR (DMSO-$d_6$) |

-continued

| Chemical Structure | Desired Product | Physicochemical Properties |
|---|---|---|
| | | δ: 1.8–2.4 (4H, m), 2.6–3.4 (2H, m), 2.5–2.9 (4H, m), 2.9–3.2 (2H, m), 5.51, 5.78 (d, respectively 1H,), 7.1–7.6 (16H, m), 8.38–8.7 (2H, m)<br>(2) MS: m/z 520 (M$^+$) |
| Ex. 154 | | (1) NMR (DMSO-d$_6$)<br>δ: 2.4–2.6 (4H, m), 2.76 (2H, t), 2.9–3.5 (2H, m), 3.4–3.8 (4H, m), 4.12 (2H, t), 4.1–4.5 (1H, m), 5.58, 5.90 (s, respectively 1H), 6.64 (2H, s), 6.8–7.1 (2H, m), 7.1–7.6 (4H, m), 7.7–8.1 (1H, m), 8.4–8.6 (2H, m)<br>(2) MS: m/z 398 (M$^+$—C$_4$H$_4$O$_4$) |
| Ex. 155 | | (1) Melting point: 154–157° C.<br>(2) Elemental analysis (for C$_{21}$H$_{24}$N$_4$O$_2$S)<br>    C    H    N    S<br>Calculated: 63.61  6.10  14.13  8.09<br>(%)<br>Found:    63.45  6.12  13.93  8.26<br>(%) |
| Ex. 156 | | (1) Melting point: 120–125° C.<br>(2) Elemental analysis (for C$_{22}$H$_{23}$N$_3$O$_2$SCl$_2$)<br>    S    Cl<br>Calculated: 6.90  15.27<br>(%)<br>Found:    6.76  14.90<br>(%) |
| Ex. 157 | | (1) Melting point: 120–126° C. |

-continued

| Chemical Structure | Desired Product Physicochemical Properties |
|---|---|
| Ex. 158 <br> (structure with thiazole, pyridine, CONHCH₂-pyridine-OCH₂CH(CH₃)₂ ·3HCl) | (2) Elemental analysis (for C₂₀H₂₉N₄O₂SCl₃) <br>  Calculated:  S <br>  (%)      6.47 <br>  Found:    6.53 <br>  (%) |
| Ex. 159 <br> (structure with thiazole, pyridine, CONHCH₂-Cl-phenyl-OCH₂CH(CH₃)₂ ·2HCl) | (1) Melting point: 107–113° C. <br> (2) Elemental analysis (for C₂₁H₂₈N₃O₂SCl₃) <br>   C    H    N    S <br>  Calculated: 51.17 5.73 8.53 6.51 <br>  (%) <br>  Found:    51.29 5.63 8.55 6.52 <br>  (%) |
| Ex. 160 <br> (structure with thiazole, pyridine, CONHCH₂-NO₂-phenyl-OCH₂CH(CH₃)₂ ·2HCl) | (1) Melting point: 115–118° C. <br> (2) Elemental analysis (for C₂₁H₂₈N₄O₅SCl₂) <br>   C    H    N    S    Cl <br>  Calculated: 50.10 5.61 11.21 6.37 14.09 <br>  (%) <br>  Found:    50.03 5.71 11.03 6.37 13.96 <br>  (%) |
| Ex. 161 <br> (structure with thiazole, pyridine, CON-piperidine-CH₂C(CH₃)₂-phenyl-COOH) | (1) Melting point: 75° C. <br> (2) NMR (DMSO-d₆): <br> δ: 0.58–0.90, 1.08–1.35 (m, respectively 6H), 1.30 (s, 6H), 1.50–4.63 (m, 13H), 5.55, 5.89 (s, respectively 1H), 6.64 (s, 2H), 7.09–7.48 (m, 6H), 7.69–8.00 (m, 1H), 8.40–8.68 (m, 2H) |
|  | (1) Melting point: 129–132° C. |

-continued

| Chemical Structure | Desired Product Physicochemical Properties |
|---|---|
| Ex. 162 (structure with thiophene-pyridine, piperidine-CON, N-(CH₂)₃CH(OCH₃)₂, phenyl-CH=CH-COOH) | (2) Elemental analysis (for C₂₈H₃₆N₄O₆S)<br>　　　　C　　H　　N　　S<br>Calculated: 60.41　6.52　10.06　5.76 (%)<br>Found:　　60.01　6.39　9.92　5.89 (%) |
| Ex. 163 (structure with N(CH₂)₅OCH₃, cinnamic acid) | (1) Melting point: 145–146° C.<br>(2) Elemental analysis (for C₂₃H₃₄N₄O₆S)<br>　　　　C　　H　　N　　S<br>Calculated: 55.85　6.93　11.33　6.48 (%)<br>Found:　　55.73　6.86　11.15　6.49 (%) |
| Ex. 164 (structure with N-CH₂CH₂CH(diphenyl), cinnamic acid) | (1) Melting point: 169–172° C.<br>(2) Elemental analysis (for C₃₂H₃₆N₄O₅S)<br>　　　　C　　H　　N　　S<br>Calculated: 65.29　6.16　9.52　5.45 (%)<br>Found:　　65.55　6.10　9.44　5.70 (%) |
| Ex. 165 (chloropyridine-thiophene structure with piperazine, N-(CH₂)₃, cinnamic acid) | (1) Melting point: 145–146° C.<br>(2) Elemental analysis (for C₂₆H₃₁N₄O₅SCl)<br>　　　　C　　H　　N　　S　　Cl<br>Calculated: 57.08　5.71　10.24　5.86　6.48 (%)<br>Found:　　57.04　5.65　10.19　5.74　6.67 (%) |
| Ex. 166 (methylpyridine-thiophene structure with piperazine, N-(CH₂)₃, cinnamic acid) | (1) NMR (DMSO-d₆):<br>δ: 1.52–1.96 (2H, m), 2.12–2.74 (11H, m) 2.83–3.77 (9H, m), 4.26 (1H, q, J=7Hz), 5.52 (0.5H, s), 5.80 (0.5H, s), 6.63 (2H, s), 7.00–7.40 (6H, m), 7.60–7.89 (1H, m), 8.41–8.60 (1H, m),<br>(2) MS: m/z 410 (M⁺—C₄H₄O₄) |
| (next entry) | (1) NMR (CDCl₃) |

| Chemical Structure | Physicochemical Properties |
|---|---|
| Ex. 167 (pyridine-thiazole-piperidine with N-(CH₂)₃-phenyl-CH=CH-COOH, SCH₂CH₃ substituent) | δ: 1.38 (3H, t, J=7Hz), 1.62–2.04 (2H, m), 2.22–2.82 (8H, m), 2.84–3.86 (9H, m), 3.99–4.39 (1H, m), 5.84 (1H,br d,J=14Hz), 6.00 (1H, br s), 6.90–7.46 (6H, m), 7.63–7.98 (1H, m), 8.41–8.60 (1H, m)<br>(2) MS: m/z 410 (M⁺—C₄H₄O₄) |
| Ex. 168 (similar structure with Cl substituent) | (1) NMR (DMSO-d₆)<br>δ: 1.52–1.92 (2H, m), 2.16–2.84 (8H, m), 2.97–3.81 (6H, m), 4.18–4.46 (1H, m) 5.74 (0.4H, s), 6.02 (0.6H, s), 6.62 (2H, s), 7.01–7.54 (6H, m), 7.82–8.42 (2H, m),<br>(2) MS: m/z 430, 432 (M⁺—C₄H₄O₄) |
| Ex. 169 (piperidine with two CH₃ groups, N-(CH₂)₃-phenyl-CH=CH-COOH) | (1) Melting point: 75° C.<br>(2) NMR (CDCl₃ + DMSO-d₆):<br>δ: 0.96–1.24 (m, 6H), 1.56–1.88 (m, 2H), 2.38–4.44 (m, 13H), 5.58 (s), 5.95 (d) (respectively 1H), 6.76 (s, 2H), 7.07–7.42 (m, 6H), 7.77–7.97 (m, 1H), 8.45–8.60 (m, 1H), 8.69–8.77 (m, 1H), |
| Ex. 170 (N-CHCH₂CH₂-phenyl with CH₃ branch) | (1) Melting point: 68° C.<br>(2) NMR (DMSO-d₆):<br>δ: 0.93–1.24 (m, 3H), 1.35–1.94 (m, 2H), 2.28–2.73 (m, 5H), 2.89–3.68 (m, 8H), 4.13–4.37 (m, 1H), 5.57, 5.88 (s, respectively 1H), 6.65 (s, 2H), 7.13–7.48 (m, 6H), 7.74–8.01 (m, 1H), 8.40–8.69 (m, 2H) |
| Ex. 171 (N-CH₂CH₂CH-phenyl with OCH₃ branch) | (1) NMR (CDCl₃):<br>δ: 1.6–2.2 (2H, m), 2.2–2.7 (6H, m), 2.8–3.3 (2H, m), 3.00 (3H, s), 3.6–3.8 (4H, m), 4.0–4.4 (2H, m), 5.6, 6.0 (m, respectively,) 7.2–7.6 (6H, m), 7.7–8.0 (1H, m), 8.4–8.7 (1H, m), 8.7–8.9 (1H, m),<br>(2) MS: m/z 426 (M⁺) |
| Ex. 171 (cont.) | (1) NMR (CDCl₃): |

-continued

| Chemical Structure | Desired Product Physicochemical Properties |
|---|---|
| Ex. 172 (structure with biphenyl-CH2-C(=O)-N-piperidine-CON-CH-CH2-thiazolopyridine) | (1) δ: 2.52–2.83 (4H, m), 2.85–4.33 (10H, m), 5.62 (0.5H, m), 5.99 (0.5H, s), 7.18–8.16 (10H, m), 8.45–8.66 (2H, m) 8.71–8.85 (1H, m)<br>(2) MS: m/z 472 (M+) |
| Ex. 173 (structure with cyclohexyl-N-CH2CH2-NHCO- and COCOOC2H5 on N, thiazolopyridine) | (1) Elemental analysis (for C16H24N4OS)<br>    C    H    N    S<br>Calculated: 59.97  7.55  17.48  10.01 (%)<br>Found:     59.77  7.56  17.22  10.22 (%)<br>(2) MS: m/z 321 (M+ + 1) |
| Ex. 174 (structure with 4-(2-carboxyvinyl)-α,α-dimethylbenzyl group on piperidine N, thiazolopyridine) | (1) Melting point: 90° C.<br>(2) Elemental analysis (for C28H35N4O4S·H2O)<br>    C    H    N    S<br>Calculated: 58.34  6.43  8.50  4.87 (%)<br>Found:     58.34  6.22  8.38  5.76 (%) |
| Ex. 175 (structure with N—(CH2)3S(=O)— phenyl with CH=CH-COOH, piperidine, thiazolopyridine) | (1) NMR (DMSO-d6):<br>δ: 1.42–1.94 (2H, m), 2.11–2.61 (6H, m), 2.64–3.19 (2H, m), 3.19–3.72 (6H, m), 4.15–4.43 (1H, m), 5.61 (0.5H, s), 5.92 (0.5H, s), 6.67 (2H, s), 7.30–8.09 (7H, m), 8.45–8.78 (2H, m)<br>(2) MS: m/z 445 (M+ + 1-C4H4O4) |
| Ex. 175 (structure with N—(CH2)3SO2— phenyl with CH=CH-COOH, piperidine, thiazolopyridine) | (1) NMR (DMSO-d6)<br>δ: 1.48–1.91 (2H, m), 2.12–2.60 (6H, m), 2.79–3.74 (8H, m), 4.08–4.37 (1H, m), 5.56 (1H, s), 5.87 (1H, s), 6.63 (2H, s), 7.24–7.51 (1H, m), 7.51–8.02 (6H, m), 8.39–8.73 (2H, m)<br>(2) MS: m/z 4.60 (M+—C4H4O4) |

The anti-PAF activity of the compounds according to the invention has been confirmed by the following test: Effect on platelet activating factor (PAF)-induced platelet aggregation in plasma Method: Nine volumes of blood were drawn from the central ear artery of male rabbit (Japan white, 3 kg) directly into plastic syringe containing 1 volume of 3.8% sodium citrate. The blood was centrifuged at 270×g for 10 minutes at room temperature and the platelet rich plasma (PRP) was removed. The pellet was further centrifuged at 1,100×g for 15 minutes. The supernatant was used as platelet poor plasma (PPP). The platelet concentration was adjusted to $5 \times 10^5$ cells/μl with PPP. Platelet aggregation was measured by the method of G. V. R. Born and M. J. Cross [Journal of Physiology, 168, 178–195 (1963)] using a HEMA TRACER (Nikou Bio Science, Japan). Varying concentration of compounds were added to the PRP 2 minutes prior to PAF ($10^{-8}$ M). The extent of platelet aggregation was determined by the maximum change of light transmission, assigning the transmission of unstimulated PRP to be 0% and that of PPP to be as 100%. Percent inhibition with compound was calculated by dividing the percent aggregation in the presence of compound by that in the control, and then the $IC_{50}$ values were calculated. Results: As shown in Table 1, a lot of compounds of the present invention inhibited the PAF-induced rabbit platelet aggregation in plasma ($IC_{50}$ value of at least $10^{-5}$ M). Especially, the compounds of Examples 37, 49, 67, 71, 81, 83, 85, 90, 91, 119 and 142 were potent inhibitors having $IC_{50}$ values of $2.8 \times 10^{-8}$ to $8.5 \times 10^{-8}$ M, while these compounds did not inhibit the platelet aggregation induced by ADP ($3 \times 10^{-6}$ M), arachidonic acid ($1 \times 10^{-4}$ M) or collagen (10 μg/ml) (data not shown). These results suggest that the compounds of this invention are specific antagonists of PAF.

TABLE 1

| Example No. | $IC_{50}$ (μM) |
| --- | --- |
| 20 | 0.8 |
| 22 | 0.790 |
| 23 | 0.430 |
| 24 | 0.250 |
| 32 | 0.490 |
| 34 | 0.950 |
| 36 | 0.860 |
| 37 | 0.054 |
| 46 | 0.650 |
| 48 | 0.450 |
| 49 | 0.085 |
| 50 | 0.800 |
| 54 | 0.240 |
| 55 | 0.160 |
| 56 | 0.120 |
| 57 | 0.200 |
| 58 | 0.390 |
| 59 | 0.210 |
| 60 | 0.760 |
| 61 | 0.770 |
| 63 | 0.500 |
| 64 | 0.390 |
| 65 | 0.120 |
| 66 | 0.430 |
| 67 | 0.071 |
| 71 | 0.064 |
| 72 | 0.900 |
| 76 | 0.900 |
| 77 | 0.430 |
| 78 | 0.280 |
| 80 | 0.340 |
| 81 | 0.028 |
| 82 | 0.160 |

TABLE 1-continued

| Example No. | $IC_{50}$ (μM) |
| --- | --- |
| 83 | 0.034 |
| 84 | 0.220 |
| 85 | 0.072 |
| 89 | 0.400 |
| 90 | 0.067 |
| 91 | 0.071 |
| 92 | 0.260 |
| 93 | 0.630 |
| 97 | 0.120 |
| 105 | 0.940 |
| 117 | 0.260 |
| 118 | 0.630 |
| 119 | 0.079 |
| 120 | 0.170 |
| 121 | 0.19 |
| 123 | 0.18 |
| 124 | 0.18 |
| 125 | 0.45 |
| 126 | 0.18 |
| 127 | 0.46 |
| 128 | 0.97 |

While the invention has been described in detail and with reference to specific embodiments thereof, it will be apparent to one skilled in the art that various changes and modifications can be made therein without departing from the spirit and scope thereof.

What is claimed is:

1. A saturated heterocyclic carboxamide compound of the formula (I) or a pharmaceutically acceptable salt thereof:

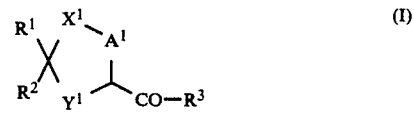

wherein $R^1$ represents a substituted or unsubstituted 5- or 6-membered heterocyclic group wherein the hetero atom is at least one member selected from the group consisting of oxygen, sulfur and nitrogen, which may be condensed with a benzene ring; $R^2$ represents a hydrogen atom, a lower alkyl group, or an $R^1$ group defined above; $X^1$ represents an oxygen atom, a sulfur atom, or a methylene group, which may be substituted by a lower alkyl group; $Y^1$ represents an oxygen atom, a sulfur atom, or a group of the formula $>N-R^4$, wherein $R^4$ is a hydrogen atom, a lower alkyl group, a carboxyl group, an acyl group or a lower alkoxycarbonyl group; $A^1$ represents a methylene group or an ethylene group, each of which may be substituted by a lower alkyl group; $R^3$ represents a group of the formula

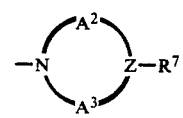

in which:

$A^2$ and $A^3$, which may be the same or different, each represents a lower alkylene group containing 1 to 3 carbon atoms, Z is a nitrogen atom and $R^7$ is a hydrogen atom, a substituted or unsubstituted hydrocarbon group or a carboxyl, acyl, lower alkoxycarbonyl, carbamoyl, or mono- or di-lower alkylaminocarbonyl group, wherein substituents on said heterocyclic and hydrocarbon groups are selected from the group consisting of halo, lower alkyl, hydroxy, mercapto, alkoxy, lower alkylthio, cycloalkyl-lower alkoxy, cycloalkyl-lower alkylthio, aryl, aralkyloxy, aralkylthio, aryloxy, arylthio, arylsulfinyl, arylsulfonyl, aryloxy-lower alkoxy, aryloxy-lower alkylthio, arylthio-lower alkoxy, arylthio-lower alkylthio, oxo, thioxo, carboxyl, lower alkoxycarbonyl, acyl, cyano, carbamoyl, mono- or di-lower alkylaminocarbonyl, nitro, amino, mono- or di-lower alkylamino, mono-or diaralkylamino and N-aralkyl-N-lower alkylamino, and wherein said cycloalkyl contains 3 to 7 carbon atoms and said aryl is phenyl or naphthyl.

2. A saturated heterocyclic carboxamide compound or a pharmaceutically acceptable salt thereof as claimed in claim 1, wherein $R^1$ is a pyridyl group, a quinolyl group, a pyrrolyl group, a piperidyl group, a pyrazinyl group or a furyl group, each of which may be substituted by one or two substituents each selected from the group consisting of a lower alkyl group, a lower alkoxy group, a lower alkoxycarbonyl group and a dimethylamino group, said pyridyl group may be in the pyridone form; $R^2$ is a hydrogen atom, a lower alkyl group or a pyridyl group; $X^1$ is a sulfur atom, an oxygen atom or a methylene group; $Y^1$ is an oxygen atom or $>N-R^4$, wherein $R^4$ is a hydrogen atom, a lower alkyl group, an acyl group or a lower alkoxycarbonyl group; $A^1$ is a methylene or ethylene group, which may be substituted by one or two lower alkyl groups; $R^3$ is

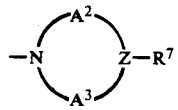

in which $A^2$ and $A^3$, which may be the same or different, each is a lower alkylene group containing 1 to 3 carbon atoms; Z is a nitrogen atom; $R^7$ is a hydrogen atom, a substituted or unsubstituted hydrocarbon group, an acyl group, a lower alkoxycarbonyl group, a carbamoyl group or a mono- or di-alkylaminocarbonyl group, wherein substituents on said hydrocarbon group are selected from the group consisting of halo, lower alkyl, hydroxy, mercapto, alkoxy, lower alkylthio, cycloalkyl-lower alkoxy, cycloalkyl-lower alkylthio, aryl, aralkyloxy, aralkylthio, aryloxy, arylthio, arylsulfinyl, arylsulfonyl, aryloxy-lower alkoxy, aryloxy-lower alkylthio, arylthio-lower alkoxy, arylthio-lower alkylthio, oxo, thioxo, carboxyl, lower alkoxycarbonyl, acyl, cyano, carbamoyl, mono- or di-lower alkylaminocarbonyl, nitro, amino, mono- or di-lower alkylamino, mono- or diaralkylamino and N-aralkyl-N-lower alkylamino, and wherein said cycloalkyl contains 3 to 7 carbon atoms and said aryl is phenyl or naphthyl.

3. A saturated heterocyclic carboxamide compound or a pharmaceutically acceptable salt thereof as claimed in claim 2, wherein $R^1$ is a pyridyl group, which may be substituted by one or two substituents each selected from the group consisting of a lower alkyl group, a lower alkoxycarbonyl group, or a dimethylamino group; $R^2$ is a hydrogen atom; $X^1$ is a sulfur atom; $Y^1$ is $>N-R^4$, in which $R^4$ is a hydrogen atom, a lower alkyl, an acyl group or a lower alkoxycarbonyl group; $A^1$ is a methylene group, which may be substituted by one or two lower alkyl groups; and $R^3$ is as defined in claim 2.

4. A saturated heterocyclic carboxamide compound or a pharmaceutically acceptable salt thereof as claimed in claim 3, wherein $R^3$ is

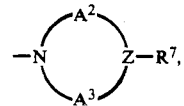

in which $R^7$ is a hydrogen atom, a substituted or unsubstituted hydrocarbon group, an acyl group, a lower alkoxycarbonyl group, a carbamoyl group or a mono- or di-alkylaminocarbonyl group; and $R^1$, $R^2$, $X^1$, $Y^1$, $A^1$ and any substitutents on said hydrocarbon group are as defined in claim 3.

5. A saturated heterocyclic carboxamide compound or a pharmaceutically acceptable salt thereof as claimed in claim 4, wherein $R^1$ is a pyridyl group; $R^2$ is a hydrogen atom; $X^1$ is a sulfur atom; $Y^1$ is $>NH$; $A^1$ is a methylene group; and $R^3$ is

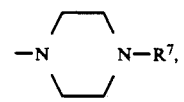

in which $R^7$ is an aryl-lower alkyl group.

6. A saturated heterocyclic carboxamide compound or a pharmaceutically acceptable salt thereof as claimed in claim 1, wherein said compound is 1-(3-phenylpropyl)-4-[2-(3-pyridyl)thiazolidin-4-ylcarbonyl]piperazine.

7. A saturated heterocyclic carboxamide compound or a pharmaceutically acceptable salt thereof as claimed in claim 1, wherein said compound is 1-decyl-4-[2-(3-pyridyl)thiazolidin-4-ylcarbonyl]piperazine.

8. A saturated heterocyclic carboxamide compound or a pharmaceutically acceptable salt thereof as claimed in claim 1, wherein said compound is 1-(4-oxo-4-phenylbutyl)-4-[2-(3-pyridyl)thiazolidin-4-ylcarbonyl]piperazine.

9. A saturated heterocyclic carboxamide compound or a pharmaceutically acceptable salt thereof as claimed in claim 1, wherein said compound is 1-(3-phenylbutyl)-4-[2-(3-pyridyl)-thiazolidin-4-ylcarbonyl]piperazine.

10. A pharmaceutical composition useful for antagonizing the physiological activities of platelet activating factor (PAF) comprised of a therapeutically effective amount of the saturated heterocyclic carboxamide compound of claim 1 and a pharmaceutically acceptable carrier.

11. The pharmaceutically composition of claim 10 wherein said compound is 1-(3-phenylpropyl)-4-[2-(3-pyridyl)thiazolidin-4-ylcarbonyl]piperazine or an acid addition salt thereof.

12. The pharmaceutical compound of claim 10 wherein said compound is 1-decyl-4-[2-(3-pyridyl)-thiazolidin-4-ylcarbonyl]piperazine or an acid addition salt thereof.

13. The pharmaceutical composition of claim 10 wherein said compound is 1-(4-oxo-4-phenylbutyl)-4-[2-(3-pyridyl)thiazolidin-4-ylcarbonyl]piperazine or an acid addition salt thereof.

14. A method for antagonizing the physiological activities of platelet activating factor (PAF) in a host, which comprises administering to said host an antagonizing-effective amount of the pharmaceutical composition of claim 10.

15. The method of claim 14 wherein said compound is 1-(3-phenylpropyl)-4-[2-(3-pyridyl)thiazolidin-4-ylcarbonyl]piperazine.

16. The method of claim 14 wherein said compound is 1-decyl-4-[2-(3-pyridyl)thiazolidin-4-ylcarbonyl]piperazine.

17. The method of claim 14 wherein said compound is 1-(4-oxo-4-phenylbutyl)-4-[2-(3-pyridyl)thiazolidin-4-ylcarbonyl]piperazine.

* * * * *